United States Patent
Phadke et al.

(10) Patent No.: US 7,365,068 B2
(45) Date of Patent: *Apr. 29, 2008

(54) SUBSTITUTED ARYL ACYLTHIOUREAS AND RELATED COMPOUNDS; INHIBITORS OF VIRAL REPLICATION

(75) Inventors: Avinash Phadke, Branford, CT (US); Dawei Chen, Middletown, CT (US); Milind Deshpande, Madison, CT (US); Andrew Thurkauf, Ridgefield, CT (US); Xiangzhu Wang, Branford, CT (US); Yiping Shen, Branford, CT (US); Cuixian Liu, Branford, CT (US); Jesse Quinn, Windsor, CT (US); Junko Ohkanda, Osaka (JP); Shouming Li, Cheshire, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/131,013

(22) Filed: May 17, 2005

(65) Prior Publication Data

US 2006/0025416 A1    Feb. 2, 2006

Related U.S. Application Data

(60) Provisional application No. 60/572,156, filed on May 18, 2004.

(51) Int. Cl.
*A61K 31/496*   (2006.01)
*A61K 31/444*   (2006.01)
*A61K 31/5377*  (2006.01)
*C07D 211/78*   (2006.01)
*C07D 401/02*   (2006.01)
*C07D 401/06*   (2006.01)
*C07D 413/02*   (2006.01)
*C07D 413/06*   (2006.01)

(52) U.S. Cl. .................. 514/235.5; 514/355; 514/357; 514/336; 514/253.01; 544/124; 544/360; 546/329; 546/316

(58) Field of Classification Search .......... 514/253.01, 514/355, 336, 357, 235; 544/124, 360; 546/329, 546/316
See application file for complete search history.

(56) References Cited

U.S. PATENT DOCUMENTS

| | | | |
|---|---|---|---|
| 3,699,110 A | 10/1972 | Dixon | |
| 3,931,244 A | 1/1976 | Archibald et al. | |
| 3,966,968 A | 6/1976 | Andree et al. | |
| 4,082,765 A | 4/1978 | Kirkpatrick | |
| 4,160,037 A | 7/1979 | Kaugars | |
| 4,338,257 A | 7/1982 | Patel | |
| 4,350,706 A | 9/1982 | Brouwer et al. | |
| 4,533,676 A | 8/1985 | Sirrenberg et al. | |
| 4,602,109 A | 7/1986 | Chou et al. | |
| 4,607,044 A | 8/1986 | Wellinga et al. | |
| 4,638,088 A | 1/1987 | Chou et al. | |
| 4,659,736 A | 4/1987 | Schluter et al. | |
| 4,665,097 A | 5/1987 | Cain | |

(Continued)

FOREIGN PATENT DOCUMENTS

CA          2170222          8/1996

(Continued)

OTHER PUBLICATIONS

Douglass et al. Journal of American Chemical Society, 1934, 56, p. 1609.*

(Continued)

*Primary Examiner*—Rebecca Anderson
*Assistant Examiner*—Yong Chu
(74) *Attorney, Agent, or Firm*—Cantor Colburn LLP

(57) ABSTRACT

The invention provides compounds and pharmaceutically acceptable salts of Formula I

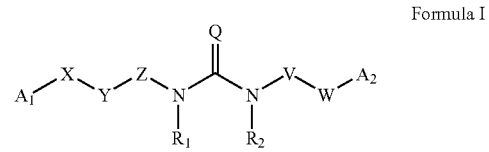

Formula I wherein the variables $A_1$, $A_2$, $R_1$, $R_2$, V, W, X, Y, and Z are defined herein. Certain compounds of Formula I described herein which possess potent antiviral activity. The invention particularly provides compounds of Formula I that are potent and/or selective inhibitors of Hepatitis C virus replication. The invention also provides pharmaceutical compositions containing one or more compound of Formula I, or a salt, solvate, or acylated prodrug of such compounds, and one or more pharmaceutically acceptable carriers, excipients, or diluents.

The invention further comprises methods of treating patients suffering from certain infectious diseases by administering to such patients an amount of a compound of Formula I effective to reduce signs or symptoms of the disease or disorder. These infectious diseases include viral infections, particularly HCV infections. The invention is particularly includes methods of treating human patients suffering from an infectious disease, but also encompasses methods of treating other animals, including livestock and domesticated companion animals, suffering from an infectious disease.

Methods of treatment include administering a compound of Formula I as a single active agent or administering a compound of Formula I in combination with on or more other therapeutic agent.

19 Claims, No Drawings

U.S. PATENT DOCUMENTS

| | | | |
|---|---|---|---|
| 4,707,478 | A | 11/1987 | Studt et al. |
| 4,774,260 | A | 9/1988 | Sirrenberg et al. |
| 4,868,215 | A | 9/1989 | Bisabri-Ershadi et al. |
| 4,873,264 | A | 10/1989 | Chou et al. |
| 4,880,838 | A | 11/1989 | Chou et al. |
| 4,920,135 | A | 4/1990 | Wellinga et al. |
| 5,001,266 | A | 3/1991 | Rigterink et al. |
| 5,166,180 | A | 11/1992 | Jenkins |
| 5,266,707 | A | 11/1993 | Matsumoto et al. |
| 5,344,842 | A | 9/1994 | Missbach |
| 5,424,204 | A | 6/1995 | Aoyama et al. |
| 5,437,996 | A | 8/1995 | Kojiri et al. |
| 5,449,812 | A | 9/1995 | Schnabel et al. |
| 5,589,365 | A | 12/1996 | Kojiri et al. |
| 5,591,842 | A | 1/1997 | Kojiri et al. |
| 5,656,642 | A | 8/1997 | Fujioka et al. |
| 5,723,409 | A | 3/1998 | Schnabel et al. |
| 5,728,699 | A | 3/1998 | Toriyabe et al. |
| 5,840,917 | A | 11/1998 | Oi et al. |
| 5,849,666 | A | 12/1998 | Kehne et al. |
| 5,874,615 | A | 2/1999 | Verbrugge et al. |
| 5,922,740 | A | 7/1999 | Braunlich et al. |
| 6,060,484 | A | 5/2000 | Fritz et al. |
| 6,093,742 | A | 7/2000 | Salituro et al. |
| 6,133,258 | A | 10/2000 | Shishikura et al. |
| 6,136,826 | A | 10/2000 | Fujioka et al. |
| 6,169,092 | B1 | 1/2001 | Braunlich et al. |
| 6,174,905 | B1 | 1/2001 | Suzuki et al. |
| 6,207,715 | B1 | 3/2001 | Bloom et al. |
| 6,255,349 | B1 | 7/2001 | Bloom et al. |
| 6,268,387 | B1 | 7/2001 | Connor et al. |
| 6,335,350 | B1 | 1/2002 | Connor et al. |
| 6,376,504 | B1 | 4/2002 | Uckun et al. |
| 6,399,657 | B1 | 6/2002 | Braunlich et al. |
| 6,420,396 | B1 | 7/2002 | Albers et al. |
| 6,469,034 | B1 | 10/2002 | Uckun et al. |
| 6,528,528 | B2 | 3/2003 | Connor et al. |
| 6,610,715 | B1 | 8/2003 | Youn et al. |
| 6,677,360 | B2 | 1/2004 | Albers et al. |
| 6,677,372 | B2 | 1/2004 | Braulich et al. |
| 6,780,873 | B2 | 8/2004 | Crooks et al. |
| 6,864,289 | B1 | 3/2005 | Tohnishi et al. |
| 2002/0099210 | A1 | 7/2002 | Alexander et al. |
| 2002/0128301 | A1 | 9/2002 | Zhou et al. |
| 2003/0109578 | A1 | 6/2003 | Braunlich et al. |
| 2003/0109579 | A1 | 6/2003 | Sauerberg et al. |
| 2003/0125318 | A1 | 7/2003 | Alanine et al. |
| 2003/0195231 | A1 | 10/2003 | Takemoto et al. |
| 2004/0009982 | A1 | 1/2004 | Tohnishi et al. |
| 2004/0014754 | A1 | 1/2004 | Crooks et al. |
| 2004/0029877 | A1 | 2/2004 | Crooks et al. |
| 2004/0030132 | A1 | 2/2004 | Albers et al. |
| 2004/0034041 | A1 | 2/2004 | Dhanak et al. |
| 2004/0132727 | A1 | 7/2004 | Sakai et al. |
| 2004/0138205 | A1* | 7/2004 | Chen et al. ............ 514/217.04 |
| 2004/0147535 | A1 | 7/2004 | Crooks et al. |
| 2004/0147569 | A1 | 7/2004 | Suzuki et al. |
| 2004/0147741 | A1 | 7/2004 | Sundermann et al. |
| 2004/0162287 | A1 | 8/2004 | Sundermann et al. |
| 2004/0229872 | A1 | 11/2004 | Friderichs et al. |
| 2005/0054654 | A1 | 3/2005 | Huth et al. |

FOREIGN PATENT DOCUMENTS

| | | |
|---|---|---|
| CN | 1183409 | 6/1998 |
| EP | 0 518 376 A1 | 12/1992 |
| EP | 1 251 130 A1 | 10/2002 |
| JP | 56-025148 | 3/1981 |
| JP | 61-106551 | 5/1986 |
| JP | 06-003787 A2 | 1/1994 |
| JP | 06-287171 A2 | 10/1994 |
| JP | 11-335375 A2 | 12/1999 |
| JP | 2002-506854 | 3/2002 |
| JP | 2002 533301 | 10/2002 |
| JP | 2002 533444 | 10/2002 |
| JP | 2002 536435 | 10/2002 |
| JP | 2002 540111 | 11/2002 |
| JP | 2003 501459 | 1/2003 |
| JP | 2003 502371 | 1/2003 |
| JP | 2004 553861 | 6/2004 |
| JP | 2004 504304 | 8/2005 |
| WO | WO 94 03976 A1 | 2/1997 |
| WO | WO 97 11050 A1 | 3/1997 |
| WO | WO 97 17970 A1 | 5/1997 |
| WO | WO 97 30047 A1 | 8/1997 |
| WO | WO 98 42323 A1 | 10/1998 |
| WO | WO 99 59586 A1 | 11/1999 |
| WO | WO 00 34261 A3 | 6/2000 |
| WO | WO 00 35864 A1 | 6/2000 |
| WO | WO 00 57869 A2 | 10/2000 |
| WO | 0076495 A1 | 12/2000 |
| WO | WO 03 037869 A1 | 5/2003 |
| WO | WO 03 097604 A1 | 11/2003 |
| WO | WO 03 097605 A1 | 11/2003 |
| WO | WO 03 099812 A1 | 12/2003 |
| WO | WO 2004 020416 A2 | 3/2004 |
| WO | 2004046095 A1 | 6/2004 |
| WO | WO 2005 063293 A1 | 7/2005 |

OTHER PUBLICATIONS

Baltabaev, U.A. et al. "Synthesis of the Nicotinoylthioureas Compounds," *Azerbaidzhanskii Kim. Zhur.* (2002) 4: 97-99.

Baltabaev, U.A. et al. "Antiinflammatory Activity of New Aryl- and Aroylthioureas," *Pharmaceutical Chemistry Journal* (2000) 36(2): 77-79.

Bloom, J.D. et al. "Thiourea of Herpes Virus. Part 1: Bis-(aryl)thiourea Inhibitors of CMV," *Bioorganic & Medicinal Chemistry Letters* (2003) 13: 2929-2932.

Daugulis, O. and Avotins, F. "N-(3-Acetyl-2,2-Dimethylcyclobutyl)Acetyl-N'-Alkryl(aryl thioureas)," *Latvijas Kimijas Zurnals* (1993) 6: 714-719.

Douglass, I.B. and Dains, F.B., "Some Derivatives of Benzoyl and Furoyl Isothicyanates and Their Use in Synthesizing Heterocyclic Compounds," *Journal of the American Chemical Society* (1934) 56(3): 719-721.

Douglass, I.B. and Forman, L. E. "Nicotinyl Isothiocyanate and Some of Its Derivatives," *Journal of the American Chemical Society* (1934) 56(7):1609.

Du, X. et al., "Aryl Ureas Represent A New Class of Anti-Trypanosomal Agents," *Chemistry & Biology* (2000) 7(9): 733-742.

Goerdeler, J. and Jonas, K. "Substituierte Thiazolin-dione-(4.5) und ihre Thermische Spaltung in Isocyanate und Senföle," *Chemische Berichte* (1966) 99(11): 3572-3581.

Goerdeler, J. and Wobig, D. "Das Dualistische Verhalten von Carbamoyl-isothiocyanaten, I," *Liebigs Annalen Der Chem* (1970) 731: 120-141.

Koščik, D. et al. "New Synthesis of 2-Amino-4-oxopyrido [3,2-e]-1,3-thiazines and 1-Alkyl(aryl)pyrido [3,2-e]-2-thiouracils," *Collection Czechoslovak Chem. Comm.* (1983) 48: 3315-3328.

Kulka, M. "Base-Catalysed Ring Opening of N-(Aminothioxomethyl-5,6-dihydro-2-methyl-1,4-oxathiin-3-carboxamides," *Canadian Journal of Chemistry* (1980) 58(19): 2044-2048.

Kutschy, P. et al. "Synthesis of Some Analogs of Indole Phytoalexines Brassinin and Methoxybrassenin B and Their Positional Isomers," *Collection of Czechoslovak Chemical Communications* (1999) 64(2): 348-362.

Ludovici, D.W. et al. "Evolution of Anti-HIV Drug Candidates. Part 1: From Apha-Anilinophenylacetamide (Alpha-APA) to Imidoyl Thiourea (ITU)," *Biorganic & Medicinal Chemistry Letters* (2001) 11: 2225-2228.

Matosiuk, D. et al. "Synthesis of New 1-Aryl-3-piperidinylcarbonylimidazoldine-2-ones and 2-thiones," *Acta Poloniae Pharmaceutica —Drug Research* (1996) 53(1): 75-77.

Matsuo, M. et al. "New 2-Aryliminoimidazolidines I. Synthesis and Antihypertensive Properties of 2-(2-Phenoxyphenylimino)imidazolidines and Related Compounds," *Chemical and Pharmaceutical Bulletin* (1985) 33(10): 4409-4421.

Mishra, V. et al., "Synthesis of Aryl Semicarbazone of 4-Aminoacetophenone and Their Anti-HIV Activity," *Pharmaceutica Acta Helvetiae* (1998) 73(4): 215-218.

Misra, V.S. and Saxena, A., "N-(2-Dibenzothiophenyl)-N' -alkyl and N' -aryl Thioureas, N-(2-Dibenzothiophenyl) and N-(2-Dibenzothiophenyl-5-dioxide) Amidines," *Journal für Praktische Chemie 4 Reihe Band* (1967) 36: 256-259.

Mitin, N.I. et al, "Effect of Adamantine-Containing Compounds On Aujeszky's And Avian Influenza Disease Viruses," *Fiziologicheski Aktivnye Veschestva* (1977) 9: 31-35.

Mukmeneva, N.A. et al. "3-Benzoylthiourea Derivatives as Antioxidants for Polymers," *Russian Journal Applied of Chemistry* (1994) 67(4): 565-567.

Otazo-Sanchez, E. et al. "Aroylthioureas: New Organic Ionophores for Heavy-Metal Ion Slective Electrodes," *Journal of the Chemical Society Perkin Translations* (2001) 2(11): 2211-2218.

Patel, N.B. and Bhagat, P.R. "2- [4' -(p-Acetamidophenylcarbonyl) Piperazin-1'-yl] -3-(N-Aryl-Thioureidocarbonyl) Pyridines as Antibacterial Agents," *Indian Journal of Heterocyclic Chemistry* (2002) 12: 83-84.

Patel, N.B. and Bhagat, P.R. "Antibacterial Study of 2-(p-Tolyl Sulfonamido)-3-(N-Arylthioureido Carbonyl) Pyridine Derivatives," *Oriental Journal of Chemistry* (2002) 18(3): 551-554.

Praceus, Chr. et al. "Inhibition of Vaccinia Virus In Vitro By Substituted Monophenylthioureas," *Natruwissenschaften* (1964) 51(4): 94-95.

Rashan, L.J. et al. "Synthesis and Biological Evaluation of N-Salicyloyl-N-Benzyl Thiorue and 2,2-Dimethyl-4-oxo-6-Methoxy Benzo-1,3-Dioxin," *Il Farmaco* (1991) 46(5): 677-683.

Rasmussen, C.R. et al. "Improved Procedures For the Preparation of Cycloalkyl-, Arylalkyl-, and Arylthioureas," *Department of Chemical Research* (1988) 6: 456-459.

Reynaud, P. et al. "Preparation de quelques p-alcoxphenyl-3 thiourees: leur activite <in vitro> et <in vivo> sur la souche H37RV du bacilli tuberculeux," *Chimie Therapeutique* (1966)7: 421-424.

Schuster, G. "Structurally Dependent Effects of Substituted Thioureas on the Concentration of Potato Virus X in Nicotiana tabacum L," *Zentralblatt fur Bakteriologie, Parasitenkunde, Infektionskraheitin un Hygiene Mikrobiolo. Der Landw.* (1978) 133(7-8): 686-689.

Sengupta, A.K. and Ramrakhyani, A. K. "Studies on Potential Pesticides, Part V. Synthesis of Some New Aryl Ureas and Thioureas and Their Insecticidal Activity," *Indian Journal of Chemistry* (1976) 53(1): 203-204.

Seth, P.P. "Efficient Solution Phase Synthesis of 2-(N-acyl)-aminobenzimidazoles," *Tetrahedron Letters* (2002) 43: 7303-7306.

Shearer, B.G. et al., "Substituted N-Phenylisothioureas: Potent Inhibitors of Human Nitric Oxide Synthase with Neuronal Isoform Selectivity," *Journal of Medicinal Chemistry* (1997) 40(12): 1901-1905.

Taniguchi, K. et al. "New 2-Aryliminoimidazolidines. II. Synthesis and Antihypertensive Activity of 2-(Biphenylimino)-imidazolidines," *Chem. Pharm. Bull.* (1992) 40(1): 240-244.

Weinstein, L. et al. "Studies on the Antiviral Activity of Urea Derivatives," *Antibodies and Chemotherapy* (1957) VII(8): 443-448.

List of compounds from MDL Information Systems, Inc.

List of Compounds from Chembridge Corp.

International Search Report for International Application No. PCT/US2005/017308, mailed Jul. 20, 2006.

Written Opinion for International Application No. PCT/US2005/01738, mailed Jul. 20, 2006.

* cited by examiner

SUBSTITUTED ARYL ACYLTHIOUREAS AND RELATED COMPOUNDS; INHIBITORS OF VIRAL REPLICATION

CROSS REFERENCE TO RELATED APPLICATIONS

This application claims priority from U.S. Provisional Patent Application No. 60/572,156 filed May 18, 2004, which is hereby incorporated by reference in its entirety.

FIELD OF THE INVENTION

The present invention provides arylthiourea derivatives and related compounds, useful as antiviral agents. Certain arylthiourea derivatives and related compounds disclosed herein are potent and/or selective inhibitors of viral replication, particularly Hepatitis C virus replication. The invention also provides pharmaceutical compositions containing one or more arylthiourea derivative or related compound and one or more pharmaceutically acceptable carriers, excipients, or diluents. Such pharmaceutical compositions may contain an arylthiourea derivative or related compound as the only active agent or may contain a combination of an arylthiourea derivative or related compound and one or more other pharmaceutically active agents. The invention also provides methods for treating Hepatitis C viral infections in mammals.

BACKGROUND

In the 1940's the disease originally referred to as viral hepatitis was distinguished into two separate disorders termed infectious hepatitis (hepatitis A, HAV) and homologous serum hepatitis (hepatitis B, HBV). Transfusion of blood products had been demonstrated to be a common route of transmission of viral hepatitis. HBV was originally assumed to be the causative agent of post-transfusion hepatitis as the epidemiological and clinical features of the disorder did not fit those of HAV.

Soon after a radioimmunoassay for hepatitis B surface antigen (HBsAg) became available as a tool for identifying patients infected with HBV, it became apparent that most patients having post-transfusion hepatitis were negative for HBsAg. Thus, hepatitis following blood transfusion that was not caused by hepatitis A or hepatitis B and was subsequently referred to as non-A, non-B hepatitis.

The causative agent of non-A, non-B hepatitis (hepatitis C virus, HCV) was discovered in 1989 via screening of cDNA expression libraries made from RNA and DNA from chimpanzees infected with serum from a patient with post-transfusion non-A, non-B hepatitis. To identify portions of the genome that encoded viral proteins, the libraries were screened with antibodies from patients who had non-A, non-B hepatitis. These investigators went on to show that the virus they identified was responsible for the vast majority of cases of non-A, non-B hepatitis.

The hepatitis C virus is one of the most prevalent causes of chronic liver disease in the United States. It accounts for about 15 percent of acute viral hepatitis, 60 to 70 percent of chronic hepatitis, and up to 50 percent of cirrhosis, end-stage liver disease, and liver cancer. Almost 4 million Americans, or 1.8 percent of the U.S. population, have antibodies to HCV (anti-HCV), indicating ongoing or previous infection with the virus. Hepatitis C causes an estimated 8,000 to 10,000 deaths annually in the United States. Hepatitis C virus (HCV) infection occurs throughout the world, and, prior to its identification, represented the major cause of transfusion-associated hepatitis. The seroprevalence of anti-HCV in blood donors from around the world has been shown to vary between 0.02% and 1.23%. HCV is also a common cause of hepatitis in individuals exposed to blood products. There have been an estimated 150,000 new cases of HCV infection each year in the United States alone during the past decade.

The acute phase of HCV infection is usually associated with mild symptoms. However, evidence suggests that only 15%-20% of the infected people will clear HCV. Among the group of chronically infected people, 10-20% will progress to life-threatening conditions known as cirrhosis and another 1-5% will develop a liver cancer called hepatocellular carcinoma. Unfortunately, the entire infected population is at risk for these life-threatening conditions because no one can predict which individual will eventually progress to any of them.

HCV is a small, enveloped, single-stranded positive RNA virus in the Flaviviridae family. The genome is approximately 10,000 nucleotides and encodes a single polyprotein of about 3,000 amino acids. The polyprotein is processed by host cell and viral proteases into three major structural proteins and several non-structural proteins necessary for viral replication. Several different genotypes of HCV with slightly different genomic sequences that correlate with differences in response to treatment with interferon alpha have since been identified.

HCV replicates in infected cells in the cytoplasm, in close association with the endoplasmic reticulum. Incoming positive sense RNA is released and translation is initiated via an internal initiation mechanism. Internal initiation is directed by a cis-acting RNA element at the 5' end of the genome; some reports have suggested that full activity of this internal ribosome entry site, or IRES, is seen with the first 700 nucleotides, which spans the 5' untranslated region (UTR) and the first 123 amino acids of the open reading frame (ORF). All the protein products of HCV are produced by proteolytic cleavage of a large (approximately 3000 amino acid) polyprotein, carried out by one of three proteases: the host signal peptidase, the viral self-cleaving metalloproteinase, NS2, or the viral serine protease NS3/4A. The combined action of these enzymes produces the structural proteins (C, E1 and E2) and non-structural (NS2, NS3, NS4A, NS4B, NS5A, and NS5B) proteins that are required for replication and packaging of viral genomic RNA. NS5B is the viral RNA-dependent RNA polymerase (RDRP) that is responsible for the conversion of the input genomic RNA into a negative stranded copy (complimentary RNA, or cRNA; the cRNA then serves as a template for transcription by NS5B of more positive sense genomic/messenger RNA.

An effective vaccine is greatly needed, yet development is unlikely in the near future because: i) lack of an efficient cell culture system and small animal models; ii) a weak neutralizing humoral and protective cellular immune response; iii) marked genetic variability of the virus, and iv) the lack of a viral proofreading mechanism.

Several institutions and laboratories are attempting to identify and develop anti-HCV drugs. Currently the only effective therapy against HCV is alpha-interferon, which reduces the amount of virus in the liver and blood (viral load) in only a small proportion of infected patients. Alpha interferon was first approved for use in HCV treatment more than ten years ago. Alpha interferon is a host protein that is made in response to viral infections and has natural antiviral activity. These standard forms of interferon, however, are now being replaced by pegylated interferons (peginterferons). Peginterferon is alpha interferon that has been modified chemically by the addition of a large inert molecule of polyethylene glycol. At the present time, the optimal regimen appears to be a 24- or 48-week course of the combination of pegylated alpha interferon and the nucleoside Ribavarin, an oral antiviral agent that has activity against a broad range of viruses. By itself, Ribavarin has little effect on HCV, but adding it to interferon increases the sustained response rate by two- to three-fold. Nonetheless, response rates to the combination interferon/Ribavarin therapy are moderate, in the range 50-60%, although response rates for selected genotypes of HCV (notably genotypes 2 and 3) are typically higher. Among patients who become HCV RNA negative during treatment, a significant proportion relapse when therapy is stopped.

In addition, there are often significant adverse side effects associated with each of these agents. Patients receiving interferon often present with flu-like symptoms. Pegylated interferon has been associated with bone marrow suppressive effects. Importantly, alpha interferon has multiple neuropsychiatric effects. Prolonged therapy can cause marked irritability, anxiety, personality changes, depression, and even suicide or acute psychosis. Interferon therapy has also been associated with relapse in people with a previous history of drug or alcohol abuse.

Side effects of Ribavarin treatment include histamine-like side effects (itching and nasal stuffiness) and anemia due to dose related hemolysis of red cells and histamine like side effects.

Taken together, the proceeding facts indicate a significant need for effective small molecule inhibitors of hepatitis C virus replication that do not suffer from the above-mentioned drawbacks.

SUMMARY OF THE INVENTION

The invention provides compounds of Formula I (shown below) and includes certain aryl acylthiourea derivatives and related compounds, which possess antiviral activity. The invention provides compounds of Formula I that are potent and/or selective inhibitors of Hepatitis C virus replication. The invention also provides pharmaceutical compositions containing one or more compound of Formula I, or a salt, solvate, or acylated prodrug of such compounds, and one or more pharmaceutically acceptable carriers, excipients, or diluents.

The invention further comprises methods of treating patients suffering from certain infectious diseases by administering to such patients an amount of a compound of Formula I effective to reduce signs or symptoms of the disease or disorder. These infectious diseases include viral infections, particularly HCV infections. The invention is particularly includes methods of treating human patients suffering from an infectious disease, but also encompasses methods of treating other animals, including livestock and domesticated companion animals, suffering from an infectious disease.

Methods of treatment include administering a compound of Formula I as a single active agent or administering a compound of Formula I in combination with one or more other therapeutic agents.

Thus in a first aspect the invention includes compounds of Formula I:

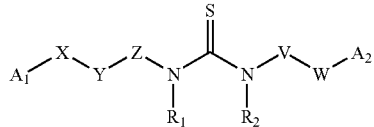

Formula I or a pharmaceutically acceptable salt thereof.

$A_1$ and $A_2$ are independently optionally substituted $C_1$-$C_{12}$alkyl, optionally substituted mono- or di-($C_1$-$C_8$alkyl)amino, optionally substituted $C_2$-$C_{12}$alkenyl, optionally substituted $C_3$-$C_8$cycloalkyl, a partially unsaturated or aromatic carbocyclic group, or an optionally substituted saturated, partially unsaturated, or aromatic heterocyclic group; wherein at least one of $A_1$ and $A_2$ is an optionally substituted aromatic carbocyclic group or an optionally substituted aromatic heterocyclic group.

X and W are independently O, S, NR, or absent, where R is hydrogen, optionally substituted $C_1$-$C_6$alkyl, or optionally substituted aryl($C_0$-$C_4$alkyl).

V is $C_1$-$C_6$ alkyl, $C_2$-$C_6$alkenyl, $C_3$-$C_7$cycloalkyl, or absent; and Y is $C_1$-$C_6$ alkyl, $C_1$-$C_6$ alkyl substituted with $C_3$-$C_7$cycloalkyl, $C_2$-$C_6$alkenyl, $C_3$-$C_7$cycloalkyl, or absent; wherein when V is absent, W is absent; and Z is carbonyl, thiocarbonyl, imino, or $C_1$-$C_6$alkylimino.

$R_1$ and $R_2$ are independently hydrogen or $R_1$ and $R_2$ are independently $C_1$-$C_6$alkyl, $C_2$-$C_6$ alkenyl, or $C_2$-$C_6$ alkynyl, each of which is substituted with 0 to 3 substituents independently chosen from halogen, hydroxy, amino, $C_1$-$C_4$alkoxy, $C_1$-$C_2$haloalkyl, and $C_1$-$C_2$haloalkoxy, or $R_1$ and $R_2$ are joined to form a 5- to 7-membered saturated or mono-unsaturated ring optionally containing one additional heteroatom chosen from N, S, and O, which 5- to 7-membered saturated or mono-unsaturated ring is substituted with 0 to 3 substituents independently chosen from halogen, hydroxy, amino, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

$R_1$ and $R_2$ are independently hydrogen or $R_1$ and $R_2$ are independently $C_1$-$C_6$alkyl, $C_2$-$C_6$ alkenyl, or $C_2$-$C_6$ alkynyl, each of which is substituted with 0 to 3 substituents independently chosen from halogen, hydroxy, amino, $C_1$-$C_4$alkoxy, $C_1$-$C_2$haloalkyl, and $C_1$-$C_2$haloalkoxy, or $R_1$ and $R_2$ are joined to form a 5- to 7-membered saturated or mono-unsaturated ring optionally containing one additional heteroatom chosen from N, S, and O, which 5- to 7-membered saturated or mono-unsaturated ring is substituted with 0 to 3 substituents independently chosen from halogen, hydroxy, amino, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

Certain compounds of Formula I disclosed herein exhibit good activity in an HCV replication assay, such as the HCV replicon assay set forth in Example 8, which follows. Preferred compounds of Formula I exhibit an $EC_{50}$ of about 10 micromolar or less, or more preferably an $EC_{50}$ of about 1 micromolar or less; or still more preferably an $EC_{50}$ of about 500 nanomolar or less in an HCV replicon assay.

DETAILED DESCRIPTION OF THE INVENTION

Chemical Description and Terminology

Prior to setting forth the invention in detail, it may be helpful to provide definitions of certain terms to be used herein. Compounds of the present invention are described using standard nomenclature. Unless defined otherwise, all technical and scientific terms used herein have the same meaning as is commonly understood by one of skill in the art to which this invention belongs.

Formula I includes all subformulae thereof. For example Formula I includes compounds of Formulae IA-VII and Formulae 1-34.

In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, the single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Where a compound exists in various tautomeric forms, the invention is not limited to any one of the specific tautomers, but rather includes all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. V, W, X, Y, Z, $A_1$, $A_2$, $R_1$, and $R_2$. Unless otherwise specified, each variable within such a formula is defined independently of other variables. Thus, if a group is said to be substituted, e.g. with 0-2 R*, then the group may be substituted with up to two R* groups and R* at each occurrence is selected independently from the definition of R*. Also, combinations of substituents and/or variables are permissible only if such combinations result in stable compounds.

The term "substituted", as used herein, means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

The phrase "optionally substituted" indicates that such groups may either be unsubstituted or substituted at one or more of any of the available positions, typically 1, 2, 3, or 4 positions, by one or more suitable groups such as those disclosed herein.

Suitable groups that may be present on a "substituted" position include, but are not limited to, e.g., halogen; cyano; hydroxyl; nitro; azido; alkanoyl (such as a $C_2$-$C_6$ alkanoyl group such as acyl or the like); carboxamido; alkyl groups (including cycloalkyl groups, having 1 to about 8 carbon atoms, or 1 to about 6 carbon atoms); alkenyl and alkynyl groups (including groups having one or more unsaturated linkages and from 2 to about 8, or 2 to about 6 carbon atoms); alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

A dash ("-") that is not between two letters or symbols is used to indicate a point of attachment for a substituent. For example, —$(CH_2)C_3$-$C_8$cycloalkyl is attached through carbon of the methylene ($CH_2$) group.

A bond represented by a combination of a solid and dashed line, i.e. -----, may be either a single or double bond.

A "pendant ring" is a ring, such as an aryl or heteroaryl ring, joined to another group by one covalent bond. A biphenyl group is an example of phenyl rings that are pendant from each other. When a ring is said to be "pendant" from a group or atom, it is bound to that an atom in that group or the atom via one single covalent bond.

A "spiro" compound is a bicyclic compound having one and only one carbon common to both rings.

As used herein, "alkyl" includes both branched and straight chain saturated aliphatic hydrocarbon groups, having the specified number of carbon atoms, generally from 1 to about 12 carbon atoms. The term $C_1$-$C_6$alkyl as used herein indicates an alkyl group having from 1 to about 6 carbon atoms. When $C_0$-$C_n$ alkyl is used herein in conjunction with another group, for example, aryl$C_0$-$C_4$ alkyl, the indicated group, in this case aryl, is either directly bound by a single covalent bond ($C_0$), or attached by an alkyl chain having the specified number of carbon atoms, in this case from 1 to about 4 carbon atoms. Examples of alkyl include, but are not limited to, methyl, ethyl, n-propyl, isopropyl, n-butyl, 3-methylbutyl, t-butyl, n-pentyl, and sec-pentyl.

For certain embodiments described herein preferred alkyl groups are lower alkyl groups; those alkyl groups having from 1 to about 8 carbon atoms, from 1 to about 6 carbon atoms, or from 1 to about 4 carbons atoms, e.g. $C_1$-$C_8$, $C_1$-$C_6$, and $C_1$-$C_4$ alkyl groups.

"Alkenyl" as used herein, indicates a straight or branched hydrocarbon chain comprising one or more unsaturated carbon-carbon bonds, which may occur in any stable point along the chain. Alkenyl groups described herein typically have from 2 to about 12 carbon atoms. For some embodiments described herein alkenyl groups are lower alkenyl groups, those alkenyl groups having from 2 to about 8 carbon atoms, e.g. $C_2$-$C_8$, $C_2$-$C_6$, and $C_2$-$C_4$ alkenyl groups. Examples of alkenyl groups include ethenyl, propenyl, and butenyl groups.

"Alkynyl" as used herein, indicates a straight or branched hydrocarbon chain comprising one or more triple carbon-carbon bonds that may occur in any stable point along the chain, such as ethynyl and propynyl. Alkynyl groups described herein typically have from 2 to about 12 carbons atoms. Preferred alkynyl groups are lower alkynyl groups, those alkynyl groups having from 2 to about 8 carbon atoms, e.g. $C_2$-$C_8$, $C_2$-$C_6$, and $C_2$-$C_4$ alkynyl groups.

"Alkoxy" indicates an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Alkenyloxy" indicates an alkenyl group as define above with the indicated number of carbon atoms attached through an oxygen bridge (—O—). Examples of alkenyloxy groups include, but are not limited to, prop-1-enyloxy, but-1-enyloxy.

In the term "Alkoxy(alkyl)" alkoxy and alkyl are as defined above and the point of attachment is on the alkyl group. For example $C_1$-$C_6$alkoxy($C_1$-$C_4$alkyl) indicates an alkoxy group having from 1 to about 6 carbon atoms attached through its oxygen atom to an alkyl group having from 1 to about 4 carbon atoms and further attached to the core molecule through a carbon atom in the $C_1$-$C_4$alkyl portion.

"Alkyloxoacetylamino" is a group of the formula

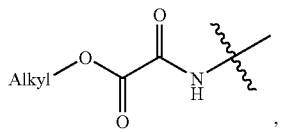

wherein the alkyl is an alkyl group as defined herein having the indicated number of carbon atoms.

"Alkanoyl" indicates an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3$(C=O)—.

As used herein the term "alkanoyloxy" indicates an alkanoyl group as defined above, having the indicated number of carbon atoms, attached through an oxygen (—O—) bridge. Examples of alkanoyloxy groups include groups of the formula $CH_3(CH_2)(C=O)$—O— and the like.

As used herein the term "mono- and/or di-alkylcarboxamide" refers to groups of formula (alkyl$_1$)-NH—(C=O)— and (alkyl$_1$)(alkyl$_2$)—N—(C=O)— in which the alkyl$_1$ and alkyl$_2$ groups are independently chosen alkyl groups as defined above having the indicated number of carbon atoms.

Mono and/or di-alkylcarboxamide also refers to groups of the formula —NH(C=O)(alkyl$_1$) and —N(alkyl$_2$)(C=O)(alkyl$_1$), carboxamide groups in which the point of attachment is the nitrogen atom, in which the alkyl$_1$ and alkyl$_2$ groups are independently chosen alkyl groups as defined above having the indicated number of carbon atoms.

As used herein the term "mono- and/or di-alkylsulfonamide" refers to groups of formula (alkyl$_1$)-NH—(SO$_2$)— and (alkyl$_1$)(alkyl$_2$)-N—(SO$_2$)— in which the alkyl$_1$ and alkyl$_2$ groups are independently chosen alkyl groups as defined above having the indicated number of carbon atoms.

As used herein, "alkylsulfinyl" means alkyl-(SO)—, where the alkyl group is an alkyl group as defined above having the indicated number of carbon atoms. An exemplary alkylsulfinyl group is ethylsulfinyl.

As used herein, "alkylsulfonyl" means alkyl-(SO$_2$)—, where the alkyl group is an alkyl group as defined above having the defined number of carbon atoms. An exemplary alkylsulfonyl group is methylsulfonyl.

As used herein, "alkylthio" means alkyl-S—, where the alkyl group is an alkyl group as defined above having the indicated number of carbon atoms. An exemplary alkylthio group is methylthio.

As used herein the term "alkoxycarbonyl" indicates an alkoxy group, as defined above, having the indicated number of carbon atoms, attached through a keto (—(C=O)—) bridge. The alkoxy moiety of the alkoxycarbonyl group has the indicated number of carbon atoms, and the carbon of the keto bridge is not included in this number. $C_3$alkoxycarbonyl group indicates, for example, groups of the formula $CH_3(CH_2)_2$—O—(C=O)— or $(CH_3)_2(CH)$—O—(C=O)—.

As used herein "aminoalkyl" is an alkyl group as defined herein, having the indicated number of carbon atoms, and substituted with at least one amino substituent (—NH$_2$). When indicated, aminoalkyl groups, like other groups described herein, may be additionally substituted.

As used herein, the term "mono- and/or di-alkylamino" indicates secondary or tertiary alkyl amino groups, wherein the alkyl groups are as defined above and have the indicated number of carbon atoms. The point of attachment of the alkylamino group is on the nitrogen. The alkyl groups are independently chosen. Examples of mono- and di-alkylamino groups include ethylamino, dimethylamino, and methyl-propyl-amino. "Mono- and/or dialkylaminoalkyl" groups are mono- and/or di-alkylamino groups attached through an alkyl linker having the specified number of carbon atoms, for example a di-methylaminoethyl group. Tertiary amino substituents may by designated by nomenclature of the form N—R—N—R', indicating that the groups R and R' are both attached to a single nitrogen atom.

As used herein, the term "aryl" indicates aromatic groups containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

In the term "aryl(alkyl)", aryl and alkyl are as defined above, and the point of attachment is on the alkyl group. "Aryl($C_0$-$C_4$alkyl)" indicates an aryl group that is directly attached via a single covalent bond (aryl($C_0$alkyl) or attached through an alkyl group having from 1 to about 4 carbon atoms. The term aryl(alkyl) encompasses, but is not limited to, benzyl, phenylethyl, and piperonyl.

The term "carbocyclic group" indicates a 3 to 8 membered saturated, partially unsaturated, or aromatic ring containing only carbon ring atoms or a 6-11 membered saturated, partially unsaturated, or aromatic bicyclic carbocyclic ring system. Unless otherwise indicated, the carbocyclic ring may be attached to its pendant group at any carbon atom that results in a stable structure. When indicated the carbocyclic rings described herein may be substituted on any available ring carbon if the resulting compound is stable. Carbocyclic groups include, cycloalkyl groups, such as cyclopropyl and cyclohexyl; cycloalkenyl groups, such as cyclohexenyl, bridged cycloalkyl groups; and aryl groups, such as phenyl.

"Cycloalkyl" as used herein, indicates a monocyclic or multicyclic saturated hydrocarbon ring group, having the specified number of carbon atoms, usually from 3 to about 10 ring carbon atoms. Monocyclic cycloalkyl groups typically have from 3 to about 8 carbon ring atoms or from 3 to about 7 carbon ring atoms. Multicyclic cycloalkyl groups may have 2 or 3 fused cycloalkyl rings or contain bridged or caged cycloalkyl groups. Cycloalkyl substituents may be pendant from a substituted nitrogen or carbon atom, or a substituted carbon atom that may have two substituents may have a cycloalkyl group, which is attached as a spiro group. Examples of cycloalkyl groups include cyclopropyl, cyclobutyl, cyclopentyl, or cyclohexyl as well as bridged or caged saturated ring groups such as norbornane or adamantane.

In the term "cycloalkyl(alkyl)", cycloalkyl and alkyl are as defined above, and the point of attachment is on the alkyl group. This term encompasses, but is not limited to, cyclopropylmethyl, cyclohexylmethyl, and cyclohexylmethyl.

As used herein the term "cycloalkylcarboxamide" refers to a cycloalkyl group as defined above attached through an —NH—(C=O)— linker where the cycloalkyl group is covalently bound to the nitrogen atom.

As used herein "haloalkyl" indicates both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and pentafluoroethyl.

"Haloalkoxy" indicates a haloalkyl group as defined above attached through an oxygen bridge (oxygen of an alcohol radical).

"Halo" or "halogen" as used herein refers to fluoro, chloro, bromo, or iodo.

As used herein, "heteroaryl" indicates a stable 5- to 7-membered monocyclic aromatic ring which contains from 1 to 3, or in some embodiments from 1 to 2, heteroatoms chosen from N, O, and S, with remaining ring atoms being carbon, or a stable bicyclic or tricyclic system containing at least one 5 to 7 membered aromatic ring which contains from 1 to 3, or in some embodiments from 1 to 2, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, and isoxazolyl.

The term "heterocycloalkyl" indicates a saturated monocyclic group containing from 1 to about 3 heteroatoms chosen from N, O, and S, with remaining ring atoms being carbon, or a saturated bicyclic ring system having at least one N, O, or S ring atom with the remaining atoms being carbon. Monocyclic heterocycloalkyl groups have from 4 to about 8 ring atoms, and more typically have from 5 to 7 ring atoms. Bicyclic heterocycloalkyl groups typically have from about five to about 12 ring atoms. The size of a heterocycloalkyl group may be given by the number of ring carbon atoms the group contains. For example, a $C_2$-$C_7$heterocycloalkyl group contains from 2 to about 7 ring carbon atoms with the remaining ring atoms, up to about 3 per ring, being chosen from N, O, and S. Preferred heterocycloalkyl groups include $C_2$-$C_7$ monocyclic heterocycloalkyl groups and $C_5$-$C_{10}$ bicyclic heterocycloalkyl groups. Examples of heterocycloalkyl groups include morpholinyl, piperazinyl, piperidinyl, and pyrrolidinyl groups.

The term "heterocyclic group" indicates a 5 to 8-membered saturated, partially unsaturated, or aromatic ring containing from 1 to about 4 heteroatoms chosen from N, O, and S, with remaining ring atoms being carbon, or a 7 to 11 membered bicyclic saturated, partially unsaturated, or aromatic heterocyclic ring system or a 10 to 15-membered tricyclic ring system, containing at least 1 heteroatom in the multiple ring system chosen from N, O, and S and containing up to about 4 heteroatoms independently chosen from N, O, and S in each ring of the multiple ring system. Unless otherwise indicated, the heterocyclic ring may be attached to its pendant group at any heteroatom or carbon atom that results in a stable structure. When indicated the heterocyclic rings described herein may be substituted on carbon or on a nitrogen atom if the resulting compound is stable. A nitrogen atom in the heterocycle may optionally be quaternized. It is preferred that the total number of heteroatoms in a heterocyclic groups is not more than 4 and that the total number of S and O atoms in a heterocyclic group is not more than 2, more preferably not more than 1. Examples of heterocyclic groups include, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, dihydroisoindolyl, 5,6,7,8-tetrahydroisoquinoline, pyridinyl, pyrimidinyl, furanyl, thienyl, pyrrolyl, pyrazolyl, pyrrolidinyl, morpholinyl, piperazinyl, piperidinyl, and pyrrolidinyl.

Additional examples of heterocyclic groups include, but are not limited to 1,1-dioxo-thieno-tetrahydrothiopyranyl, 1,1-dioxothiochromanyl, 1,4-dioxanyl, 5-pteridinyl, tetrahydroindazolyl, azetidinyl, benzimidazolyl, benzisoxazinyl, benzodioxanyl, benzodioxolyl, benzofurazanyl, benzoisoxolyl, benzopyranyl, benzopyrazolyl, benzotetrahydrofuranyl, benzotetrahydrothienyl, benzothiopyranyl, benzotriazolyl, benzoxazinyl, benzoxazolinonyl, benzoxazolyl, beta-carbolinyl, carbazolyl, carbolinyl, chromanonyl, chromanyl, cinnolinyl, coumarinyl, dihydroazetidinyl, dihydrobenzisothiazinyl, dihydrobenzisoxazinyl, dihydrobenzodioxinyl, dihydrobenzofuranyl, dihydrobenzoimidazolyl, dihydrobenzothiophenyl, dihydrobenzoxazolyl, dihydrocoumarinyl, dihydroindolyl, dihydroisocoumarinyl, dihydroisooxazolyl, dihydroisoquinolinonyl, dihydroisothiazolyl, dihydrooxadiazolyl, dihydropyrazinyl, dihydropyrazolyl, dihydropyridinyl, dihydropyrimidinyl, dihydropyrrolyl, dihydroquinolinonyl, dihydroquinolinyl, dihydrotetrazolyl, dihydrothiadiazolyl, dihydrothiazolyl, dihydrothienyl, dihydrotriazolyl, hexahydroazepinyl, imidazopyrazinyl, imidazopyridazinyl, imidazopyridinyl, imidazopyridinyl, imidazopyrimidinyl, imidazothiadiazolyl, imidazothiazolyl, imidazothiophenyl, indolinyl, indolizinyl, isobenzotetrahydrofuranyl, isobenzotetrahydrothienyl, isobenzothienyl, isochromanyl, isocoumarinyl, isoindolinonyl, isoindolinyl, isoquinolyl, isothiazolyl, isoxazolyl, methylenedioxybenzyl, naphthyridinyl, oxadiazolyl, oxazolopyridinyl, oxazolyl, oxetanyl, oxopiperidinyl, oxopyrazolyl, oxopyridinyl, phenothiazinyl, phenoxazinyl, phthalazinyl, purinyl, pyrazinyl, pyrazolopyrazinyl, pyrazolopyridazinyl, pyrazolopyridyl, pyrazolopyrimidinyl, pyrazolothiophenyl, pyrazolotriazinyl, pyridazinyl, pyridopyridinyl, quinazolinyl, quinolinyl, quinoxalinyl, tetrahydrofuranyl, tetrahydroimidazopyrazinyl, tetrahydroimidazopyridazinyl, tetrahydroimidazopyridyl, tetrahydroimidazopyrimidyl, tetrahydroisoquinolinyl, tetrahydropyranyl, tetrahydropyrazolopyrazinyl, tetrahydropyrazolopyridinyl, tetrahydropyrazolopyrimidyl, tetrahydroquinolinyl, tetrahydrothienyl, tetrahydrotriazolopyrimidyl, tetrahydrotriazolopyrazinyl, tetrahydrotriazolopyridazinyl, tetrahydrotriazopyridinyl, tetrazolopyridinyl, tetrazolyl, thiadiazolyl, thienotetrahydrothiopyranyl, thienyl, thiochromanyl, triazinyl, triazolopyrazinyl, triazolopyridazinyl, triazolopyridyl, triazolopyrimidinyl, triazolothiophenyl, and where possible, N-oxides thereof.

As used herein an "imino" group is a group of the formula C=N, where the carbon atom additionally contains two single bonds. An "alkylimino" group contains an alkyl group as defined above covalently bound to the nitrogen atom of an imino group. When specified the alkyl portion of an alkylimino group may be optionally substituted.

As used herein a "thiocarbonyl" group is a group of the formula C=S, where the carbon atom additionally contains two single bonds.

The term "pharmaceutically acceptable salts" includes derivatives of the disclosed compounds wherein the parent compound is modified by making non-toxic acid or base salts thereof, and further refers to pharmaceutically acceptable solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, flimaric, toluenesulfonic, methanesulfonic, ethane disulfonic, oxalic, isethionic, HOOC—$(CH_2)_n$—COOH where n is 0-4, and the like. Certain embodiments within the invention include hydrochloric acid and trifluoroacetic acid salts of the compounds disclosed herein. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts may be found, e.g., in *Remington's Pharmaceutical Sciences*, 17th ed., Mack Publishing Company, Easton, Pa., p. 1418 (1985).

The term "prodrugs" includes any compounds that become compounds of Formula I when administered to a mammalian subject, e.g., upon metabolic processing of the prodrug. Examples of prodrugs include, but are not limited to, acetate, formate and benzoate and the like derivatives of functional groups (such as alcohol or amine groups) in the compounds of Formula I.

The term "therapeutically effective amount" of a compound of this invention means an amount effective, when administered to a human or non-human patient, to provide a therapeutic benefit such as an amelioration of symptoms, e.g., an amount effective to decrease the symptoms of a viral infection, and preferably an amount sufficient to reduce the symptoms of an HCV infection. In certain circumstances a patient suffering from a viral infection may not present symptoms of being infected. Thus a therapeutically effective amount of a compound is also an amount sufficient to prevent a significant increase or significantly reduce the detectable level of virus or viral antibodies in the patient's blood, serum, or tissues. A significant increase or reduction in the detectable level of virus or viral antibodies is any detectable change that is statistically significant in a standard parametric test of statistical significance such as Student's T-test, where $p<0.05$.

A "replicon" as used herein includes any genetic element, for example, a plasmid, cosmid, bacmid, phage or virus capable of replication largely under its own control a replicon may be either RNA or DNA and may be single or double stranded.

"nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule can be described herein according to the normal convention of providing the sequence in the 5' to 3' direction.

VIRAL INHIBITORS

As disclosed above, the invention provides compounds and salts of Formula I as defined above.

Additionally the invention includes compounds and salts of Formula I, which has the same chemical structure as Formula I shown above,

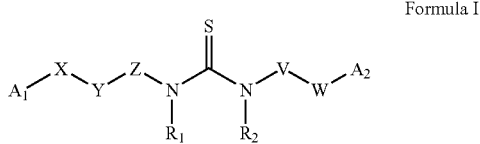

Formula I but in which the variables $A_1$, $A_2$, $R_1$, $R_2$, X, Y, Z, V, and W are defined as follows:

$A_1$ and $A_2$ are independently $C_1$-$C_{12}$alkyl, $C_2$-$C_{12}$alkenyl, $C_3$-$C_8$ cycloalkyl, or a partially unsaturated or aromatic carbocyclic group, or a saturated, partially unsaturated, or aromatic heterocyclic group; each of which $A_1$ and $A_2$ is substituted with 0 to 5 substituents independently chosen from (a), (b), and (c).

Where (a) is independently chosen from halogen, hydroxy, cyano, amino, nitro, oxo, —COOH, —CONH$_2$, —SO$_2$NH$_2$, —SH, $C_1$-$C_2$haloalkyl, and $C_1$-$C_2$haloalkoxy, (b) is independently chosen from $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl, and (c) is -GR$_a$ where G is chosen from —(CH$_2$)$_n$—, $C_2$-$C_4$alkenyl, $C_2$-$C_4$alkynyl, —(CH$_2$)$_n$O(CH$_2$)$_m$—, and —(CH$_2$)$_n$N(CH$_2$)$_m$—, where n and m are independently 0, 1, 2, 3, or 4; and R$_a$ is independently chosen at each occurrence from $C_3$-$C_8$cycloalkyl, $C_2$-$C_7$monocyclic heterocycloalkyl, $C_5$-$C_{10}$bicyclicheterocycloalkyl, indanyl, tetrahydronapthyl, tetrahydroisoquinolinyl, tetrahydropyridyl, aryl, and heteroaryl.

Each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_2$-$C_4$alkanoyl, $C_1$-$C_4$alkoxycarbonyl, $C_1$-$C_2$haloalkyl, $C_1$-$C_2$haloalkoxy, and phenyl;

wherein at least one of $A_1$ and $A_2$ is a carbocyclic group or heterocyclic group substituted with 0 to 5 substituents independently chosen from (a), (b), and (c).

X and W are independently O, S, NR, or absent, where R is hydrogen or R is $C_1$-$C_6$alkyl or aryl($C_0$-$C_4$alkyl), each of which is substituted with 0 to 5 substituents independently chosen from halogen, hydroxy, cyano, amino, nitro, oxo, C1-C2haloalkyl, C1-C2haloalkoxy, C1-C6alkyl, C1-C6alkoxy, and mono- and di-(C1-C6alkyl)amino.

V is $C_1$-$C_6$ alkyl, $C_2$-$C_6$alkenyl, $C_3$-$C_7$cycloalkyl, or absent; Y is $C_1$-$C_6$ alkyl, $C_1$-$C_6$ alkyl substituted with $C_3$-$C_7$cycloalkyl, $C_2$-$C_6$alkenyl, $C_3$-$C_7$cycloalkyl, or absent; and when V is absent, W is absent.

Z is carbonyl, thiocarbonyl, or imino.

$R_1$ and $R_2$ are independently hydrogen; or $C_1$-$C_6$alkyl, $C_2$-$C_6$ alkenyl, or $C_2$-$C_6$ alkynyl, each of which is substituted with 0 to 3 substituents independently chosen from halogen, hydroxy, amino, $C_1$-$C_4$alkoxy, $C_1$-$C_2$haloalkyl, and $C_1$-$C_2$haloalkoxy, or $R_1$ and $R_2$ are joined to form a 5- to 7-membered saturated or mono-unsaturated ring optionally containing one additional heteroatom chosen from N, S, and O, which 5- to 7-membered saturated or mono-unsaturated ring is substituted with 0 to 3 substituents independently chosen from halogen, hydroxy, amino, $C_1$-$C_4$alkyl, $C_1$-$C_4$alkoxy, mono- and di-($C_1$-$C_4$alkyl) amino, $C_1$-$C_2$haloalkyl, and $C_1$-$C_2$haloalkoxy.

Such compounds will be referred to as compound of Formula IA.

The invention also includes compounds and salts of Formula I and Formula IA wherein when X is absent, Y is also absent.

The invention provides compounds and pharmaceutically acceptable salts of Formula IB, wherein

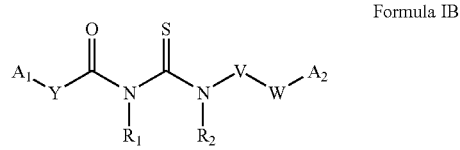

Formula IB $A_1$ is di-($C_1$-$C_8$alkyl)amino, an N—($C_1$-$C_6$alkyl)-N-phenyl-amino group, an N—($C_1$-$C_6$alkyl)-N-pyridyl amino group, a 5- to 7-membered monocyclic heterocycloalkyl group covalently bound to a point of attachment in Formula IB via a Nitrogen atom, a 5- to 7-membered monocyclic partially unsaturated heterocyclic group covalently bound to a point of attachment in Formula IB via a Nitrogen atom, a 5- to 7-membered heterocycloalkyl group covalently bound to a point of attachment in Formula IB via a Carbon atom which is adjacent to a Nitrogen atom, or an 8- to 11-membered bicyclic heterocycloalkyl in which the rings are fused or spiro covalently bound to a point of attachment in Formula IB via a Nitrogen atom.

$A_2$ is $C_3$-$C_8$ cycloalkyl, a partially unsaturated or aromatic carbocyclic group, or a saturated, partially unsaturated, or aromatic heterocyclic group.

Each of which $A_1$ and $A_2$ is substituted with 0 to 5 substituents independently chosen from (a), (b), and (c), where (a) is independently chosen from halogen, hydroxy, cyano, amino, nitro, oxo, —COOH, —CONH$_2$, —SO$_2$NH$_2$, —SH, $C_1$-$C_2$haloalkyl, and $C_1$-$C_2$haloalkoxy, (b) is independently chosen from $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl, and (c) is -GR$_a$ where G is chosen from —(CH$_2$)$_n$—, $C_2$-$C_4$alkenyl, $C_2$-$C_4$alkynyl, —(CH$_2$)$_n$O(CH$_2$)$_m$—, and —(CH$_2$)$_n$N(CH$_2$)$_m$—, where n and m are independently 0, 1, 2, 3, or 4; and R$_a$ is independently chosen at each occurrence from $C_3$-$C_8$cycloalkyl, $C_2$-$C_7$monocyclic heterocycloalkyl, $C_5$-$C_{10}$bicyclicheterocycloalkyl, indanyl, tetrahydronapthyl, aryl, and heteroaryl. Each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_2$-$C_4$alkanoyl, $C_1$-$C_4$alkoxycarbonyl, $C_1$-$C_2$haloalkyl, $C_1$-$C_2$haloalkoxy, and phenyl.

W is O, S, NR, or absent, where R is hydrogen or R is $C_1$-$C_6$alkyl or aryl($C_0$-$C_4$alkyl), each of which is substituted with 0 to 5 substituents independently chosen from halogen, hydroxy, cyano, amino, nitro, oxo, $C_1$-$C_2$haloalkyl, $C_1$-$C_2$haloalkoxy, $C_1$-$C_6$alkyl, $C_1$-$C_6$alkoxy, and mono- and di-($C_1$-$C_6$alkyl)amino.

V is $C_1$-$C_6$ alkyl, $C_2$-$C_6$alkenyl, $C_3$-$C_7$cycloalkyl, or absent; and when V is absent, W is absent.

Y is $C_1$-$C_6$ alkyl substituted with 0 or 1 of $C_3$-$C_7$cycloalkyl, a 5- to 7-membered monocyclic heterocycloalkyl, or 8- to 11-membered bicyclic heterocycloalkyl in which the rings are fused or spiro; each of which substituted with 0 to 3 substituents independently chosen from halogen, hydroxy, cyano, amino, nitro, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy; or Y is absent.

$R_1$ and $R_2$ are independently hydrogen, or $C_1$-$C_6$alkyl, $C_2$-$C_6$ alkenyl, or $C_2$-$C_6$ alkynyl, each of which is substituted with 0 to 3 substituents independently chosen from halogen, hydroxy, amino, $C_1$-$C_4$alkoxy, $C_1$-$C_2$haloalkyl, and $C_1$-$C_2$haloalkoxy, or $R_1$ and $R_2$ are joined to form a 5- to 7-membered saturated or mono-unsaturated ring optionally containing one additional heteroatom chosen from N, S, and O, which 5- to 7-membered saturated or mono-unsaturated ring is substituted with 0 to 3 substituents independently chosen from halogen, hydroxy, amino, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

The invention provides compounds and salts of Formula IB in which V and W are absent.

The invention provides compounds and salts of Formula IB in which Y is absent; or in which Y is —$CH_2$—, or in which Y is —$CH_2$— substituted with $C_3$-$C_6$cycloalkyl, pyrrolidinyl, or piperidinyl.

The invention also provides compounds and salts of Formula IB in which $R_1$ and $R_2$ are independently hydrogen or $C_1$-$C_4$alkyl, and other embodiments of Formula IB in which $R_1$ and $R_2$ are independently hydrogen or methyl.

The invention provides compounds and salts of Formula IB in which $A_2$ is $C_5$-$C_7$cycloalkyl, phenyl, pyridyl, naphthyl, pyrimidinyl, pyrazinyl, benzothiazolyl, benzodioxyl, quinolinyl, or isoquinolinyl, each of which is substituted with 0 to 5 substituents independently chosen from (a), (b), and (c).

Where:
(a) is chosen from halogen, hydroxy, cyano, amino, nitro, oxo, —COOH, —$CONH_2$, —$SO_2NH_2$, —SH, $C_1$-$C_2$haloalkyl, and $C_1$-$C_2$haloalkoxy, (b) is chosen from $C_1$-$C_6$alkyl, $C_2$-$C_6$alkenyl, $C_2$-$C_6$alkynyl, $C_1$-$C_6$alkoxy, $C_2$-$C_6$alkanoyl, and $C_1$-$C_8$alkoxycarbonyl, and (c) is -$GR_a$ where G is chosen from —$(CH_2)_n$—, $C_2$-$C_4$alkenyl, $C_2$-$C_4$alkynyl, —$(CH_2)_nO(CH_2)_m$—, and —$(CH_2)_nN(CH_2)_m$—, where n and m are independently 0, 1, 2, 3, or 4; and Ra is independently chosen at each occurrence from $C_3$-$C_8$cycloalkyl, piperidinyl, piperazinyl, morpholinyl, tetrahydroisoquinolinyl, indanyl, tetrahydronaphthyl, phenyl, pyridyl, benzothiophenyl, and benzofuranyl. Each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_2$-$C_4$alkanoyl, $C_1$-$C_4$alkoxycarbonyl, $C_1$-$C_2$haloalkyl, $C_1$-$C_2$haloalkoxy, and phenyl.

The invention also includes compounds of Formula II

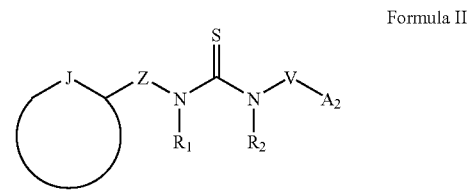

Formula II and the pharmaceutically acceptable salts thereof.

In Formula II the variables $A_2$, $R_1$, $R_2$, J, V, and Z carry the following definitions:

$A_2$ is $C_3$-$C_8$ cycloalkyl, or a partially unsaturated or aromatic carbocyclic group, or a saturated, partially unsaturated, or aromatic heterocyclic group substituted with 0 to 5 substituents independently chosen from:

(a) halogen, hydroxy, cyano, amino, nitro, oxo, —COOH, —$CONH_2$, —$SO_2NH_2$, —SH, $C_1$-$C_2$haloalkyl, and $C_1$-$C_2$haloalkoxy, and (b) $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl, and (c) -$GR_a$ where G is chosen from —$(CH_2)_n$—, $C_2$-$C_4$alkenyl, $C_2$-$C_4$alkynyl, —$(CH_2)_nO(CH_2)_m$—, and —$(CH_2)_nN(CH_2)_m$—, where n and m are independently 0, 1, 2, 3, or 4; and Ra is independently chosen at each occurrence from $C_3$-$C_8$cycloalkyl, $C_2$-$C_7$monocyclic heterocycloalkyl, $C_5$-$C_{10}$bicyclicheterocycloalkyl, indanyl, tetrahydronapthyl, aryl, and heteroaryl, each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_2$-$C_4$alkanoyl, $C_1$-$C_4$alkoxycarbonyl, $C_1$-$C_2$haloalkyl, $C_1$-$C_2$haloalkoxy, and phenyl.

V is $C_1$-$C_6$ alkyl, $C_2$-$C_6$alkenyl, or absent.

Z is carbonyl, thiocarbonyl, or imino.

$R_1$ and $R_2$ are independently hydrogen, or $C_1$-$C_6$alkyl, $C_2$-$C_6$ alkenyl, or $C_2$-$C_6$ alkynyl, each of which is substituted with 0 to 3 substituents independently chosen from halogen, hydroxy, amino, $C_1$-$C_4$alkoxy, $C_1$-$C_2$haloalkyl, and $C_1$-$C_2$haloalkoxy, or $R_1$ and $R_2$ are joined to form a 5- to 7-membered saturated or mono-unsaturated ring optionally containing one additional heteroatom chosen from N, S, and O, which 5- to 7-membered saturated or mono-unsaturated ring is substituted with 0 to 3 substituents independently chosen from halogen, hydroxy, amino, $C_1$-$C_4$alkyl, $C_1$-$C_4$alkoxy, mono- and di-($C_1$-$C_4$alkyl) amino, $C_1$-$C_2$haloalkyl, and $C_1$-$C_2$haloalkoxy.

The group:

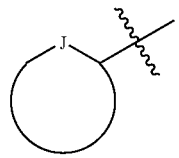

is a group of Formula (i)
that is a saturated, partially unsaturated, or aromatic heterocyclic group where J is O, S, or $NR_3$ substituted with 0 to 5 substituents independently chosen from: (a), (b), and (c) above.

$R_3$ is
(d) hydrogen, $C_1$-$C_2$haloalkyl, or $C_1$-$C_2$haloalkoxy;
(e) $C_1$-$C_6$alkyl, $C_2$-$C_6$alkenyl, $C_2$-$C_6$alkynyl, $C_1$-$C_4$alkoxy($C_1$-$C_4$alkyl), or amino($C_1$-$C_6$)alkyl,
(f) -$LR_b$, where L is chosen from —$(CH_2)_r$—, $C_2$-$C_4$alkenyl, $C_2$-$C_4$alkynyl, —$(CH_2)_rO(CH_2)_s$—, and —$(CH_2)_rN(CH_2)_s$—, where r and s are independently 0, 1, 2, 3, or 4; and Rb is chosen from $C_3$-$C_8$cycloalkyl, $C_2$-$C_7$monocyclic heterocycloalkyl, $C_5$-$C_{10}$bicyclicheterocycloalkyl, indanyl, tetrahydronapthyl, aryl, and heteroaryl; each of which (e) and (f) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_1$-$C_2$haloalkyl, $C_1$-$C_2$haloalkoxy, and phenyl.

Certain embodiments of the invention pertain to compounds and salts of Formula II in which Z is carbonyl.

Additional embodiments pertain to compounds and salts of Formula I in which V is absent or V is $C_1$-$C_4$alkyl.

The invention includes compounds and salts of Formula II wherein $R_1$ and $R_2$ are independently hydrogen or methyl.

The invention further provides compounds and salts of Formula II in which $A_2$ is $C_5$-$C_7$cycloalkyl, phenyl, pyridyl, pyrimidinyl, pyrazinyl, naphthyl, benzothiazolyl, benzodioxyl, quinolinyl, or isoquinolinyl, each of which is substituted with 0 to 5 substituents independently chosen from (a), (b), and (c), where (a), (b), and (c) carry the definitions set forth above for these variables in Formula II.

In certain embodiments the invention provides compounds and salts of Formula II wherein $A_2$ is $C_5$-$C_7$cycloalkyl, phenyl, pyridyl, naphthyl, pyrimidinyl, pyrazinyl, benzothiazolyl, benzodioxyl, quinolinyl, or isoquinolinyl, each of which is substituted with 0 to 5 substituents independently chosen from (a), (b), and (c) where (a) is chosen from halogen, hydroxy, cyano, amino, nitro, oxo, —COOH, —$CONH_2$, —$SO_2NH_2$, —SH, $C_1$-$C_2$haloalkyl, and $C_1$-$C_2$haloalkoxy, (b) is chosen from $C_1$-$C_6$alkyl, $C_2$-$C_6$alkenyl, $C_2$-$C_6$alkynyl, $C_1$-$C_6$alkoxy, $C_2$-$C_6$alkanoyl, $C_1$-$C_8$alkoxycarbonyl, and (c) is -$GR_a$ where G is chosen from —$(CH_2)_n$—, $C_2$-$C_4$alkenyl, $C_2$-$C_4$alkynyl, —$(CH_2)_nO(CH_2)_m$—, and —$(CH_2)_nN(CH_2)_m$—, where n and m are independently 0, 1, 2, 3, or 4; and I, is chosen from $C_3$-$C_8$cycloalkyl, piperidinyl, piperazinyl, morpholinyl, tetrahydroisoquinolinyl, indanyl, tetrahydronaphthyl, phenyl, pyridyl, benzothiophenyl, and benzofuranyl; each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_2$-$C_4$alkanoyl, $C_1$-$C_4$alkoxycarbonyl, $C_1$-$C_2$haloalkyl, $C_1$-$C_2$haloalkoxy, and phenyl.

The invention pertains to compounds and salts of Formula II wherein

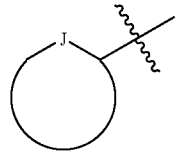

is a group of Formula (i)
where Formula (i) is a heteroaryl group that is pyridyl, pyrimidinyl, thienyl, pyrrolyl, furanyl, pyrazolyl, imidazolyl, thiazolyl, triazolyl, thiadiazolyl, oxazolyl, isoxazolyl, benzofuranyl, benzothiazolyl, benzothiophenyl, benzoxadiazolyl, benzo[d]oxazolyl, dihydrobenzodioxynyl, indolyl, pyrazolopyrimidinyl, or thienylpyrazolyl oriented such that the heteroatom J is adjacent (separated by one single, double or aromatic covalent bond) to the point of attachment of the group of Formula (i) in Formula II and the group of Formula (i) is substituted with 0 to 5 substituent independently chosen from (a), (b), and (c), where (a), (b) and (c) carry the definitions set forth for these variables in Formula II.

J is S, O, or $NR_3$.
$R_3$ is
(d) hydrogen, $C_1$-$C_2$haloalkyl, or $C_1$-$C_2$haloalkoxy;
(e) $C_1$-$C_6$alkyl, $C_2$-$C_6$alkenyl, $C_2$-$C_6$alkynyl, $C_1$-$C_4$alkoxy($C_1$-$C_4$alkyl), or amino($C_1$-$C_6$)alkyl, or
(f) -$LR_b$ where L is chosen from —$(CH_2)_r$—, $C_2$-$C_4$alkenyl, $C_2$-$C_4$alkynyl, —$(CH_2)_rO(CH_2)_s$—, and —$(CH_2)_rN(CH_2)_s$—, where r and s are independently 0, 1, 2, 3, or 4; and $R_b$ is chosen from $C_3$-$C_8$cycloalkyl, $C_2$-$C_7$monocyclic heterocycloalkyl, $C_5$-$C_{10}$bicyclicheterocycloalkyl, indanyl, tetrahydronapthyl, aryl, and heteroaryl; each of which (e) and (f) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_1$-$C_2$haloalkyl, $C_1$-$C_2$haloalkoxy, and phenyl.

Certain embodiments of the invention pertain to compounds and salts of Formula II in wherein

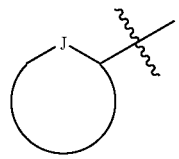

is a group of Formula (i)

where Formula (i) is a heteroaryl group that is pyridyl, pyrimidinyl, thienyl, pyrrolyl, furanyl, pyrazolyl, imidazolyl, thiazolyl, triazolyl, thiadiazolyl, oxazolyl, isoxazolyl, benzofuranyl, benzothiazolyl, benzothiophenyl, benzoxadiazolyl, benzo[d]oxazolyl, dihydrobenzodioxynyl, indolyl, pyrazolopyrimidinyl, or thienylpyrazolyl oriented such that the heteroatom J is adjacent (separated by one single, double or aromatic covalent bond) to the point of attachment of the group of Formula (i) in Formula II. The group of Formula (i)

is substituted with 0 to 5 substituents independently chosen from: (a) halogen, hydroxy, cyano, amino, nitro, oxo, —COOH, —CONH$_2$, —SO$_2$NH$_2$, —SH, C$_1$-C$_2$haloalkyl, and C$_1$-C$_2$haloalkoxy, and (b) C$_1$-C$_6$alkyl, C$_2$-C$_6$alkenyl, C$_2$-C$_6$alkynyl, C$_1$-C$_6$alkoxy, C$_2$-C$_6$alkanoyl, C$_1$-C$_9$alkoxycarbonyl, and (c) -GR$_a$ where G is chosen from —(CH$_2$)$_n$—, C$_2$-C$_4$alkenyl, C$_2$-C$_4$alkynyl, —(CH$_2$)$_n$O(CH$_2$)$_m$—, and —(CH$_2$)$_n$N(CH$_2$)$_m$—, where n and m are independently 0, 1, 2, 3, or 4; and Ra is chosen from C$_3$-C$_8$cycloalkyl, piperidinyl, piperazinyl, morpholinyl, tetrahydroisoquinolinyl, indanyl, tetrahydronaphthyl, phenyl, pyridyl, benzothiophenyl, and benzofuranyl; each of which (b) and (c) is substituted with 0 to 5 substituents independently chosen from halogen, hydroxy, amino, C$_1$-C$_4$alkyl, C$_1$-C$_4$alkoxy, mono- and di-(C$_1$-C$_4$alkyl)amino, C$_2$-C$_4$alkanoyl, C$_1$-C$_4$alkoxycarbonyl, C$_1$-C$_2$haloalkyl, C$_1$-C$_2$haloalkoxy, and phenyl.

J is S, O, or NR$_3$.

R$_3$ is (d) hydrogen, (e) C$_1$-C$_6$alkyl, or (f) -LR$_b$ where L is chosen from —(CH$_2$)$_r$—, —(CH$_2$)$_r$O(CH$_2$)$_s$—, and —(CH$_2$)$_r$N(CH$_2$)$_s$—, where r and s are independently 0, 1, 2, 3, or 4; and R$_b$ is chosen from C$_3$-C$_8$cycloalkyl, piperidinyl, piperazinyl, morpholinyl, indanyl, tetrahydronapthyl, phenyl, and pyridyl; each of which (e) and (f) is substituted with 0 to 5 substituents independently chosen from halogen, hydroxy, amino, C$_1$-C$_4$alkyl, C$_1$-C$_4$alkoxy, mono- and di-(C$_1$-C$_4$alkyl)amino, C$_1$-C$_2$haloalkyl, C$_1$-C$_2$haloalkoxy, and phenyl.

The invention includes compounds and salts of Formula III in which V and W are absent.

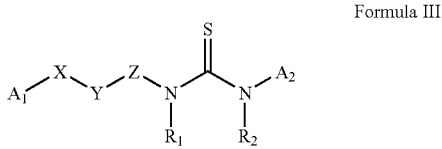

Formula III

The variables A$_1$, X, Y, Z, R$_1$, and R$_2$ in Formula III carry the definitions set forth in Formula I or alternatively in Formula IA. In certain compounds and salts of Formula II$_1$, R$_1$ and R$_2$ are both hydrogen.

The invention includes compounds and salts of Formula IV in which V and W are both absent:

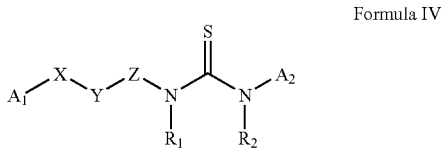

Formula IV

The variables A$_1$, X, Y, Z, R$_1$, and R$_2$ in Formula IV carry the definitions set forth in Formula I or alternatively in Formula IA. In certain compounds and salts of Formula IV R$_1$ and R$_2$ are both hydrogen.

The invention also includes compounds and salts of Formula V in which V and W are both absent, and Z is carbonyl:

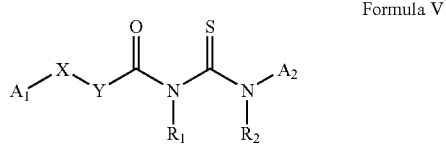

Formula V

The variables A$_1$, X, Y, R$_1$, and R$_2$ in Formula V carry the definitions set forth in Formula I or alternatively in Formula IA. In certain compounds and salts of Formula V R$_1$ and R$_2$ are both hydrogen.

The invention includes compounds and salt of Formula VI in which V is C$_1$-C$_2$alkyl and W is absent.

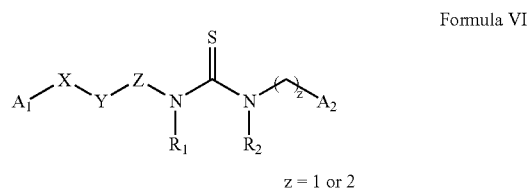

Formula VI z = 1 or 2

The variables A$_1$, X, Y, Z, R$_1$, and R$_2$ in Formula 1-4 carry the definitions set forth in Formula I or alternatively in Formula IA. In certain compounds and salts of Formula VI R$_1$ and R$_2$ are both hydrogen.

The invention also includes compounds and salts of Formula VI in which X and Y are absent, and Z is carbonyl. The invention further includes compounds and salts of Formula VI in which X is oxygen, Y is C$_1$-C$_2$ alkyl, and Z is carbonyl.

The invention includes compounds and salts of any of the above Formulae in which R$_1$ and R$_2$ are independently hydrogen or C$_1$-C$_4$alkyl, C$_2$-C$_4$alkenyl, or C$_2$-C$_4$alkynyl, each of which is substituted with 0 to 3 substituents independently chosen from halogen, hydroxy, amino, C$_1$-C$_4$alkoxy, C$_1$-C$_2$haloalkyl, and C$_1$-C$_2$haloalkoxy. In certain compounds and salt of the above Formulae R$_1$ and R$_2$ are independently hydrogen, methyl, or ethyl. The invention also includes compounds and salts of the above Formulae in which R$_1$ and R$_2$ are both hydrogen.

The invention includes compounds and salts of any of the above Formulae which R$_1$ and R$_2$ are joined to form a 5- to 7-membered saturated or mono-unsaturated ring optionally containing one additional heteroatom chosen from N, S, and O, which 5- to 7-membered saturated or mono-unsaturated ring is substituted with 0 to 3 substituents independently chosen from halogen, hydroxy, amino, C$_1$-C$_4$alkyl, C$_1$-C$_4$alkoxy, mono- and di-(C$_1$-C$_4$alkyl)amino, C$_1$-C$_2$haloalkyl, and C$_1$-C$_2$haloalkoxy.

The invention also includes compounds and salts of any of the above Formulae in which R$_1$ and R$_2$ are joined to form a 5- to 7-membered saturated or mono-unsaturated ring containing no additional heteroatoms, which 5- to 7-membered saturated or mono-unsaturated ring is substituted with 0 to 3 substituents independently chosen from halogen, hydroxy, amino, C$_1$-C$_2$alkyl, and C$_1$-C$_2$alkoxy.

For example the invention includes compounds and salts of Formula VII

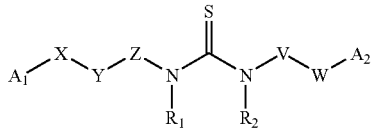

Formula VII where $R_4$ represents 0 to 2 substituents independently chosen from halogen, hydroxy, amino, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy. The variables $A_1$, $A_2$, V, W, X, Y, and Z carry the definitions set forth in Formula I or alternatively in Formula IA. In certain compounds of Formula VII Z is carbonyl.

The invention also includes compounds and salts of Formula VIII:

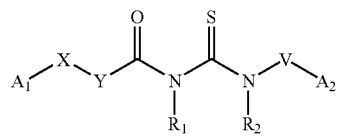

Formula VIII where V and Y are $C_1$-$C_4$ alkyl. The variables $A_1$, $A_2$, V, and X carry the definitions set forth in Formula I or alternatively in Formula IA. For compounds of Formula VIII it is preferred that $R_1$ and $R_2$ are hydrogen.

The invention includes compounds and salts of Formula I, IA, III, IV, VI, and VII in which Z is thiocarbonyl.

The invention includes compounds and salts of Formula I, IA, III, IV, VI, and VII in which Z is imino or $C_1$-$C_6$alkylimino. In other embodiments the invention includes compounds and salts of Formula I, IA, III, IV, 1-4, and 1-5 in which Z is imino or methylimino.

The invention includes compounds and salts of Formula I, IA, III, IV, VI, and VII in which Z is carbonyl.

The invention includes compounds and salts of any of the above formulae in which X is oxygen and Y is —$CH_2$—.

The invention includes compounds and salts of any of the above formulae in which X and Y are absent.

The invention includes compounds and salts of any of the above formulae in which:
  $A_1$ is $C_1$-$C_6$alkyl, $C_3$-$C_8$cycloalkyl, a partially unsaturated or aromatic carbocyclic group, or a saturated, partially unsaturated, or aromatic heterocyclic group and $A_2$ is phenyl, naphthyl, pyridyl, pyrazinyl, or pyrimidinyl.
  Each of $A_1$ and $A_2$ is substituted with 0 to 5 substituents independently chosen from:
  (a) halogen, hydroxy, cyano, amino, nitro, oxo, —COOH, —$CONH_2$, —$SO_2NH_2$, —SH, $C_1$-$C_2$haloalkyl, and $C_1$-$C_2$haloalkoxy, and
  (b) $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl, and
  (c) -$GR_a$ where G is chosen from —$(CH_2)_n$—, $C_2$-$C_4$alkenyl, $C_2$-$C_4$alkynyl, —$(CH_2)_nO(CH_2)_m$—, and —$(CH_2)_nN(CH_2)_m$—, where n and m are independently 0, 1, 2, 3, or 4; and $R_a$ is chosen from $C_3$-$C_8$cycloalkyl, $C_2$-$C_7$monocyclic heterocycloalkyl, $C_5$-$C_{10}$bicyclicheterocycloalkyl, indanyl, tetrahydronapthyl, aryl, and heteroaryl; each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_2$-$C_4$alkanoyl, $C_1$-$C_4$alkoxycarbonyl, $C_1$-$C_2$haloalkyl, $C_1$-$C_2$haloalkoxy, and phenyl.

The invention includes compounds and salts of any of the above formulae in which $A_1$ is $C_1$-$C_6$alkyl, $C_3$-$C_8$cycloalkyl, a partially unsaturated or aromatic carbocyclic group, or a saturated, partially unsaturated, or aromatic heterocyclic group and $A_2$ is phenyl, naphthyl, pyridyl, pyrimidinyl, pyrazinyl, or phenyl fused to a 5- to 7-membered heterocycloalkyl ring containing 1 or 2 heteroatoms chosen from N, O, and S.

$A_2$ is substituted with 0 to 5 substituents independently chosen from:
  (i) halogen, hydroxy, cyano, amino, nitro, $C_1$-$C_2$haloalkyl, and $C_1$-$C_2$haloalkoxy, and
  (ii) $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_6$alkoxycarbonyl, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl,
  (iii) -$GR_a$ where G is chosen from —$(CH_2)_n$—, $C_2$-$C_4$alkenyl, $C_2$-$C_4$alkynyl, —$(CH_2)_nO(CH_2)_m$—, and —$(CH_2)_nN(CH_2)_m$—, where n and m are independently 0, 1, 2, 3, or 4; and Ra is chosen from $C_3$-$C_8$cycloalkyl, piperidinyl, piperazinyl, morpholinyl, thiomorpholinyl, tetrahydrofuranyl, pyrrolidinyl, decahydroquinolinyl, decahydroisoquinolinyl, indanyl, tetrahydronapthyl, phenyl, pyridyl, pyrimidinyl, and thienyl; each of which (ii) and (iii) is substituted with 0 to 3 substituents independently chosen from halogen, hydroxy, amino, $C_1$-$C_4$alkyl, $C_1$-$C_4$alkoxy, mono- and di-($C_1$-$C_4$alkyl)amino, $C_1$-$C_2$haloalkyl, $C_1$-$C_2$haloalkoxy, and phenyl.

The invention includes compounds and salts of any of the above formulae in which $A_1$ is an aryl, partially unsaturated heterocyclic group, or heteroaryl group.

$A_1$ is substituted with 0 to 5 substituents independently chosen from:
  (a) halogen, hydroxy, cyano, amino, nitro, oxo, —COOH, —$CONH_2$, —$SO_2NH_2$, —SH, $C_1$-$C_2$haloalkyl, and $C_1$-$C_2$haloalkoxy,
  (b) $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl, and
  (c) -$GR_a$ where G is chosen from —$(CH_2)_n$—, $C_2$-$C_4$alkenyl, $C_2$-$C_4$alkynyl, —$(CH_2)_nO(CH_2)_m$—, and —$(CH_2)_nN(CH_2)_m$—, where n and m are independently 0, 1, 2, 3, or 4; and $R_a$ is chosen from $C_3$-$C_8$cycloalkyl, $C_2$-$C_7$monocyclic heterocycloalkyl, $C_5$-$C_{10}$bicyclicheterocycloalkyl, indanyl, tetrahydronapthyl, aryl, and heteroaryl; each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_2$-$C_4$alkanoyl, $C_1$-$C_4$alkoxycarbonyl, $C_1$-$C_2$haloalkyl, $C_1$-$C_2$haloalkoxy, and phenyl.

The invention includes compounds and salts of any of the above formulae in which $A_1$ is phenyl, naphthyl, pyridyl, pyrimidinyl, thienyl, pyrrolyl, furanyl, pyrazolyl, imidazolyl, thiazolyl, triazolyl, thiadiazolyl, oxazolyl, isoxazolyl, benzofuranyl, benzothiazolyl, benzothiophenyl, benzoxadiazolyl, benzo[d]oxazolyl, dihydrobenzodioxynyl, indolyl, pyrazolopyrimidinyl, thienylpyrazolyl, benzopyranyl, or 4H-chromenyl, $A_1$ is substituted with 0 to 5 substituents independently chosen from (a) halogen, hydroxy, cyano, amino, nitro, oxo, —COOH, —CONH$_2$, —SO$_2$NH$_2$, —SH, $C_1$-$C_2$haloalkyl, and $C_1$-$C_2$haloalkoxy, (b) $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl, and (c) -$GR_a$ where G is chosen from —(CH$_2$)$_n$—, $C_2$-$C_4$alkenyl, $C_2$-$C_4$alkynyl, —(CH$_2$)$_n$O(CH$_2$)$_m$—, and —(CH$_2$)$_n$N(CH$_2$)$_m$—, where n and m are independently 0, 1, 2, 3, or 4; and $R_a$ is chosen from $C_3$-$C_8$cycloalkyl, $C_2$-$C_7$monocyclic heterocycloalkyl, $C_5$-$C_{10}$bicyclicheterocycloalkyl, indanyl, tetrahydronapthyl, aryl, and heteroaryl; each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_1$-$C_2$haloalkyl, $C_1$-$C_2$haloalkoxy, and phenyl.

The invention also includes compounds and salts of any of the above formulae in which $A_1$ is phenyl, naphthyl, pyridin-2-yl, pyridin-3-yl, pyridin-4-yl, pyrimidin-2-yl, pyrimidinyl-4-yl, pyrimidin-5-yl, thien-2-yl, thien-3-yl, thiazol-4-yl, pyrrol-1-yl, pyrrol-2-yl, pyyrol-3-yl, furan-2-yl, furan-3-yl, pyrazol-1-yl, pyrazol-2-yl pyrazol-4-yl, pyrazol-5-yl, imdiazol-1-yl, imdiazol-2-yl, imdiazol-4-yl, imdiazol-5-yl, thiazol-2-yl, thiazol-3-yl, thiazol-5-yl, 1,2,3-triazol-4-yl, 1,2,3-thiadiazol-4-yl, 1,2,3-thiadiazol-5-yl, oxazol-2-yl, isoxazol-4-yl, isoxazol-5-yl, isoxazol-3-yl, isoxazol-4-yl, isoxazol-5-yl, benzofuran-2-yl, benzofuran-3-yl, benzopyran-2-yl, benzopyran-3-yl, benzopyran-4-yl, benzo[d]oxazol-2-yl benzo[d]thiazol-2-yl, benzo[b]thiophen-2-yl, 4H-chromen-2-yl, benzo[c][1,2,5]oxadiazolyl, 2,3-dihydrobenzo[b][1,4]dioxin-2-yl, pyrazolo[1,5-a]pyrimidin-6-yl, dihydrobenzo[b][1,4]dioxin-3-yl, indol-2-yl, pyrazolo[1,5-a]pyrimidin-5-yl, 1H-thieno[2,3-c]pyrazol-4-yl, or 1H-thieno[2,3-c]pyrazol-5-yl.

In this embodiment $A_1$ is substituted with 0 to 5 substituents independently chosen from (a) halogen, hydroxy, cyano, amino, nitro, oxo, —COOH, —CONH$_2$, —SO$_2$NH$_2$, —SH, $C_1$-$C_2$haloalkyl, and C I—C$_2$haloalkoxy, (b) $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl, and (c) -$GR_a$ where G is chosen from —(CH$_2$)$_n$—, $C_2$-$C_4$alkenyl, $C_2$-$C_4$alkynyl, —(CH$_2$)$_n$O(CH$_2$)$_m$—, and —(CH$_2$)$_n$N(CH$_2$)$_m$—, where n and m are independently 0, 1, 2, 3, or 4; and $R_a$ is chosen from $C_3$-$C_8$cycloalkyl, $C_2$-$C_7$monocyclic heterocycloalkyl, $C_5$-$C_{10}$bicyclicheterocycloalkyl, indanyl, tetrahydronapthyl, aryl, and heteroaryl; each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_1$-$C_2$haloalkyl, $C_1$-$C_2$haloalkoxy, and phenyl.

Alternatively the possible substituents on $A_1$ may be 0 to 5 substituents independently chosen from (a) halogen, hydroxy, cyano, amino, nitro, oxo, $C_1$-$C_2$haloalkyl, and $C_1$-$C_2$haloalkoxy, and (b) $C_1$-$C_6$alkyl, $C_1$-$C_6$alkoxy, $C_1$-$C_4$alkoxy($C_1$-$C_4$alkyl), amino($C_1$-$C_4$)alkyl, mono- and di-($C_1$-$C_4$alkyl)amino, mono- and di-($C_1$-$C_4$alkyl)amino$C_1$-$C_4$alkyl; and (c) -$GR_a$ where G is from —(CH$_2$)$_n$—, —(CH$_2$)$_n$O(CH$_2$)$_m$—, and —(CH$_2$)$_n$N(CH$_2$)$_m$—, and $R_a$ is $C_3$-$C_8$cycloalkyl, 5 or 6-membered heterocycloalkyl containing 1 or 2 heteroatoms independently chosen from O, S, and N, 5- or 6-membered heteroaryl containing 1, 2, or 3 heteroatoms independently chosen from O, S, and N, indanyl, and phenyl, each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_2$alkyl)amino, and $C_1$-$C_2$haloalkyl, and $C_1$-$C_2$haloalkoxy.

The invention also includes compounds and salts of any of the above formulae in which $A_1$ is $C_1$-$C_6$ alkyl, $C_3$-$C_7$cycloalkyl, or $C_2$-$C_7$monocyclic heterocycloalkyl.

$A_1$ in this embodiment is substituted with 0 to 5 substituents independently chosen from:

(a) halogen, hydroxy, cyano, amino, nitro, oxo, —COOH, —CONH$_2$, —SO$_2$NH$_2$, —SH, $C_1$-$C_2$haloalkyl, and $C_1$-$C_2$haloalkoxy, (b) $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl, and (c) -$GR_a$ where G is chosen from —(CH$_2$)$_n$—, $C_2$-$C_4$alkenyl, $C_2$-$C_4$alkynyl, —(CH$_2$)$_n$O(CH$_2$)$_m$—, and —(CH$_2$)$_n$N(CH$_2$)$_m$—, where n and m are independently 0, 1, 2, 3, or 4; and $R_a$ is chosen from $C_3$-$C_8$cycloalkyl, $C_2$-$C_7$monocyclic heterocycloalkyl, $C_5$-$C_{10}$bicyclicheterocycloalkyl, indanyl, tetrahydronapthyl, aryl, and heteroaryl; each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_2$-$C_4$alkanoyl, $C_1$-$C_4$alkoxycarbonyl, $C_1$-$C_2$haloalkyl, $C_1$-$C_2$haloalkoxy, and phenyl.

The invention further includes compounds and salts of any of the above formulae in which $A_1$ is $C_1$-$C_6$ alkyl, $C_3$-$C_7$cycloalkyl, pyrrolidinyl, piperidinyl, piperazinyl, or morpholinyl.

$A_1$ is substituted with 0 to 5 substituents independently chosen from:

(a) halogen, hydroxy, cyano, amino, nitro, oxo, —COOH, —CONH$_2$, —SO$_2$NH$_2$, —SH, $C_1$-$C_2$haloalkyl, and $C_1$-$C_2$haloalkoxy;

(b) $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl, and (c) -GR$_a$ where G is chosen from —(CH$_2$)$_n$—, $C_2$-$C_4$alkenyl, $C_2$-$C_4$alkynyl, —(CH$_2$)$_n$O(CH$_2$)$_m$—, and —(CH$_2$)$_n$N(CH$_2$)$_m$—, where n and m are independently 0, 1, 2, 3, or 4; and R$_a$ is chosen from $C_3$-$C_8$cycloalkyl, and phenyl.

The invention includes compounds and pharmaceutically acceptable salts of Formula 1

Formula 1
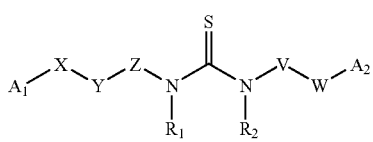

In Formula 1 the variables $A_1$, V, W, X, Y, Z, $R_1$, and $R_2$ are defined as follows:

$A_1$ is an optionally substituted di-alkylamino, an optionally substituted aryl group, an optionally substituted 5- or 6-membered heteroaryl group, an optionally substituted bicyclic heteroaryl group having a 5-membered heteroaryl ring fused to a phenyl ring, an optionally substituted partially unsaturated or aromatic heterocyclic group having two 6-membered rings, an optionally substituted 5- to 7-membered heterocycloalkyl group containing at least one nitrogen atom and 0 or 1 additional heteroatoms, an optionally substituted partially unsaturated 5- to 7-membered heterocycloalkyl group containing at least one nitrogen atom and 0 or 1 additional heteroatoms, or a fused or spiro 8 to 11-membered bicyclic heterocycloalkyl group containing at least one nitrogen atom and 0 to 3 additional heteroatoms.

$A_2$ is (i)
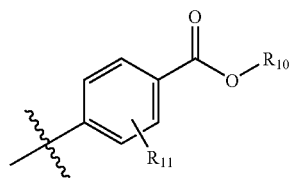

(ii)
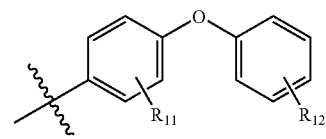

(iii)
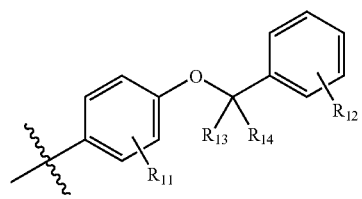

(iv)
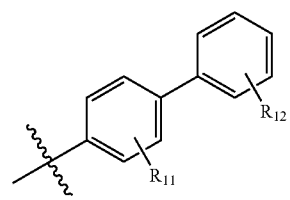

(v)
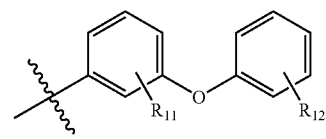

(vi)
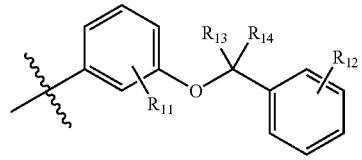

(vii)
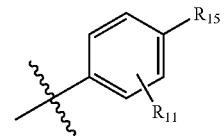

(viii)
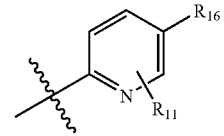

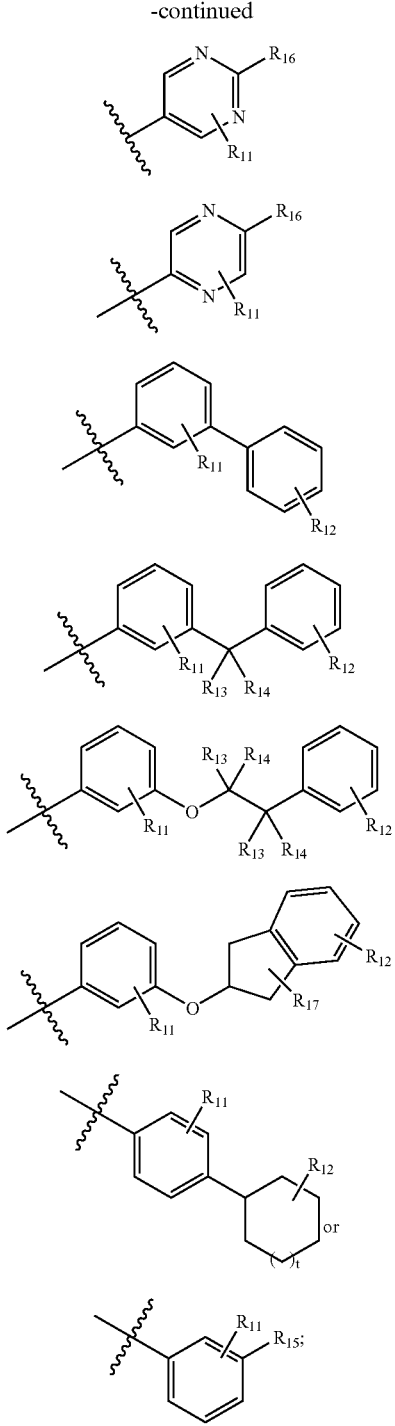

X and W are independently O, S, NR, or absent, where R is hydrogen, optionally substituted $C_1$-$C_6$alkyl, or optionally substituted aryl($C_0$-$C_4$alkyl).

V is $C_1$-$C_6$ alkyl, $C_2$-$C_6$alkenyl, $C_3$-$C_7$cycloalkyl, or absent.

Y is $C_1$-$C_6$ alkyl, $C_1$-$C_6$ alkyl substituted with $C_3$-$C_7$cycloalkyl, $C_2$-$C_6$alkenyl, $C_3$-$C_7$cycloalkyl, or absent; wherein when V is absent, W is absent.

Z is carbonyl, thiocarbonyl, imino, or $C_1$-$C_6$alkylimino.

The variable t is 0 or 1;

$R_1$ and $R_2$ are independently hydrogen, or $R_1$ and $R_2$ are independently $C_1$-$C_6$alkyl, $C_2$-$C_6$ alkenyl, or $C_2$-$C_6$ alkynyl, each of which is substituted with 0 to 3 substituents independently chosen from halogen, hydroxy, amino, $C_1$-$C_4$alkoxy, $C_1$-$C_2$haloalkyl, and $C_1$-$C_2$haloalkoxy, or $R_1$ and $R_2$ are joined to form a 5- to 7-membered saturated or mono-unsaturated ring optionally containing one additional heteroatom chosen from N, S, and O, which 5- to 7-membered saturated or mono-unsaturated ring is substituted with 0 to 3 substituents independently chosen from halogen, hydroxy, amino, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

$R_{10}$ is $C_1$-$C_6$alkyl.

$R_{11}$ and $R_{12}$ each represent 0 to 3 substituents independently chosen from halogen, hydroxy, cyano, $C_1$-$C_6$alkyl, $C_1$-$C_6$alkoxy, mono- and di-($C_1$-$C_6$alkyl)amino, $C_2$-$C_6$alkanoyl, $C_1$-$C_2$haloalkyl, $C_1$-$C_2$haloalkoxy, and phenyl.

$R_{13}$ and $R_{14}$ are independently chosen at each occurrence from hydrogen and $C_1$-$C_4$alkyl.

$R_{15}$ is $C_4$-$C_6$alkoxy or $C_4$-$C_6$alkyl.

$R_{16}$ is $C_2$-$C_6$alkoxy or $C_2$-$C_6$alkyl.

$R_{17}$ represents 0 to 2 substituents independently chosen from halogen, methyl, and methoxy.

The invention also includes certain compounds and salts of Formula 1 (above), which will be referred to as compounds of Formula 1A, in which the variables $A_2$ and $R_{10}$-$R_{17}$ carry the definitions set forth above for compounds and salts of Formula 1, but in which the variables, $A_1$, V, W, X, Y, Z, $R_1$ and $R_2$ are defined as follows:

$A_1$ is a di-($C_1$-$C_6$alkyl)amino, an aryl group, a 5- or 6-membered heteroaryl group, a bicyclic heteroaryl group having a 5-membered heteroaryl ring fused to a phenyl ring, a partially unsaturated or aromatic heterocyclic group having two 6-membered rings, a 5- to 7-membered heterocycloalkyl group containing at least one nitrogen atom and 0 or 1 additional heteroatoms, a partially unsaturated 5- to 7-membered heterocycloalkyl group containing at least one nitrogen atom and 0 or 1 additional heteroatoms, or a fused or spiro 8 to 11-membered bicyclic heterocycloalkyl group containing at least one nitrogen atom and 0 to 3 additional heteroatoms; each of which $A_1$ is substituted with 0 to 5 substituents independently chosen from:

(a) halogen, hydroxy, cyano, amino, nitro, oxo, —COOH, —CONH$_2$, —SO$_2$NH$_2$, —SH, $C_1$-$C_2$haloalkyl, and $C_1$-$C_2$haloalkoxy, (b) $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl, and (c) -GR$_a$ where G is chosen from —(CH$_2$)$_n$—, $C_2$-$C_4$alkenyl, $C_2$-$C_4$alkynyl, —(CH$_2$)$_n$O(CH$_2$)$_m$—, and —(CH$_2$)$_n$N(CH$_2$)$_m$—, where n and m are independently 0, 1, 2, 3, or 4; and R$_a$ is chosen from $C_3$-$C_8$cycloalkyl, $C_2$-$C_7$monocyclic heterocycloalkyl, $C_5$-$C_{10}$bicyclicheterocycloalkyl, indanyl, tetrahydronapthyl, aryl, and heteroaryl.

each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_2$-$C_4$alkanoyl, $C_1$-$C_4$alkoxycarbonyl, $C_1$-$C_2$haloalkyl, $C_1$-$C_2$haloalkoxy, and phenyl;

X and W are independently O, S, NR, or absent, where R is hydrogen or R is $C_1$-$C_6$alkyl or aryl($C_0$-$C_4$alkyl), each of which is substituted with 0 to 5 substituents independently chosen from halogen, hydroxy, cyano, amino, nitro, oxo, $C_1$-$C_2$haloalkyl, $C_1$-$C_2$haloalkoxy, $C_1$-$C_6$alkyl, $C_1$-$C_6$alkoxy, and mono- and di-($C_1$-$C_6$alkyl)amino.

V is independently $C_1$-$C_6$ alkyl, $C_2$-$C_6$alkenyl, $C_3$-$C_7$cycloalkyl, or absent.

Y is $C_1$-$C_6$ alkyl, $C_1$-$C_6$ alkyl substituted with $C_3$-$C_7$cycloalkyl, $C_2$-$C_6$alkenyl, $C_3$-$C_7$cycloalkyl, or absent; wherein when V is absent, W is absent.

Z is carbonyl, thiocarbonyl, or imino.

$R_1$ and $R_2$ are independently hydrogen, or $R_1$ and $R_2$ are independently $C_1$-$C_6$alkyl, $C_2$-$C_6$ alkenyl, or $C_2$-$C_6$ alkynyl, each of which is substituted with 0 to 3 substituents independently chosen from halogen, hydroxy, amino, $C_1$-$C_4$alkoxy, $C_1$-$C_2$haloalkyl, and $C_1$-$C_2$haloalkoxy, or $R_1$ and $R_2$ are joined to form a 5- to 7-membered saturated or mono-unsaturated ring optionally containing one additional heteroatom chosen from N, S, and O, which 5- to 7-membered saturated or mono-unsaturated ring is substituted with 0 to 3 substituents independently chosen from halogen, hydroxy, amino, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

In certain embodiments the invention provides compounds and salts of Formula 1 and Formula 1A in which Z is thiocarbonyl; or in which Z is imino or $C_1$-$C_6$alkylimino; or in which Z is imino or methylimino; or in which Z is carbonyl.

The invention provides compounds and salts of Formula 1 and Formula 1A in which X is oxygen and Y is —CH$_2$—; and also provides compounds and salts of Formula 1 and Formula 1A in which X is oxygen and Y is —CH$_2$CH$_2$—; and further provides compounds and salts of Formula 1 and Formula 1A in which X and Y are absent.

The invention provides compounds and salts of Formula 1 and Formula 1A in which V and W are absent; or in other embodiments in which V is $C_1$-$C_2$alkyl and W is absent.

The invention provides compounds and salts of Formula 1 and Formula 1A in which $R_1$ and $R_2$ are independently hydrogen, or $C_1$-$C_4$alkyl, $C_2$-$C_4$alkenyl, or $C_2$-$C_4$alkynyl, each of which is substituted with 0 to 3 substituents independently chosen from halogen, hydroxy, amino, $C_1$-$C_4$alkoxy, $C_1$-$C_2$haloalkyl, and $C_1$-$C_2$haloalkoxy. In certain embodiments $R_1$ and $R_2$ are independently hydrogen, methyl, or ethyl. In other embodiment $R_1$ and $R_2$ are both hydrogen.

The invention provides compounds and salts of Formula 1 and Formula 1A in which:

$R_1$ and $R_2$ are joined to form a 5- to 7-membered saturated or mono-unsaturated ring optionally containing one additional heteroatom chosen from N, S, and O, which 5- to 7-membered saturated or mono-unsaturated ring is substituted with 0 to 3 substituents independently chosen from halogen, hydroxy, amino, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy. In some embodiments $R_1$ and $R_2$ are joined to form a 5- to 7-membered saturated or mono-unsaturated ring containing no additional heteroatoms, which 5- to 7-membered saturated or mono-unsaturated ring is substituted with 0 to 3 substituents independently chosen from halogen, hydroxy, amino, $C_1$-$C_2$alkyl, and $C_1$-$C_2$alkoxy.

The invention includes compounds and salts of Formula 1 and Formula 1A in which:

$A_1$ is aryl, a partially unsaturated heterocyclic group, or heteroaryl group; substituted with 0 to 5 substituents independently chosen from (a), (b), and (c).

Wherein:

(a) is halogen, hydroxy, cyano, amino, nitro, oxo, —COOH, —CONH$_2$, —SO$_2$NH$_2$, —SH, $C_1$-$C_2$haloalkyl, and $C_1$-$C_2$haloalkoxy, and (b) is $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl, and (c) is -GR$_a$ where G is chosen from —(CH$_2$)$_n$—, $C_2$-$C_4$alkenyl, $C_2$-$C_4$alkynyl, —(CH$_2$)$_n$O(CH$_2$)$_m$—, and —(CH$_2$)$_n$N(CH$_2$)$_m$—, where n and m are independently 0, 1, 2, 3, or 4; and R$_a$ is chosen from $C_3$-$C_8$cycloalkyl, $C_2$-$C_7$monocyclic heterocycloalkyl, $C_5$-$C_{10}$bicyclicheterocycloalkyl, indanyl, tetrahydronapthyl, aryl, and heteroaryl. Each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_2$-$C_4$alkanoyl, $C_1$-$C_4$alkoxycarbonyl, $C_1$-$C_2$haloalkyl, $C_1$-$C_2$haloalkoxy, and phenyl.

In some embodiments $A_1$ in Formula 1 or Formula 1A is phenyl, naphthyl, pyridyl, pyrimidinyl, thienyl, pyrrolyl, furanyl, pyrazolyl, imidazolyl, thiazolyl, triazolyl, thiadiazolyl, oxazolyl, isoxazolyl, benzofuranyl, benzothiazolyl, benzothiophenyl, benzoxadiazolyl, benzo[d]oxazolyl, dihydrobenzodioxynyl, indolyl, pyrazolopyrimidinyl, thienylpyrazolyl, or 4H-chromenyl, each of which is substituted with 0 to 5 substituents independently chosen from (a), (b), and (c).

Wherein (a) is halogen, hydroxy, cyano, amino, nitro, oxo, —COOH, —CONH$_2$, —SO$_2$NH$_2$, —SH, $C_1$-$C_2$haloalkyl, and $C_1$-$C_2$haloalkoxy, (b) is $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl, and (c) is -GR$_a$ where G is chosen from —(CH$_2$)$_n$—, $C_2$-$C_4$alkenyl, $C_2$-$C_4$alkynyl, —(CH$_2$)$_n$O(CH$_2$)$_m$—, and —(CH$_2$)$_n$N(CH$_2$)$_m$—, where n and m are independently 0, 1, 2, 3, or 4; and R$_a$ is chosen from $C_3$-$C_8$cycloalkyl, $C_2$-$C_7$monocyclic heterocycloalkyl, $C_5$-$C_{10}$bicyclicheterocycloalkyl, indanyl, tetrahydronapthyl, aryl, and heteroaryl. Each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_1$-$C_2$haloalkyl, $C_1$-$C_2$haloalkoxy, and phenyl.

The invention includes compounds and salts of Formula 1 and Formula 1A in which $A_1$ is phenyl, naphthyl, pyridin-2-yl, pyridin-3-yl, pyridin-4-yl, pyrimidin-2-yl, pyrimidinyl-4-yl, pyrimidin-5-yl, thien-2-yl, thien-3-yl, thiazol-4-yl, pyrrol-1-yl, pyrrol-2-yl, pyyrol-3-yl, furan-2-yl, furan-3-yl, pyrazol-1-yl, pyrazol-2-yl pyrazol-4-yl, pyrazol-5-yl, imdiazol-1-yl, imdiazol-2-yl, imdiazol-4-yl, imdiazol-5-yl, thiazol-2-yl, thiazol-3-yl, thiazol-5-yl, 1,2,3-triazol-4-yl, 1,2,3-thiadiazol-4-yl, 1,2,3-thiadiazol-5-yl, oxazol-2-yl, isoxazol-4-yl, isoxazol-5-yl, isoxazol-3-yl, isoxazol-4-yl, isoxazol-5-yl, benzofuran-2-yl, benzofuran-3-yl, benzopyran-2-yl, benzopyran-3-yl, benzopyran-4-yl, benzo[d]oxazol-2-yl benzo[d]thiazol-2-yl, benzo[b]thiophen-2-yl, 4H-chromen-2-yl, benzo[c][1,2,5]oxadiazolyl, 2,3-dihydrobenzo[b][1,4]dioxin-2-yl, pyrazolo[1,5-a]pyrimidin-6-yl, dihydrobenzo[b][1,4]dioxin-3-yl, indol-2-yl, pyrazolo[1,5-a]pyrimidin-5-yl, 1H-thieno[2,3-c]pyrazol-4-yl, or 1H-thieno[2,3-c]pyrazol-5-yl.

Each of which $A_1$ is substituted with 0 to 5 substituents independently chosen from
- (a) halogen, hydroxy, cyano, amino, nitro, oxo, —COOH, —CONH$_2$, —SO$_2$NH$_2$, —SH, $C_1$-$C_2$haloalkyl, and $C_1$-$C_2$haloalkoxy, and
- (b) $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl, and
- (c) -GR$_a$ where G is chosen from —(CH$_2$)$_n$—, $C_2$-$C_4$alkenyl, $C_2$-$C_4$alkynyl, —(CH$_2$)$_n$O(CH$_2$)$_m$—, and —(CH$_2$)$_n$N(CH$_2$)$_m$—, where n and m are independently 0, 1, 2, 3, or 4; and R$_a$ is chosen from $C_3$-$C_8$cycloalkyl, $C_2$-$C_7$monocyclic heterocycloalkyl, $C_5$-$C_{10}$bicyclicheterocycloalkyl, indanyl, tetrahydronapthyl, aryl, and heteroaryl. Each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_1$-$C_2$haloalkyl, $C_1$-$C_2$haloalkoxy, and phenyl.

In some embodiments (a), (b), and (c) are defined as follows:
- (a) is halogen, hydroxy, cyano, amino, nitro, oxo, $C_1$-$C_2$haloalkyl, and $C_1$-$C_2$haloalkoxy,
- (b) is $C_1$-$C_6$alkyl, $C_1$-$C_6$alkoxy, $C_1$-$C_4$alkoxy($C_1$-$C_4$alkyl), amino($C_1$-$C_4$)alkyl, mono- and di-($C_1$-$C_4$alkyl)amino, mono- and di-($C_1$-$C_4$alkyl)amino$C_1$-$C_4$alkyl; and
- (c) is -GR$_a$ where G is from —(CH$_2$)$_n$—, —(CH$_2$)$_n$O(CH$_2$)$_m$—, and —(CH$_2$)$_n$N(CH$_2$)$_m$—, and R$_a$ is $C_3$-$C_8$cycloalkyl, 5 or 6-membered heterocycloalkyl containing 1 or 2 heteroatoms independently chosen from O, S, and N, 5- or 6-membered heteroaryl containing 1, 2, or 3 heteroatoms independently chosen from O, S, and N, indanyl, and phenyl. Each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_2$alkyl)amino, and $C_1$-$C_2$haloalkyl, $C_1$-$C_2$haloalkoxy.

Alternatively, $A_1$ in Formula 1 or Formula 1A is substituted with 0 to 3 substituents independently chosen from halogen, hydroxy, cyano, amino, nitro, oxo, $C_1$-$C_2$haloalkyl, $C_1$-$C_2$haloalkoxy, $C_1$-$C_6$alkyl, $C_1$-$C_6$alkoxy, $C_1$-$C_4$alkoxy($C_1$-$C_4$alkyl), amino($C_1$-$C_4$)alkyl, mono- and di-($C_1$-$C_4$alkyl)amino, and mono- and di-($C_1$-$C_4$alkyl)amino$C_1$-$C_4$alkyl.

The invention includes compounds and salts of Formula 1 and Formula 1A in which $A_1$ is $C_1$-$C_6$ alkyl, $C_3$-$C_7$cycloalkyl, or $C_2$-$C_7$monocyclic heterocycloalkyl, each of which is substituted with 0 to 5 substituents independently chosen from (a), (b), and (c).

Wherein:
- (a) is halogen, hydroxy, cyano, amino, nitro, oxo, —COOH, —CONH$_2$, —SO$_2$NH$_2$, —SH, $C_1$-$C_2$haloalkyl, and $C_1$-$C_2$haloalkoxy,
- (b) is $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl, and
- (c) is -GR$_a$ where G is chosen from —(CH$_2$)$_n$—, $C_2$-$C_4$alkenyl, $C_2$-$C_4$alkynyl, —(CH$_2$)$_n$O(CH$_2$)$_m$—, and —(CH$_2$)$_n$N(CH$_2$)$_m$—, where n and m are independently 0, 1, 2, 3, or 4; and R$_a$ is chosen from $C_3$-$C_8$cycloalkyl, $C_2$-$C_7$monocyclic heterocycloalkyl, $C_5$-$C_{10}$bicyclicheterocycloalkyl, indanyl, tetrahydronapthyl, aryl, and heteroaryl. Each of which (b) and (c) is substituted with 0 to 5 substituents independently chosen from halogen, hydroxy, amino, $C_1$-$C_4$alkyl, $C_1$-$C_4$alkoxy, mono- and di-($C_1$-$C_4$alkyl)amino, $C_2$-$C_4$alkanoyl, $C_1$-$C_4$alkoxycarbonyl, $C_1$-$C_2$haloalkyl, $C_1$-$C_2$haloalkoxy, and phenyl.

In certain embodiments the invention provides compounds and salts of Formula 1 and Formula 1A in which:

$A_1$ is $C_1$-$C_6$ alkyl, $C_3$-$C_7$cycloalkyl, pyrrolidinyl, piperidinyl, piperazinyl, or morpholinyl; each of which is substituted with 0 to 3 substituents independently chosen from (a), (b), and (c).

Wherein:
- (a) is halogen, hydroxy, cyano, amino, nitro, oxo, —COOH, —CONH$_2$, —SO$_2$NH$_2$, —SH, $C_1$-$C_2$haloalkyl, and $C_1$-$C_2$haloalkoxy,
- (b) is $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl, and
- (c) is -GR$_a$ where G is chosen from —(CH$_2$)$_n$—, $C_2$-$C_4$alkenyl, $C_2$-$C_4$alkynyl, —(CH$_2$)$_n$O(CH$_2$)$_m$—, and —(CH$_2$)$_n$N(CH$_2$)$_m$—, where n and m are independently 0, 1, 2, 3, or 4; and R$_a$ is chosen from $C_3$-$C_8$cycloalkyl, and phenyl.

The invention further pertains to compounds and salts of Formula 2 to Formula 16.
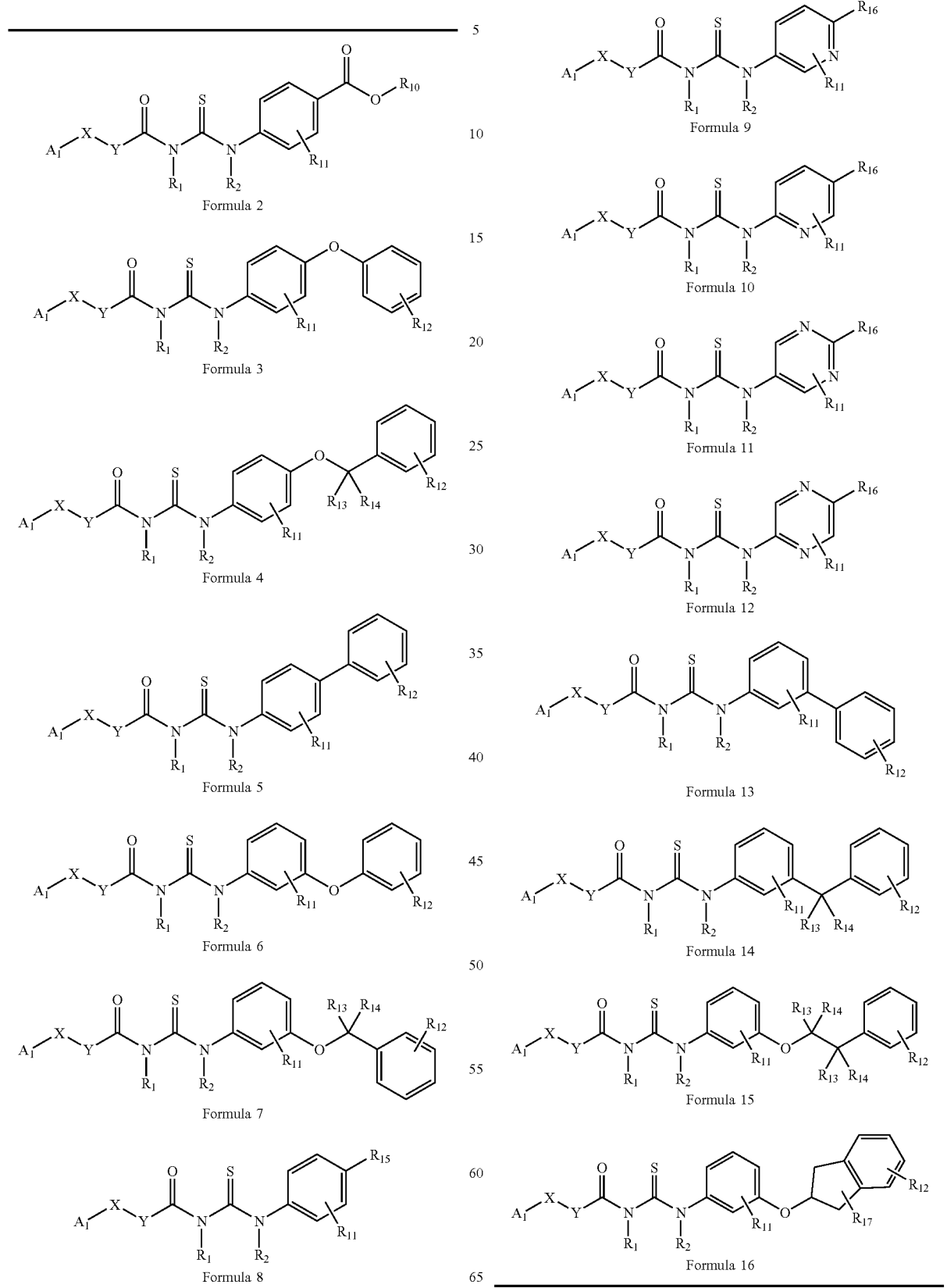

The variables $A_1$, X, and Y in Formula 2-16 carry the definitions set forth in Formula I, Formula IA, or Formula 1.

$R_1$ and $R_2$ are independently hydrogen or methyl.

$R_{10}$ is $C_1$-$C_6$alkyl.

$R_{11}$ and $R_{12}$ each represent 0 to 3 substituents independently chosen from halogen, hydroxy, cyano, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

$R_{13}$ and $R_{14}$ are independently chosen at each occurrence from hydrogen or methyl.

$R_{15}$ represents $C_4$-$C_6$alkoxy or $C_4$-$C_6$alkyl.

$R_{16}$ is $C_2$-$C_6$alkoxy or $C_2$-$C_6$alkyl.

$R_{17}$ represents 0 to 2 substituents independently chosen from halogen, methyl, and methoxy.

In other embodiments the invention provides compounds and salts of Formulae 2 to 16 in which X is NR (which carries the definition set forth for Formula 1) and Y is —CH$_2$— or —CH$_2$CH$_2$—. In still other embodiments the invention provides compounds and salts of Formulae 2 to 16 in which X is O and Y is —CH$_2$— or —CH$_2$CH$_2$—; or in which X and Y are absent.

The $A_1$ Variable

The invention provides compounds and salts of Formulae 1 to 16 in which $A_1$ is pyrazinyl, pyridyl, or quinoxolinyl, each of which is substituted with 0 to 3 substituents independently chosen from halogen, hydroxy, cyano, amino, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

The invention provides compounds and pharmaceutically acceptable thereof of Formula 17 to 29

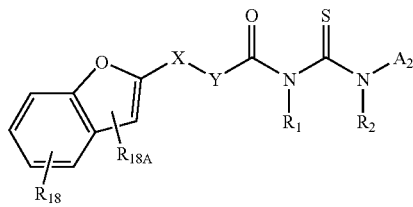

Formula 17

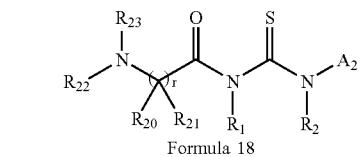

Formula 18

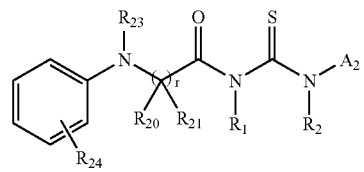

Formula 19

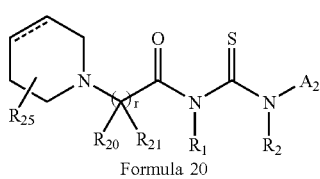

Formula 20

-continued

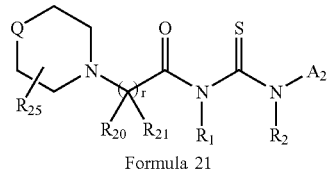

Formula 21

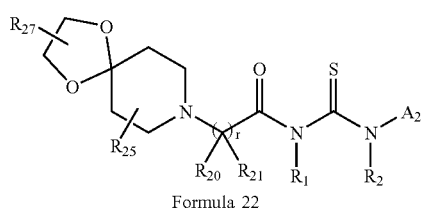

Formula 22

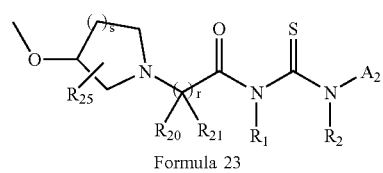

Formula 23

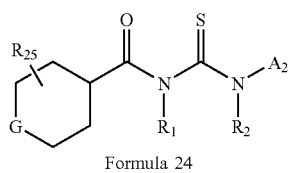

Formula 24

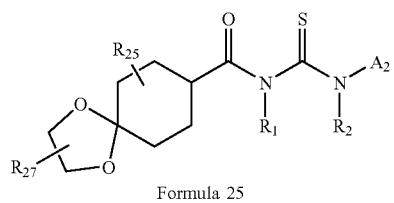

Formula 25

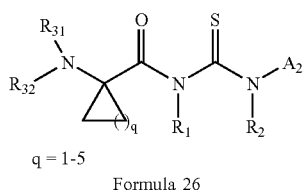

q = 1-5

Formula 26

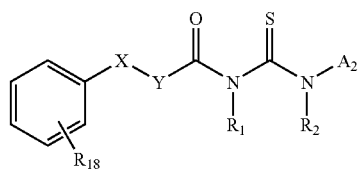

Formula 27

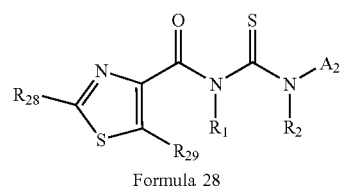

Formula 28

-continued

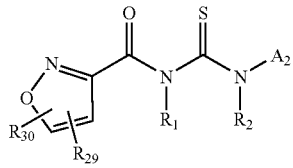

Formula 29

The variables $A_2$, $R_1$, and $R_2$ in Formulae 17-29 carry the definition set forth for compounds of Formula I and Formula IA. In certain embodiments the variables $A_1$, $R_1$, and $R_2$ carries the definitions set forth for compounds and salts of Formula 1. In certain embodiments these variables carry the definitions set forth below for compounds of Formulae 17-29.

Thus in Formulae 17-29 the variables r, s, Q, X, Y, $R_1$, $R_2$, $R_{18A}$, $R_{18}$, $R_{20}$, $R_{21}$, $R_{22}$, $R_{23}$, $R_{24}$, $R_{25}$, $R_{27}$, $R_{28}$, $R_{29}$, and $R_{30}$ are defined as follows q is an integer from 1 to 5;

r is 1, 2, or 3.

s is 1, 2, or 3;

X and Y are absent; and $R_1$ and $R_2$ are independently hydrogen or methyl, in other embodiments X is oxygen and Y is —CH$_2$—.

$R_{18A}$ is hydrogen, halogen, hydroxy, cyano, amino, $C_1$-$C_4$alkyl, $C_1$-$C_4$alkoxy, mono- and di-($C_1$-$C_4$alkyl)amino, $C_1$-$C_2$haloalkyl, or $C_1$-$C_2$haloalkoxy.

$R_{18}$ represents 0 to 3 substituents independently chosen from halogen, hydroxy, cyano, amino, nitro, $C_1$-$C_4$alkyl, $C_1$-$C_4$alkoxy, mono- and di-($C_1$-$C_4$alkyl)amino, $C_1$-$C_2$haloalkyl, $C_1$-$C_2$haloalkoxy, and phenyl.

$R_{20}$ and $R_2$, are independently selected from hydrogen and $C_1$-$C_4$alkyl; or $R_{20}$ and $R_{21}$ are joined to form a $C_3$-$C_7$cycloalkyl group.

$R_{22}$ and $R_{23}$ are independently chosen $C_1$-$C_6$ alkyl groups; each of which is substituted with 0 to 5 substituents independently chosen from halogen, hydroxy, cyano, amino, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

$R_{24}$ represents 0 to 3 substituents independently chosen from halogen, hydroxy, cyano, amino, nitro, —COOH, —CONH$_2$, —SO$_2$NH$_2$, —SH, $C_1$-$C_2$haloalkyl, $C_1$-$C_2$haloalkoxy, $C_1$-$C_6$alkyl, $C_2$-$C_6$alkenyl, $C_2$-$C_6$alkynyl, $C_1$-$C_6$alkoxy, $C_2$-$C_6$alkenyloxy, $C_1$-$C_4$alkoxy($C_1$-$C_4$alkyl), amino($C_1$-$C_6$)alkyl, mono- and di-($C_1$-$C_6$alkyl)amino, mono- and di-($C_1$-$C_4$alkyl)amino$C_1$-$C_4$alkyl, $C_2$-$C_6$alkanoyl, $C_2$-$C_8$alkanoyloxy, $C_1$-$C_8$alkoxycarbonyl, -mono- and di-($C_1$-$C_6$alkyl)carboxamide, ($C_3$-$C_7$cycloalkyl)carboxamide, mono- and di-($C_1$-$C_6$alkyl)sulfonamide, $C_1$-$C_6$alkylthio, aryl($C_0$-$C_4$alkyl)thio, $C_1$-$C_6$alkylsulfinyl, and $C_1$-$C_6$alkylsulfonyl. In certain embodiments $R_{24}$ represents 0 to 3 substituents independently chosen from halogen, hydroxy, cyano, amino, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

$R_{25}$ and $R_{27}$ each represent 0 to 3, or in some embodiments 0 to 2 substituents independently chosen from halogen, hydroxy, cyano, amino, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy. In certain embodiments the invention includes compounds and salts of Formula 24 and Formula 25 in which $R_{25}$ represents a di-($C_1$-$C_6$alkyl)amino substituent and 0 to 2 additional substituents independently chosen from halogen, hydroxy, cyano, amino, $C_1$-$C_4$alkyl, $C_1$-$C_4$alkoxy, mono- and di-($C_1$-$C_6$alkyl)amino, $C_1$-$C_2$haloalkyl, and $C_1$-$C_2$haloalkoxy.

$R_{28}$ is phenyl or pyridyl, each of which is substituted with 0 to 3 substituents independently chosen from halogen, hydroxy, cyano, amino, nitro, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

$R_{29}$ is hydrogen, methyl or ethyl.

$R_{30}$ is a 5-membered heteroaryl substituent containing 1 nitrogen atom and 0 or 1 additional heteroatoms chosen from N, O, or S; substituted with 0 to 2 substituents independently chosen from halogen, $C_1$-$C_2$alkyl, and $C_1$-$C_2$alkoxy.

$R_{31}$ and $R_{32}$ are independently chosen from $C_1$-$C_6$alkyl and phenyl; each of which is substituted with 0 to 3 substituents independently chosen from halogen, hydroxy, cyano, amino, nitro, $C_1$-$C_4$alkyl, $C_1$-$C_4$alkoxy, mono- and di-($C_1$-$C_4$alkyl)amino, $C_1$-$C_2$haloalkyl, and $C_1$-$C_2$haloalkoxy.

G is O, S, SO$_2$, or NR$_{26}$; where $R_{26}$ is hydrogen or $R_{26}$ is $C_1$-$C_6$alkyl, phenyl, pyridyl, or pyrimidinyl, each of which is substituted with 0 to 3 substituents independently chosen from halogen, hydroxy, cyano, amino, $C_1$-$C_4$alkyl, $C_1$-$C_4$alkoxy, mono- and di-($C_1$-$C_6$alkyl)amino, $C_1$-$C_2$haloalkyl, and $C_1$-$C_2$haloalkoxy.

Q is O, S, or NR$_{26}$; where $R_{26}$ is hydrogen or $R_{26}$ is $C_1$-$C_6$alkyl, phenyl, pyridyl, or pyrimidinyl, each of which is substituted with 0 to 3 substituents independently chosen from halogen, hydroxy, cyano, amino, $C_1$-$C_4$alkyl, $C_1$-$C_4$alkoxy, mono- and di-($C_1$-$C_6$alkyl)amino, $C_1$-$C_2$haloalkyl, and $C_1$-$C_2$haloalkoxy.

The invention includes compounds and salts of Formula 17-29 in which $A_2$ carries the definitions set forth for compounds and salts of any of the above formula, e.g. the definitions of $A_2$ set forth for Formulae I, IA, 1, and which occur in Formulae 2-16. The variable $A_2$ does not appear in Formulae 2-16 as each of these structures has a defined group in place of $A_2$. For example, Formula 3 has a 4-phenoxy-phenyl group at the $A_2$ position. Thus the invention includes compounds and salts of Formula 17-29 in which $A_2$ is any of the groups appearing at the $A_2$ position in Formulae 2-16.

The invention include compounds and salts of Formula I, IA, and 1-16 in which $A_1$ is 5-membered heteroaryl group selected from furan-2-yl, furan-3-yl, isoxazol-3-yl, isoxazol-4-yl, thiophen-2-yl, thiophen-3-yl, pyrrol-2-yl, pyrrol-3-yl, and pyrazolyl; each of which is substituted with 0 to 3 substituents independently chosen from halogen, hydroxy, cyano, amino, nitro, $C_1$-$C_4$alkyl, $C_2$-$C_4$alkenyl, $C_1$-$C_4$alkoxy, mono- and di-($C_1$-$C_4$alkyl)amino, $C_1$-$C_2$haloalkyl, $C_1$-$C_2$haloalkoxy, and phenyl. In such compounds X may be oxygen and Y may be —CH$_2$—, or X and Y may be absent.

The invention include compounds and salts of Formula I, IA, and 1-16 in which $A_1$ is 5-membered heteroaryl group selected from furan-2-yl, furan-3-yl, isoxazol-3-yl, isoxazol-4-yl, thiophen-2-yl, thiophen-3-yl, pyrrol-2-yl, pyrrol-3-yl, and pyrazolyl; each of which is substituted with 0 to 2 substituents independently chosen from halogen, $C_1$-$C_4$alkyl, $C_1$-$C_4$alkoxy, $C_1$-$C_2$haloalkyl, and $C_1$-$C_2$haloalkoxy, and phenyl and is substituted with one 5-membered heteroaryl substituent containing one nitrogen atom and 0 or 1 additional heteroatoms chosen from N, O, and S, which 5-membered heteroaryl substituent is substituted with 0 to 2 substituents independently chosen from halogen, $C_1$-$C_2$alkyl, and $C_1$-$C_2$alkoxy. In such compounds X may be oxygen and Y may be —$CH_2$—, or X and Y may be absent.

The invention also includes compounds and salts of Formula I, IA, and 1-16 in which $A_1$ is pyridin-2-yl or pyridin-3-yl, each of which is substituted with 0 to 3 substituents independently chosen from halogen, hydroxy, cyano, amino, nitro, $C_1$-$C_4$alkyl, $C_1$-$C_4$alkoxy, mono- and di-($C_1$-$C_4$alkyl) amino, $C_1$-$C_2$haloalkyl, $C_1$-$C_2$haloalkoxy, and phenyl. In such compounds X may be oxygen and Y may be —$CH_2$—, or X and Y may be absent.

Additionally the following provisos apply to certain preferred compounds of Formula I, IA, II, and Formula 1 and the subformulae thereof when V, W, X, and Y are absent, Z is carbonyl, and $R_1$ and $R_2$ are both hydrogen:

When $A_1$ is 4-chlorophenyl, $A_2$ is not 4-phenyloxyphenyl;
When $A_1$ is 3,4,5-trimethoxyphenyl, $A_2$ is not 4-chlorophenyl;
When $A_1$ is 3-methylphenyl; $A_2$ is not 4-phenyloxyphenyl;
When $A_1$ is 4-methoxyphenyl; $A_2$ is not 4-phenyloxyphenyl;
When $A_1$ is 2,4-dichlorophenyl; $A_2$ is not 4-phenyloxyphenyl;
When $A_1$ is 2-nitrophenyl; $A_2$ is not 4-phenyloxyphenyl;
When $A_1$ is cyclopropyl; $A_2$ is not 4-phenyloxyphenyl;
When $A_1$ is 4-tert-butyl-phenyl; $A_2$ is not 4-phenyloxyphenyl;
When $A_1$ is phenyl or phenyl substituted with 0 to 3 substituents independently chosen from halogen, nitro, $C_1$-$C_4$alkyl, and $C_1$-$C_4$alkoxy; $A_2$ is not 4-(4-chlorophenyloxy)phenyl;
When $A_1$ is benzofuran-2-yl or benzofuran-2-yl substituted with methyl; $A_2$ is not 4-(4-chlorophenyloxy) phenyl;
When $A_1$ is naphthyl or thienyl; $A_2$ is not 4-(4-chlorophenyloxy)phenyl;
When $A_1$ is phenyl; $A_2$ is not 4-(3,5-di-trifluormethyl-phenyloxy)phenyl;
When $A_1$ is 1,5-dimethyl-2-chloro-pyrrol-3-yl, $A_2$ is not 4-(4-ntirophenyloxy)-(3,5-dichlorophenyl)-; and
When $A_1$ is 2-halo-phenyl, 2,6-di-halo-phenyl, or 2-methylphenyl; $A_2$ is not 4-phenyloxyphenyl substituted with 0 to 5 substituents independently chosen from halogen, $C_1$-$C_4$alkyl, methoxy, trifluoromethyl, trifluoromethoxy, and trifluoromethylthio.

The Invention further includes compounds of Formula 30

Formula 30

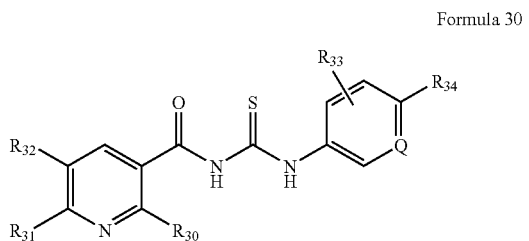

and the pharmaceutically acceptable salts thereof.
Wherein:
$R_{30}$, $R_{31}$, and $R_{32}$ are all hydrogen; or
$R_{30}$ is hydroxyl, halogen, cyano, $C_1$-$C_4$alkyl, $C_1$-$C_4$alkoxy, mono- or di-($C_1$-$C_2$alkyl)amino$C_0$-$C_2$alkyl, or 5- or 6-membered heterocycloalkyl, and $R_3$, and $R_{32}$ are both hydrogen; or $R_{31}$ is hydroxyl, halogen, cyano, $C_1$-$C_4$alkyl, $C_1$-$C_4$alkoxy, mono- or di-($C_1$-$C_2$alkyl)amino$C_0$-$C_2$alkyl, mono- or di-($C_1$-$C_2$alkyl)amino$C_1$-$C_2$alkoxy, hydroxy($C_1$-$C_4$alkyl), $C_1$-$C_2$alkanoyloxy($C_0$-$C_2$alkyl), $C_1$-$C_2$alkyloxoacetylamino, $H_2N$—C(O)—C(O)—HN—, mono- or di-$C_1$-$C_2$alkylcarboxamide, and $R_{30}$ and $R_{32}$ are both hydrogen; or $R_{31}$ is 5- to -7-membered heterocycloalkyl($C_0$-$C_2$alkyl), 5- to -7 membered heterocycloalkyl($C_1$-$C_2$alkoxy), (5-to-7-membered heterocycloalkyl)-C(O)—, each of which heterocycloalkyl is substituted with 0 or 1 methyl or ethyl substituents; and $R_{30}$ and $R_{32}$ are both hydrogen; or $R_{32}$ is hydroxyl, halogen, cyano, $C_1$-$C_4$alkyl, $C_1$-$C_4$alkoxy, mono- or di-($C_1$-$C_2$alkyl)amino$C_0$-$C_2$alkyl, 5- or -6-membered heterocycloalkyl, or 5- or 6-membered heteroaryl, and $R_{30}$ and $R_3$, are both hydrogen;

Q is N or C—$R_{35}$.

$R_{33}$ is 0, 1, or 2 methyl substituents.

$R_{34}$ is hydrogen, $C_4$-$C_{10}$alkyl, $C_4$-$C_{10}$alkoxy, mono- or di-($C_1$-$C_6$alkyl)amino; or $R_{34}$ is phenyl($C_0$-$C_2$alkoxy), $C_3$-$C_{10}$cycloalkyl($C_0$-$C_2$alkoxy), 5- to 7-membered heterocycloalkyl, each of which is substituted with 0 or 1 trifluoromethyl, trifluoromethoxy, $C_1$-$C_6$alkyl, $C_1$-$C_6$alkoxy, or phenyl;

$R_{35}$ is hydrogen, halogen, cyano, $C_1$-$C_4$alkyl, $C_1$-$C_4$alkoxy, trifluormethyl, or trifluoromethoxy; or $R_{35}$ is phenyl($C_0$-$C_2$alkoxy) or indanyl($C_0$-$C_2$alkoxy); each of which is substituted with 0 or 1 $C_1$-$C_4$alkyl; or $R_{34}$ and $R_{35}$ are joined to form a 5- to 6-membered partially unsaturated ring having 1 or 2 ring oxygen atoms, and substituted with 0 or 1 phenyl.

Wherein $R_{34}$ is not hydrogen when Q is N or CH.

Compounds of Formula 30 in which at least one of the following conditions are met are included herein:

(a) $R_{30}$, $R_{31}$, and $R_{32}$ are all hydrogen.
(b) $R_{30}$ is fluoro, $C_1$-$C_2$alkyl, or 1-pyrrolidinyl, and $R_{31}$ and $R_{32}$ are both hydrogen.
(c) $R_{31}$ is hydroxyl, halogen, cyano, $C_1$-$C_4$alkyl, $C_1$-$C_4$alkoxy, mono- or di-($C_1$-$C_2$alkyl)amino$C_0$-$C_2$alkyl, mono- or di-($C_1$-$C_2$alkyl)amino$C_1$-$C_2$alkoxy, hydroxy($C_1$-$C_4$alkyl), $C_1$-$C_2$alkanoyloxy($C_0$-$C_2$alkyl), $C_1$-$C_2$alkyloxoacetylamino, aminooxalamido, mono- or di-$C_1$-$C_2$alkylcarboxamide, and $R_{30}$ and $R_{32}$ are both hydrogen.
(d) $R_{31}$ is 5- to -7-membered heterocycloalkyl($C_0$-$C_2$alkyl), heterocycloalkyl($C_1$-$C_2$alkoxy), (heterocycloalkyl)-C(O)—, wherein the heterocycloalkyl is a morpholinyl, thiomorpholinyl, piperazinyl, or piperidinyl group, each of which is substituted with 0 or 1 methyl or ethyl substituents; and $R_{30}$ and $R_{32}$ are both hydrogen.
(e) $R_{32}$ is hydroxyl, bromo, $C_1$-$C_4$alkyl, furanyl, thienyl, pyridinyl, or pyrimidinyl, and $R_{30}$ and $R_{31}$ are both hydrogen.
(f) Q is N.
(g) Q is C—$R_{35}$.
(h) $R_{33}$ is 0 substituents, $R_{34}$ is $C_4$-$C_{10}$alkyl or $C_4$-$C_{10}$alkoxy; and $R_{35}$ is hydrogen, halogen, methyl, methoxy, or trifluoromethyl.
(i) $R_{33}$ is 0 substituents, $R_{34}$ is hydrogen, and $R_{35}$ is phenyl($C_0$-$C_2$alkoxy) or indanyloxy.

The Invention includes compounds and pharmaceutically acceptable salts of Formula 31-34
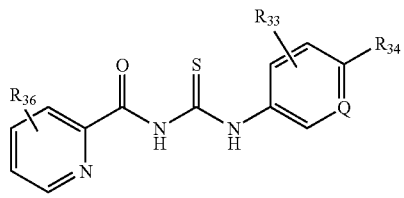
Formula 31
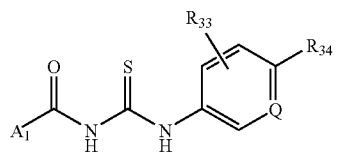
Formula 32
Within Formula 32, A₁ is a 6-membered heteroaryl or heterocyclic group of the formula:
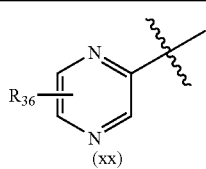
(xx)
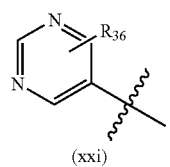
(xxi)
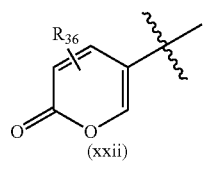
(xxii)
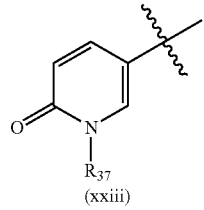
(xxiii)
Or A₁ is a 6,6-heteroaryl, 5,6-heteroaryl, 5,6-heteroaryl or 5,5-heteroaryl group of the formula:
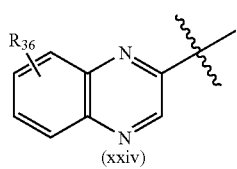
(xxiv)
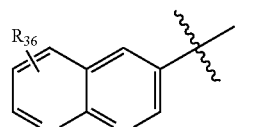
(xxv)
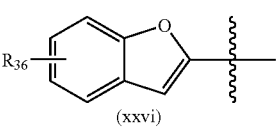
(xxvi)
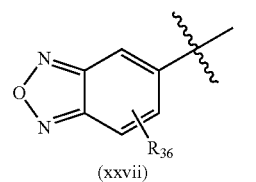
(xxvii)
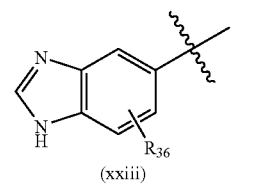
(xxiii)
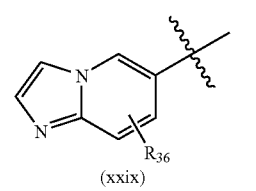
(xxix)
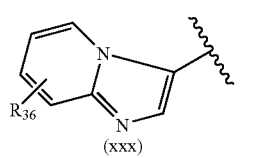
(xxx)
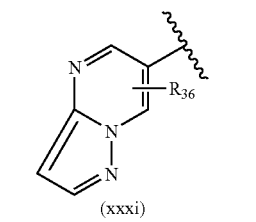
(xxxi)
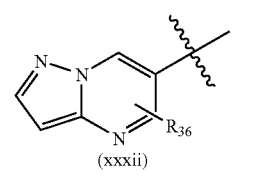
(xxxii)
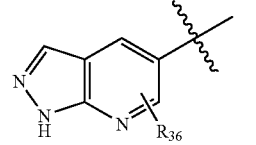

(xxxiii)

or

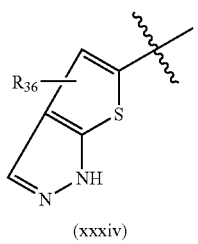

(xxxiv)

In structures xxv to xxxiv, above, the substituent $R_{36}$ is 0 or 1 or more substituents, which are attached to either of the two shown rings.

Or $A_1$ is a 5 membered heteroaryl group of the formula

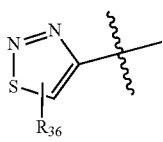
(xxxv)

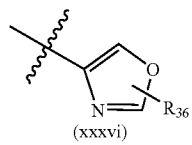
(xxxvi)

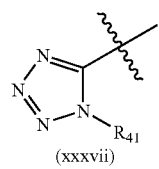
(xxxvii)

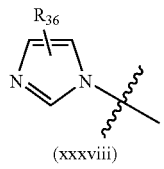
(xxxviii)

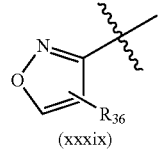
(xxxix)

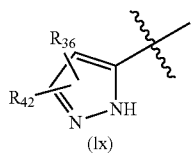
(lx)

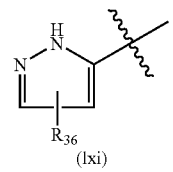
(lxi)

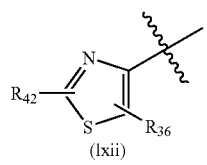
(lxii)

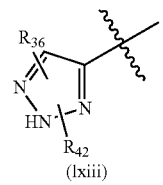
(lxiii)

Also included herein are compounds and pharmaceutically acceptable salts of Formula 33

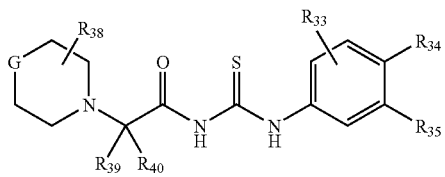

Formula 33

Wherein, within Formula 31-33:
G is O, NH, or $CH_2$.
Q is N or C—$R_{35}$.
$R_{33}$ is 0, 1, or 2 methyl substituents.
$R_{34}$ is hydrogen, $C_4$-$C_{10}$alkyl, $C_4$-$C_{10}$alkoxy, mono- or di-($C_1$-$C_6$alkyl)amino; or
$R_{34}$ is phenyl(CO—$C_2$alkoxy), $C_3$-$C_{10}$cycloalkyl($C_0$-$C_2$alkoxy), 5- to 7-membered heterocycloalkyl, each of which is substituted with 0 or 1 trifluoromethyl, trifluoromethoxy, $C_1$-$C_6$alkyl, $C_1$-$C_6$alkoxy, or phenyl;
$R_{35}$ is hydrogen, halogen, cyano, $C_1$-$C_4$alkyl, $C_1$-$C_4$alkoxy, trifluoromethyl, or trifluoromethoxy; or
$R_{35}$ is phenyl($C_0$-$C_2$alkoxy) or indanyl($C_0$-$C_2$alkoxy); each of which is substituted with 0 or 1 $C_1$-$C_4$alkyl.
Wherein $R_{34}$ is not hydrogen when Q is N or CH.
$R_{36}$ is 0 or 1 or more substituents independently chosen from hydroxyl, halogen, cyano, $C_1$-$C_4$alkyl, $C_1$-$C_4$alkoxy, mono- and di-($C_1$-$C_2$alkyl)amino$C_0$-$C_2$alkyl, trifluormethyl, and trifluoromethoxy.
$R_{37}$ is $C_1$-$C_4$alkyl, which is substituted with 0 or 1 hydroxyl, —C(O)OH, or —C(O)$NH_2$.
$R_{38}$ is 0 or 1 or more methyl substituents, though it is preferred that $R_{40}$ is 0 substituents.
$R_{39}$ and $R_{40}$ are independently hydrogen or methyl, though it is preferred that both $R_{39}$ and $R_{40}$ are hydrogen.
$R_{41}$ is hydrogen, $C_1$-$C_6$alkyl, $C_3$-$C_7$cycloalkyl($C_0$-$C_2$alkyl), or benzyl.

$R_{42}$ is 0 or 1 pyridyl or phenyl substituents, each of which is substituted with 0, 1, or 2 substituents independently chosen from halogen, hydroxy, methyl, and methoxy.

Compounds of Formula 31-33 in which at least one of the following conditions are met are included herein:
(a) Q is N.
(b) Q is C—$R_{35}$.
(c) $R_{33}$ is 0 substituents, $R_{34}$ is $C_4$-$C_{10}$alkyl or $C_4$-$C_{10}$alkoxy; and $R_{35}$ is hydrogen, halogen, methyl, methoxy, or trifluoromethyl.
(d) $R_{33}$ is 0 substituents, $R_{34}$ is hydrogen, and $R_{35}$ is phenyl($C_0$-$C_2$alkoxy).
(e) $R_{36}$ is 0 substituents.
(f) $R_{37}$ is methyl.

Without wishing to be bound to any particular theory, it is believed that the anti-HCV activity of compounds of Formula I is due to their inhibit replication of the HCV replicon. Preferred compounds of Formula I exhibit an $EC_{50}$ of about 10 micromolar or less, or more preferably an $EC_{50}$ of about 1 micromolar or less; or an $EC_{50}$ of about 500 nanomolar or less in an HCV replicon assay, such as the assay of Example 7.

Preferred compounds of Formula I will have certain pharmacological properties. Such properties include, but are not limited to oral bioavailability, low toxicity, low serum protein binding and desirable in vitro and in vivo half-lives.

The invention includes packaged pharmaceutical formulations. Such packaged formulations include a pharmaceutical composition containing one or more compounds or salts of Formula I in a container and instructions for using the composition to treat a patient suffering from Hepatitis C infection (HCV infection).

PHARMACEUTICAL PREPARATIONS

Compounds and salts of Formula 1 can be administered as the neat chemical, but are preferably administered as a pharmaceutical composition or formulation. Accordingly, the invention provides pharmaceutical formulations comprising a compound or pharmaceutically acceptable salt of Formula 1, together with one or more pharmaceutically acceptable carrier, excipients, adjuvant, diluent, or other ingredient.

Compounds of general Formula 1 may be administered orally, topically, parenterally, by inhalation or spray, sublingually, transdermally, via buccal administration, rectally, as an ophthalmic solution, or by other means, in dosage unit formulations containing conventional non-toxic pharmaceutically acceptable carriers, excipients, adjuvants, and vehicles.

In addition to the subject compound, the compositions of the invention may contain a pharmaceutically acceptable carrier, one or more compatible solid or liquid filler diluents or encapsulating substances, which are suitable for administration to an animal. Carriers must be of sufficiently high purity and sufficiently low toxicity to render them suitable for administration to the animal being treated. The carrier can be inert or it can possess pharmaceutical benefits of its own. The amount of carrier employed in conjunction with the compound is sufficient to provide a practical quantity of material for administration per unit dose of the compound.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, and corn oil; polyols such as propylene glycol, glycerine, sorbitol, mannitol, and polyethylene glycol; alginic acid; emulsifiers, such as the TWEENS; bioavailability enhancers, such as lauroyl macroglycerides, including GELUCIRE, wetting agents, such sodium lauryl sulfate; coloring agents; flavoring agents; tableting agents, stabilizers; antioxidants; preservatives; pyrogen-free water; isotonic saline; and phosphate buffer solutions.

In particular, pharmaceutically acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil.

Optional active agents may be included in a pharmaceutical composition, which do not substantially interfere with the activity of the compound of the present invention.

Effective concentrations of one or more of the compounds of the invention including pharmaceutically acceptable salts, esters or other derivatives thereof are mixed with a suitable pharmaceutical carrier, excipients, adjuvant, or vehicle. In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as Tween, or dissolution in aqueous sodium bicarbonate. Derivatives of the compounds, such as salts of the compounds or prodrugs of the compounds may also be used in formulating effective pharmaceutical compositions.

Upon mixing or addition of the compound(s) of Formula I, the resulting mixture may be a solution, suspension, emulsion or the like. The form of the resulting mixture depends upon a number of factors, including the intended mode of administration and the solubility of the compound in the chosen carrier or vehicle. The effective concentration sufficient for ameliorating the symptoms of the disease, disorder or condition treated and may be empirically determined.

The pharmaceutical compositions containing compounds of general Formula I may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations.

Oral formulations contain between 0.1 and 99% of a compound of the invention and usually at least about 5% (weight %) of a compound of the present invention. Some embodiments contain from about 25% to about 50% or from 5% to 75% of a compound of invention.

Liquids Formulations

Compounds of the invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

Orally administered compositions also include liquid solutions, emulsions, suspensions, powders, granules, elixirs, tinctures, syrups, and the like. The pharmaceutically acceptable carriers suitable for preparation of such compositions are well known in the art. Oral formulations may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such formulations may also contain a demulcent.

Suspensions

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Emulsions

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible Powders

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets and Capsules

Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Injectable and Parenteral Formulations

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid are useful in the preparation of injectables.

Compounds of Formula I may be administered parenterally in a sterile medium. Parenteral administration includes subcutaneous injections, intravenous, intramuscular, intrathecal injection or infusion techniques. The drug, depending on the vehicle and concentration used, can either be suspended or dissolved in the vehicle. Advantageously, adjuvants such as local anesthetics, preservatives and buffering agents can be dissolved in the vehicle. In compositions for parenteral administration the carrier comprises at least about 90% by weight of the total composition.

Suppositories

Compounds of Formula I may also be administered in the form of suppositories for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Topical Formulations

Compounds of the invention may be formulated for local or topical application, such as for topical application to the skin and mucous membranes, such as in the eye, in the form of gels, creams, and lotions and for application to the eye or for intracisternal or intraspinal application. Topical compositions of the present invention may be in any form including, for example, solutions, creams, ointments, gels, lotions, milks, cleansers, moisturizers, sprays, skin patches, and the like.

Such solutions may be formulated as 0.01%-10% isotonic solutions, pH about 5-7, with appropriate salts. Compounds of the invention may also be formulated for transdermal administration as a transdermal patch.

Topical compositions containing the active compound can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Emollients, such as stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl-palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

The compounds of the invention may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other Formulations

Other compositions useful for attaining systemic delivery of the subject compounds include sublingual, buccal and nasal dosage forms. Such compositions typically comprise one or more of soluble filler substances such as sucrose, sorbitol and mannitol, and binders such as acacia, microcrystalline cellulose, carboxymethyl cellulose and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

Additional Components

The compositions of the present invention may also optionally comprise an activity enhancer. The activity enhancer can be chosen from a wide variety of molecules that function in different ways to enhance antimicrobial effects of compounds of the present invention. Particular classes of activity enhancers include skin penetration enhancers and absorbtion enhancers.

Pharmaceutical compositions of the invention may also contain additional active agents can be chosen from a wide variety of molecules, which can function in different ways to enhance the antimicrobial or therapeutic effects of a compound of the present invention. These optional other active agents, when present, are typically employed in the compositions of the invention at a level ranging from about 0.01% to about 15%. Some embodiments contain from about 0.1% to about 10% by weight of the composition. Other embodiments contain from about 0.5% to about 5% by weight of the composition.

Packaged Formulations

The invention includes packaged pharmaceutical formulations. Such packaged formulations include a pharmaceutical composition containing one or more compounds or salts of Formula I in a container and instructions for using the composition to treat an animal (typically a human patient) suffering from a microorganism infection) or prevent a microorganism infection in an animal.

In all of the foregoing the compounds of the invention can be administered alone or as mixtures, and the compositions may further include additional drugs or excipients as appropriate for the indication.

METHODS OF TREATMENT

The invention includes methods of treating viral infections, particularly HCV infections, by administering an effective amount of one or more compounds of Formula I to patient suffering from a viral infection. An effective amount of a compound of Formula I may be an amount sufficient to reduce the symptoms of viral infection. An effective amount of a compound of Formula I may be an amount sufficient to reduce viral replication. Alternatively an effective amount of a compound of Formula I may be an amount sufficient to significantly reduce the amount of virus (viral load) or viral antibodies detectable in a patient's tissues or bodily fluids.

Inhibition of hepatitis C virus replication may be measured by any technique known to the artisan. For example, inhibition may be measured by clinical observation, or laboratory tests such as $EC_{50}$. Hepatitis C virus replication may be measured by an HCV replicon replication assay, such as the assay of Example 7. In another embodiment, inhibition of hepatitis C virus replication may be measured by a decrease in nucleotide or protein production. An effective amount of a compound of Formula I includes any amount that provides a reduction in HCV replication of at least about 10%, at least about 25%, at least about 35%, at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% as compared with HCV replication prior to administration of one or more compounds of the invention.

In an embodiment of the present invention, inhibition of hepatitis C virus replication may be measured by a decrease hepatitis C viral load or viral antibodies of at least about 10%, at least about 25%, at least about 35%, at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% as compared with hepatitis C viral load or viral antibodies prior to administration of one or more compounds of the invention.

Methods of treatment include administering an amount of a compound of Formula I sufficient to reduce or relieve the jaundice, fatigue, dark urine, abdominal pain, loss of appetite, and nausea associated with HCV infection.

The invention also pertains to methods of treating viral infections, other than HCV infections, including Herpes simplex (HSV) infections, Hepatitis B infections, retroviral infections including HIV-AIDS, Cytomegalovirus (CMV) infections, measles, mumps, Lassa fever, Influenza A and B infections, and Picorna virus infections.

Compounds of Formula I are thought to ameliorate the HCV disease process by virtue of their inhibition of the replication of the Hepatitis C virus. The compounds provided herein may be virucidal, in that they actually kill the active virus, in addition to independently inhibiting viral replication. The provided compounds may also function through mechanisms that involve a combination of virucidal activity and inhibition of replication.

Methods of treatment encompassed by the invention include administering to a patient infected with a virus or at risk for viral infection an effective amount of compound of Formula I as the sole active and administering a compound of Formula I together with one or more other active agents, such another antiviral agent, particularly an anti-viral agent effective against HCV infection. The invention includes administering one or more compounds of Formula I together with one or more a protease inhibitor, a polymerase inhibitor, a p7 inhibitor, a viral entry inhibitor, a fusion inhibitor such as as FUZEON (Trimeris), an anti-fibrotic, drug which targets inosine monophosphate dehydrogenase inhibitors (IMPDH)) such as MERIMEPADIB (Vertex Pharmaceuticals Inc.), synthetic thymosin alpha 1, such as or ZADAXIN (SciClone Pharmaceuticals Inc.), therapeutic vaccine, immunomodulator, and helicase inhibitor.

The invention includes administering one or more compounds of Formula I together with compounds effective against HCV, including but not limited to un-pegylated interferon alpha, Peg-interferon, Peg-interferon alpha 2b, Ribavarin, natural interferon, Albuferon, interferon beta-1a, IL-10, interferon gamma-1b, AMANTADINE.

Methods of treatment and disease prevention also include administering an effective amount of compound of Formula I together with an effective amount of one or more antiviral agents that is a nucleoside analogue, including but not limited to Vidarabine, Acyclovir, Gancyclovir, VALCYTE (valganciclovir), Penciclovir, Famciclovir, BVDU, Broavir, FIAC, FIAU, (S)-HPMPA, (S)-HPMPC, Nevirapine, Delavirdine, and nucleoside-analog reverse transcriptase inhibitors such as AZT (Zidovudine), ddI (Didansosine), ddC (Zalcitabine), d4T (Stavudine), 3TC (Lamivudine) to a patient infected with a virus or at risk for viral infection.

Methods of treatment and disease prevention further include administering an effective amount compound of Formula I together with an effective amount one or more antiviral agents that is a non-nucleoside analogue antiviral compound, including but not limited to Amantadine, Rimantadine, Relenza, Tamiflu, Pleconaril, and protease inhibitors such as Saquinavir, Ritonavir, Indinavir, and Nelfinavir to a patient infected with a virus or at risk for viral infection.

Methods of treatment also include inhibiting HCV replication in vivo, in a patient infected with HCV, by administering a sufficient concentration of a compound of Formula I to inhibit HCV replicon replication in vitro. By "sufficient concentration" of a compound administered to the patient is meant the concentration of the compound available in the patient's system to combat the infection. Such a concentration by be ascertained experimentally, for example by assaying blood concentration of the compound, or theoretically, by calculating bioavailability.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

SYNTHESIS OF COMPOUNDS

An illustration of the preparation of compounds of the present invention is given in below in Examples 1 to 6. Those having skill in the art will recognize that the starting materials may be varied and additional steps employed to produce compound encompassed by the present invention.

EXAMPLES

SCHEMES

Scheme I

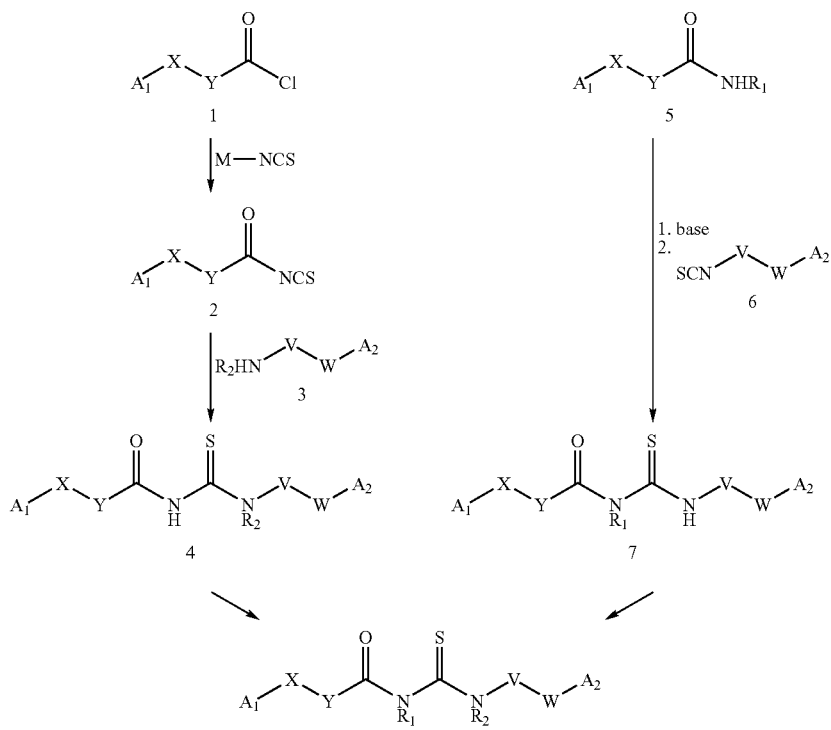

General Formula I, wherein Z is carbonyl

A general method of preparing the compounds of the present invention is shown in Scheme I and further illustrated by the following synthetic examples. As shown, an acid chloride 1 (or bromide) is reacted with a metal or ammonium thiocyanate in an appropriate solvent to provide the corresponding acylisothiocyanate 2. Reaction of 2 with an appropriate primary ($R_2$=H) or secondary amine 3 gives the acylthiourea 4. Further alkylation, when desirable, may be carried out on 4 to provide compounds of general Formula I. In this scheme, the Z group of Formula I is represented by a carbonyl. Alternatively, compounds of general Formula I may be prepared by treatment of a primary ($R_1$=H) or secondary amide 5 with base followed by reaction of the resulting anion with an appropriately substituted isothiocyanate 6 to provide the acylthiourea 7. Further alkylation, when desirable, may be carried out on 7 to provide compounds of general Formula I.

The reaction to form the acid chloride is generally carried out in a solvent. Suitable solvents in this case are inert organic solvents that do not change under the reaction conditions. These preferably include ethers, such as diethyl ether or tetrahydrofuranyl, or tertiary butyl methyl ether; halogenohydrocarbons such as dichloromethane, trichloromethane, tetrachloromethane, 1,2-dichloroethane, trichloroethane, tetrachloroethane, 1,2-dichloroethane or trichloroethylene, hydrocarbons such as benzene, xylene, toluene, hexane, heptane, cyclohexane or mineral oil fractions, nitromethane, or acetonitrile. It is also possible to employ mixtures of these solvents.

Reaction of the acid chloride with ammonium or potassium thiocyanate is typically carried out in a solvent in which the inorganic thiocyanate is moderately soluble. In some cases, water may be added to increase solubility. The percentage of water added may vary from one percent to 90 percent, with 50% (v/v) typically being most preferred.

Other alkali thiocyanates may be employed. For example lithium thiocyanate has increased solubility in tetrahydrofuran and therefore may allow the use of smaller amounts of aqueous components. Cesium, rubidium, strontium, and barium can all be used as counter ions to the thiocyanate, as is well known to one normally skilled in the art.

Example 1

PREPARATION OF 4-[3-(NAPHTHALENE-2-CARBONYL)-THIO-UREIDO]-BENZOIC ACID BUTYL ESTER

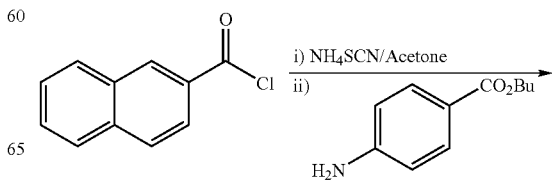

-continued

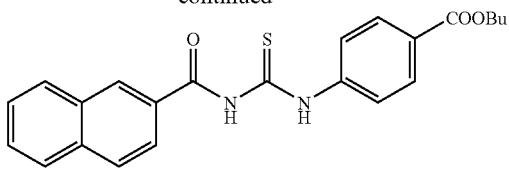

2-Naphthoyl chloride (190 mg, 1 mmol) is added to a solution of ammonium thiocyanate (200 mg, about 3 mmol) in acetone (5 ml) and stirred at room temperature for 1 hour. Butyl 4-aminobenzoate (180 mg, 0.93 mmol) is added to the reaction mixture. Stirring is continued overnight at room temperature. The solid, which forms is filtered and washed with water (2×5 ml) followed by acetone/hexane (3:1) (2×10 ml) and dried. The product (140 mg) is characterized by NMR (Bruker, 300 MHz) and MS. $^1$H NMR (300 MHz, CDCl$_3$) δ (Ppm): 12.9 (s, 1H), 9.27 (1H), 8.43 (s, 1H), 8.11 (d, 2H, J=6.0), 7.99 (d, 2H, J=6.0), 7.91 (m, 4H), 7.65 (m, 2H), 4.34 (t, 2H, J=6.6 Hz), 1.81-1.72 (m, 2H), 1.55-1.43 (m, 2H), 0.99 (t, 3H, J=7.3 Hz). MS (APCI) m/z 407 [M+H]$^+$.

Example 2

Preparation of 4-[3-Methyl-3-(2-phenoxy-acetyl)-thioureido]benzoic acid butyl ester

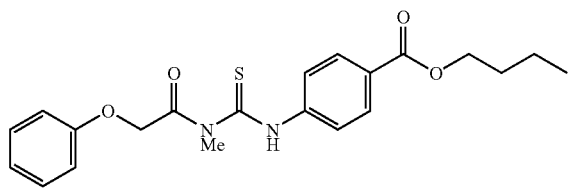

t-BuOK (0.55 mL of 1.0 N solution) in THF is added to a solution of phenoxy-N-methylacetamide (83 mg, 0.5 mmol) in THF (5 mL). After 5 minutes, butyl-4-isothiocyanatobenzoate (118 mg, 0.5 mmol) is added in one portion and the resultant mixture is stirred overnight. The crude mixture is filtered through a silica pad. After purification on silica eluting with 25% EtOAc in hexane, the desired acylthiouraea is obtained as a yellow oil (20 mg). 1H NMR (300 MHz, CDCl$_3$): δ 12.38 (s, 1H), 9.44 (s, 1H), 8.10 (d, 2H, J=8.7 Hz), 7.86 (d, 2H, J=6.9 Hz), 7.42-7.35 (m, 2H), 7.11 (t, 1H, J=7.4 Hz), 7.02-6.98 (m, 2H), 4.64 (s, 2H), 4.34 (t, 2H, J=6.6 Hz), 1.81-1.72 (m, 2H), 1.55-1.43 (m, 2H), 0.99 (t, 3H, J=7.3 Hz). MS (APCI) m/z 387 [M+H]$^+$.

Example 3

Synthesis of 1-(3-Phenoxy-phenyl)-3-(pyridine-3-carbonyl)-thiourea (Compound 1)

Synthetic Scheme:

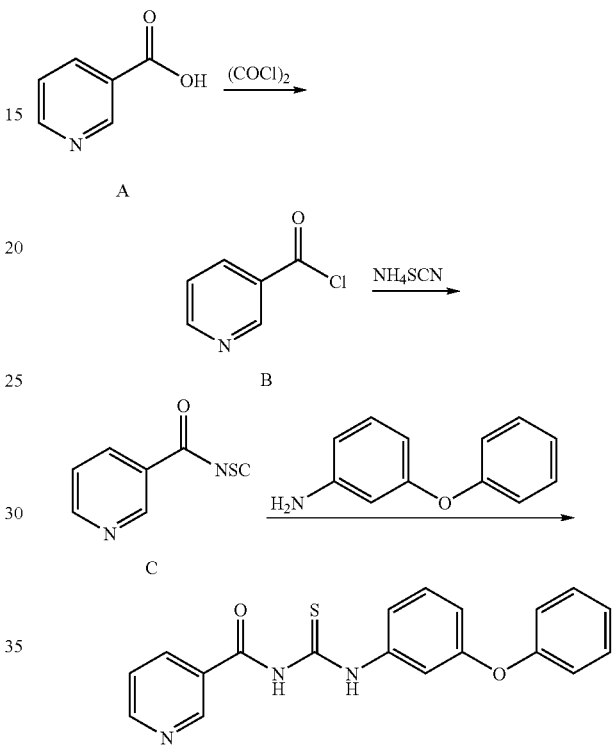

Compound 1

Oxalyl chloride (2.8 mL, 32 mmol) is added to a suspension of nicotinic acid (3.7 g, 30 mmol) in methylene chloride (35 ml) followed by 2 drops of DMF. The reaction is refluxed for 1.5 h and all the volatiles are removed on a rotovap. Alternatively, rather than convert nicotinic acid to the acid chloride, commercially available nicotinyl chloride hydrochloride may be used. The solid is resuspended in methylene chloride/acetone (1:1) (50 ml) and an acetone (10 ml) solution of ammonium thiocyanate (3.5 g, 45 mmol) is added. The reaction is stirred for 1 h at room temperature followed by the addition of 3-phenoxy aniline. The stirring is continued over night at room temperature. The solvent is evaporated and the residue suspended in water (100 ml) and extracted with methylene chloride (3×75 ml). The organic layers are combined, dried over sodium sulphate, filtered to remove any insoluble materials and evaporated. The residue is purified by column chromatography on silica gel and crystallized from methanol to give the desired product. MP: 144.5-145.5° C., 1H NMR (300 MHz, DMSO): δ 12.330 (s, 1H), 11.93 (s, 1H), 9.07 (s, 1H), 8.80 (m, 1H), 8.300 (d, 2H, J=8.1 Hz), 7.955 (s, 1H), 7.81 (d, 1H, J=9.0 Hz), 7.57 (m, 1H), 7.299 (d, 1H, J=9.0 Hz), 4.13 (t, 2H, J=6.2 Hz), 1.77-1.72 (m, 2H,), 1.44-1.34 (m, 4H), 0.92-0.87 (t, 3H, J=7.1). MS (APCI) m/z 350.1 [M+H]$^+$.

Example 4

SYNTHESIS OF 1-(4-PENTYLOXY-3-TRIFLUOROMETHYL-PHE-NYL)-3-(PYRIDINE-3-CARBONYL)-THIOUREA

Alternate Name: 1nicotinoyl-3-(4-(pentyloxy)-3(trifluoromethyl)phenyl)thiourea (Compound 2)

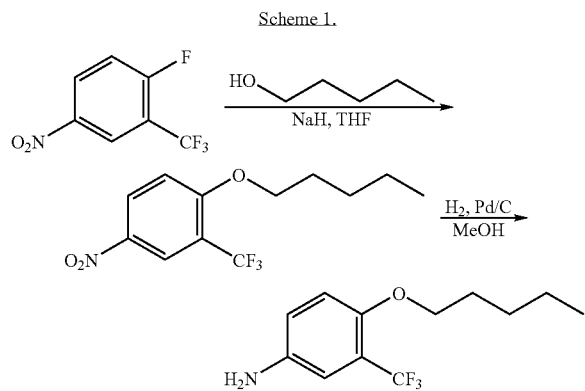

Step 1. Synthesis of 4-nitro-1-pentyloxy-2-trifluoromethyl-benzene

NaH (0.7 g, 17.5 mmol) is added to a solution of 1-pentanol (5 ml) in dry THF (25 ml). After stirring at room temperature for 30 min, 3.50 g (16.7 mmole) of 1-fluoro-4-nitro-2-trifluoromethylbenzene is added, and stirring is continued at room temperature overnight. The reaction is quenched with water and extracted with ethylacetate, dried over sodium sulfate and evaporated to dryness. The residue is purified by chromatography on silica gel, eluted with 33% dichloromethane/hexane. Removal of solvent provides 4-nitro-1-pentyloxy-2-trifluoromethyl-benzene as pale yellow oil.

Step 2. Synthesis of 1-(4-pentyloxy-3-trifluoromethyl-phenyl)-3-(pyridine-3-carbonyl)-thiourea A solution of 4-nitro-1-pentyloxy-2-trifluoromethyl-benzene (4.6 g, 16.6 mmole) in Methanol (120 ml) is hydrogenated in presence of 10% Pd/C (0.2 g) with hydrogen filled in a balloon at room temperature overnight. Filtration over CELITE and concentration gave the desired product as a brownish oil. MS: 248 (M+1).

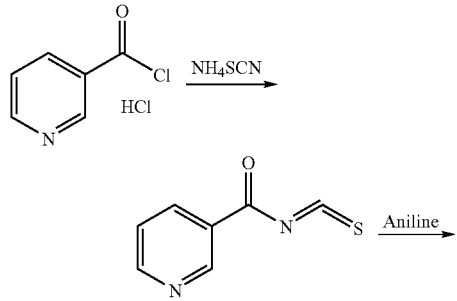

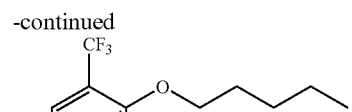

Compound 2

A solution of ammonium thiocyanate (4.5 g, 60 mmol) in acetone (25 ml) is added to a suspension of nicotinyl chloride hydrochloride (3.6 g, 20 mmol) in acetone (50 ml). The reaction is stirred for 1 h at room temperature followed by the addition of a solution of 4-pentyloxy-3-trifluoromethyl aniline (4.9 g, 20 mmol) in methylene chloride (25 ml). Stirring is continued over night at room temperature. The solvent is evaporated and the residue suspended in water (100 ml) and extracted with ethylacetate (3×75 ml). The organic extract is washed successively with 10% aq. NaHCO$_3$ solution (×1), water, and brine. The organic layer is dried over sodium sulphate and evaporated. The residue is crystallized from methanol to give the desired product 1H NMR (300 MHz, CDCl$_3$): δ 12.34 (s, 1H), 9.35 (s, 1H), 9.16 (s, 1H), 8.91-8.88 (d, 1H, J=6.4 Hz), 8.23-8.20 (t, 1H, J=2.2 Hz), 7.85-7.81 (d, 1H, J=12 Hz), 7.54-7.50 (q, 2H, J=4.8 Hz), 7.04 (d, 1H, J=8.7, 1.0 Hz), 4.10-4.06 (t, 2H, J=6.3 Hz), 1.92-1.83 (m, 2H), 1.50-1.42 (m, 4H), 0.97-0.93 (m, 3H). MS (APCI) m/z 412.14 [M+H]$^+$.

Example 5

SYNTHESIS OF 1-[3-(BIPHENYL-4-YLMETHOXY)-PHENYL]-3-(2-MORPHOLIN-4-YL-ACETYL)-THIOUREA (Compound 3)

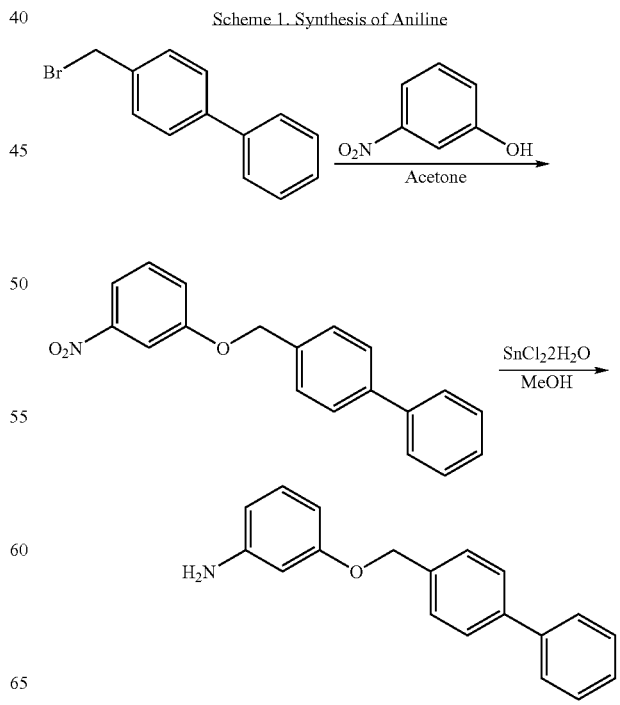

Step 1. 4-(3-Nitro-phenoxymethyl)-biphenyl

A mixture of 3-Nitro-phenol (3.5 g, 25 mmole), 4-Bromomethyl-biphenyl (4.94 g, 20 mmole) and Potassium carbonate (3.8 g, 30 mmole) in 75 mL of acetone is stirred for 16 hr at room temperature. After removal of the solvent, the residue is taken up in ethyl acetate, washed with 1 N NaOH and brine, dried over Na$_2$SO$_4$, and concentrated to yield a solid. The solid is washed with methanol and dried under vacuum to afford 4-(3-Nitro-phenoxymethyl)-biphenyl.

Step 2. 3-(Biphenyl-4-ylmethoxy)-aniline

Tin (II) chloride (13.6 g (60 mmole)) is added to a solution of 4-(3-Nitro-phenoxymethyl)-biphenyl (4.6 g, 15 mmole) in 120 ml methanol. The reaction mixture is refluxed for 12 hr. The reaction is cooled to room temperature, 4 N of NaOH solution is added with stirring to adjust pH=8. The resulting mixture is filtered through a plug of CELITE, the filtrate concentrated and taken up in ethyl acetate. The organic layer is washed with brine and dried over Na$_2$SO$_4$, and concentrated. The resulting solid is washed with little methanol to yield 3-(Biphenyl-4-ylmethoxy)-aniline as a yellow solid. MS: 276(M+1).

methylene chloride (50 ml), followed by 2 drops of DMF at 0° C. The suspension is stirred at room temperature for 1.5 h. All the volatiles are removed on a rotovap. The yellow solid is re-suspended in 80 ml of acetone, and 2.9 g (38 mmole) ammonium thiocyanate is added. The reaction is stirred for 1.5 h at room temperature to give a brownish suspension. A solution of 3-(Biphenyl-4-ylmethoxy)-aniline (1.8 g, 6.7 mmole) in 50 mL of dichloromethane is added into the above suspension. The stirring is continued over night at room temperature. After removal of insoluble salts, the solvent is evaporated and the residue dissolved in ethyl acetate, washed with 5% aq. NaHCO$_3$ and brine, dried over sodium sulfate and concentrated. The residue is purified by flash chromatography on silica gel (30-50% EtOAc/Hexanes), and further purified on Prep-LC/MS, yielding the desired light yellow solid product. 1H NMR (300 MHz, CDCl$_3$): δ 12.20 (s, 1H), 10.12 (brs, 1H), 7.66-7.61 (m, 5H), 7.55-7.52 (m, 2H), 7.50-7.35 (m, 1H), 7.33-7.30 (m, 1H), 7.19 (dd, 1H, J=8.0, 1.0 Hz), 6.93 (ddd, 1H, J=8.2, 2.4, 0.8 Hz), 5.14 (s, 2H), 3.84 (t, 4H, J=4.4 Hz), 3.21 (brs, 2H), 2.66 (brs, 4H). MS (APCI) m/z 462 [M+H]$^+$.

Scheme 2. Synthesis of 1-[3-(Biphenyl-4-ylmethoxy)-phenyl]-3(2-morpholin-4-yl-acetyl)-thiourea

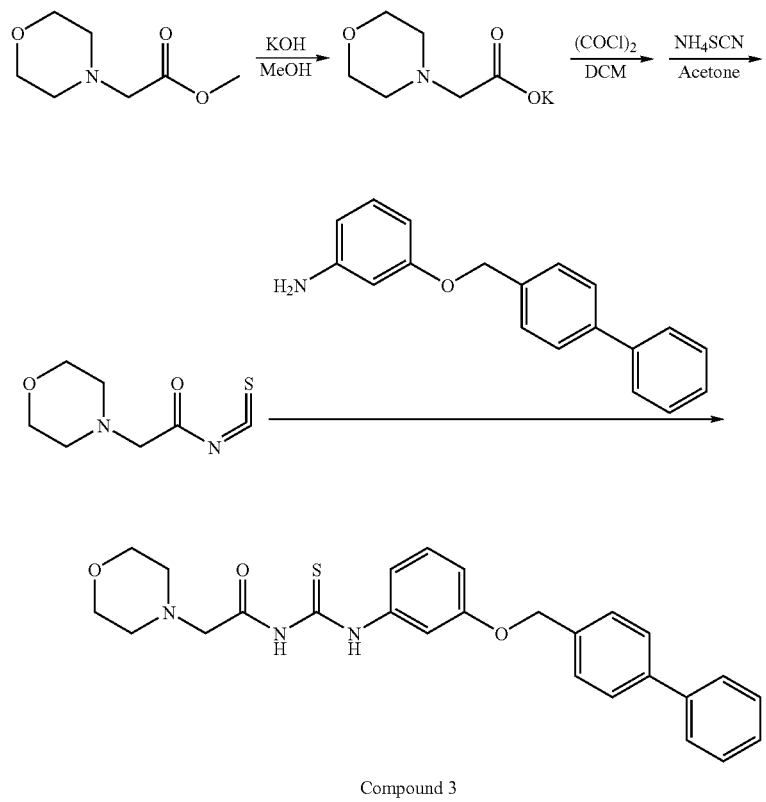

Compound 3

Methyl morpholinoacetate, (8.25 g, 52 mmol) is hydrolyzed with KOH (85%, 3.42 g, 52 mmol) in 100 mL of methanol at 80° C. for 16 h. After removal of solvent, the residue is dried under vacuum to give off-white potassium salt power, 9.6 g (100%).

Oxalyl chloride (2.7 mL, 30 mmol) is added to a suspension of the above potassium salt (2.75 g, 15 mmol) in

Example 6

ADDITIONAL ARYL ACYL THIOUREA COMPOUNDS

The compounds disclosed in Table I and Table II are made via the synthetic procedures set forth in Scheme I and further illustrated in Examples 1 to 5.

The following methods were used to obtain the mass spectral data provided for the compounds of TABLE II.

Method A

Retention time (TR) is measured in a gradient of 30-100% B over 3.00 minutes followed by 100% B for 1 minute. Buffer A is 0.1% trifluoroacetic acid in water and buffer B is 0.1% trifluoroacetic acid in acetonitrile. An analytical Phenomenex Luna C8 column is used with a flow rate of 2.5 mL/min. All HPLC/MS analytical runs are run at a wavelength of 220 nm using a Gilson 151 UVNVIS detector followed by a ThermoFinnigan Surveyor MSQ.

Method B

Retention time (TR) is measure in a gradient of 10-100% B in 3.00 minutes followed by 100% B for 1 minute. Buffer A is 0.1% trifluoroacetic acid in water and buffer B is 0.1% trifluoroacetic acid in acetonitrile. An analytical Phenomenex Luna C8 column is used with a flow rate of 2.5 mL/min. All HPLC/MS analytical runs are run at a wavelength of 220 nm using a Gilson 151 UVNVIS detector followed by a ThermoFinnigan Surveyor MSQ.

TABLE I

| Cmp # | Structure | Name |
|---|---|---|
| 4 | 0137025 | 1-(4-pentylphenyl)-3-(1,2,3-thiadiazole-4-carbonyl)thiourea |
| 5 | 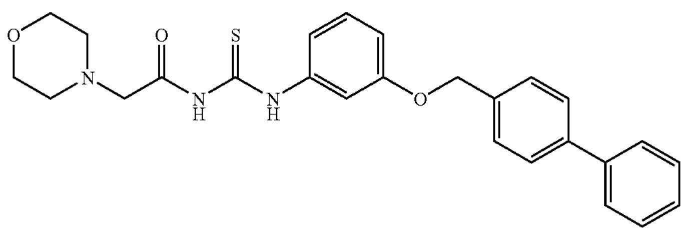 | 1-(3-(4-phenyl-benzyloxy)phenyl)-3-(2-morpholinoacetyl)thiourea |
| 6 | 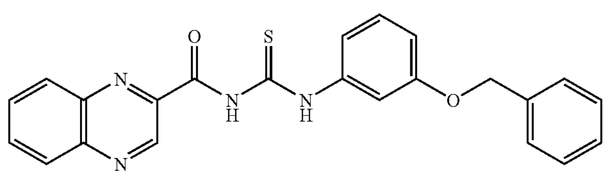 | 1-(3-(benzyloxy)phenyl)-3-(quinoxaline-2-carbonyl)thiourea |
| 7 | 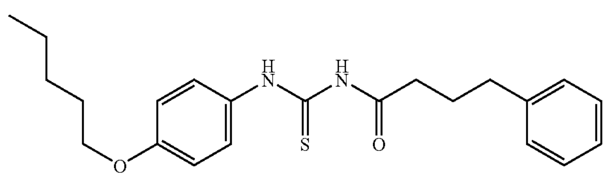 | 1-(4-(pentyloxy)phenyl)-3-(4-phenylbutanoyl)thiourea |
| 8 | 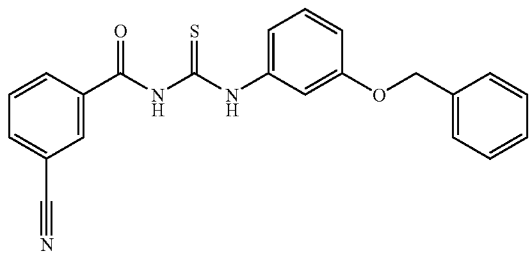 | 1-(3-cyanobenzoyl)-3-(3-benzyloxy-phenyl)thiourea |

TABLE I-continued
| | | |
|---|---|---|
| 9 | 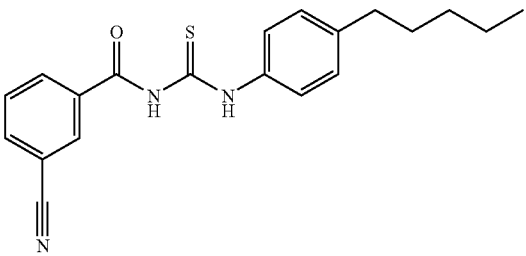 | 1-(3-cyanobenzoyl)-3-(4-pentylphenyl)thiourea |
| 10 | 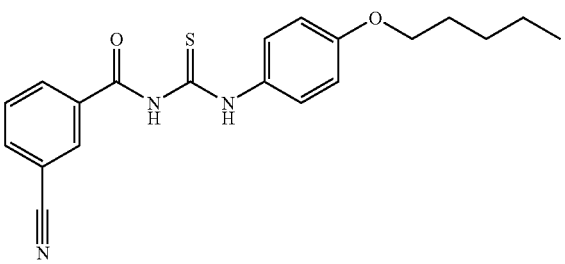 | 1-(3-cyanobenzoyl)-3-(4-pentyloxy-phenyl)thiourea |
| 11 | 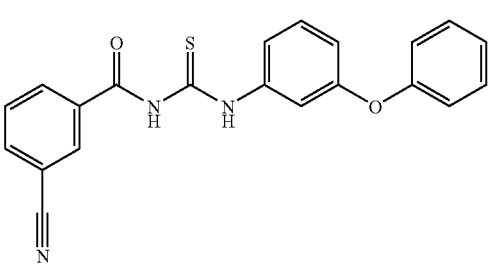 | 1-(3-cyanobenzoyl)-3-(3-phenoxy-phenyl)thiourea |
| 12 | 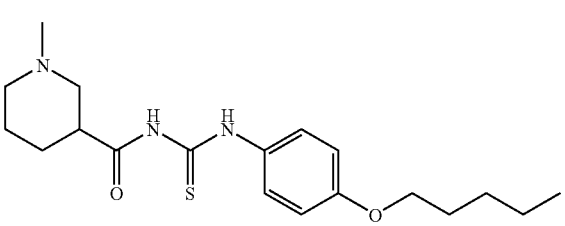 | 1-(1-methylpiperidine-3-carbonyl)-3-(4-pentyloxyphenyl)thiourea |
| 13 | 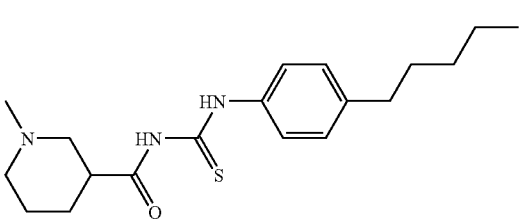 | 1-(1-methylpiperidine-3-carbonyl)-3-(4-pentylphenyl)thiourea |
| 14 | 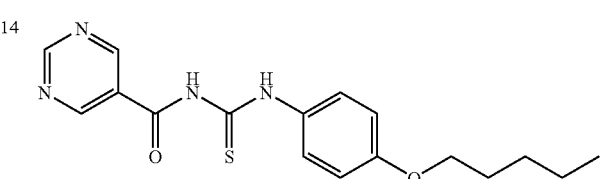 | 1-(4-(pentyloxy)phenyl)-3-(quinoxaline-7-carbonyl)thiourea |
| 15 | 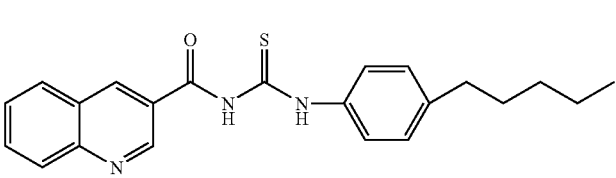 | 1-(4-pentylphenyl)-3-(quinoline-3-carbonyl)thiourea |

TABLE I-continued

| 16 | 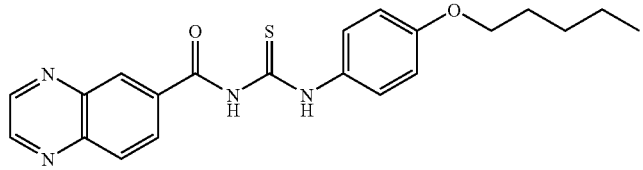 | 1-(4-(pentyloxy)phenyl)-3-(quinoxaline-7-carbonyl)thiourea |
| --- | --- | --- |
| 17 | 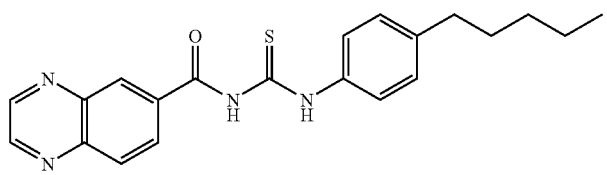 | 1-(4-pentylphenyl)-3-(quinoxaline-7-carbonyl)thiourea |
| 18 | 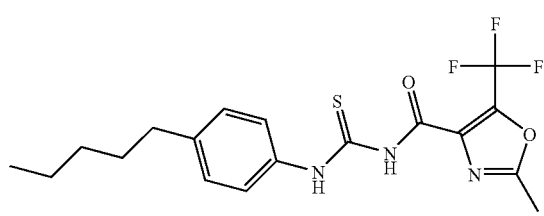 | 1-(2-methyl-5-(trifluoromethyl)oxazole-4-carbonyl)-3-(4-pentylphenyl)thiourea |
| 19 | 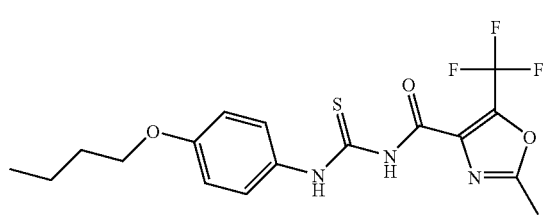 | 1-(2-methyl-5-(trifluoromethyl)oxazole-4-carbonyl)-3-(4-(pentyloxy)phenyl)thiourea |
| 20 | 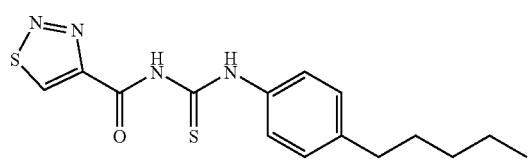 | 1-(4-pentylphenyl)-3-(1,2,3-thiadiazole-4-carbonyl)thiourea |
| 21 | 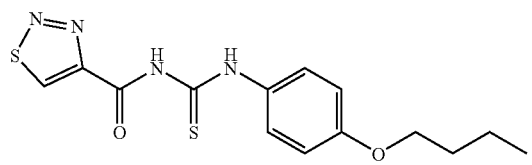 | 1-(4-pentoxyphenyl)-3-(1,2,3-thiadiazole-4-carbonyl)thiourea |
| 22 | 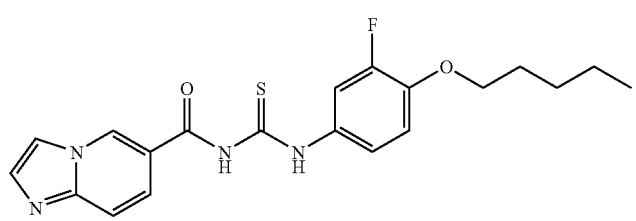 | 1-(3-fluoro-4-(pentyloxy)phenyl)-3-(H-imidazo[1,2-a]pyridine-6-carbonyl)thiourea |

TABLE II

| CPD # | STRUCTURE | NAME | MS | method |
|---|---|---|---|---|
| 23 | 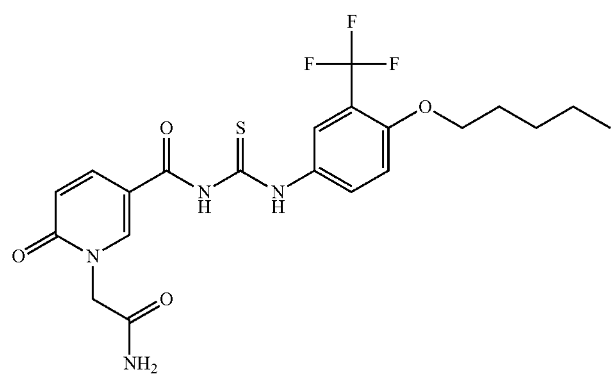 | 1-(1-(2-amino-2-oxoethyl)-2-oxo-1,2-dihydropyridine-5-carbonyl)-3-(4-(pentyloxy)-3-(trifluoromethyl)phenyl)thiourea | HPLC (tR) = 2.12 min MS (APCI) m/z 468 [M − 16]+ | A |
| 24 | 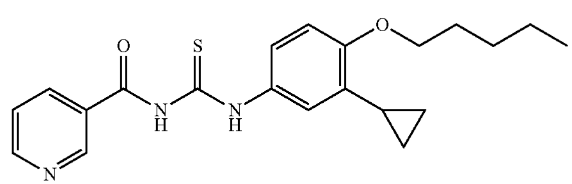 | 1-(3-cyclopropyl-4-(pentyloxy)phenyl)-3-nicotinoylthiourea | HPLC (tR) = 2.02 min MS (APCI) m/z 384 [M + H]+ | A |
| 25 | 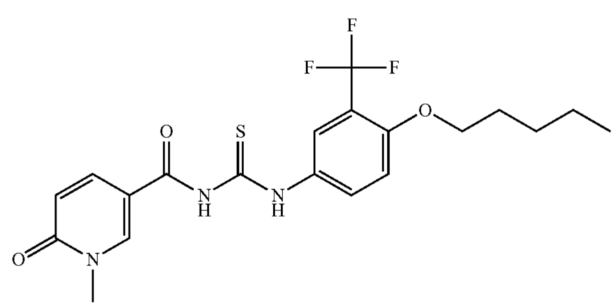 | 1-(1-methyl-2-oxo-1,2-dihydropyridine-5-carbonyl)-3-(4-(pentyloxy)-3-(trifluoromethyl)phenyl)thiourea | HPLC (tR) = 3.01 min MS (APCI) m/z 442 [M + H]+ | B |

TABLE II-continued

| CPD # | STRUCTURE | NAME | MS | method |
|---|---|---|---|---|
| 26 | 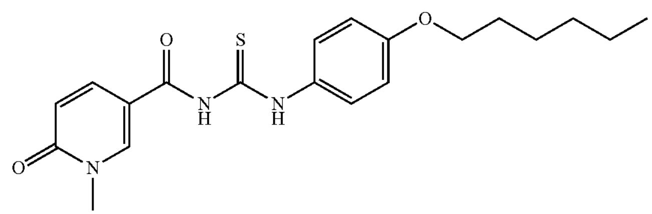 | 1-(4-(hexyloxy)phenyl)-3-(1-methyl-2-oxo-1,2-dihydropyridine-5-carbonyl)thiourea | HPLC (tR) = 2.92 min MS (APCI) m/z 388 [M + H]+ | B |
| 27 | 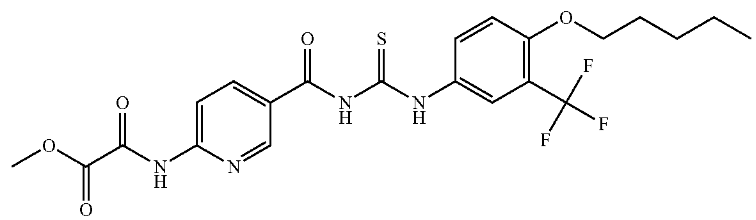 | 2-oxo-2-(5-((3-(4-(pentyloxy)phenyl)thioureido)carbonyl)pyridin-2-ylamino)acetate | HPLC (tR) = 2.32 min MS (APCI) m/z 514 [M + H]+ | A |
| 28 | 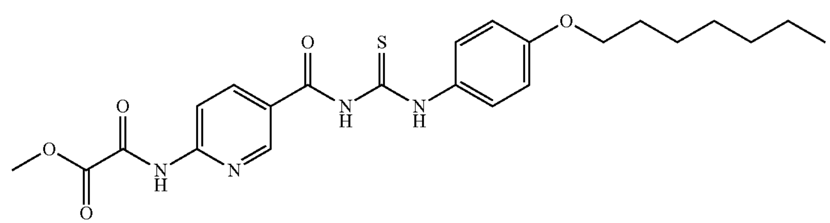 | methyl 2-(5-(3-(4-(heptyloxy)phenyl)thioureido)carbonyl)pyridin-2-ylamino)-2-oxoacetate | HPLC (tR) = 2.30 min MS (APCI) m/z 474 [M + H]+ | A |
| 29 | 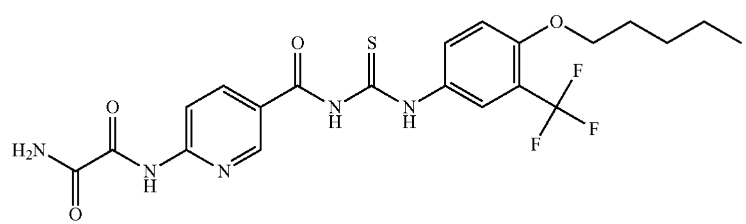 | 1-(6-(2-amino-2-oxoacetamideo)nicotinoyl)-3-(4-(pentyloxy)-3-(trifluoromethyl)phenyl)thiourea | HPLC (tR) = 2.06 min MS (APCI) m/z 498 [M + H]+ | A |

TABLE II-continued

| CPD # | STRUCTURE | NAME | MS | method |
|---|---|---|---|---|
| 30 | 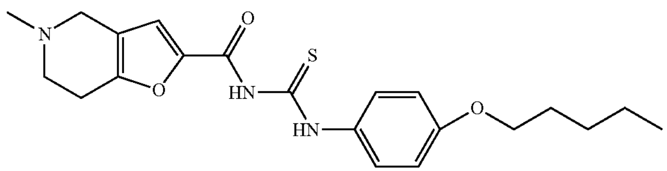 | 1-(5-methyl-4,5,6,7-tetrahydrofuro[3,2-c]pyridine-2-carbonyl)-3-(4-(pentyloxy)phenyl)thiourea | HPLC (tR) = 1.35 min MS (APCI) m/z 402 [M + H]+ | A |
| 31 | 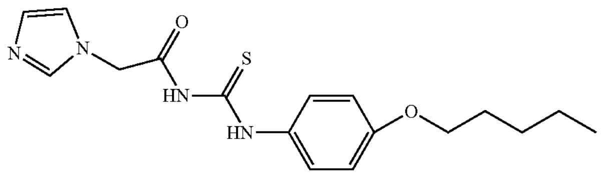 | 1-(2-(1H-imidazol-1-yl)acetyl)-3-(4-(pentyloxy)phenyl)thiourea | HPLC (tR) = 2.46 min MS (APCI) m/z 347 [M + H]+ | A |
| 32 | 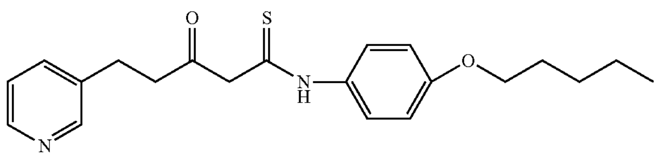 | 1-(4-(pentyloxy)phenyl)-3-(3-(pyridin-3-yl)propanoyl)thiourea | HPLC (tR) = 1.37 min MS (APCI) m/z 372 [M + H]+ | A |
| 33 | 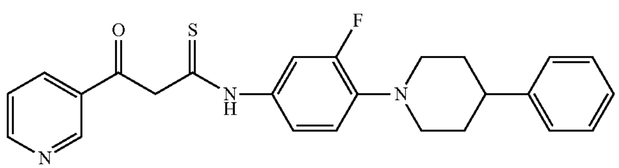 | 1-(3-fluoro-4-(4-phenylpiperidin-1-yl)phenyl)-3-nicotinoylthiourea | HPLC (tR) = 1.61 min MS (APCI) m/z 436 [M + H]+ | A |
| 34 | 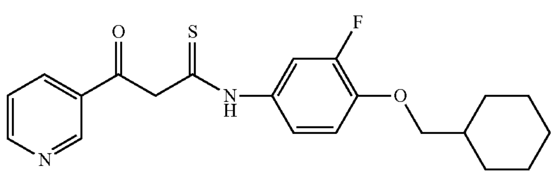 | 1-(4-(cyclohexylmethoxy)-3-fluorophenyl)-3-nicotinoylthiourea | HPLC (tR) = 1.94 min MS (APCI) m/z 388 [M + H]+ | A |

TABLE II-continued

| CPD # | STRUCTURE | NAME | MS | method |
|---|---|---|---|---|
| 35 | 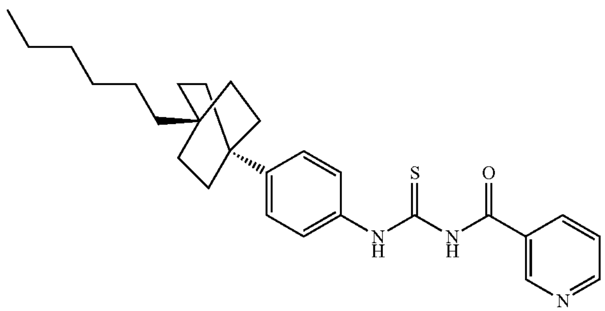 | 1-(4-(4-hexylbicyclo[2.2.2]octan-1-yl)phenyl)-3-nicotinoylthiourea | HPLC (tR) = 4.35 min MS (APCI) m/z 450 [M + H]+ | B |
| 36 | 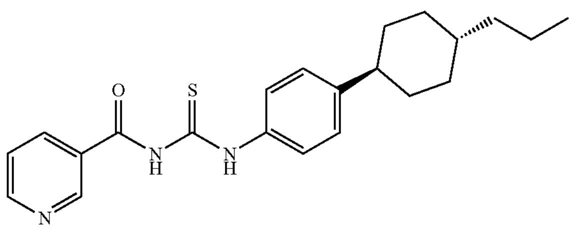 | 1-nicotinoyl-3-(4-((1S,4r)-4-propylcyclohexyl)phenyl)thiourea | HPLC (tR) = 3.37 min MS (APCI) m/z 382 [M + H]+ | B |
| 37 | 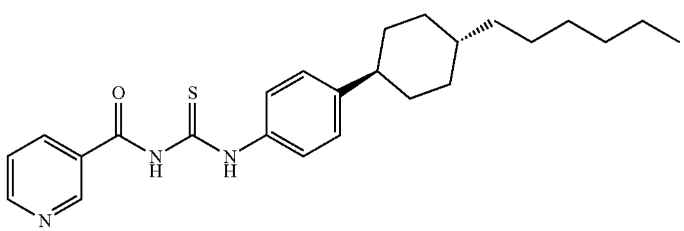 | 1-(4-((1s,4r)-4-hexylcyclohexyl)phenyl)-3-nicotinoylthiourea | HPLC (tR) = 4.13 min MS (APCI) m/z 424 [M + H]+ | B |
| 38 | 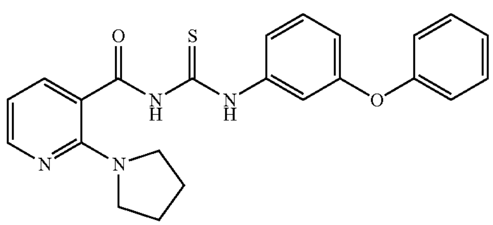 | 1-(3-phenoxyphenyl)-3-(2-(pyrrolidin-1-yl)nicotinoyl)thiourea | HPLC (tR) = 1.4 min MS (APCI) m/z 419 [M + H]+ | A |

TABLE II-continued

| CPD # | STRUCTURE | NAME | MS | method |
|---|---|---|---|---|
| 39 | 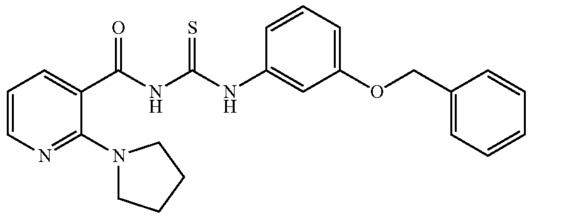 | 1-(3-(benzyloxy)phenyl)-3-(2-(pyrrolidin-1-yl)nicotinoyl)thiourea | HPLC (tR) = 1.40 min MS (APCI) m/z 433 [M + H]+ | A |
| 40 | 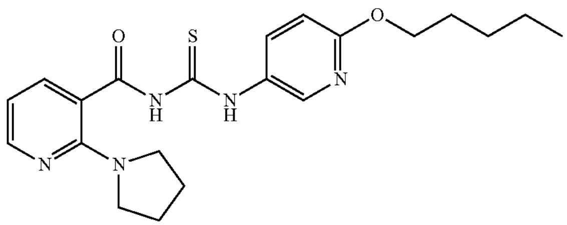 | 1-(6-(pentyloxy)pyridin-3-yl)-3-(2-(pyrrolidin-1-yl)nicotinoyl)thiourea | HPLC (tR) = 1.39 min MS (APCI) m/z 414 [M + H]+ | A |
| 41 | 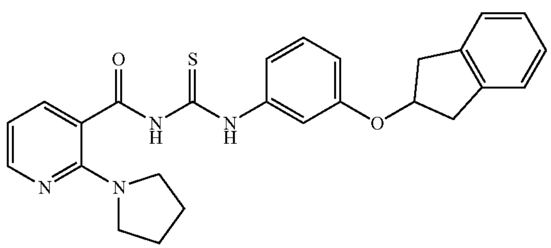 | 1-(3-(2,3-dihydro-1H-inden-2-yloxy)phenyl)-3-(2-(pyrrolidin-1-yl)nicotinoyl)thiourea | HPLC (tR) = 1.49 min MS (APCI) m/z 459 [M + H]+ | A |
| 42 | 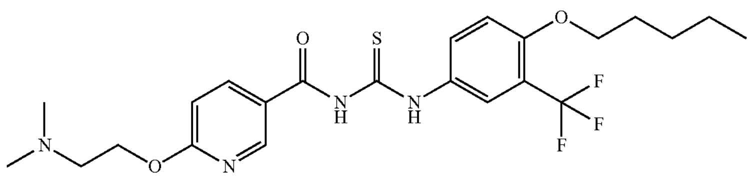 | 1-(6-(2-(dimethylamino)ethoxy)nicotinoyl)-3-(4-(pentyloxy)-3-(trifluoromethyl)phenyl)thiourea | HPLC (tR) = 1.55 min MS (APCI) m/z 499 [M + H]+ | B |

TABLE II-continued

| CPD # | STRUCTURE | NAME | MS | method |
|---|---|---|---|---|
| 43 | 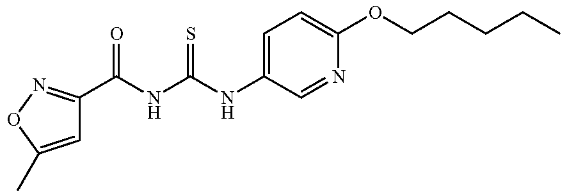 | 1-(5-methylisoxazole-3-carbonyl)-3-(6-(pentyloxy)pyridin-3-yl)thiourea | HPLC (tR) = 2.27 min MS (APCI) m/z 349 [M + H]+ | A |
| 44 | 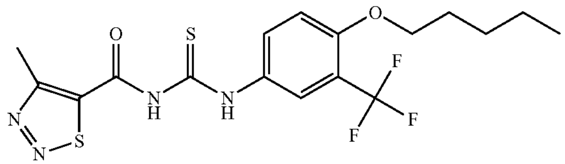 | 1-(4-methyl-1,2,3-thiadiazole-5-carbonyl)-3-(4-(pentyloxy)-3-(trifluoromethyl)phenyl)thiourea | HPLC (tR) = 2.41 min MS (APCI) m/z 433 [M + H]+ | A |
| 45 | 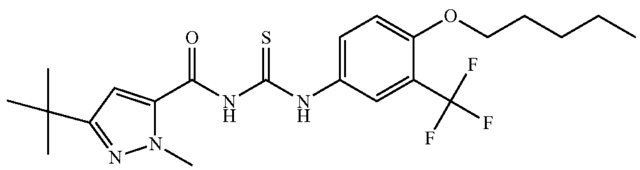 | 1-(3-tert-butyl-1-methyl-1H-pyrazole-5-carbonyl)-3-(4-(pentyloxy)-3-(trifluoromethyl)phenyl)thiourea | HPLC (tR) = 3.05 min MS (APCI) m/z 470 [M + H]+ | A |
| 46 | 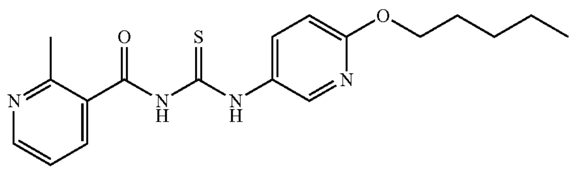 | 1-(2-methylnicotinoyl)-3-(6-(pentyloxy)pyridin-3-yl)thiourea | HPLC (tR) = 1.34 min MS (APCI) m/z 359 [M + H]+ | A |
| 47 | 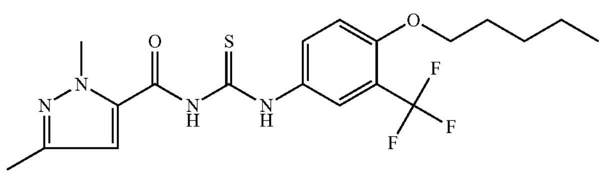 | 1-(1,3-dimethyl-1H-pyrazole-5-carbonyl)-3-(4-(pentyloxy)-3-(trifluoromethyl)phenyl)thiourea | HPLC (tR) = 2.47 min MS (APCI) m/z 428 [M + H]+ | A |

TABLE II-continued

| CPD # | STRUCTURE | NAME | MS | method |
|---|---|---|---|---|
| 48 | 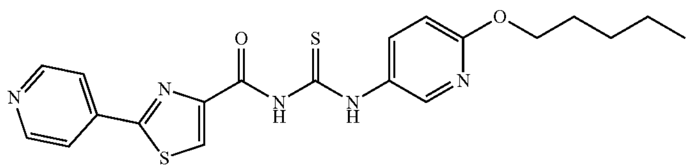 | 1-(6-(pentyloxy)pyridin-3-yl)-3-(2-(pyridin-4-yl)thiazole-4-carbonyl)thiourea | HPLC (tR) = 1.56 min MS (APCI) m/z 428 [M + H]+ | A |
| 49 | 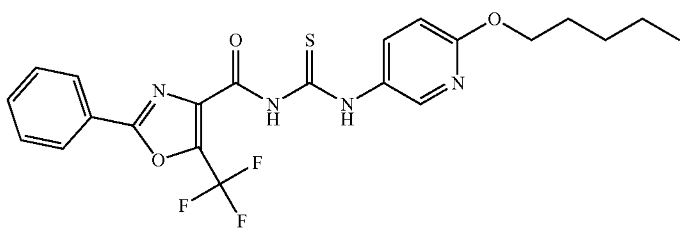 | 1-(6-(pentyloxy)pyridin-3-yl)-3-(2-phenyl-5-(trifluoromethyl)oxazole-4-carbonyl)thiourea | HPLC (tR) = 3.09 min MS (APCI) m/z 479 [M + H]+ | A |
| 50 | 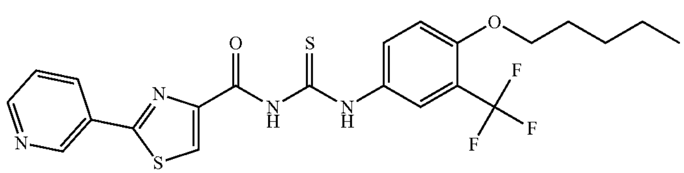 | 1-(4-(pentyloxy)-3-(trifluoromethyl)phenyl)-3-(2-(pyridin-3-yl)thiazole-4-carbonyl)thiourea | HPLC (tR) = 2.17 min MS (APC) m/z 495 [M + H]+ | A |
| 51 | 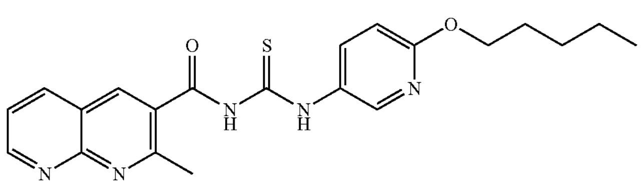 | 1-(2-methyl-1,8-naphthyridine-3-carbonyl)-3-(6-(pentyloxy)pyridin-3-yl)thiourea | HPLC (tR) = 1.56 min MS (APCI) m/z 410 [M + H]+ | A |

TABLE II-continued

| CPD # | STRUCTURE | NAME | MS | method |
|---|---|---|---|---|
| 52 | 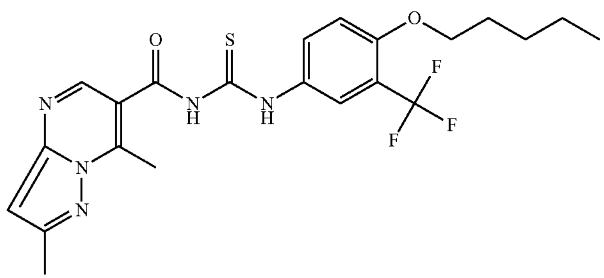 | 1-(2,7-dimethylpyrazolo[1,5-a]pyrimidine-6-carbonyl)-3-(4-(pentyloxy)-3-(trifluoromethyl)phenyl)thiourea | HPLC (tR) = 2.43 min MS (APCI) m/z 480 [M + H]+ | A |
| 53 | 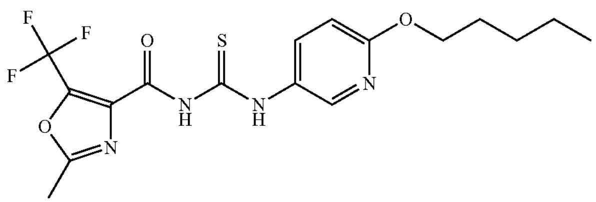 | 1-(2-methyl-5-(trifluoromethyl)oxazole-4-carbonyl)-3-(6-(pentyloxy)pyridin-3-yl)thiourea | HPLC (tR) = 2.51 min MS (APCI) m/z 417 [M + H]+ | A |
| 54 | 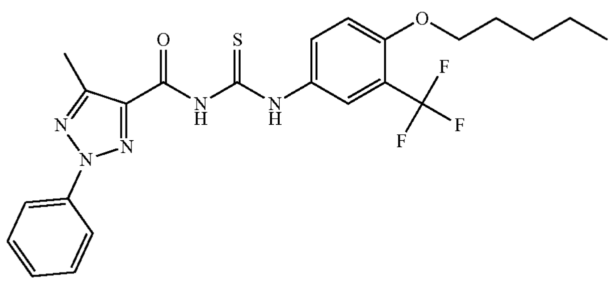 | 1-(4-methyl-2-phenyl-2H-1,2,3-triazole-5-carbonyl)-3-(4-(pentyloxy)-3-(trifluoromethyl)phenyl)thiourea | HPLC (tR) = 3.61 min MS (APCI) m/z 492 [M + H]+ | A |
| 55 | 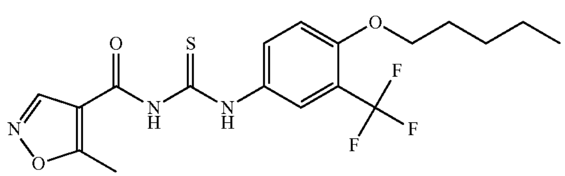 | 1-(5-methylisoxazole-4-carbonyl)-3-(4-(pentyloxy)-3-(trifluoromethyl)phenyl)thiourea | HPLC (tR) = 2.44 min MS (APCI) m/z 416 [M + H]+ | A |

TABLE II-continued

| CPD # | STRUCTURE | NAME | MS | method |
|---|---|---|---|---|
| 56 | 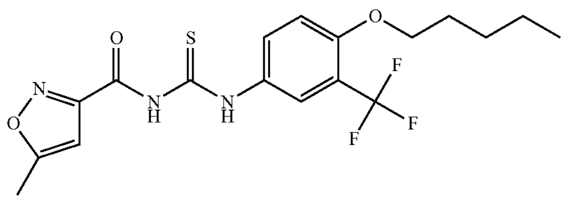 | 1-(5-methylisoxazole-3-carbonyl)-3-(4-(pentyloxy)-3-(trifluoromethyl)phenyl)thiourea | HPLC (tR) = 2.59 min MS (APCI) m/z 416 [M + H]+ | A |
| 57 | 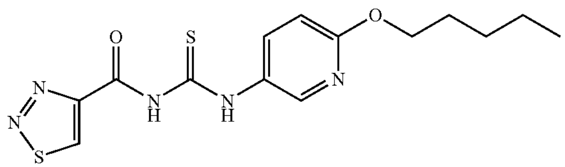 | 1-(6-(pentyloxy)pyridin-3-yl)-3-(1,2,3-thiadiazole-4-carbonyl)thiourea | HPLC (tR) = 2.15 min MS (APCI) m/z 352 [M + H]+ | A |
| 58 | 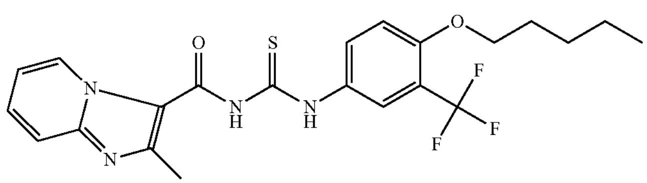 | 1-(2-methyl1H-imidazo[1,2-a]pyridine-3-carbonyl)-3-(4-(pentyloxy)-3-(trifluoromethyl)phenyl)thiourea | HPLC (tR) = 1.7 min MS (APCI) m/z 465 [M + H]+ | A |
| 59 | 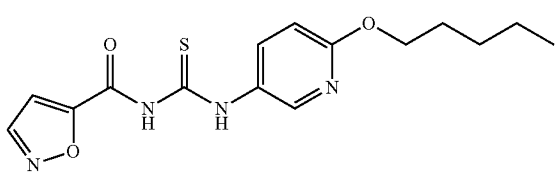 | 1-(isoxazole-5-carbonyl)-3-(6-(pentyloxy)pyridin-3-yl)thiourea | HPLC (tR) = 2.0 min MS (APCI) m/z 335 [M + H]+ | A |
| 60 | 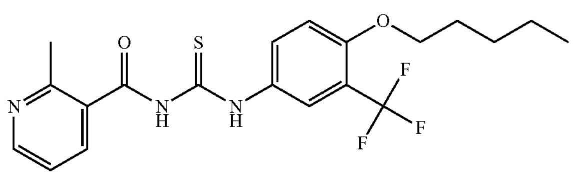 | 1-(2-methylnicotinoyl)-3-(4-(pentyloxy)-3-(trifluoromethyl)phenyl)thiourea | HPLC (tR) = 1.68 min MS (APCI) m/z 426 [M + H]+ | A |

TABLE II-continued

| CPD # | STRUCTURE | NAME | MS | method |
|---|---|---|---|---|
| 61 | 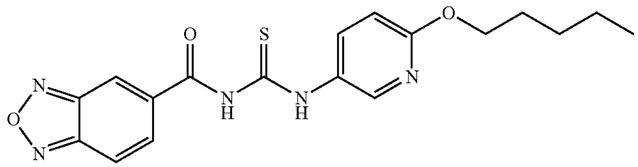 | 1-(benzo[c][1,2,5]oxadiazole-6-carbonyl)-3-(6-(pentyloxy)pyridin-3-yl)thiourea | HPLC (tR) = 2.29 min MS (APCI) m/z 386 [M + H]+ | A |
| 62 | 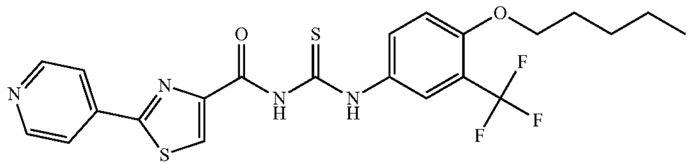 | 1-(4-(pentyloxy)-3-(trifluoromethyl)phenyl)-3-(2-(pyridin-4-yl)thiazole-4-carbonyl)thiourea | HPLC (tR) = 1.86 min MS (APCI) m/z 495 [M + H]+ | A |
| 63 | 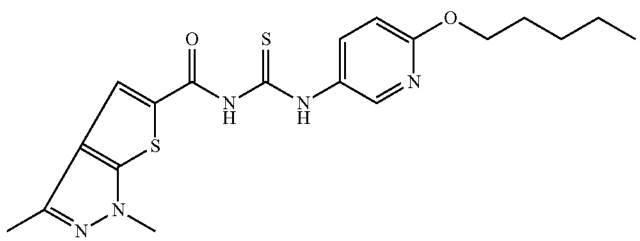 | 1-(1,3-dimethyl-1H-thieno[2,3-c]pyrazole-5-carbonyl)-3-(6-(pentyloxy)pyridin-3-yl)thiourea | HPLC (tR) = 2.31 min MS (APCI) m/z 418 [M + H]+ | A |
| 64 | 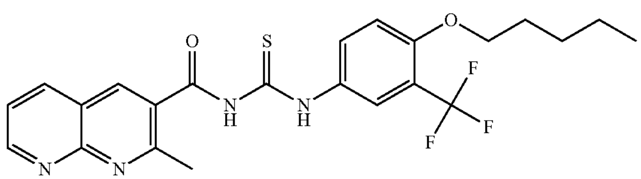 | 1-(2-methyl-1,8-naphthyridine-3-carbonyl)-3-(4-(pentyloxy)-3-(trifluoromethyl)phenyl)thiourea | HPLC (tR) = 1.88 min MS (APCI) m/z 477 [M + H]+ | A |
| 65 | 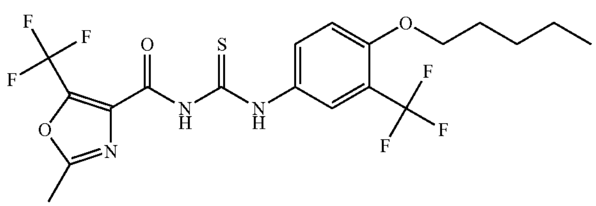 | 1-(2-methyl-5-(trifluoromethyl)oxazole-4-carbonyl)-3-(4-(pentyloxy)-3-(trifluoromethyl)phenyl)thiourea | HPLC (tR) = 2.86 min MS (APCI) m/z 484 [M + H]+ | A |

TABLE II-continued

| CPD # | STRUCTURE | NAME | MS | method |
|---|---|---|---|---|
| 66 | 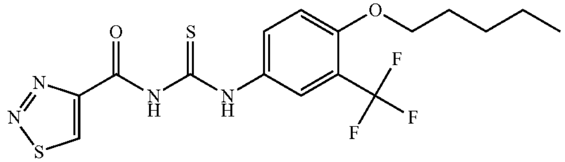 | 1-(4-(pentyloxy)-3-(trifluoromethyl)phenyl)-3-(1,2,3-thiadiazole-4-carbonyl)thiourea | HPLC (tR) = 2.48 min MS (APCI) m/z 419 [M + H]+ | A |
| 67 | 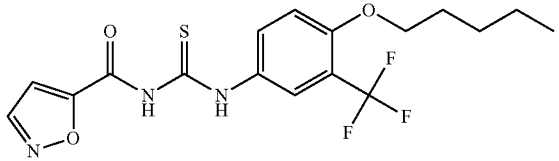 | 1-(isoxazole-5-carbonyl)-3-(4-(pentyloxy)-3-(trifluoromethyl)phenyl)thiourea | HPLC (tR) = 2.34 min MS (APCI) m/z 402 [M + H]+ | A |
| 68 | 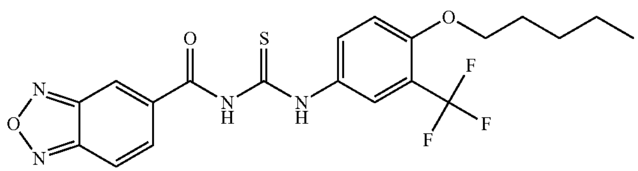 | 1-(benzo[c][1,2,5]oxadiazole-6-carbonyl)-3-(4-(pentyloxy)-3-(trifluoromethyl)phenyl)thiourea | HPLC (tR) = 2.61 min MS (APCI) m/z 453 [M + H]+ | A |
| 69 | 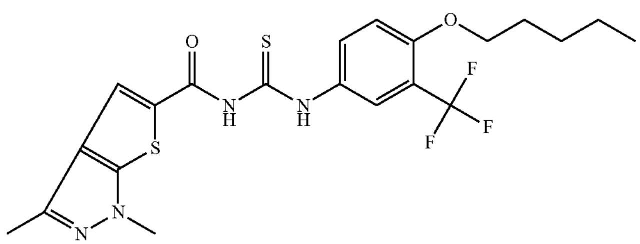 | 1-(3-fluoro-4-(pentyloxy)phenyl)-3-(4-methyl-1,2,3-thiadiazole-5-carbonyl)thiourea | HPLC (tR) = 2.69 min MS (APCI) m/z 485 [M + H]+ | A |
| 70 | 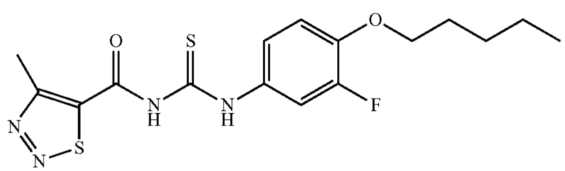 | 1-(3-fluoro-4-(pentyloxy)phenyl)-3-(4-methyl-1,2,3-thiadiazole-5-carbonyl)thiourea | HPLC (tR) = 2.29 min MS (APCI) m/z 383 [M + H]+ | A |

TABLE II-continued

| CPD # | STRUCTURE | NAME | MS | method |
|---|---|---|---|---|
| 71 | 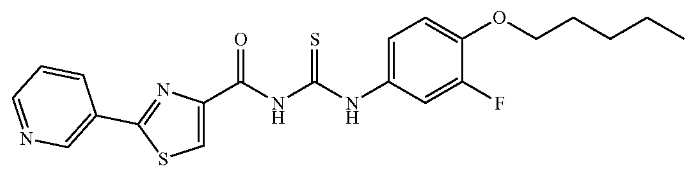 | 1-(3-fluoro-4-(pentyloxy)phenyl)-3-(2-(pyridin-3-yl)thiazole-4-carbonyl)thiourea | HPLC (tR) = 2.03 min MS (APCI) m/z 445 [M + H]+ | A |
| 72 | 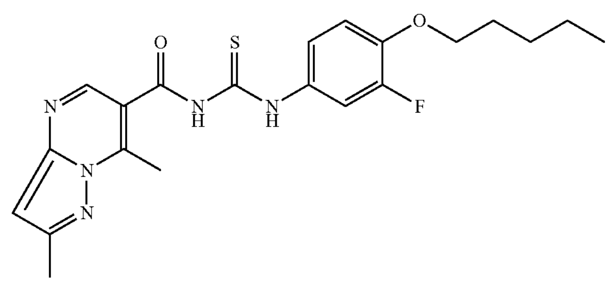 | 1-(2,7-dimethylpyrazolo[1,5-a]pyrimidine-6-carbonyl)-3-(3-fluoro-4-(pentyloxy)phenyl)thiourea | HPLC (tR) = 2.3 min MS (APCI) m/z 430 [M + H]+ | A |
| 73 | 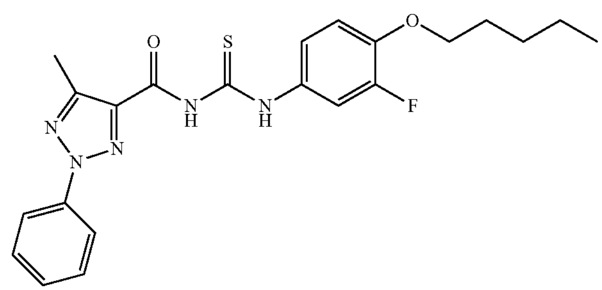 | 1-(3-fluoro-4-(pentyloxy)phenyl)-3-(4-methyl-2-phenyl-2H-1,2,3-triazole-5-carbonyl)thiourea | HPLC (tR) = 3.5 min MS (APCI) m/z 442 [M + H]+ | A |
| 74 | 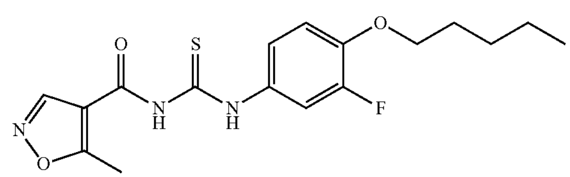 | 1-(3-fluoro-4-(pentyloxy)phenyl)-3-(5-methylisoxazole-4-carbonyl)thiourea | HPLC (tR) = 2.31 min MS (APCI) m/z 366 [M + H]+ | A |

TABLE II-continued

| CPD # | STRUCTURE | NAME | MS | method |
|---|---|---|---|---|
| 75 | 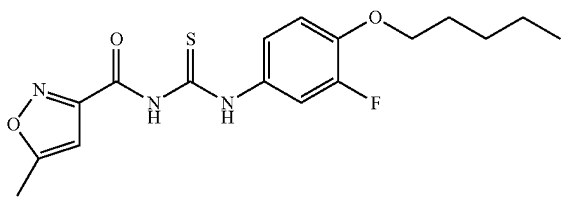 | 1-(3-fluoro-4-(pentyloxy)phenyl)-3-(5-methylisoxazole-3-carbonyl)thiourea | HPLC (tR) = 2.46 min MS (APCI) m/z 366 [M + H]+ | A |
| 76 | 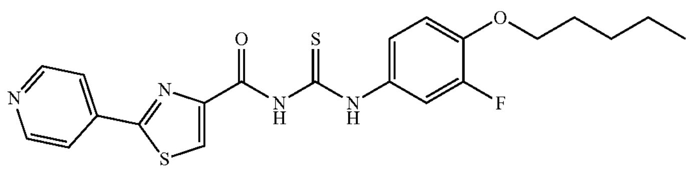 | 1-(3-fluoro-4-(pentyloxy)phenyl)-3-(2-(pyridin-4-yl)thiazole-4-carbonyl)thiourea | HPLC (tR) = 1.73 min MS (APCI) m/z 445 [M + H]+ | A |
| 77 | 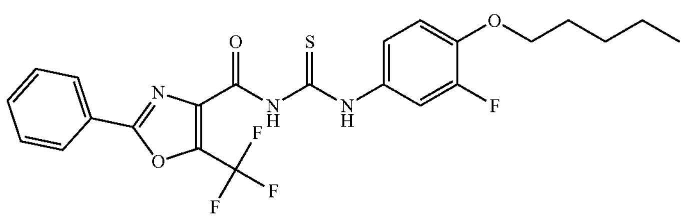 | 1-(3-fluoro-4-(pentyloxy)phenyl)-3-(2-phenyl-5-(trifluoromethyl)oxazole-4-carbonyl)thiourea | HPLC (tR) = 3.39 min MS (APCI) m/z 496 [M + H]+ | A |
| 78 | 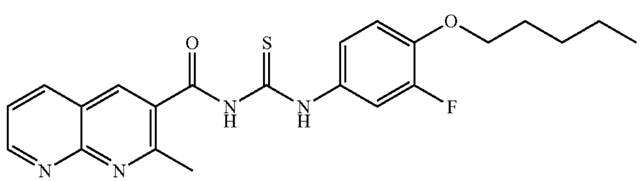 | 1-(3-fluoro-4-(pentyloxy)phenyl)-3-(2-methyl-1,8-naphthyridine-3-carbonyl)thiourea | HPLC (tR) = 1.72 min MS (APCI) m/z 427 [M + H]+ | A |
| 79 | 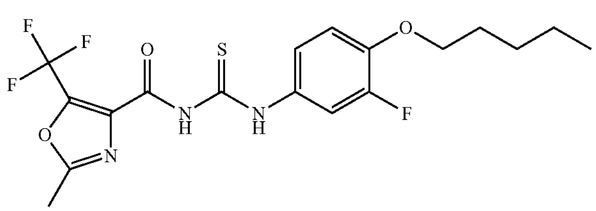 | 1-(3-fluoro-4-(pentyloxy)phenyl)-3-(2-methyl-5-(trifluoromethyl)oxazole-4-carbonyl)thiourea | HPLC (tR) = 2.69 min MS (APCI) m/z 434 [M + H]+ | A |

TABLE II-continued

| CPD # | STRUCTURE | NAME | MS | method |
|---|---|---|---|---|
| 80 | 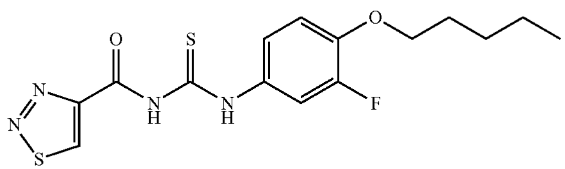 | 1-(3-fluoro-4-(pentyloxy)phenyl)-3-(1,2,3-thiadiazole-4-carbonyl)thiourea | HPLC (tR) = 2.34 min MS (APCI) m/z 369 [M + H]+ | A |
| 81 | 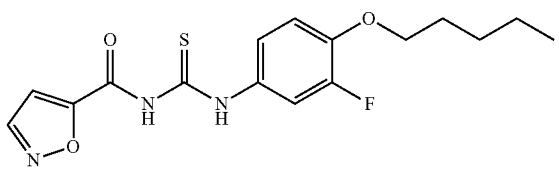 | 1-(3-fluoro-4-(pentyloxy)phenyl)-3-(isoxazole-5-carbonyl)thiourea | HPLC (tR) = 2.19 min MS (APCI) m/z 352 [M + H]+ | A |
| 82 | 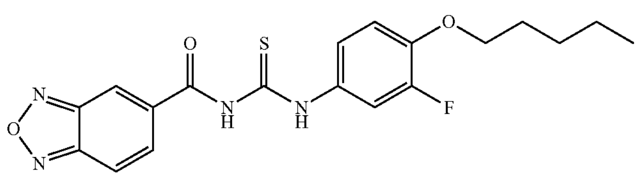 | 1-(benzo[c][1,2,5]oxadiazole-6-carbonyl)-3-(3-fluoro-4-(pentyloxy)phenyl)thiourea | HPLC (tR) = 2.47 min MS (APCI) m/z 403 [M + H]+ | A |
| 83 | 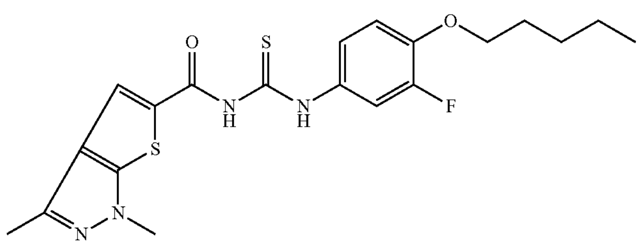 | 1-(1,3-dimethyl-1H-thieno[2,3-c]pyrazole-5-carbonyl)-3-(3-fluoro-4-(pentyloxy)phenyl)thiourea | HPLC (tR) = 2.51 min MS (APCI) m/z 435 [M + H]+ | A |
| 84 | 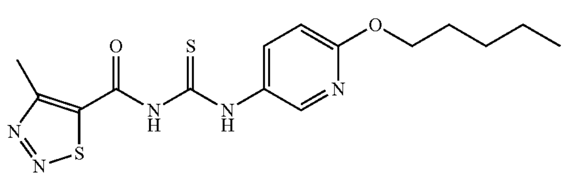 | 1-(4-methyl-1,2,3-thiadiazole-5-carbonyl)-3-(6-(pentyloxy)pyridin-3-yl)thiourea | HPLC (tR) = 2.13 min MS (APCI) m/z 366 [M + H]+ | A |

TABLE II-continued

| CPD # | STRUCTURE | NAME | MS | method |
|---|---|---|---|---|
| 85 | 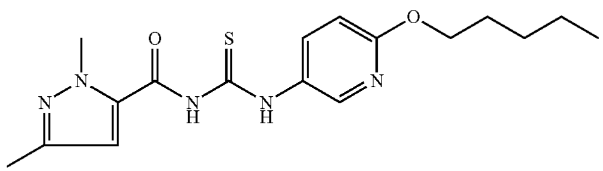 | 1-(1,3-dimethyl-1H-pyrazole-5-carbonyl)-3-(6-(pentyloxy)pyridin-3-yl)thiourea | HPLC (tR) = 2.15 min MS (APCI) m/z 362 [M + H]+ | A |
| 86 | 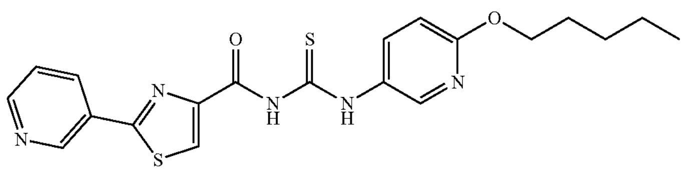 | 1-(6-(pentyloxy)pyridin-3-yl)-3-(2-(pyridin-3-yl)thiazole-4-carbonyl)thiourea | HPLC (tR) = 1.84 min MS (APCI) m/z 428 [M + H]+ | A |
| 87 | 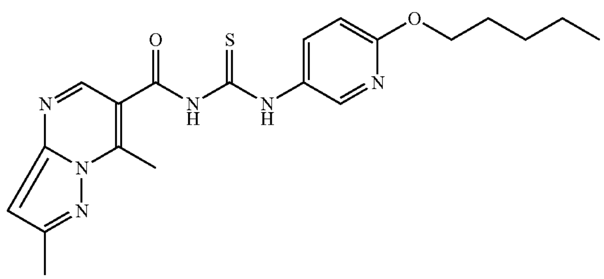 | 1-(2,7-dimethylpyrazolo[1,5-a]pyrimidine-6-carbonyl)-3-(6-(pentyloxy)pyridin-3-yl)thiourea | HPLC (tR) = 2.09 min MS (APCI) m/z 413 [M + H]+ | A |
| 88 | 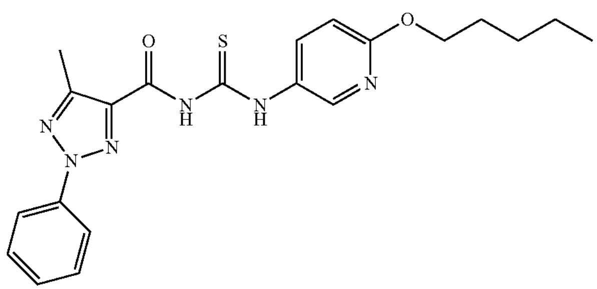 | 1-(4-methyl-2-phenyl-2H-1,2,3-triazole-5-carbonyl)-3-(6-(pentyloxy)pyridin-3-yl)thiourea | HPLC (tR) = 3.22 min MS (APCI) m/z 425 [M + H]+ | A |

TABLE II-continued

| CPD # | STRUCTURE | NAME | MS | method |
|---|---|---|---|---|
| 89 | 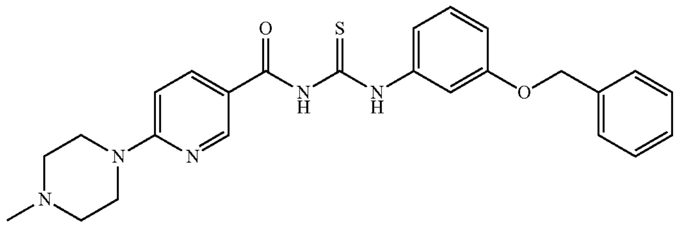 | 1-(3-(benzyloxy)phenyl)-3-(6-(4-methylpiperazin-1-yl)nicotinoyl)thiourea | HPLC (tR) = 1.45 min MS (APCI) m/z 462 [M + H]+ | A |
| 90 | 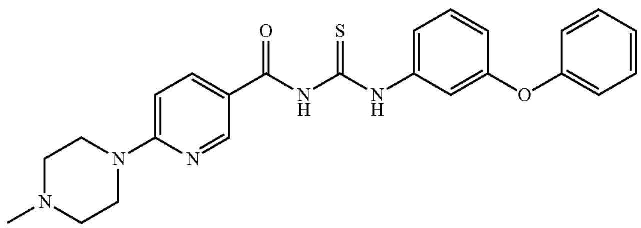 | 1-(6-(4-methylpiperazin-1-yl)nicotinoyl)-3-(3-phenoxyphenyl)thiourea | HPLC (tR) = 1.42 min MS (APCI) m/z 448 [M + H]+ | A |
| 91 | 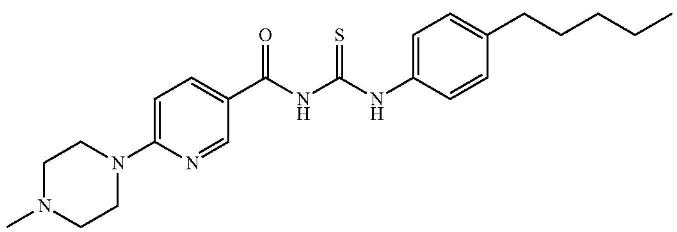 | 1-(6-(4-methylpiperazin-1-yl)nicotinoyl)-3-(4-pentylphenyl)thiourea | HPLC (tR) = 1.64 min MS (APCI) m/z 426 [M + H]+ | A |
| 92 | 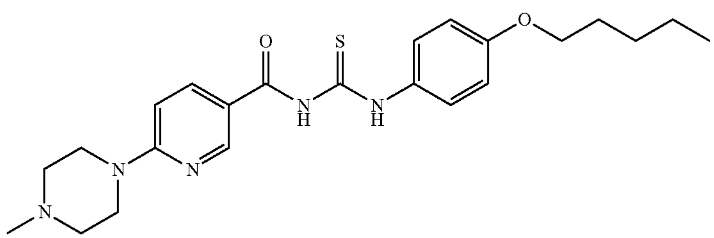 | 1-(6-(4-methylpiperazin-1-yl)nicotinoyl)-3-(4-(pentyloxy)phenyl)thiourea | HPLC (tR) = 1.57 min MS (APCI) m/z 442 [M + H]+ | A |

TABLE II-continued

| CPD # | STRUCTURE | NAME | MS | method |
|---|---|---|---|---|
| 93 | 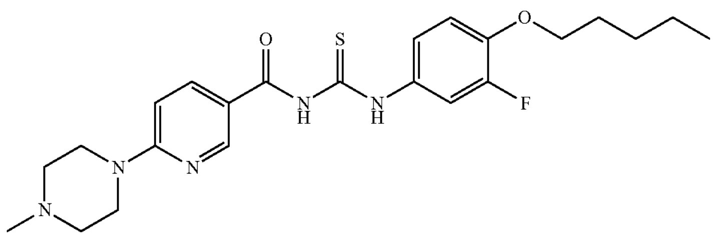 | 1-(3-fluoro-4-(pentyloxy)phenyl)-3-(6-(4-methylpiperazin-1-yl)nicotinoyl)thiourea | HPLC (tR) = 1.57 min MS (APCI) m/z 460 [M + H]+ | A |
| 94 | 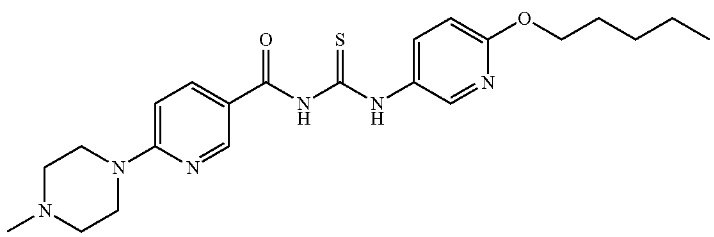 | 1-(6-(4-methylpiperazin-1-yl)nicotinoyl)-3-(6-(pentyloxy)pyridin-3-yl)thiourea | HPLC (tR) = 1.43 min MS (APCI) m/z 443 [M + H]+ | A |
| 95 | 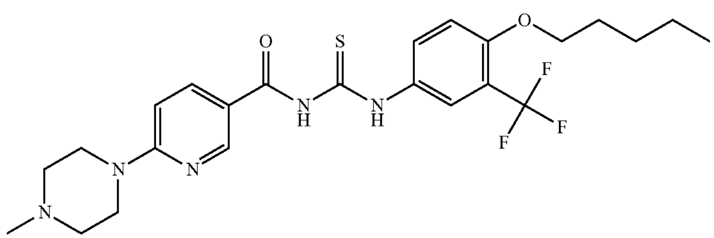 | 1-(6-(4-methylpiperazin-1-yl)nicotinoyl)-3-(4-(pentyloxy)-3-(trifluoromethyl)phenyl)thiourea | HPLC (tR) = 1.71 min MS (APCI) m/z 510 [M + H]+ | A |
| 96 | 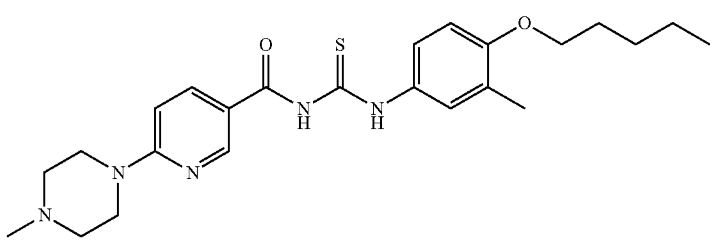 | 1-(3-methyl-4-(pentyloxy)phenyl)-3-(6-(4-methylpiperazin-1-yl)nicotinoyl)thiourea | HPLC (tR) = 1.69 min MS (APCI) m/z 456 [M + H]+ | A |

TABLE II-continued

| CPD # | STRUCTURE | NAME | MS | method |
|---|---|---|---|---|
| 97 | 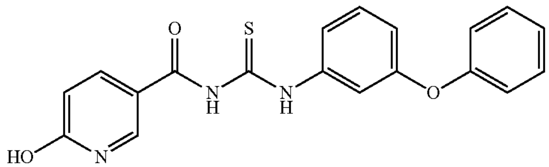 | 1-(6-hydroxynicotinoyl)-3-(3-phenoxyphenyl)thiourea | HPLC (tR) = 1.63 min MS (APCI) m/z 366.11 [M + H]+ | A |
| 98 | 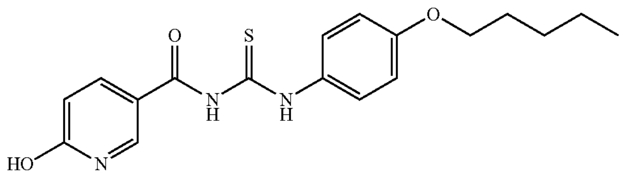 | 1-(6-hydroxynicotinoyl)-3-(4-(pentyloxy)phenyl)thiourea | HPLC (tR) = 1.79 min MS (APC) m/z 360.05 [M + H]+ | A |
| 99 | 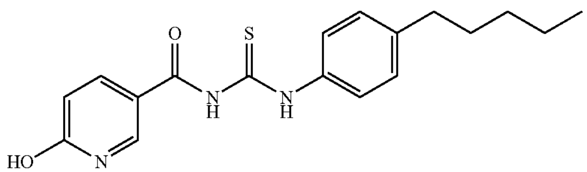 | 1-(6-hydroxynicotinoyl)-3-(4-pentylphenyl)thiourea | HPLC (tR) = 1.93 min MS (APCI) m/z 344.11 [M + H]+ | A |
| 100 | 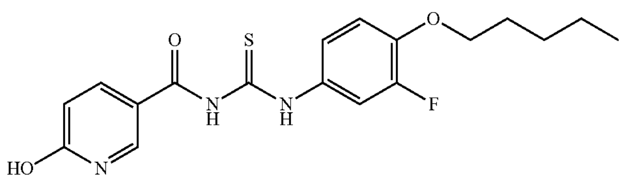 | 1-(3-fluoro-4-(pentyloxy)phenyl)-3-(6-hydroxynicotinoyl)thiourea | HPLC (tR) = 1.80 min MS (APCI) m/z 378.11 [M + H]+ | A |
| 101 | 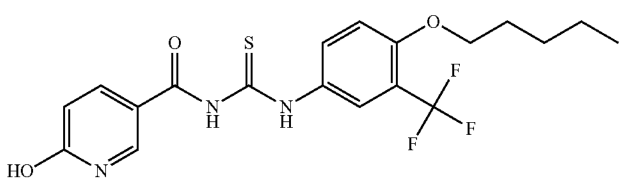 | 1-(6-hydroxynicotinoyl)-3-(4-(pentyloxy)-3-(trifluoromethyl)phenyl)thiourea | HPLC (tR) = 1.97 min MS (APCI) m/z 427.9 [M + H]+ | A |

TABLE II-continued

| CPD # | STRUCTURE | NAME | MS | method |
|---|---|---|---|---|
| 102 | 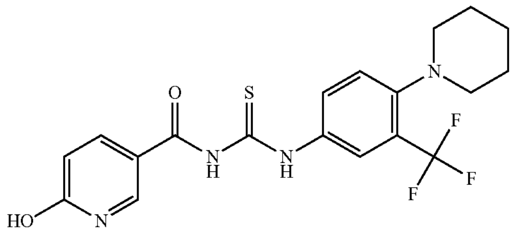 | 1-(6-hydroxynicotinoyl)-3-(4-(piperidin-1-yl)-3-(trifluoromethyl)phenyl)thiourea | HPLC (tR) = 1.96 min MS (APCI) m/z 426.04 [M + H]+ | A |
| 103 | 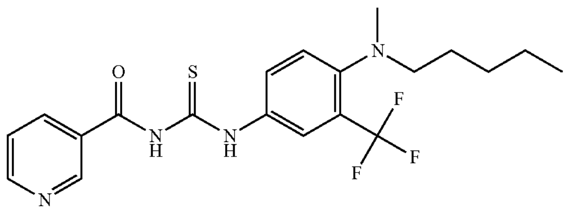 | 1-(4-(methyl(pentyl)amino)-3-(trifluoromethyl)phenyl)-3-nicotinoylthiourea | HPLC (tR) = 2.78 min MS (APCI) m/z 426.01 [M + H]+ | A |
| 104 | 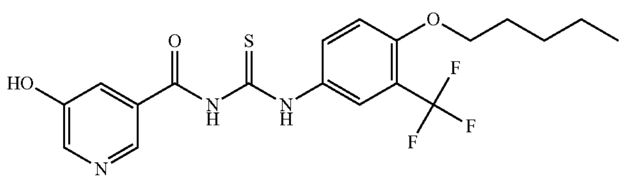 | 1-(5-hydroxynicotinoyl)-3-(4-(pentyloxy)-3-(trifluoromethyl)phenyl)thiourea | HPLC (tR) = 1.81 min MS (APCI) m/z 428.09 [M + H]+ | A |
| 105 | 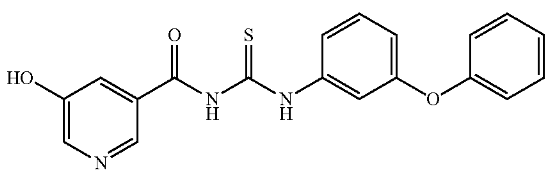 | 1-(5-hydroxynicotinoyl)-3-(3-phenoxyphenyl)thiourea | HPLC (tR) = 1.46 min MS (APCI) m/z 365.97 [M + H]+ | A |
| 106 | 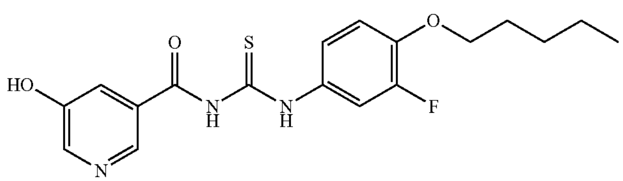 | 1-(3-fluoro-4-(pentyloxy)phenyl)-3-(5-hydroxynicotinoyl)thiourea | HPLC (tR) = 1.66 min MS (APCI) m/z 378.01 [M + H]+ | A |

TABLE II-continued

| CPD # | STRUCTURE | NAME | MS | method |
|---|---|---|---|---|
| 107 | 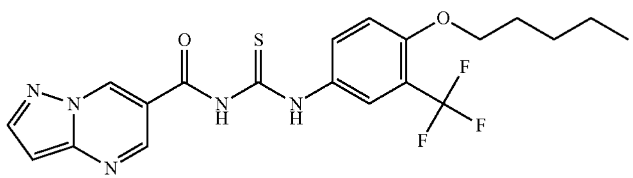 | 1-(4-(pentyloxy)-3-(trifluoromethyl)phenyl)-3-(pyrazolo[1,5-a]pyrimidine-6-carbonyl)thiourea | HPLC (tR) = 2.07 min MS (APCI) m/z 452.01 [M + H]+ | A |
| 108 | 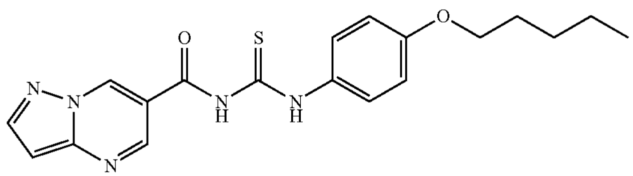 | 1-(4-(pentyloxy)phenyl)-3-(pyrazolo[1,5-a]pyrimidine-6-carbonyl)thiourea | HPLC (tR) = 1.88 min MS (APCI) m/z 384.01 [M + H]+ | A |
| 109 | 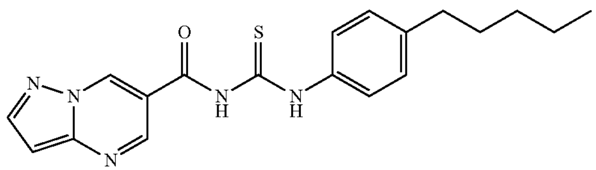 | 1-(4-(pentyl)phenyl)-3-(pyrazolo[1,5-a]pyrimidine-6-carbonyl)thiourea | HPLC (tR) = 2.0 min MS (APCI) m/z 367.88 [M + H]+ | A |
| 110 | 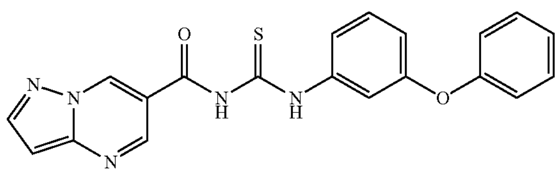 | 1-(3-phenoxyphenyl)-3-(pyrazolo[1,5-a]pyrimidine-6-carbonyl)thiourea | HPLC (tR) = 1.74 min MS (APCI) m/z 389.76 [M + H]+ | A |
| 111 | 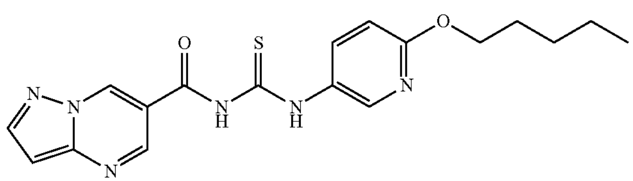 | 1-(6-(pentyloxy)pyridin-3-yl)-3-(pyrazolo[1,5-a]pyrimidine-6-carbonyl)thiourea | HPLC (tR) = 1.73 min MS (APCI) m/z 384.9 [M + H]+ | A |

TABLE II-continued

| CPD # | STRUCTURE | NAME | MS | method |
|---|---|---|---|---|
| 112 | 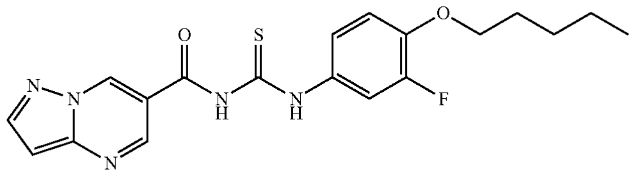 | 1-(3-fluoro-4-(pentyloxy)phenyl)-3-(pyrazolo[1,5-a]pyrimidine-6-carbonyl)thiourea | HPLC (tR) = 1.91 min MS (APCI) m/z 402.0 [M + H]+ | A |
| 113 | 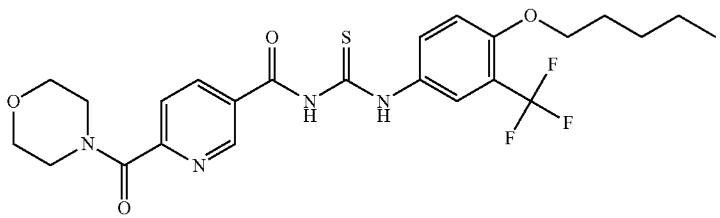 | 1-(6-(morpholine-4-carbonyl)-nicotinoyl)-3-(4-(pentyloxy)-3-(trifluoromethyl)phenyl)thiourea | HPLC (tR) = 2.14 min MS (APCI) m/z 525.12 [M + H]+ | A |
| 114 | 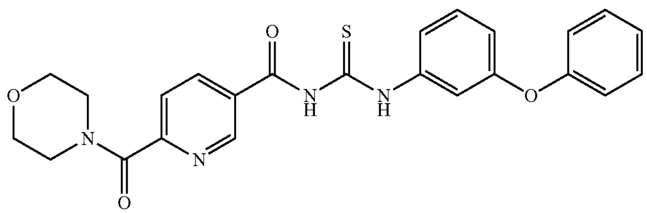 | 1-(6-(morpholine-4-carbonyl)nicotinoyl)-3-(3-phenoxyphenyl)thiourea | HPLC (tR) = 1.72 min MS (APCI) m/z 462.88 [M + H]+ | A |
| 115 | 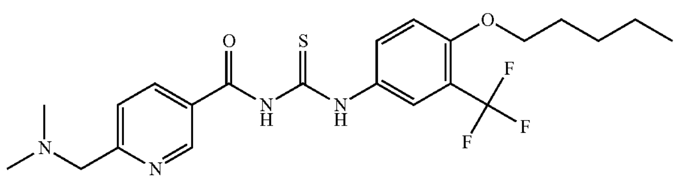 | 1-(6-((dimethylamino)methyl)nicotinoyl)-3-(4-(pentyloxy)-3-(trifluoromethyl)phenyl)thiourea | HPLC (tR) = 1.54 min MS (APCI) m/z 468.81 [M + H]+ | A |
| 116 | 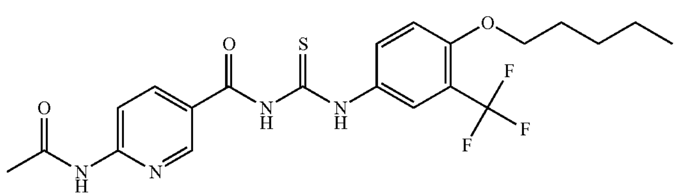 | 1-(6-(acetamidonicotinoyl)-3-(4-(pentyloxy)-3-(trifluoromethyl)phenyl)thiourea | HPLC (tR) = 2.27 min MS (APCI) m/z 470 [M + H]+ | A |

TABLE II-continued

| CPD # | STRUCTURE | NAME | MS | method |
|---|---|---|---|---|
| 117 | 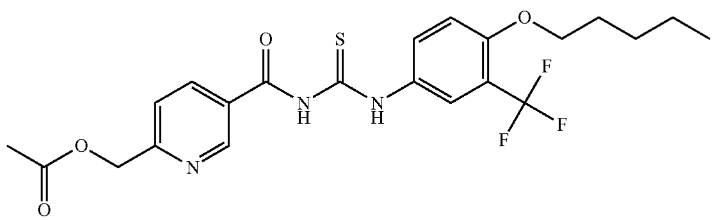 | (5-(3-(4-(pentyloxy)-3-(trifluoromethyl)phenyl)thioureido)carbonyl)pyridin-2-yl)methyl acetate | HPLC (tR) = 2.36 min MS (APCI) m/z 484.11 [M + H]+ | A |
| 118 | 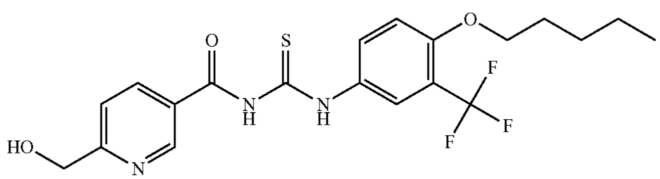 | 1-(6-(hydroxymethyl)nicotinoyl)-3-(4-(pentyloxy)-3-(trifluoromethyl)phenyl)thiourea | HPLC (tR) = 3.30 min MS (APCI) m/z 441.7 [M + H]+ | A |
| 119 | 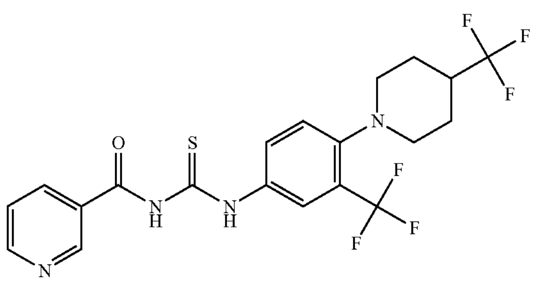 | 1-nicotinoyl-3-(3-(trifluoromethyl)-4-(4-(trifluoromethyl)piperidin-1-yl)phenyl)thiourea | HPLC (tR) = 1.99 min MS (APCI) m/z 477.67 [M + H]+ | A |
| 120 | 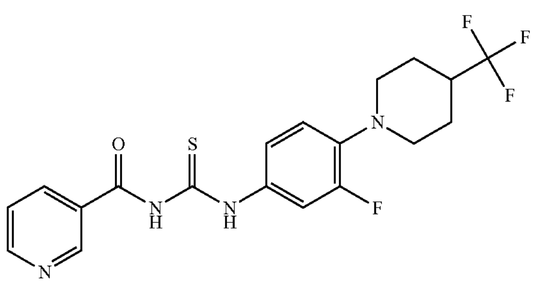 | 1-(3-fluoro-4-(4-(trifluoromethyl)piperidin-1-yl)phenyl)-3-nicotinoylthiourea | HPLC (tR) = 1.61 min MS (APCI) m/z 427.59 [M + H]+ | A |

TABLE II-continued

| CPD # | STRUCTURE | NAME | MS | method |
|---|---|---|---|---|
| 121 | 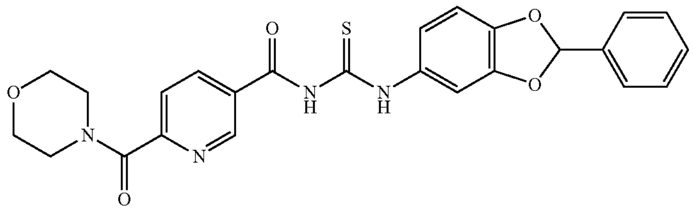 | 1-(6-(morpholine-4-carbonyl)nicotinoyl)-3-(2-phenylbenzo[d][1,3]dioxol-5-yl)thiourea | HPLC (tR) = 1.65 min MS (APCI) m/z 491.7 [M + H]+ | A |
| 122 | 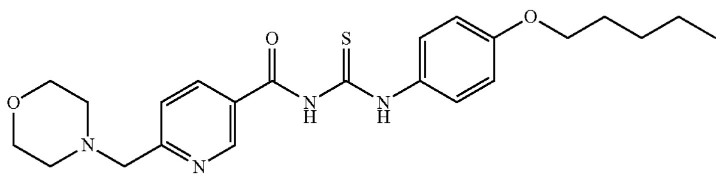 | 1-(6-(morpholinomethyl)nicotinoyl)-3-(4-(pentyloxy)phenyl)thiourea | HPLC (tR) = 1.75 min MS (APCI) m/z 443.1 [M + H]+ | A |
| 123 | 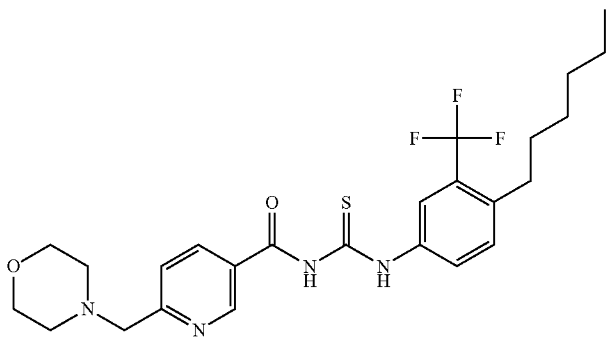 | 1-(6-(morpholinomethyl)nicotinoyl)-3-(4-(pentyloxy)-3-(trifluoromethyl)phenyl)thiourea | HPLC (tR) = 1.78 min MS (APCI) m/z 511.74 [M + H]+ | A |
| 124 | 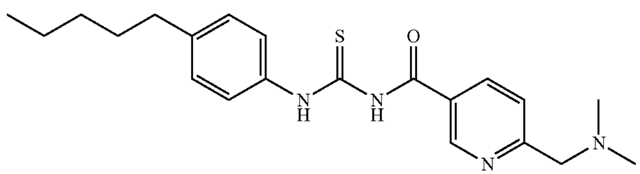 | 1-(6-((dimethylamino)methyl)nicotinoyl)-3-(4-pentylphenyl)thiourea | HPLC (tR) = 1.28 min MS (APCI) m/z 385.35 [M + H]+ | A |

TABLE II-continued

| CPD # | STRUCTURE | NAME | MS | method |
|---|---|---|---|---|
| 125 | 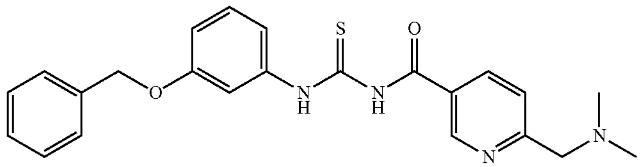 | 1-(3-(benzyloxy)phenyl)-3-(6-((dimethylamino)methyl)nicotinoyl)thiourea | HPLC (tR) = 1.18 min MS (APCI) m/z 421.78 [M + H]+ | A |
| 126 | 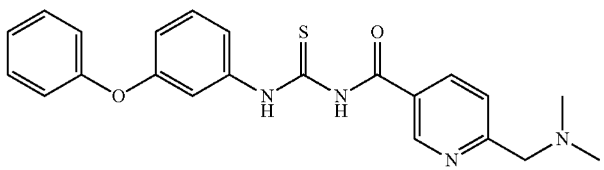 | 1-(6-((dimethylamino)methyl)nicotinoyl)-3-(3-phenoxyphenyl)thiourea | HPLC (tR) = 1.55 min MS (APCI) m/z 407.56 [M + H]+ | A |
| 127 | 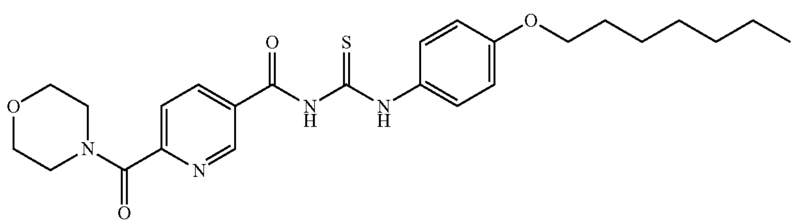 | 1-(4-(heptyloxy)phenyl)-3-(6-(morpholine-4-carbonyl)nicotinoyl)thiourea | HPLC (tR) = 2.29 min MS (APCI) m/z 485.68 [M + H]+ | A |
| 128 | 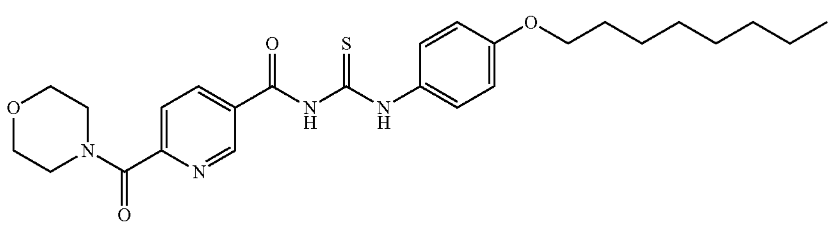 | 1-(6-(morpholine-4-carbonyl)nicotinoyl)-3-(4-(octyloxy)phenyl)thiourea | HPLC (tR) = 2.37 min MS (APCI) m/z 499.77 [M + H]+ | A |
| 129 | 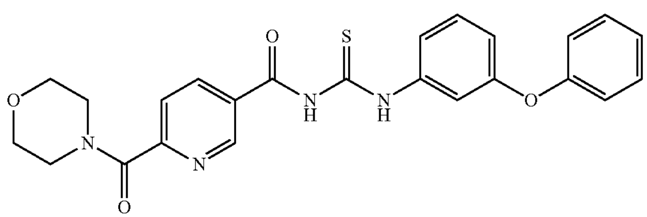 | 1-(6-(morpholine-4-carbonyl)nicotinoyl)-3-(3-phenoxyphenyl)thiourea | HPLC (tR) = 1.66 min MS (APCI) m/z 463.61 [M + H]+ | A |

TABLE II-continued

| CPD # | STRUCTURE | NAME | MS | method |
|---|---|---|---|---|
| 130 | 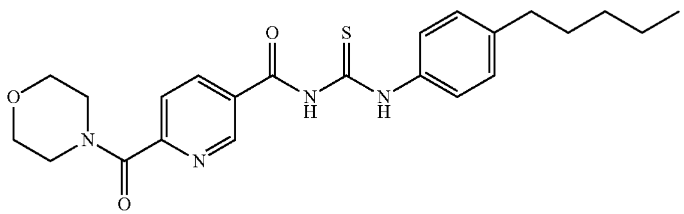 | 1-(6-(morpholine-4-carbonyl)nicotinoyl)-3-(4-pentylphenyl)thiourea | HPLC (tR) = 2.01 min MS (APCI) m/z 441.59 [M + H]+ | A |
| 131 | 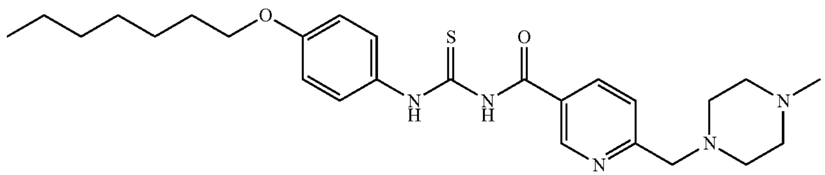 | 1-(4-(heptyloxy)phenyl)-3-(6-((4-methylpiperazin-1-yl)methyl)nicotinoyl)thiourea | HPLC (tR) = 2.29 min MS (APCI) m/z 484.64 [M + H]+ | A |
| 132 | 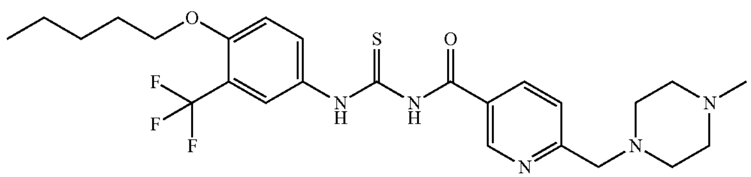 | 1-(6-((4-methylpiperazin-1-yl)methyl)nicotinoyl)-3-(4-(pentyloxy)-3-(trifluoromethyl)phenyl)thiourea | HPLC (tR) = 2.71 min MS (APCI) m/z 524.83 [M + H]+ | A |
| 133 | 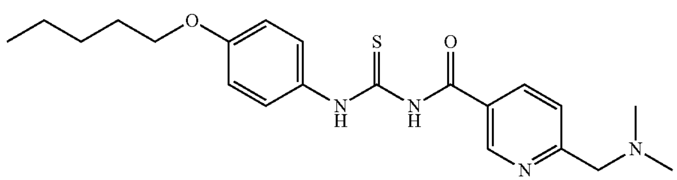 | 1-(6-((dimethylamino)methyl)nicotinoyl)-3-(4-(pentyloxy)phenyl)thiourea | HPLC (tR) = 1.61 min MS (APCI) m/z 401.64 [M + H]+ | A |
| 134 | 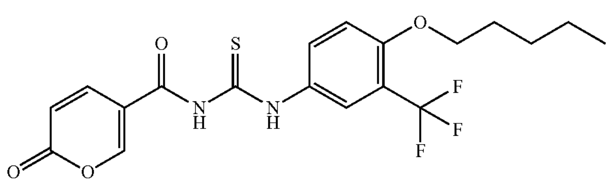 | 1-(2-oxo-2H-pyran-5-carbonyl)-3-(4-(pentyloxy)-3-(trifluoromethyl)phenyl)thiourea | HPLC (tR) = 3.46 min MS (APCI) m/z 429.42 [M + H]+ | B |

TABLE II-continued

| CPD # | STRUCTURE | NAME | MS | method |
|---|---|---|---|---|
| 135 | 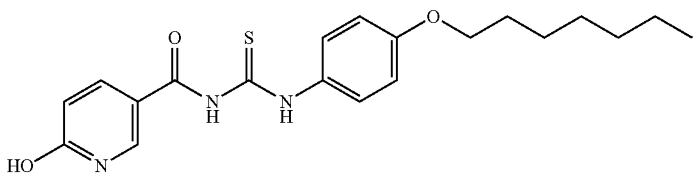 | 1-(4-(heptyloxy)phenyl)-3-(6-hydroxynicotinoyl)thiourea | HPLC (tR) = 2.49 min MS (APCI) m/z 388.6 [M + H]+ | B |
| 136 | 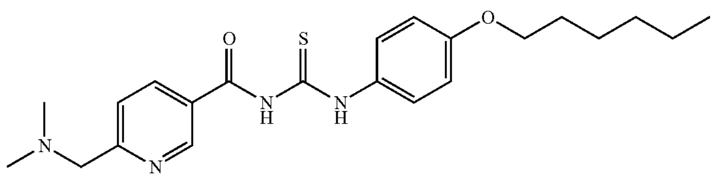 | 1-(6-((dimethylamino)methyl)nicotinoyl)-3-(4-(hexyloxy)phenyl)thiourea (APCI) m/z | HPLC (tR) = 2.90 min MS (APCI) m/z 415.7 | B |
| 137 | 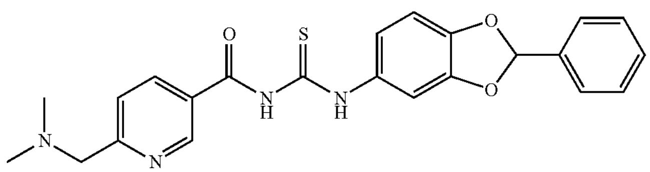 | 1-(6-((dimethylamino)methyl)nicotinoyl)-3-(2-phenylbenzo[d][1,3]dioxol-5-yl)thiourea | HPLC (tR) = 1.16 min MS (APCI) m/z 435.65 [M + H]+ | A |
| 138 | 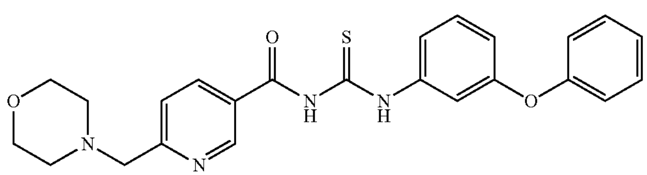 | 1-(6-(morpholinomethyl)nicotinoyl)-3-(3-phenoxyphenyl)thiourea | HPLC (tR) = 2.11 min MS (APCI) m/z 449.54 [M + H]+ | B |
| 139 | 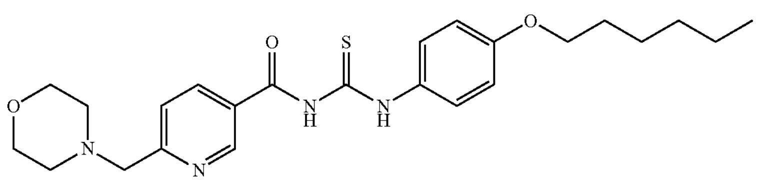 | 1-(4-(hexyloxy)phenyl)-3-(6-(morpholinomethyl)nicotinoyl)thiourea | HPLC (tR) = 2.44 min MS (APCI) m/z 457.63 [M + H]+ | B |

TABLE II-continued

| CPD # | STRUCTURE | NAME | MS | method |
|---|---|---|---|---|
| 140 | 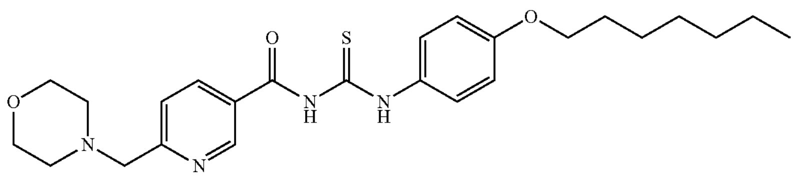 | 1-(4-(heptyloxy)phenyl)-3-(6-(morpholinomethyl)nicotinoyl)thiourea | HPLC (tR) = 2.61 min MS (APCI) m/z 471.41 [M + H]+ | B |
| 141 | 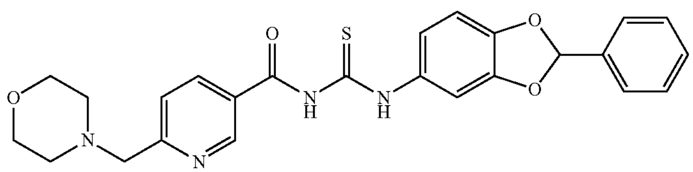 | 1-(6-(morpholinomethyl)nicotinoyl)-3-(2-phenylbenzo[d][1,3]dioxol-5-yl)thiourea | HPLC (tR) = 2.10 min MS (APCI) m/z 477.58 [M + H]+ | B |
| 142 | 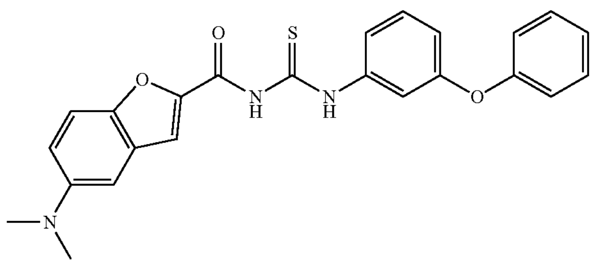 | 1-(5-(dimethylamino)benzofuran-2-carbonyl)-3-(3-phenoxyphenyl)thiourea | HPLC (tR) = 1.49 min MS (APCI) m/z 432.1 [M + H]+ | A |
| 143 | 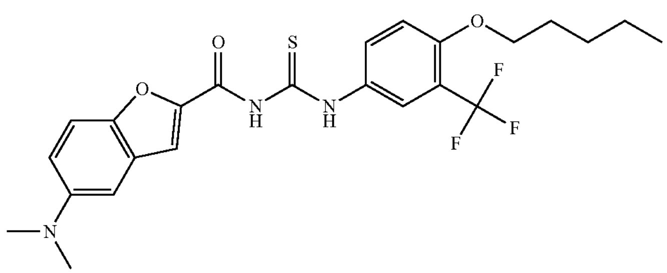 | 1-(5-(dimethylamino)benzofuran-2-carbonyl)-3-(4-(pentyloxy)-3-(trifluoromethyl)phenyl)thiourea | HPLC (tR) = 1.83 min MS (APCI) m/z 493.54 [M + H]+ | A |

TABLE II-continued

| CPD # | STRUCTURE | NAME | MS | method |
|---|---|---|---|---|
| 144 | 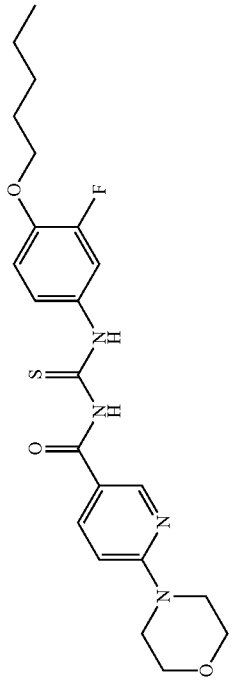 | 1-(3-fluoro-4-(pentyloxy)phenyl)-3-(6-morpholinonicotinoyl)thiourea | HPLC (tR) = 2.08 min MS (APCI) m/z 447.23 [M + H]+ | A |
| 145 | 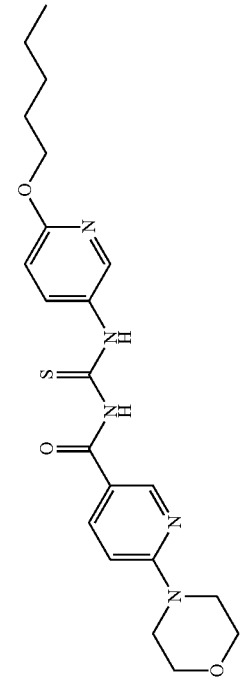 | 1-(6-morpholinonicotinoyl)-3-(6-(pentyloxy)pyridin-3-yl)thiourea | HPLC (tR) = 1.87 min MS (APCI) m/z 430.04 [M + H]+ | A |
| 146 | 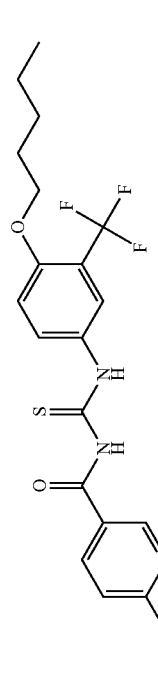 | 1-(6-cyanonicotinoyl)-3-(4-(pentyloxy)-3-(trifluoromethyl)phenyl)thiourea | HPLC (tR) = 2.38 min MS (APCI) m/z 437.12 [M + H]+ | A |
| 147 | 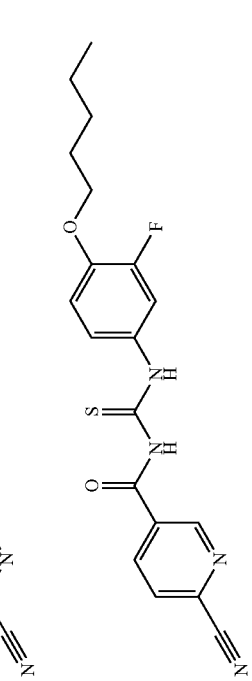 | 1-(6-cyanonicotinoyl)-3-(3-fluoro-4-(pentyloxy)phenyl)thiourea | HPLC (tR) = 2.21 min MS (APCI) m/z 387.07 [M + H]+ | A |

TABLE II-continued

| CPD # | STRUCTURE | NAME | MS | method |
|---|---|---|---|---|
| 148 | 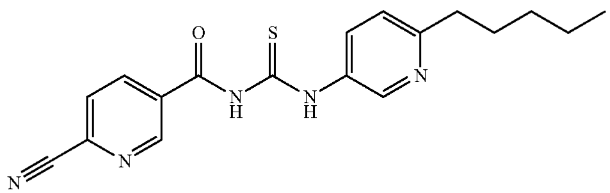 | 1-(6-cyanonicotinoyl)-3-(6-pentylpyridin-3-yl)thiourea | HPLC (tR) = 2.06 min MS (APCI) m/z 354.02 [M + H]+ | A |
| 149 | 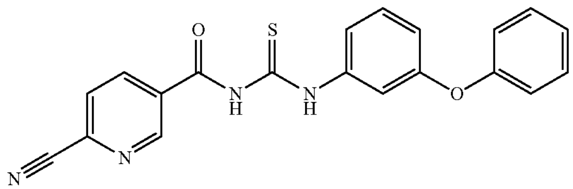 | 1-(6-cyanonicotinoyl)-3-(3-phenoxyphenyl)thiourea | HPLC (tR) = 2.01 min MS (APCI) m/z 375.02 [M + H]+ | A |
| 150 | 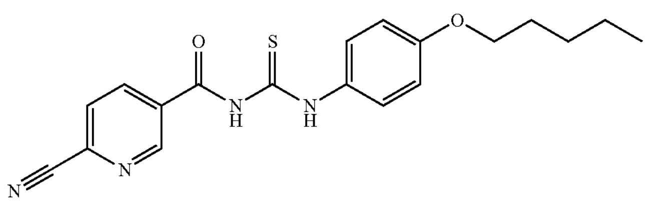 | 1-(6-cyanonicotinoyl)-3-(4-pentyloxyphenyl)thiourea | HPLC (tR) = 2.23 min MS (APCI) m/z 369.12 [M + H]+ | A |
| 151 | 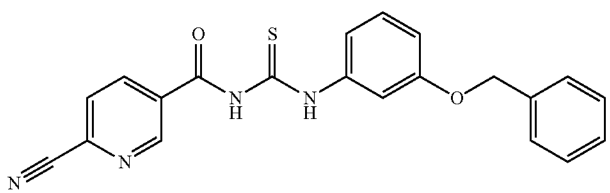 | 1-(3-(benzyloxy)phenyl)-3-(6-cyanonicotinoyl)thiourea | HPLC (tR) = 2.01 min MS (APCI) m/z 389.08 [M + H]+ | A |
| 152 | 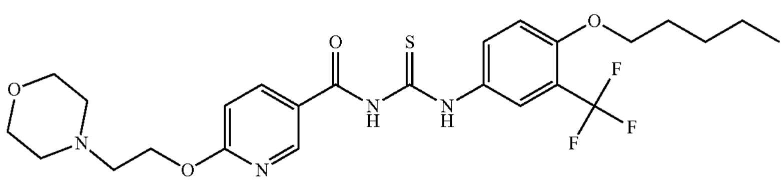 | 1-(6-(2-morpholinoethoxy)nicotinoyl)-3-(4-(pentyloxy)-3-(trifluoromethyl)phenyl)thiourea | HPLC (tR) = 1.65 min MS (APCI) m/z 541.06 [M + H]+ | A |

TABLE II-continued

| CPD # | STRUCTURE | NAME | MS | method |
|---|---|---|---|---|
| 153 | 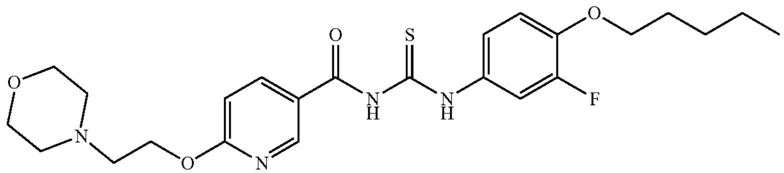 | 1-(3-fluoro-4-(pentyloxy)phenyl)-3-(6-(2-morpholinoethoxy)nicotinoyl)thiourea | HPLC (tR) = 1.51 min MS (APCI) m/z 491.07 [M + H]+ | A |
| 154 | 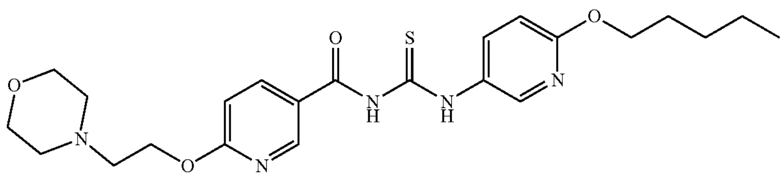 | 1-(6-(2-morpholinoethoxy)nicotinoyl)-3-(6-(pentyloxy)pyridin-3-yl)thiourea | HPLC (tR) = 1.38 min MS (APCI) m/z 474.14 [M + H]+ | A |
| 155 | 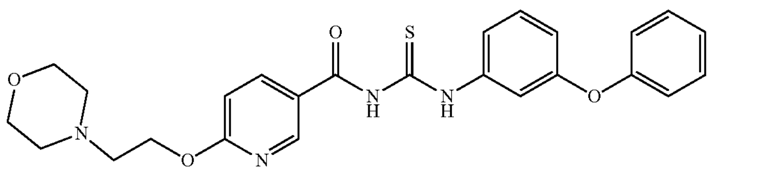 | 1-(6-(2-morpholinoethoxy)nicotinoyl)-3-(3-phenoxyphenyl)thiourea | HPLC (tR) = 1.37 min MS (APCI) m/z 479.39 [M + H]+ | A |
| 156 | 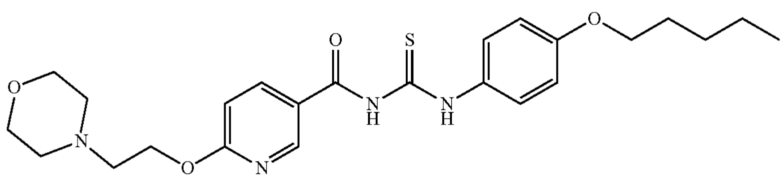 | 1-(6-(2-morpholinoethoxy)nicotinoyl)-3-(4-(pentyloxy)phenyl)thiourea | HPLC (tR) = 1.50 min MS (APCI) m/z 473.2 [M + H]+ | A |
| 157 | 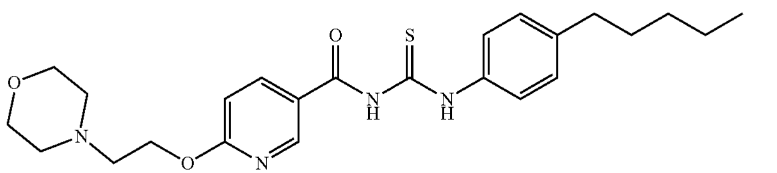 | 1-(6-(2-morpholinoethoxy)nicotinoyl)-3-(4-pentylphenyl)thiourea | HPLC (tR) = 1.59 min MS (APCI) m/z 457.14 [M + H]+ | A |

TABLE II-continued

| CPD # | STRUCTURE | NAME | MS | method |
|---|---|---|---|---|
| 158 | 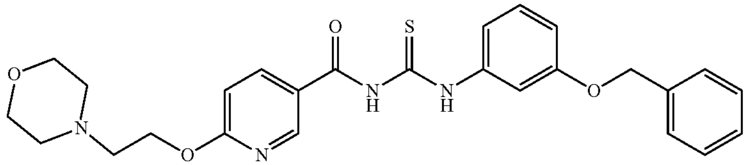 | 1-(3-(benzyloxy)phenyl)-3-(6-(2-morpholinoethoxy)nicotinoyl)thiourea | HPLC (tR) = 1.38 min MS (APCI) m/z 493.13 [M + H]+ | A |
| 159 | 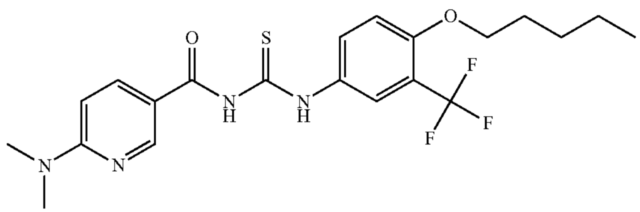 | 1-(6-(dimethylamino)nicotinoyl)-3-(4-(pentyloxy)-3-(trifluoromethyl)phenyl)thiourea | HPLC (tR) = 1.57 min MS (APCI) m/z 455.14 [M + H]+ | A |
| 160 | 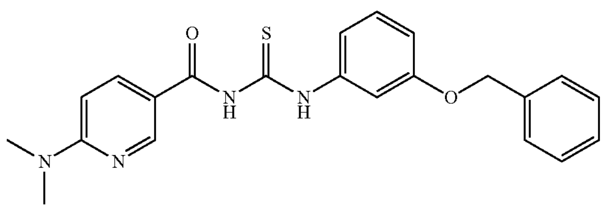 | 1-(3-(benzyloxy)phenyl)-3-(6-(dimethylamino)nicotinoyl)thiourea | HPLC (tR) = 1.30 MS (APCI) m/z 407.14 [M + H]+ | A |
| 161 | 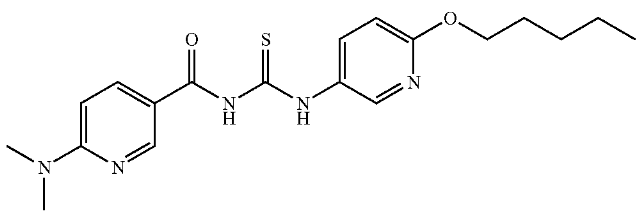 | 1-(6-(dimethylamino)nicotinoyl)-3-(6-(pentyloxy)pyridin-3-yl)thiourea | HPLC (tR) = 1.32 min MS (APCI) m/z 388.21 [M + H]+ | A |
| 162 | 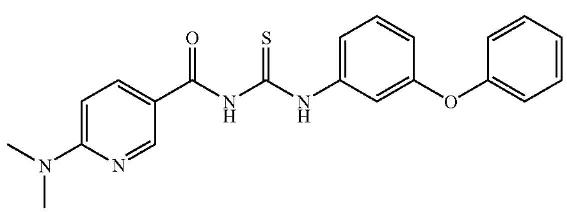 | 1-(6-(dimethylamino)nicotinoyl)-3-(3-phenoxyphenyl)thiourea | HPLC (tR) = 1.30 min MS (APCI) m/z 393.09 [M + H]+ | A |

TABLE II-continued

| CPD # | STRUCTURE | NAME | MS | method |
|---|---|---|---|---|
| 163 | 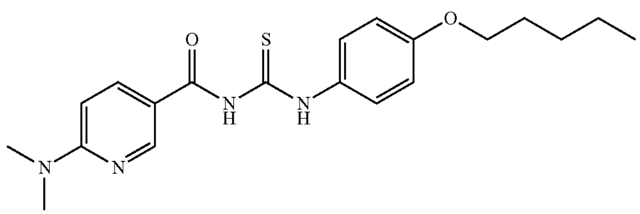 | 1-(6-(dimethylamino)nicotinoyl)-3-(4-(pentyloxy)phenyl)thiourea | HPLC (tR) = 1.43 min MS (APCI) m/z 387.16 [M + H]+ | A |
| 164 | 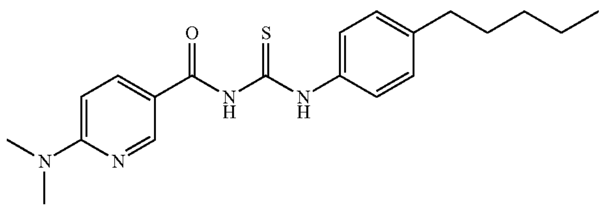 | 1-(6-(dimethylamino)nicotinoyl)-3-(4-pentylphenyl)thiourea | HPLC (tR) = 1.50 min MS (APCI) m/z 371.15 [M + H]+ | A |
| 165 | 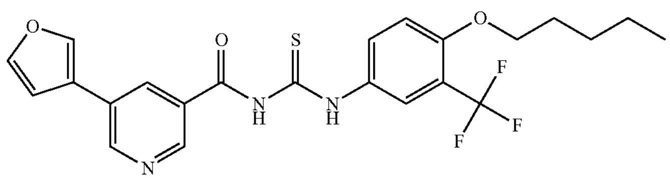 | 1-(5-(furan-3-yl)nicotinoyl)-3-(4-(pentyloxy)-3-(trifluoromethyl)phenyl)thiourea | HPLC (tR) = 2.33 min MS (APCI) m/z 478.05 [M + H]+ | A |
| 166 | 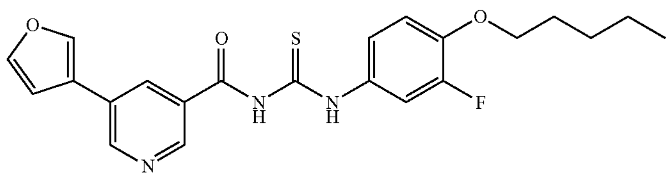 | 1-(3-fluoro-4-(pentyloxy)phenyl)-3-(5-(furan-3-yl)nicotinoyl)thiourea | HPLC (tR) = 2.20 min MS (APCI) m/z 428.09 [M + H]+ | A |
| 167 | 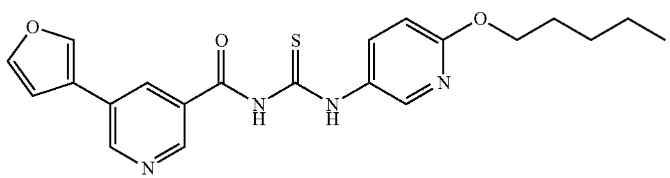 | 1-(5-(furan-3-yl)nicotinoyl)-3-(6-(pentyloxy)pyridin-3-yl)thiourea | HPLC (tR) = 2.04 min MS (APCI) m/z 411.07 [M + H]+ | A |

TABLE II-continued

| CPD # | STRUCTURE | NAME | MS | method |
|---|---|---|---|---|
| 168 | 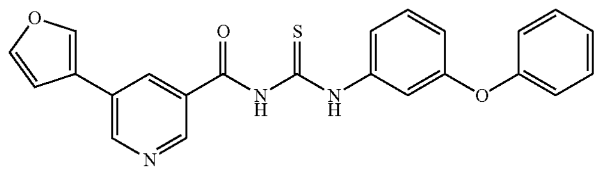 | 1-(5-(furan-3-yl)nicotinoyl)-3-(3-phenoxyphenyl)thiourea | HPLC (tR) = 2.01 min MS (APCI) m/z 416.07 [M + H]+ | A |
| 169 | 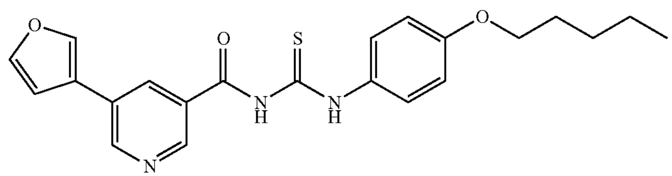 | 1-(5-(furan-3-yl)nicotinoyl)-3-(4-(pentyloxy)phenyl)thiourea | HPLC (tR) = 2.20 min MS (APCI) m/z 410.12 [M + H]+ | A |
| 170 | 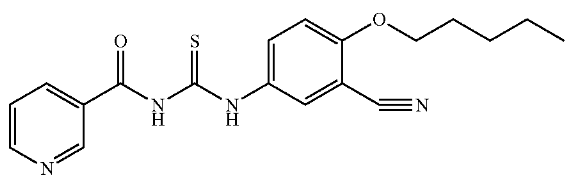 | 1-(3-cyano-4-(pentyloxy)phenyl)-3-nicotinoylthiourea | HPLC (tR) = 1.71 min MS (APCI) m/z 369.16 [M + H]+ | A |
| 171 | 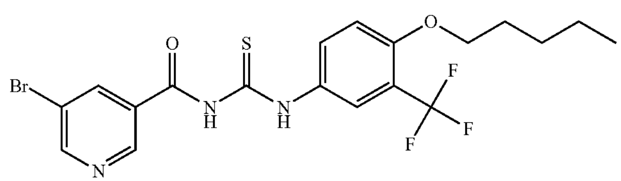 | 1-(5-bromonicotinoyl)-3-(4-(pentyloxy)-3-(trifluoromethyl)phenyl)thiourea | HPLC (tR) = 2.26 min MS (APCI) m/z 491.99 [M + H]+ | A |
| 172 | 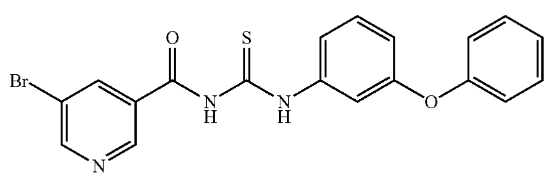 | 1-(5-bromonicotinoyl)-3-(3-phenoxyphenyl)thiourea | HPLC (tR) = 2.20 min MS (APCI) m/z 430.05 [M + H]+ | A |

TABLE II-continued

| CPD # | STRUCTURE | NAME | MS | method |
|---|---|---|---|---|
| 173 | 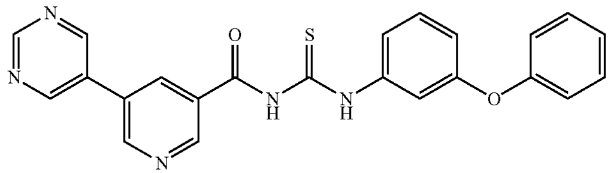 | 1-(3-phenoxyphenyl)-3-(5-pyrimidin-5-yl)nicotinoyl)thiourea | HPLC (tR) = 1.73 min MS (APCI) m/z 428.05 [M + H]+ | A |
| 174 | 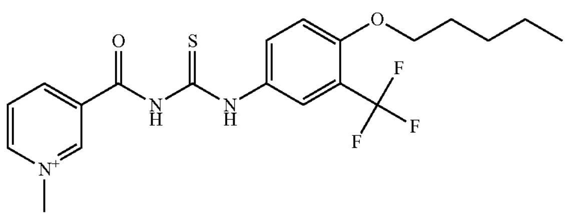 | | HPLC (tR) = 1.38 min MS (APCI) m/z 426.0 [M + H]+ | A |
| 175 | 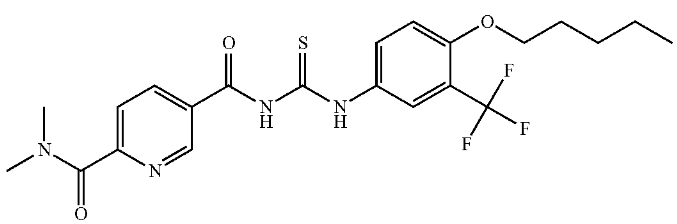 | 1-(6-(dimethylcarbamoyl)nicotinoyl)-3-(4-(pentyloxy)-3-(trifluoromethyl)phenyl)thiourea | HPLC (tR) = 2.08 min MS (APCI) m/z 483.0 [M + H]+ | A |
| 176 | 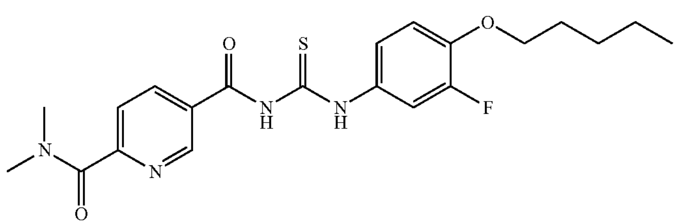 | 1-(6-(dimethylcarbamoyl)nicotinoyl)-3-(3-fluoro-4-(pentyloxy)phenyl)thiourea | HPLC (tR) = 1.96 min MS (APCI) m/z 433.11 [M + H]+ | A |

TABLE II-continued

| CPD # | STRUCTURE | NAME | MS | method |
|---|---|---|---|---|
| 177 | 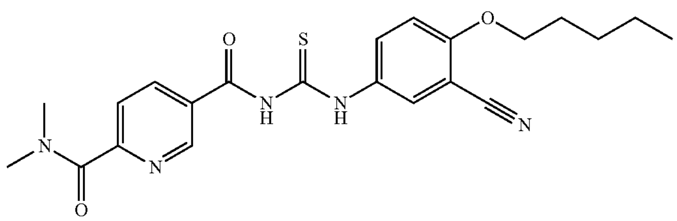 | 1-(3-cyano-4-(pentyloxy)phenyl)-3-(6-(dimethylcarbamoyl)nicotinoyl)thiourea | HPLC (tR) = 1.78 min MS (APCI) m/z 440.14 [M + H]+ | A |
| 178 | 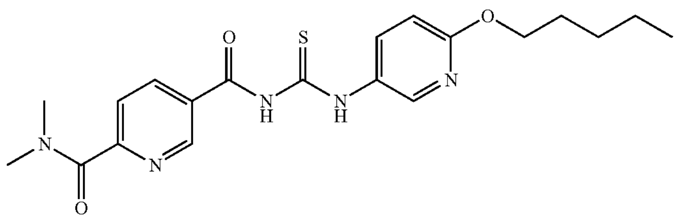 | 1-(6-(dimethylcarbamoyl)nicotinoyl)-3-(6-(pentyloxy)pyridin-3-yl)thiourea | HPLC (tR) = 1.77 min MS (APCI) m/z 416.17 [M + H]+ | A |
| 179 | 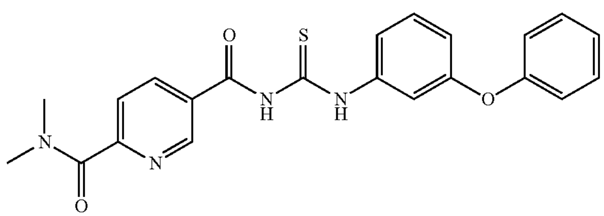 | 1-(6-(dimethylcarbamoyl)nicotinoyl)-3-(3-phenoxyphenyl)thiourea | HPLC (tR) = 1.71 min MS (APCI) m/z 421.15 [M + H]+ | A |
| 180 | 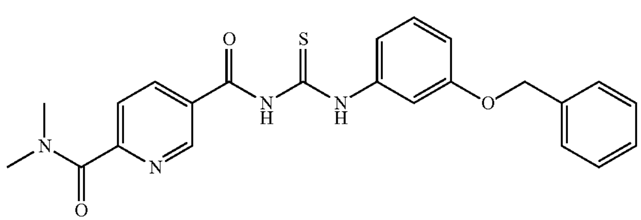 | 1-(3-(benzyloxy)phenyl)-3-(6-(dimethylcarbamoyl)nicotinoyl)thiourea | HPLC (tR) = 1.76 min MS (APCI) m/z 435.1 [M + H]+ | A |

TABLE II-continued

| CPD # | STRUCTURE | NAME | MS | method |
|---|---|---|---|---|
| 181 | 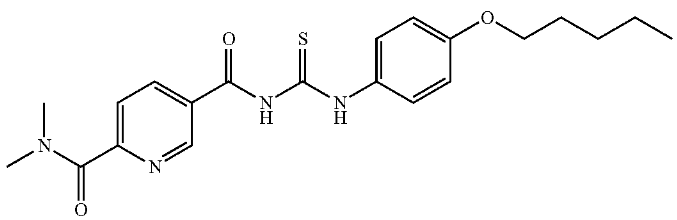 | 1-(6-(dimethylcarbamoyl)nicotinoyl)-3-(4-(pentyloxy)phenyl)thiourea | HPLC (tR) = 1.95 min MS (APCI) m/z 415.22 [M + H]+ | A |
| 182 | 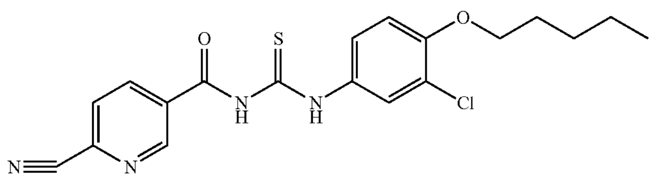 | 1-3-chloro-4-(pentyloxy)phenyl)-3-(6-cyanonicotinoyl)thiourea | HPLC (tR) = 2.09 min MS (APCI) m/z 402.95 [M + H]+ | A |
| 183 | 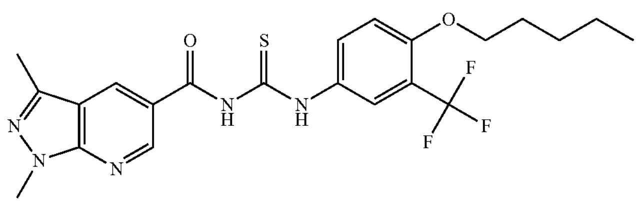 | 1-(1,3-dimethyl-1H-pyrazolo[3,4-b]pyridine-5-carbonyl)-3-(4-(pentyloxy)-3-(trifluoromethyl)phenyl)thiourea | HPLC (tR) = 2.56 min MS (APCI) m/z 479.81 [M + H]+ | A |
| 184 | 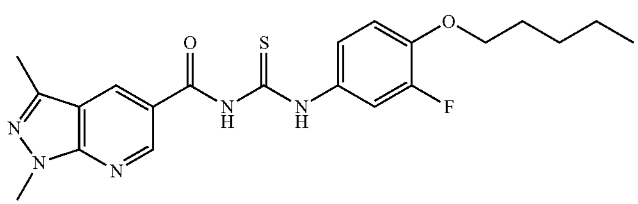 | 1-(1,3-dimethyl-1H-pyrazolo[3,4-b]pyridine-5-carbonyl)-3-(3-fluoro-4-(pentyloxy)phenyl)thiourea | HPLC (tR) = 2.40 min MS (APCI) m/z 430.00 [M + H]+ | A |
| 185 | 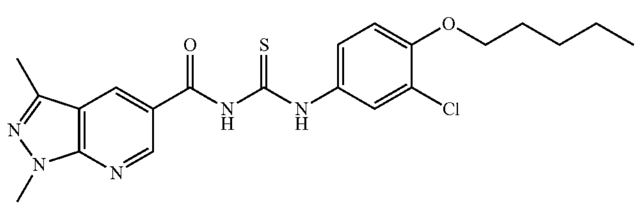 | 1-(3-chloro-4-(pentyloxy)phenyl)-3-(1,3-dimethyl-1H-pyrazolo[3,4-b]pyridine-5-carbonyl)thiourea | HPLC (tR) = 2.59 min MS (APCI) m/z 446.43 [M + H]+ | A |

TABLE II-continued

| CPD # | STRUCTURE | NAME | MS | method |
|---|---|---|---|---|
| 186 | 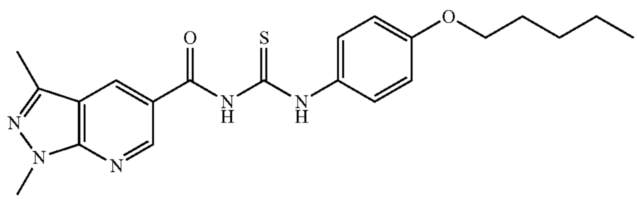 | 1-(1,3-dimethyl-1H-pyrazolo[3,4-b]pyridine-5-carbonyl)-3-(4-(pentyloxy)phenyl)thiourea | HPLC (tR) = 2.40 min MS (APCI) m/z 411.83 [M + H]+ | A |
| 187 | 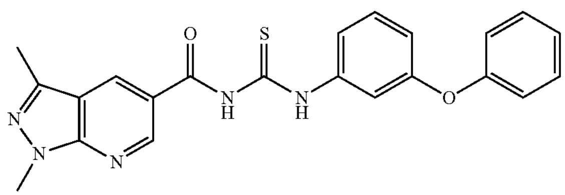 | 1-(1,3-dimethyl-1H-pyrazolo[3,4-b]pyridine-5-carbonyl)-3-(3-phenoxyphenyl)thiourea | HPLC (tR) = 2.17 min MS (APCI) m/z 417.94 [M + H]+ | A |
| 188 | 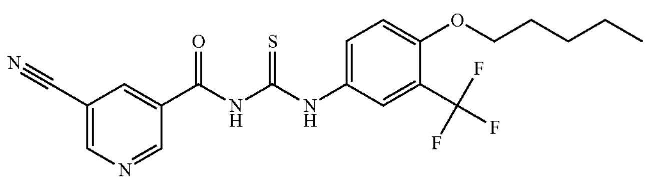 | 1-(5-cyanonicotinoyl)-3-(4-(pentyloxy)-3-(trifluoromethyl)phenyl)thiourea | HPLC (tR) = 2.32 min MS (APCI) m/z 437.50 [M + H]+ | B |
| 189 | 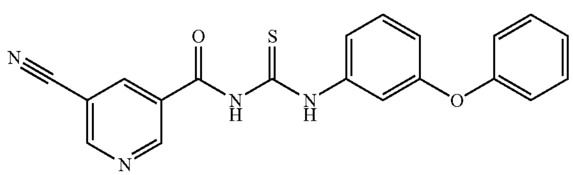 | 1-(5-cyanonicotinoyl)-3-(3-phenoxyphenyl)thiourea | HPLC (tR) = 1.96 min MS (APCI) m/z 375.21 [M + H]+ | B |
| 190 | 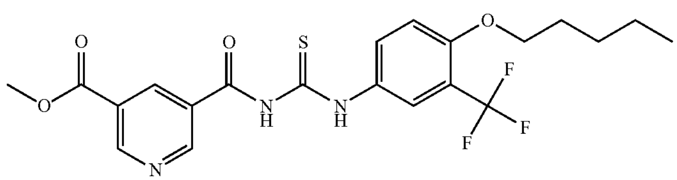 | methyl 5-((3-(4-(pentyloxy)-3-(trifluoromethyl)phenyl)thioureido)carbonyl)nicotinate | HPLC (tR) = 4.55 min MS (APCI) m/z 470.26 [M + H]+ | A |

TABLE II-continued

| CPD # | STRUCTURE | NAME | MS | method |
|---|---|---|---|---|
| 191 | 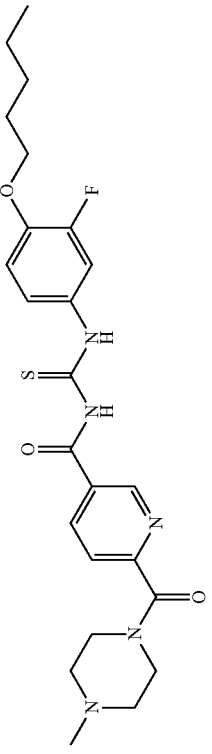 | 1-(3-fluoro-4-(pentyloxy)phenyl)-3-(6-(1-methylpiperazine-4-carbonyl)nicotinoyl)thiourea | HPLC (tR) = 1.30 min MS (APCI) m/z 488.2 [M + H]+ | A |
| 192 | 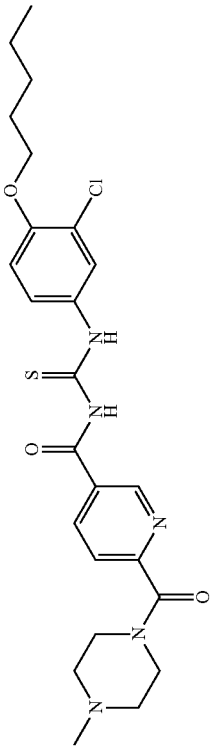 | 1-(3-chloro-4-(pentyloxy)phenyl)-3-(6-(1-methylpiperazine-4-carbonyl)nicotinoyl)thiourea | HPLC (tR) = 1.37 min MS (APCI) m/z 504.1 [M + H]+ | A |
| 193 | 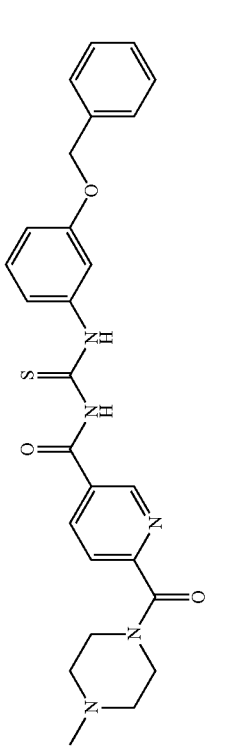 | 1-(3-(benzyloxy)phenyl)-3-(6-(1-methylpiperazine-4-carbonyl)nicotinoyl)thiourea | HPLC (tR) = 1.16 min MS (APCI) m/z 490.0 [M + H]+ | A |
| 194 | 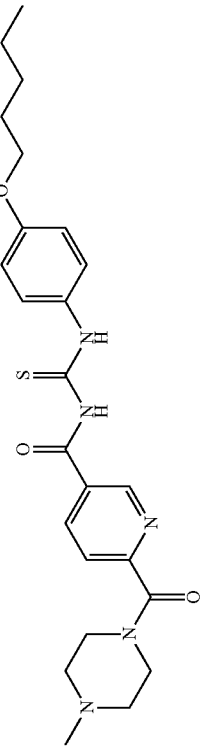 | 1-(6-(1-methylpiperazine-4-carbonyl)nicotinoyl)-3-(4-(pentyloxy)phenyl)thiourea | HPLC (tR) = 1.27 min MS (APCI) m/z 470.2 [M + H]+ | A |

TABLE II-continued

| CPD # | STRUCTURE | NAME | MS | method |
|---|---|---|---|---|
| 195 | 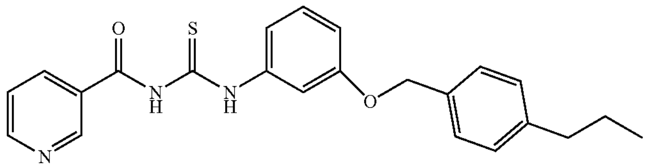 | 1-(3-(4-propylbenzyloxy)phenyl)-3-nicotinoylthiourea | HPLC (tR) = 1.94 min MS (APCI) m/z 406 [M + H]+ | A |
| 196 | 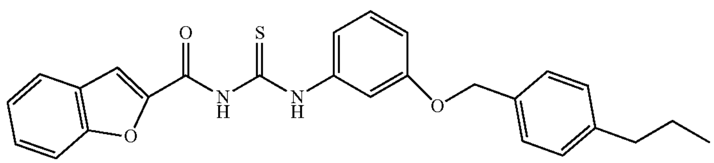 | 1-(3-(4-propylbenzyloxy)phenyl)-3-(benzofuran-2-carbonyl)thiourea | HPLC (tR) = 2.63 min MS m/z 446 [M + H]+ | A |
| 197 | 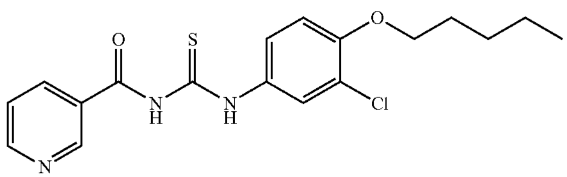 | 1-(3-chloro-4-(pentyloxy)phenyl)-3-nicotinoylthiourea | HPLC (tR) = 1.97 min MS m/z 378; 380 [M + H]+ | A |
| 198 | 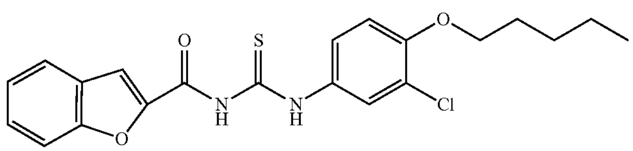 | 1-(benzofuran-2-carbonyl)-3-(3-chloro-4-(pentyloxy)phenyl)thiourea | HPLC (tR) = 2.58 min MS m/z 417, 419 [M + H]+ | A |
| 199 | 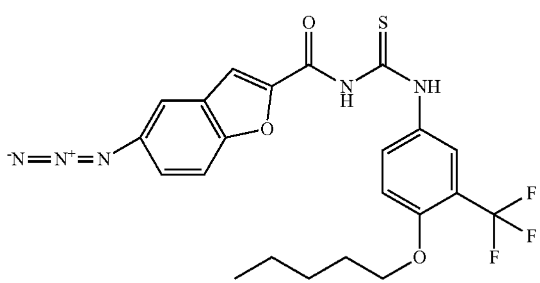 | 1-(5-azidobenzofuran-2-carbonyl)-3-(4-(pentyloxy)-3-(trifluoromethyl)phenyl)thiourea | HPLC (tR) = 2.5 min MS (APCI) m/z 492.08 [M + H]+ | A |

TABLE III

| CPD # | STRUCTURE | NAME | MS | method |
|---|---|---|---|---|
| 200 | 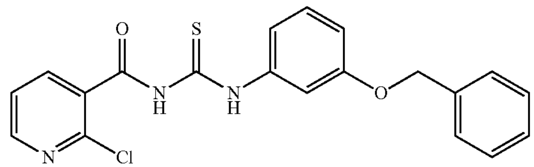 | 1-(3-(benzyloxy)phenyl)-3-(2-chloronicotinoyl)thiourea | HPLC (tR) = 2.00 min MS (APCI) m/z 398.1 [M + H]+ | A |
| 201 | 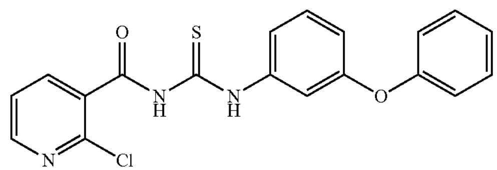 | 1-(2-chloronicotinoyl)-3-(3-phenoxyphenyl)thiourea | HPLC (tR) = 1.13 min MS (APCI) m/z 364 [M + H]+ | B |
| 202 | 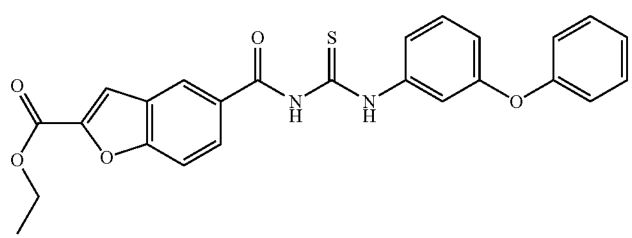 | ethyl 5-((3-(3-phenoxyphenyl)thioureido)carbonyl)benzofuran-2-carboxylate | HPLC (tR) = 2.25 min MS (APCI) m/z 384.1 [M + H]+ | A |
| 203 | 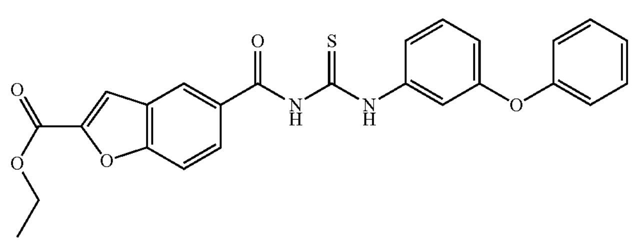 | ethyl 5-((3-(3-phenoxyphenyl)thioureido)carbonyl)benzofuran-2-carboxylate | HPLC (tR) = 2.59 min MS (APCI) m/z 461.62 [M + H]+ | A |

TABLE III-continued

| CPD # | STRUCTURE | NAME | MS | method |
|---|---|---|---|---|
| 204 | 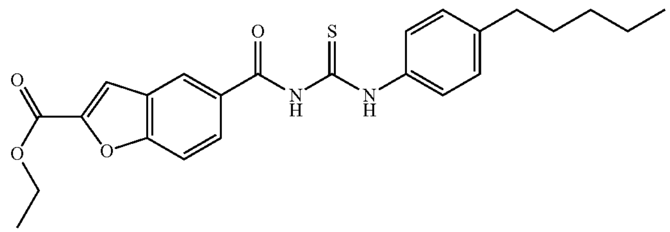 | ethyl 5-((3-(4-pentylphenyl)thioureido)carbonyl)benzofuran-2-carboxylate | HPLC (tR) = 2.57 min MS (APCI) m/z 439.66 [M + H]+ | A |
| 205 | 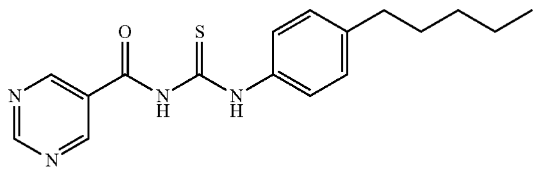 | 1-(4-pentylphenyl)-3-(pyrimidine-5-carbonyl)thiourea | HPLC (tR) = 2.17 min MS (APCI) m/z 329.49 [M + H]+ | A |
| 206 | 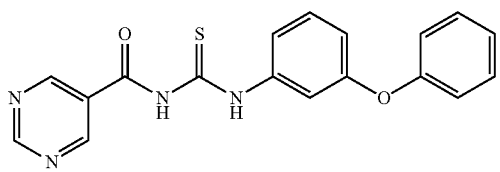 | 1-(3-phenoxyphenyl)-3-(pyrimidine-5-carbonyl)thiourea | HPLC (tR) = 1.77 min MS (APCI) m/z 351.46 [M + H]+ | A |
| 207 | 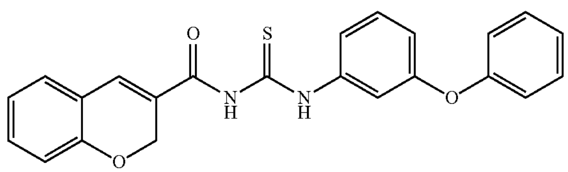 | 1-(2H-chromene-3-carbonyl)-3-(3-phenoxyphenyl)thiourea | HPLC (tR) = 2.57 min MS (APCI) m/z 403.1 [M + H]+ | A |
| 208 | 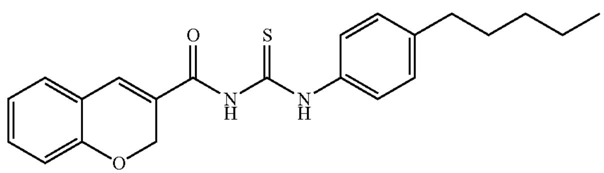 | 1-(2H-chromene-3-carbonyl)-3-(4-pentylphenyl)thiourea | HPLC (tR) = 2.85 min MS (APCI) m/z 417.2 [M + H]+ | A |

TABLE III-continued

| CPD # | STRUCTURE | NAME | MS | method |
|---|---|---|---|---|
| 209 | 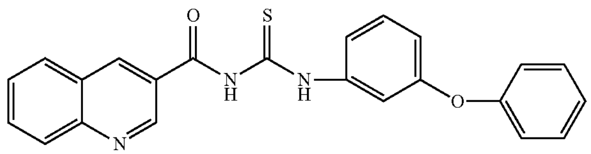 | 1-(3-phenoxyphenyl)-3-(quinoline-3-carbonyl)thiourea | HPLC (tR) = 2.13 min MS (APCI) m/z 400 [M + H]+ | B |
| 210 | 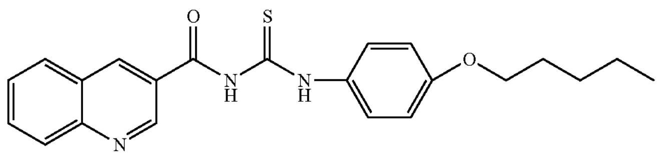 | 1-(4-(pentyloxy)phenyl)-3-(quinoline-3-carbonyl)thiourea | HPLC (tR) = 2.33 min MS (APCI) m/z 394 [M + H]+ | B |
| 211 | 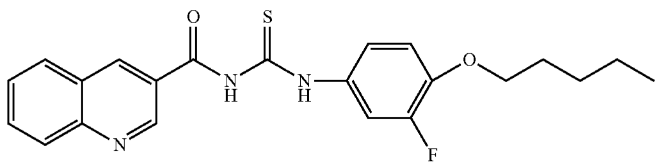 | 1-(3-fluoro-4-(pentyloxy)phenyl)-3-(quinoline-3-carbonyl)thiourea | HPLC (tR) = 2.35 min MS (APCI) m/z 412 [M + H]+ | B |
| 212 | 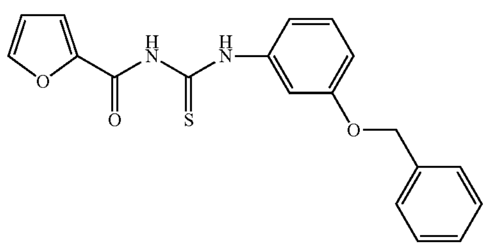 | 1-(3-(benzyloxy)phenyl)-3-(furan-2-carbonyl)thiourea | HPLC (tR) = 1.86 min MS (APCI) min 353 [M + H]+ | B |
| 213 | 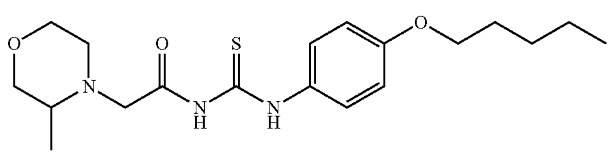 | 1-(2-(3-methylmorpholino)acetyl)-3-(4-(pentyloxy)phenyl)thiourea | HPLC (tR) = 1.39 min MS (APCI) m/z 380.62 [M + H]+ | A |

TABLE III-continued

| CPD # | STRUCTURE | NAME | MS | method |
|---|---|---|---|---|
| 214 | 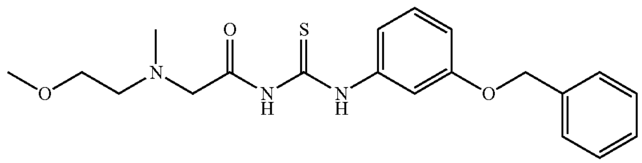 | 1-(3-(benzyloxy)phenyl)-3-(2-((2-methoxyethyl)(methyl)amino)acetyl)thiourea | HPLC (tR) = 5.89 min MS (APCI) m/z 388.1 [M + H]+ | B |
| 215 | 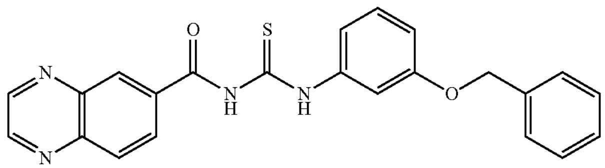 | 1-(3-(benzyloxy)phenyl)-3-(quinoxaline-7-carbonyl)thiourea | HPLC (tR) = 2.02 min MS (APCI) m/z 415.2 [M + H]+ | A |
| 216 | 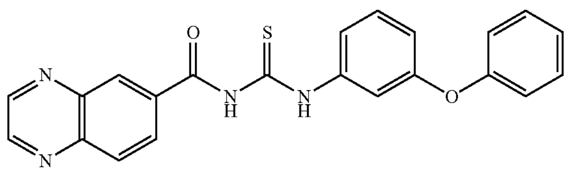 | 1-(3-phenoxyphenyl)-3-(quinoxaline-7-carbonyl)thiourea | HPLC (tR) = 2.36 min MS (APCI) m/z 400.98 [M + H]+ | A |
| 217 | 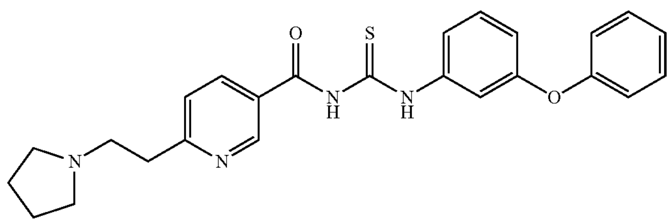 | 1-(3-phenoxyphenyl)-3-(6-(2-(pyrrolidin-1-yl)ethyl)nicotinoyl)thiourea | HPLC (tR) = 1.42 min MS (APCI) m/z 447.3 [M + H]+ | A |
| 218 | 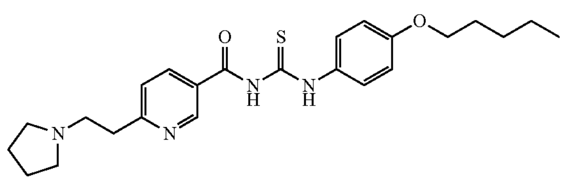 | 1-(4-(pentyloxy)phenyl)-3-(6-(2-(pyrrolidin-1-yl)ethyl)nicotinoyl)thiourea | HPLC (tR) = 1.87 min MS (APCI) m/z 441.3 [M + H]+ | A |

TABLE III-continued

| CPD # | STRUCTURE | NAME | MS | method |
|---|---|---|---|---|
| 219 | 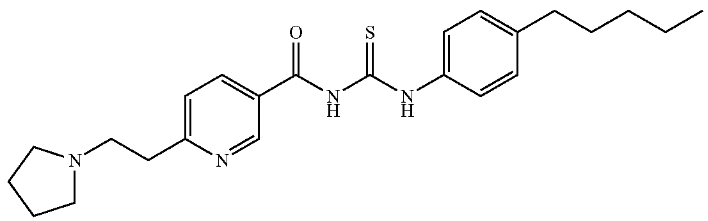 | 1-(4-pentylphenyl)-3-(6-(2-(pyrrolidin-1-yl)ethyl)nicotinoyl)thiourea | HPLC (tR) = 1.92 min MS (APCI) m/z 425.3 [M + H]+ | A |
| 220 | 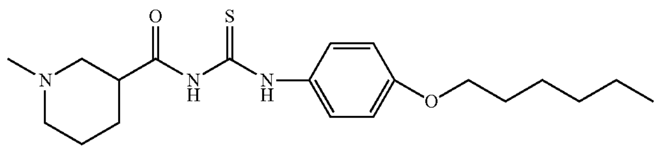 | 1-(4-(hexyloxy)phenyl)-3-(1-methylpiperidine-5-carbonyl)thiourea | HPLC (tR) = 1.24 min MS (APCI) m/z 362 [M − Me]+ | B |
| 221 | 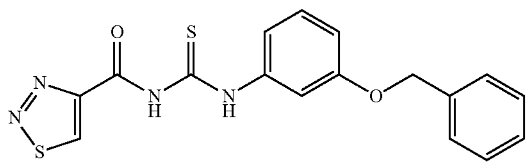 | 1-(3-(benzyloxy)phenyl)-3-(1,2,3-thiadiazole-4-carbonyl)thiourea | HPLC (tR) = 1.92 min MS (APCI) m/z 371 [M + H]+ | A |
| 222 | 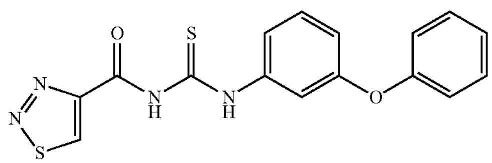 | 1-(3-phenoxyphenyl)-3-(1,2,3-thiadiazole-4-carbonyl)thiourea | HPLC (tR) = 1.92 min MS (APCI) m/z 357 [M + H]+ | A |
| 223 | 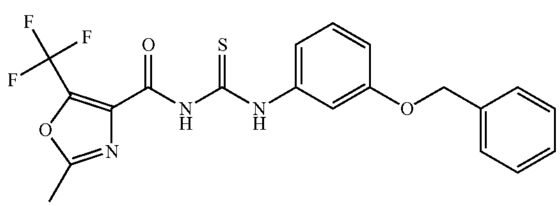 | 1-(3-(benzloxy)phenyl)-3-(2-methyl-5-(trifluoromethyl)oxazole-4-carbonyl)thiourea | HPLC (tR) = 2.20 min MS (APCI) m/z 436 [M + H]+ | A |

TABLE III-continued

| CPD # | STRUCTURE | NAME | MS | method |
|---|---|---|---|---|
| 224 | 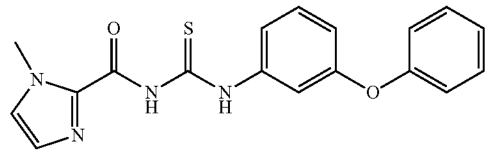 | 1-(1-methyl-1H-imidazole-2-carbonyl)-3-(3-phenoxyphenyl)thiourea | HPLC (tR) = 1.97 min MS (APCI) m/z 353 [M + H]+ | A |
| 225 | 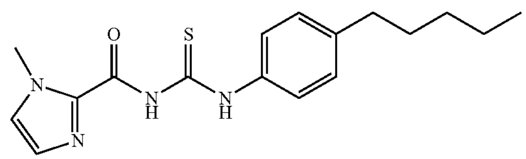 | 1-(1-methyl-1H-imidazole-2-carbonyl)-3-(4-pentylphenyl)thiourea | HPLC (tR) = 2.30 min MS (APCI) m/z 331 [M + H]+ | A |
| 226 | 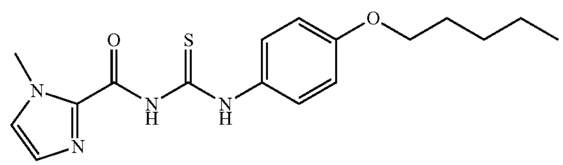 | 1-(1-methyl-1H-imidazole-2-carbonyl)-3-(4-pentylphenyl)thiourea | HPLC (tR) = 2.17 min MS (APCI) m/z 347 [M + H]+ | A |
| 227 | 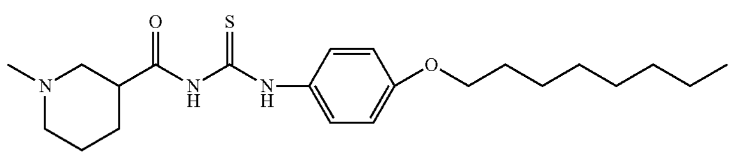 | 1-(1-methylpiperidine-3-carbonyl)-3-(4-(octyloxy)phenyl)thiourea | HPLC (tR) = 1.58 min MS (APCI) m/z 406 [M + H]+ | B |
| 228 | 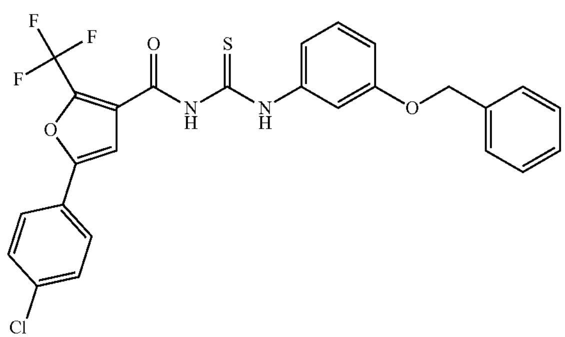 | 1-(3-(benzyloxy)phenyl)-3-(2-(4-chlorophenyl)-5-(trifluoromethyl)furan-4-carbonyl)thiourea | HPLC (tR) = 3.09 min MS (APCI) m/z 531 [M + H]+ | A |

TABLE III-continued

| CPD # | STRUCTURE | NAME | MS | method |
|---|---|---|---|---|
| 229 | 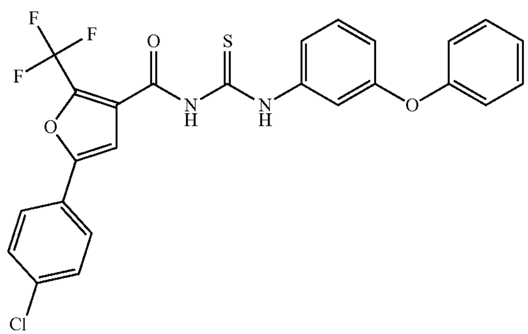 | 1-(2-(4-chlorophenyl)-5-(trifluoromethyl)furan-4-carbonyl)-3-(3-phenoxyphenyl)thiourea | HPLC (tR) = 3.14 min MS (APCI) m/z 517 [M + H]+ | A |
| 230 | 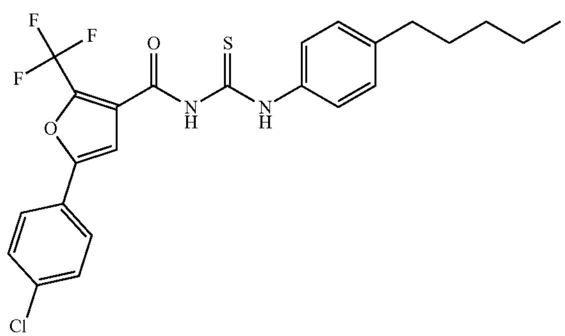 | 1-(2-(4-chlorophenyl)-5-(trifluoromethyl)furan-4-carbonyl)-3-(4-pentylphenyl)thiourea | HPLC (tR) = 2.93 min MS (APCI) m/z 495 [M + H]+ | A |
| 231 | 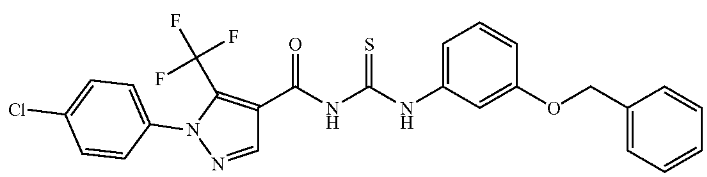 | 1-(3-(benzyloxy)phenyl)-3-(1-(4-chlorophenyl)-5-(trifluoromethyl)-1H-pyrazole-4-carbonyl)thiourea | HPLC (tR) = 2.57 min MS (APCI) m/z 531 [M + H]+ | A |
| 232 | 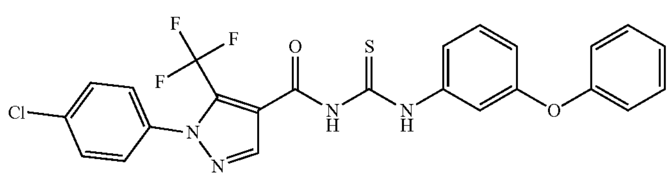 | 1-(1-(4-chlorophenyl)-5-(trifluoromethyl)-1H-pyrazole-4-carbonyl)-3-(3-phenoxyphenyl)thiourea | HPLC (tR) = 2.59 min MS (APCI) m/z 517 [M + H]+ | A |

| CPD # | STRUCTURE | NAME | MS | method |
|---|---|---|---|---|
| 233 | 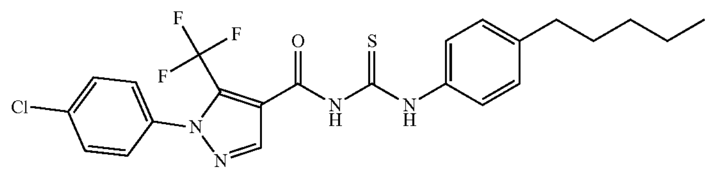 | 1-(1-(4-chlorophenyl)-5-(trifluoromethyl)-1H-pyrazole-4-carbonyl)-3-(4-pentylphenyl)thiourea | HPLC (tR) = 3.10 min MS (APCI) m/z 495 [M + H]+ | A |
| 234 | 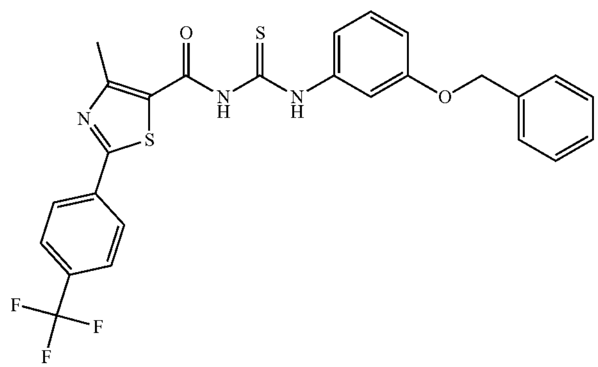 | 1-(3-(benzyloxy)phenyl)-3-(4-methyl-2-(4-(trifluoromethyl)phenyl)thiazole-5-carbonyl)thiourea | HPLC (tR) = 3.09 min MS (APCI) m/z 528 [M + H]+ | A |
| 235 | 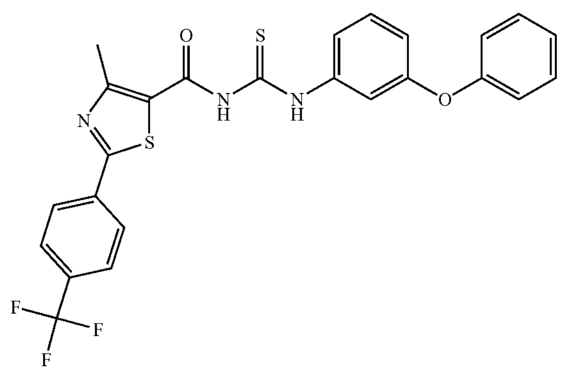 | 1-(4-methyl-2-(4-(trifluoromethyl)phenyl)thiazole-5-carbonyl)-3-(3-phenoxyphenyl)thiourea | HPLC (tR) = 3.13 min MS (APCI) m/z 514 [M + H]+ | A |

TABLE III-continued

| CPD # | STRUCTURE | NAME | MS | method |
|---|---|---|---|---|
| 236 | 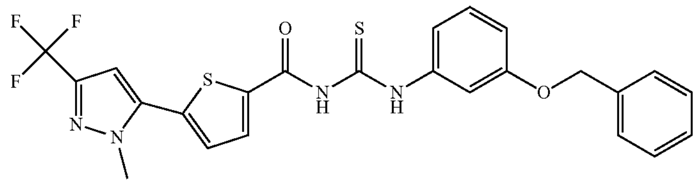 | 1-(3-(benzyloxy)phenyl)-3-(2-(1-methyl-3-(trifluoromethyl)-1H-pyrazol-5-yl)thiophene-5-carbonyl)thiourea | HPLC (tR) = 2.71 min MS (APCI) m/z 517 [M + H]+ | A |
| 237 | 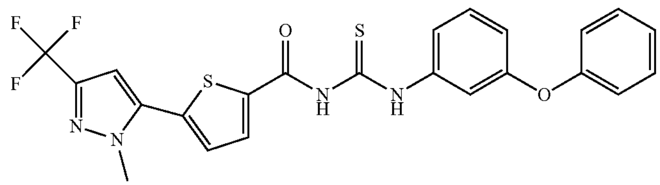 | 1-(2-(1-methyl-3-(trifluoromethyl)-1H-pyrazol-5-yl)thiophene-5-carbonyl)-3-(3-phenoxyphenyl)thiourea | HPLC (tR) = 2.75 min MS (APCI) m/z 503 [M + H]+ | A |
| 238 | 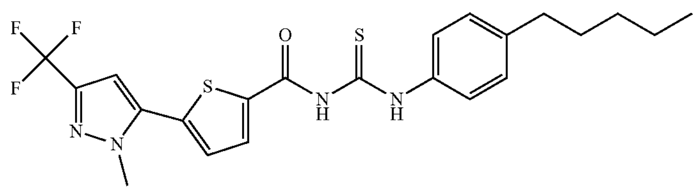 | 1-(2-(1-methyl-3-(trifluoromethyl)-1H-pyrazol-5-yl)thiophene-5-carbonyl)-3-(4-pentylphenyl)thiourea | HPLC (tR) = 3.44 min MS (APCI) m/z 481 [M + H]+ | A |
| 239 | 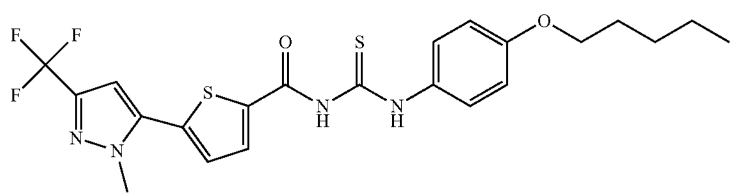 | 1-(2-(1-methyl-3-(trifluoromethyl)-1H-pyrazol-5-yl)thiophene-5-carbonyl)-3-(4-(pentyloxy)phenyl)thiourea | HPLC (tR) = 3.07 min MS (APCI) m/z 497 [M + H]+ | A |

TABLE III-continued

| CPD # | STRUCTURE | NAME | MS | method |
|---|---|---|---|---|
| 240 | 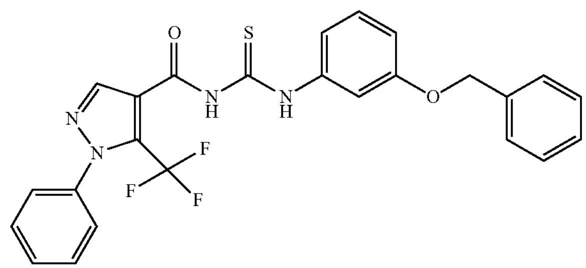 | 1-(3-(benzyloxy)phenyl)-3-(1-phenyl-5-(trifluoromethyl)-1H-pyrazole-4-carbonyl)thiourea | HPLC (tR) = 2.37 min MS (APCI) m/z 497 [M + H]+ | A |
| 241 | 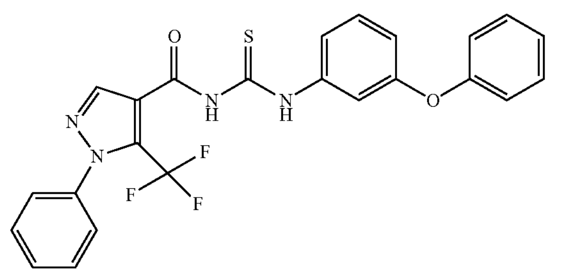 | 1-(3-phenoxyphenyl)-3-(1-phenyl-5-(trifluoromethyl)-1H-pyrazole-4-carbonyl)thiourea | HPLC (tR) = 2.38 min MS (APCI) m/z 483 [M + H]+ | A |
| 242 | 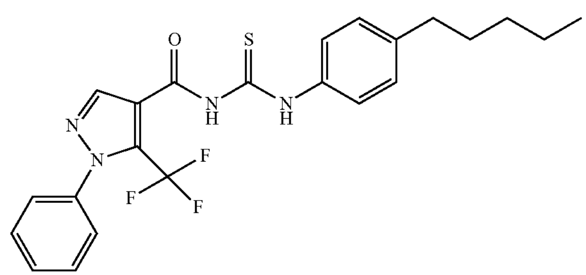 | 1-(4-pentylphenyl)-3-(1-phenyl-5-(trifluoromethyl)-1H-pyrazole-4-carbonyl)thiourea | HPLC (tR) = 2.90 min MS (APCI) m/z 461 [M + H]+ | A |

TABLE III-continued

| CPD # | STRUCTURE | NAME | MS | method |
|---|---|---|---|---|
| 243 | 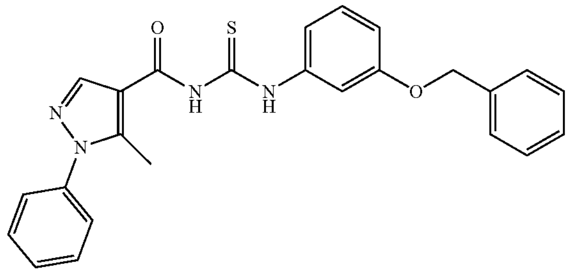 | 1-(3-(benzyloxy)phenyl)-3-(5-methyl-1-phenyl-1H-pyrazole-4-carbonyl)thiourea | HPLC (tR) = 2.34 min MS (APCI) m/z 443 [M + H]+ | A |
| 244 | 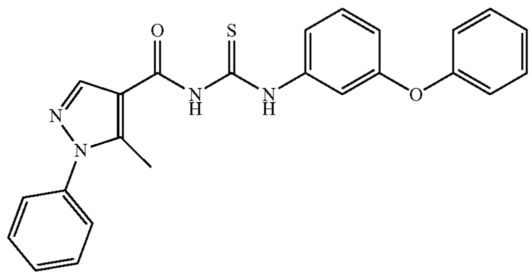 | 1-(5-methyl-1-phenyl-1H-pyrazole-4-carbonyl)-3-(3-phenoxyphenyl)thiourea | HPLC (tR) = 2.37 min MS (APCI) m/z 429 [M + H]+ | A |
| 245 | 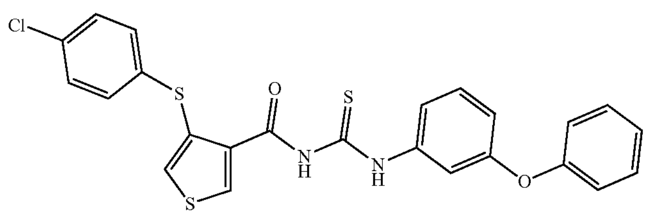 | 1-(3-(4-chlorophenylthio)thiophene-4-carbonyl)-3-(3-phenoxyphenyl)thiourea | HPLC (tR) = 3.04 min MS (APCI) m/z 499 [M + 2]+ | A |
| 246 | 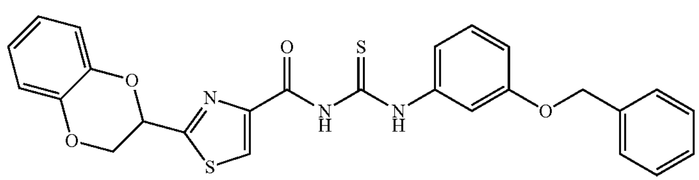 | 1-(3-(benzyloxy)phenyl)-3-(2-(2,3-dihydrobenzo[b][1,4]dioxin-2-yl)thiazole-4-carbonyl)thiourea | HPLC (tR) = 2.74 min MS (APCI) m/z 504 [M + H]+ | A |

| CPD # | STRUCTURE | NAME | MS | method |
|---|---|---|---|---|
| 247 | 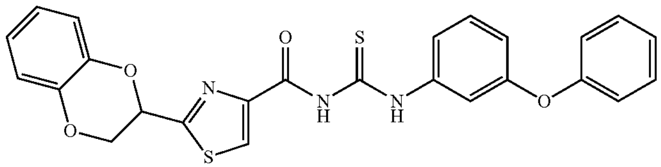 | 1-(3-(benzyloxy)phenyl)-3-(2-(2,3-dihydrobenzo[b][1,4]dioxin-2-yl)thiazole-4-carbonyl)thiourea | HPLC (tR) = 2.73 min MS (APCI) m/z 490 [M + H]+ | A |
| 248 | 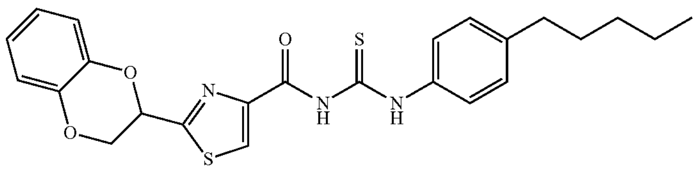 | 1-(2-(2,3-dihydrobenzo[b][1,4]dioxin-2-yl)thiazole-4-carbonyl)-3-(4-pentylphenyl)thiourea | HPLC (tR) = 3.31 min MS (APCI) m/z 468 [M + H]+ | A |
| 249 | 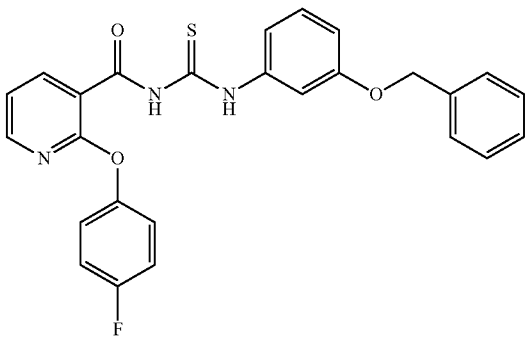 | 1-(3-(benzyloxy)phenyl)-3-(2-(4-fluorophenoxy)nicotinoyl)thiourea | HPLC (tR) = 2.46 min MS (APCI) m/z 474 [M + H]+ | A |
| 250 | 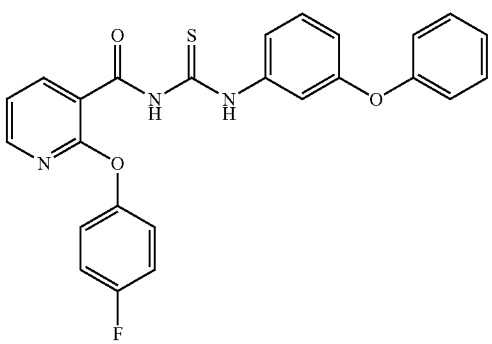 | 1-(2-(4-fluorophenoxy)nicotinoyl)-3-(3-phenoxyphenyl)thiourea | HPLC (tR) = 2.52 min MS (APCI) m/z 460 [M + H]+ | A |

TABLE III-continued

| CPD # | STRUCTURE | NAME | MS | method |
|---|---|---|---|---|
| 251 | 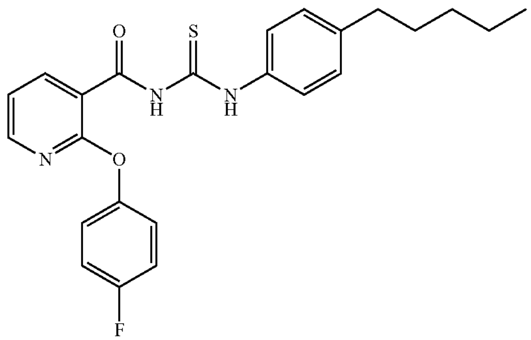 | 1-(2-(4-fluorophenoxy)nicotinoyl)-3-(4-pentylphenyl)thiourea | HPLC (tR) = 3.06 min MS (APCI) m/z 438 [M + H]+ | A |
| 252 | 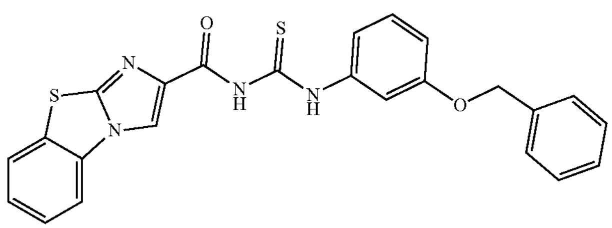 | | HPLC (tR) = 2.70 min MS (APCI) m/z 459 [M + H]+ | A |
| 253 | 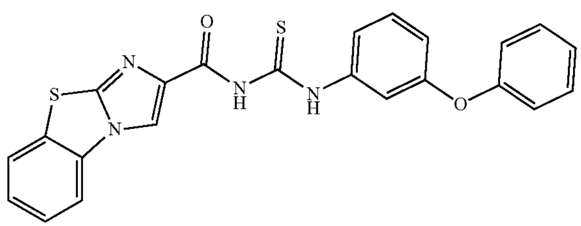 | | HPLC (tR) = 2.77 min MS (APCI) m/z 445 [M + H]+ | A |

TABLE III-continued

| CPD # | STRUCTURE | NAME | MS | method |
|---|---|---|---|---|
| 254 | 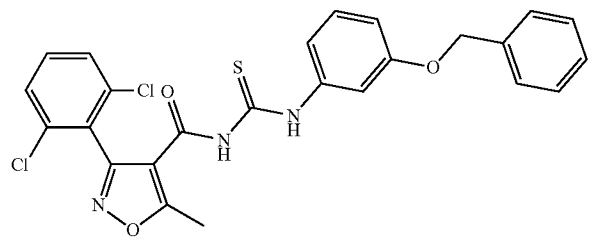 | 1-(3-(benzyloxy)phenyl)-3-(3-(2,6-dichlorophenyl)-5-methylisoxazole-4-carbonyl)thiourea | HPLC (tR) = 2.44 min MS (APCI) m/z 514 [M + 2]+ | A |
| 255 | 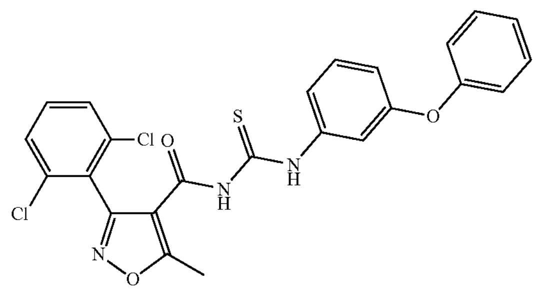 | 1-(3-(2,6-dichlorophenyl)-5-methylisoxazole-4-carbonyl)-3-(3-phenoxyphenyl)thiourea | HPLC (tR) = 2.48 min MS (APCI) m/z 500 [M + 2]+ | A |
| 256 | 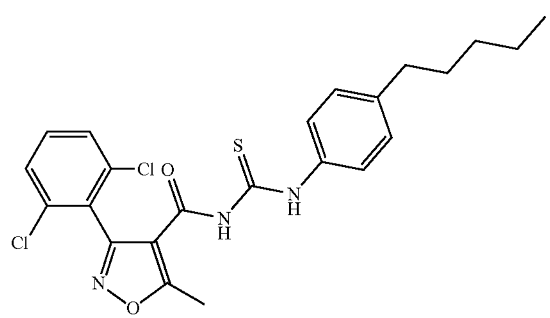 | 1-(3-(2,6-dichlorophenyl)-5-methylisoxazole-4-carbonyl)-3-(4-(pentyl)phenyl)thiourea | HPLC (tR) = 3.03 min MS (APCI) m/z 478 [M + 2]+ | A |

TABLE III-continued

| CPD # | STRUCTURE | NAME | MS | method |
|---|---|---|---|---|
| 257 | 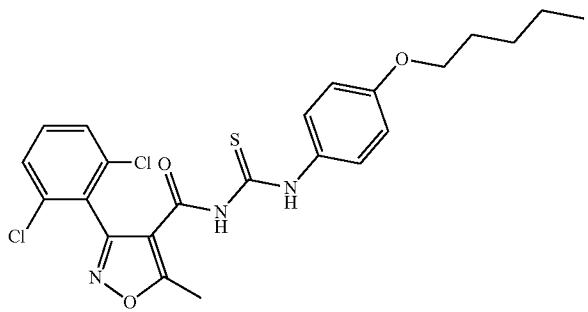 | 1-(3-(2,6-dichlorophenyl)-5-methylisoxazole-4-carbonyl)-3-(4-(pentyloxy)phenyl)thiourea | HPLC (tR) = 2.80 min MS (APCI) m/z 494 [M + H]+ | A |
| 258 | 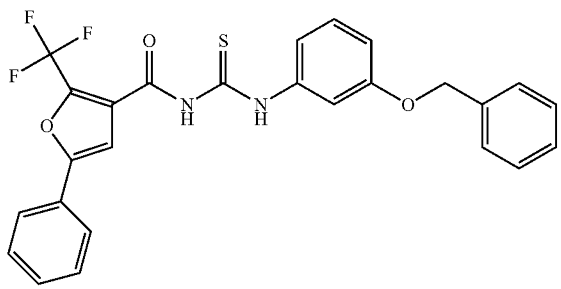 | 1-(3-(benzyloxy)phenyl)-3-(2-phenyl-5-(trifluoromethyl)furan-4-carbonyl)thiourea | HPLC (tR) = 2.91 min MS (APCI) m/z 497 [M + H]+ | A |
| 259 | 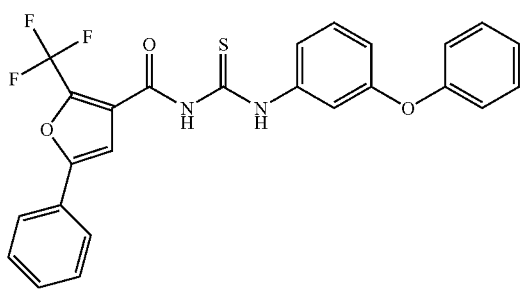 | 1-(3-phenoxyphenyl)-3-(2-phenyl-5-(trifluoromethyl)furan-4-carbonyl)thiourea | HPLC (tR) = 2.82 min MS (APCI) m/z 483 [M + H]+ | A |

TABLE III-continued

| CPD # | STRUCTURE | NAME | MS | method |
|---|---|---|---|---|
| 260 | 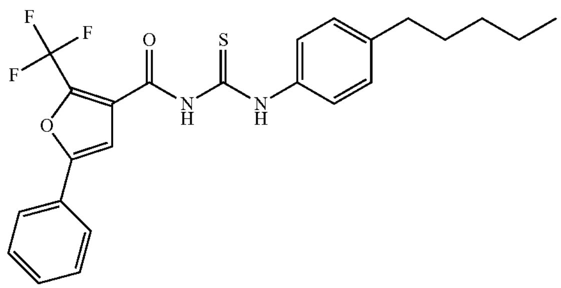 | 1-(4-pentylphenyl)-3-(2-phenyl-5-(trifluoromethyl)furan-4-carbonyl)thiourea | HPLC (tR) = 3.41 min MS (APCI) m/z 461 [M + H]+ | A |
| 261 | 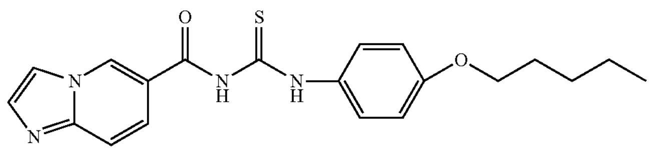 | 1-(H-imidazo[1,2-a]pyridine-6-carbonyl)-3-(4-(pentyloxy)phenyl)thiourea | | B |
| 262 | 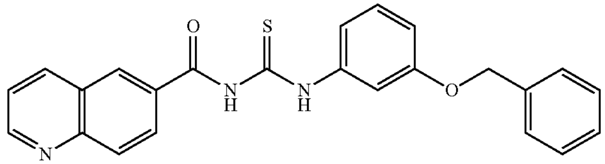 | 1-(3-(benzyloxy)phenyl)-3-(quinoline-6-carbonyl)thiourea | HPLC (tR) = 1.44 min MS (APCI) m/z 413.97 [M + H]+ | A |
| 263 | 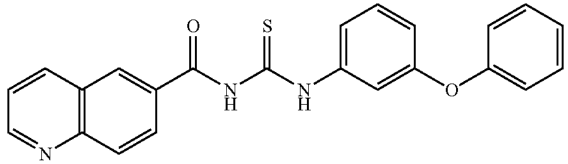 | 1-(3-phenoxyphenyl)-3-(quinoline-6-carbonyl)thiourea | HPLC (tR) = 2.12 min MS (APCI) m/z 399.96 [M + H]+ | A |
| 264 | 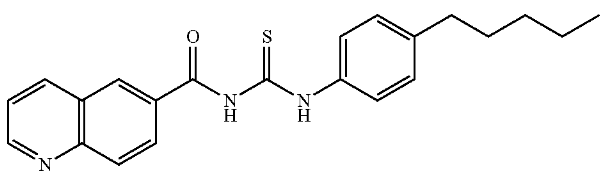 | 1-(4-pentylphenyl)-3-(quinoline-6-carbonyl)thiourea | HPLC (tR) = 2.54 min MS (APCI) m/z 377.97 [M + H]+ | A |

TABLE III-continued

| CPD # | STRUCTURE | NAME | MS | method |
|---|---|---|---|---|
| 265 | 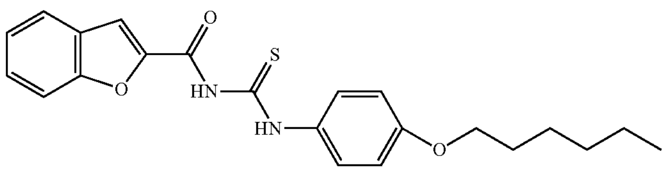 | 1-(benzofuran-2-carbonyl)-3-(4-(hexyloxy)phenyl)thiourea | HPLC (tR) = 2.94 min MS (APCI) m/z 397 [M + H]+ | B |
| 266 | 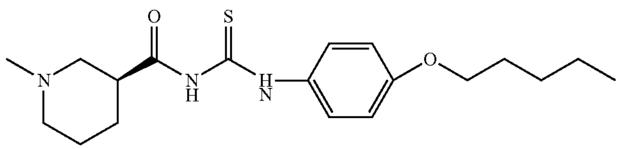 | (S)-1-(1-methylpiperidine-5-carbonyl)-3-(4-(pentyloxy)phenyl)thiourea | HPLC (tR) = 0.84 min MS (APCI) m/z 364 [M + H]+ | B |
| 267 | 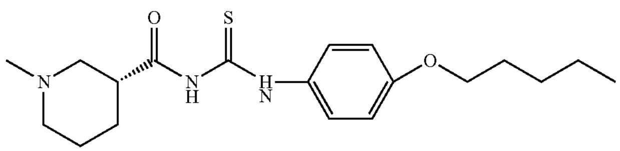 | (R)-1-(1-methylpiperidine-5-carbonyl)-3-(4-(pentyloxy)phenyl)thiourea | HPLC (tR) = 0.84 min MS (APCI) m/z 364 [M + H]+ | B |
| 268 | 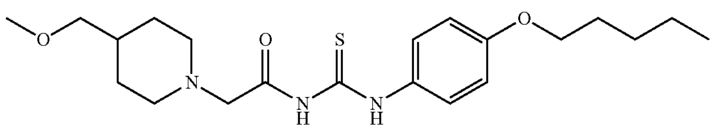 | 1-(2-(4-(methoxymethyl)piperidin-1-yl)acetyl)-3-(4-(pentyloxy)phenyl)thiourea | HPLC (tR) = 2.70 min MS (APCI) m/z 408.68 [M + H]+ | A |
| 269 | 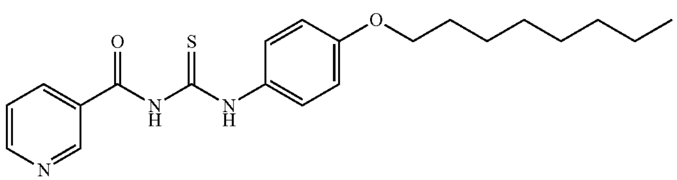 | 1-nicotinoyl-3-(4-(octyloxy)phenyl)thiourea | HPLC (tR) = 2.35 min MS (APCI) m/z 386 [M + H]+ | A |
| 270 | 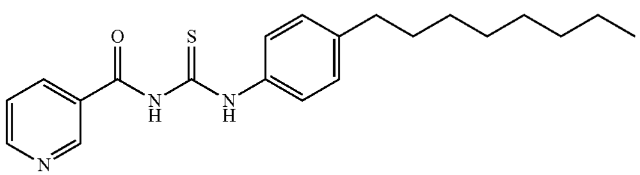 | 1-nicotinoyl-3-(4-octylphenyl)thiourea | HPLC (tR) = 2.51 min MS (APCI) m/z 370 [M + H]+ | A |

TABLE III-continued

| CPD # | STRUCTURE | NAME | MS | method |
|---|---|---|---|---|
| 271 | 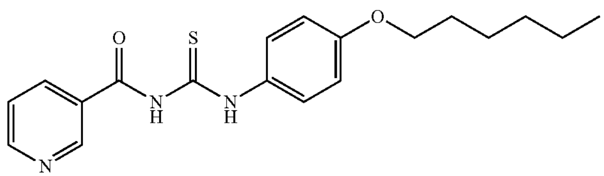 | 1-(4-(hexyloxy)phenyl)-3-nicotinoylthiourea | HPLC (tR) = 2.13 min MS (APCI) m/z 358 [M + H]+ | A |
| 272 | 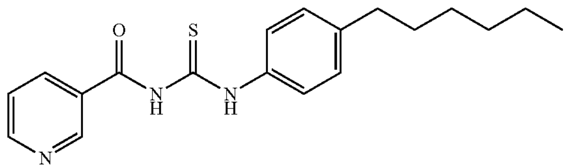 | 1-(4-hexylphenyl)-3-nicotinoylthiourea | HPLC (tR) = 2.27 min MS (APCI) m/z 342 [M + H]+ | A |
| 273 | 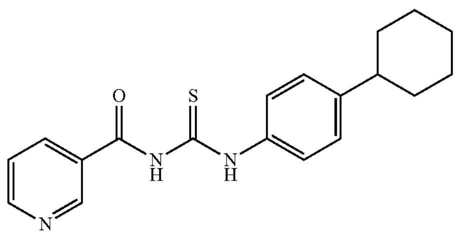 | 1-(4-cyclohexytphenyl)-3-nicotinoylthiourea | HPLC (tR) = 2.13 min MS (APCI) m/z 340 [M + H]+ | A |
| 274 | 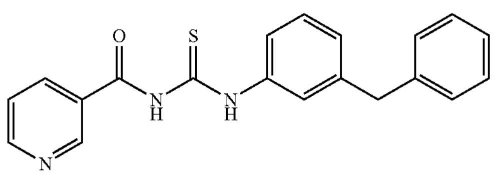 | 1-(3-benzylphenyl)-3-nicotinoylthiourea | HPLC (tR) = 1.83 min MS (APCI) m/z 348 [M + H]+ | A |
| 275 | 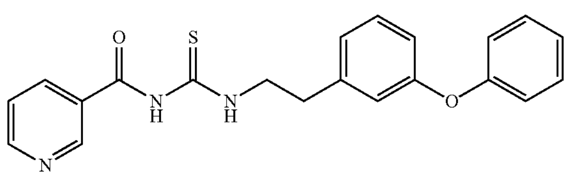 | 1-(3-phenoxyphenethyl)-3-nicotinoylthiourea | HPLC (tR) = 1.87 min MS (APCI) m/z 378 [M + H]+ | A |

TABLE III-continued

| CPD # | STRUCTURE | NAME | MS | method |
|---|---|---|---|---|
| 276 | 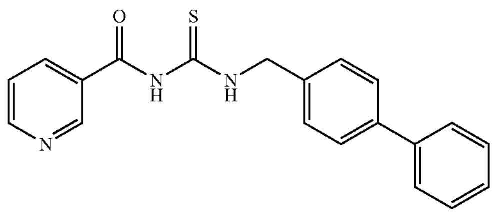 | 1-(4-phenyl-benzyl)-3-nicotinoylthiourea | HPLC (tR) = 1.79 min MS (APCI) m/z 348 [M + H]+ | A |
| 277 | 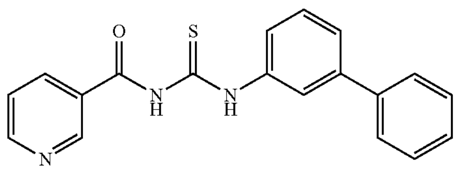 | 1-(3-phenylphenyl)-3-nicotinoylthiourea | HPLC (tR) = 1.81 min MS (APCI) m/z 334 [M + H]+ | A |
| 278 | 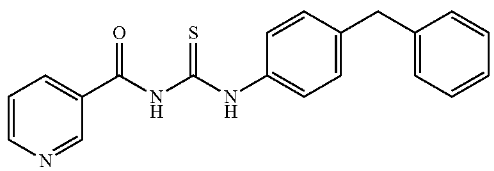 | 1-(4-benzylphenyl)-3-nicotinoylthiourea | HPLC (tR) = 1.83 min MS (APCI) m/z 348 [M + H]+ | A |
| 279 | 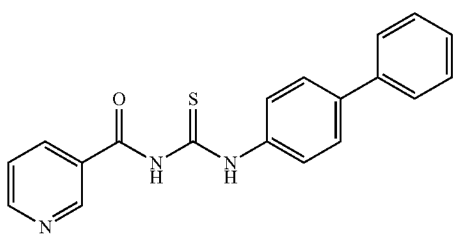 | 1-(4-phenylphenyl)-3-nicotinoylthiourea | HPLC (tR) = 1.81 min MS (APCI) m/z 334 [M + H]+ | A |
| 280 | 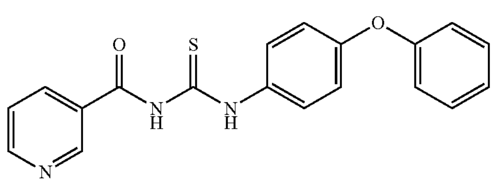 | 1-nicotinoyl-3-(4-phenoxyphenyl)thiourea | HPLC (tR) = 1.79 min MS (APCI) m/z 350 [M + H]+ | A |

TABLE III-continued

| CPD # | STRUCTURE | NAME | MS | method |
|---|---|---|---|---|
| 281 | 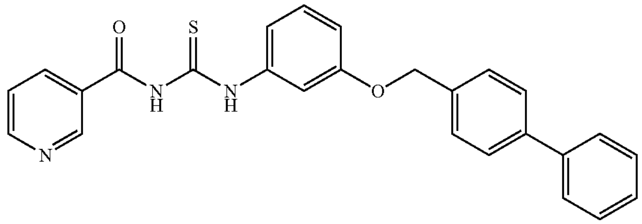 | 1-(3-(4-phenylbenzyloxy)phenyl)-3-nicotinoylthiourea | HPLC (tR) = 2.14 min MS (APCI) m/z 440 [M + H]+ | A |
| 282 | 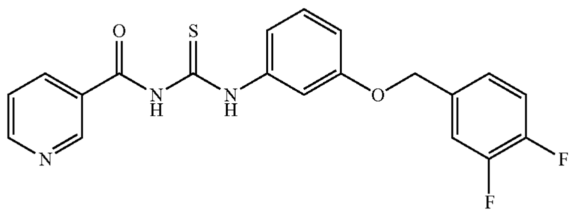 | 1-(3-(3,4-difluorobenzyloxy)phenyl)-3-nicotinoylthiourea | HPLC (tR) = 1.86 min MS (APCI) m/z 400 [M + H]+ | A |
| 283 | 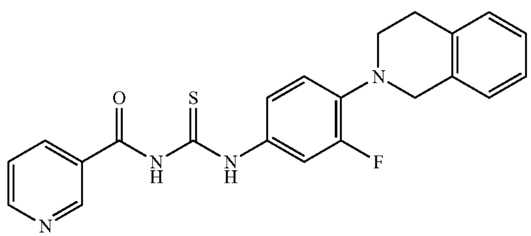 | 1-(4-(3,4-dihydroisoquinolin-2(1H)-yl)-3-fluorophenyl)-3-nicotinoylthiourea | HPLC (tR) = 1.90 min MS (APCI) m/z 407 [M + H]+ | A |
| 284 | 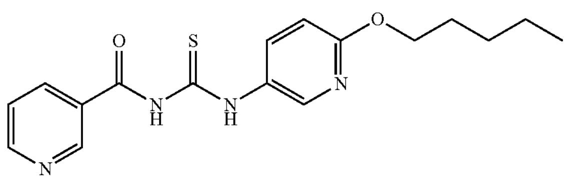 | 1-nicotinoyl-3-(6-(pentyloxy)pyridin-3-yl)thiourea | HPLC (tR) = 1.84 min MS (APCI) m/z 345 [M + H]+ | A |

| CPD # | STRUCTURE | NAME | MS | method |
|---|---|---|---|---|
| 285 | 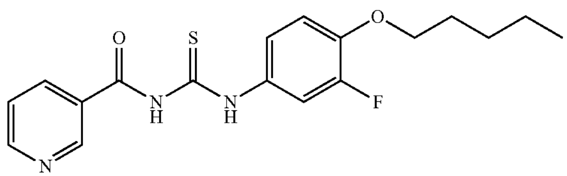 | 1-(3-fluoro-4-(pentyloxy)phenyl)-3-nicotinoylthiourea | HPLC (tR) = 1.99 min MS (APCI) m/z 362 [M + H]+ | A |
| 286 | 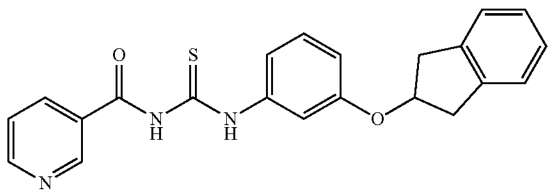 | 1-(3-(2,3-dihydro-1H-inden-2-yloxy)phenyl)-3-nicotinoylthiourea | HPLC (tR) = 1.91 min MS (APCI) m/z 390 [M + H]+ | A |
| 287 | 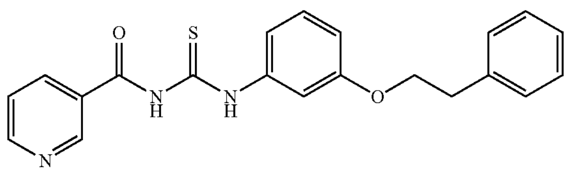 | 1-nicotinoyl-3-(3-phenethoxyphenyl)thiourea | HPLC (tR) = 1.88 min MS (APCI) m/z 378 [M + H]+ | A |
| 288 | 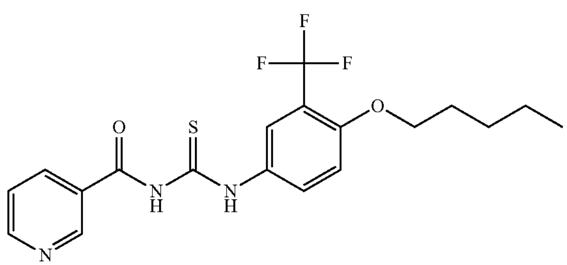 | 1-nicotinoyl-3-(4-(pentyloxy)-3-(trifluoromethyl)phenyl)thiourea | HPLC (tR) = 2.13 min MS (APCI) m/z 412 [M + H]+ | A |
| 289 | 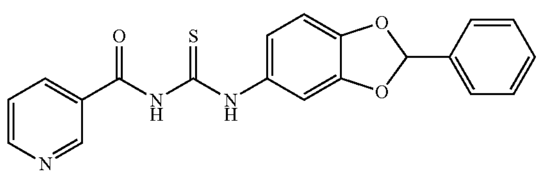 | 1-nicotinoyl-3-(2-phenylbenzo[d][1,3]dioxol-5-yl)thiourea | HPLC (tR) = 1.77 min MS (APCI) m/z 378 [M + H]+ | A |

TABLE III-continued

| CPD # | STRUCTURE | NAME | MS | method |
|---|---|---|---|---|
| 290 | 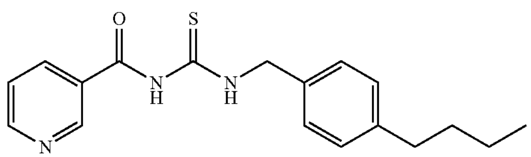 | 1-(4-butylbenzyl)-3-nicotinoylthiourea | HPLC (tR) = 1.97 min MS (APCI) m/z 328 [M + H]+ | A |
| 291 | 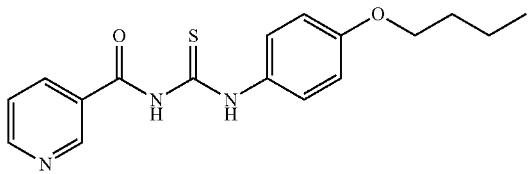 | 1-(4-butoxyphenyl)-3-nicotinoylthiourea | HPLC (tR) = 1.82 min MS (APCI) m/z 330 [M + H]+ | A |
| 292 | 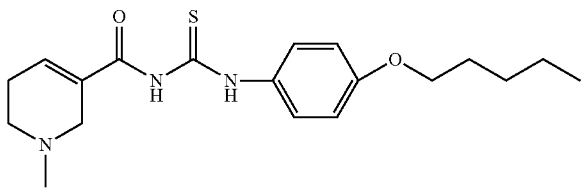 | 1-(1-methyl-1,2,3,6-tetrahydropyridine-5-carbonyl)-3-(4-(pentyloxy)phenyl)thiourea | HPLC (tR) = 2.32 min MS (APCI) m/z 346 [M − Me]+ | B |
| 293 | 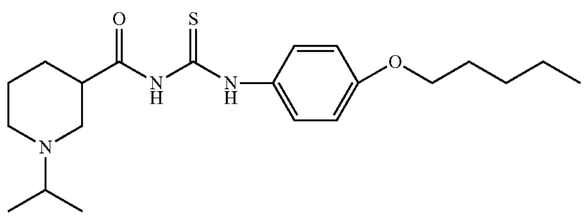 | 1-(1-isopropylpiperidine-5-carbonyl)-3-(4-(pentyloxy)phenyl)thiourea | HPLC (tR) = 0.8 min MS (APCI) m/z 391.7 [M + H]+ | B |
| 294 | 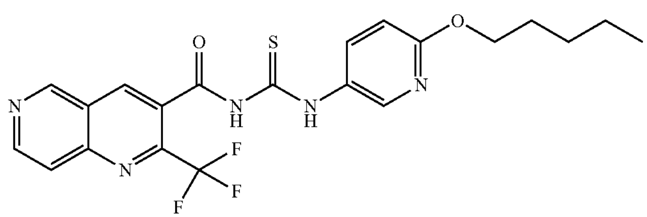 | 1-(6-(pentyloxy)pyridin-3-yl)-3-(2-(trifluoromethyl)-1,6-naphthyridine-3-carbonyl)thiourea | HPLC (tR) = 2.09 min MS (APCI) m/z 464.3 [M + H]+ | A |

TABLE III-continued

| CPD # | STRUCTURE | NAME | MS | method |
|---|---|---|---|---|
| 295 | 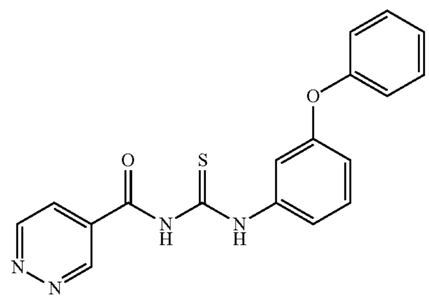 | 1-(3-phenoxyphenyl)-3-(pyridazine-4-carbonyl)thiourea | HPLC (tR) = 1.64 min MS (APCI) m/z 351 [M + H]+ | A |
| 296 | 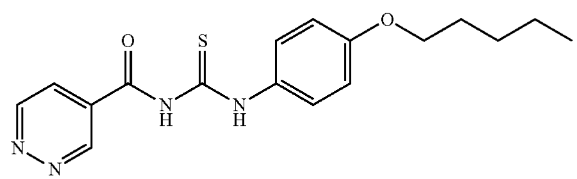 | 1-(4-(pentyloxy)phenyl)-3-(pyridazine-4-carbonyl)thiourea | HPLC (tR) = 1.86 min MS (APCI) m/z 345 [M + H]+ | A |
| 297 | 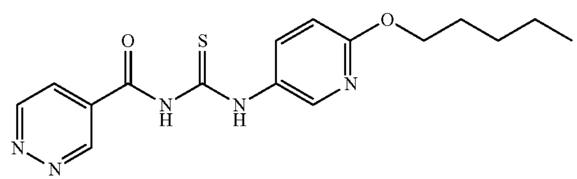 | 1-(6-(pentyloxy)pyridin-3-yl)-3-(pyridazine-4-carbonyl)thiourea | HPLC (tR) = 1.66 min MS (APCI) m/z 346 [M + H]+ | A |
| 298 | 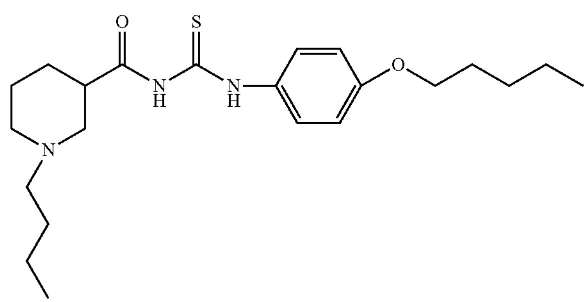 | 1-(1-butylpiperidine-5-carbonyl)-3-(4-(pentyloxy)phenyl)thiourea | HPLC (tR) = 2.02 min MS (APCI) m/z 406 [M + H]+ | B |

TABLE III-continued

| CPD # | STRUCTURE | NAME | MS | method |
|---|---|---|---|---|
| 299 | 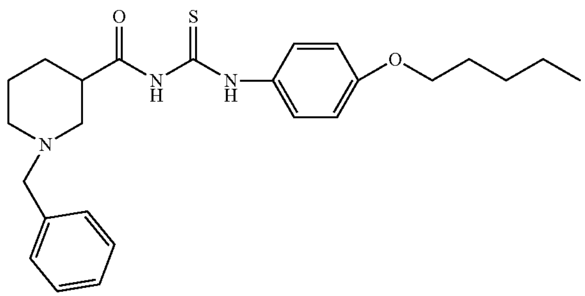 | 1-(1-benzylpiperidine-5-carbonyl)-3-(4-(pentyloxy)phenyl)thiourea | HPLC (tR) = 2.10 min MS (APCI) m/z 440 [M + H]+ | B |
| 300 | 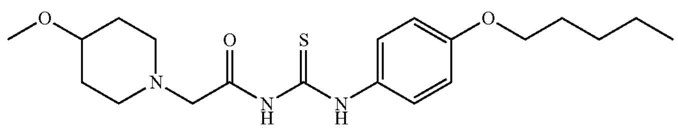 | 1-(2-(4-methoxypiperidin-1-yl)acetyl)-3-(4-(pentyloxy)phenyl)thiourea | HPLC (tR) = 1.33 min MS (APCI) m/z 394.64 [M + H]+ | A |
| 301 | 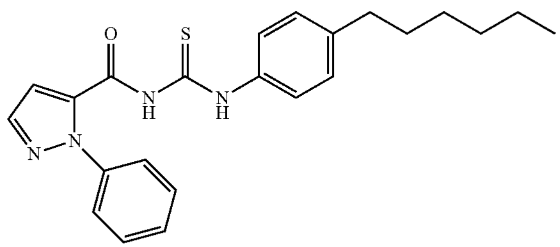 | 1-(4-hexylphenyl)-3-(1-phenyl-1H-pyrazole-5-carbonyl)thiourea | HPLC (tR) = 4.39 min MS (APCI) m/z 407 [M + H]+ | B |
| 302 | 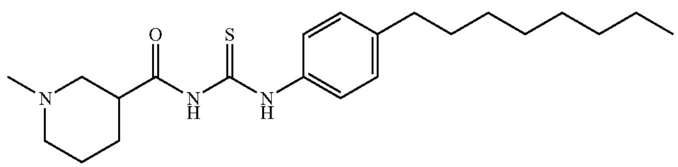 | 1-(1-methylpiperidine-5-carbonyl)-3-(4-octylphenyl)thiourea | HPLC (tR) = 3.09 min MS (APCI) m/z 390 [M + H]+ | B |
| 303 | 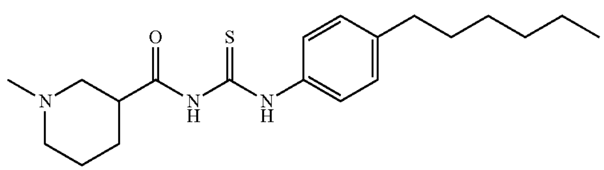 | 1-(4-hexylphenyl)-3-(1-methylpiperidine-5-carbonyl)thiourea | HPLC (tR) = 2.72 min MS (APCI) m/z 362 [M + H]+ | B |

TABLE III-continued

| CPD # | STRUCTURE | NAME | MS | method |
|---|---|---|---|---|
| 304 | 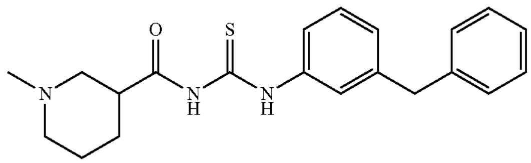 | 1-(3-benzylphenyl)-3-(1-methyl-piperidine-5-carbonyl)thiourea | HPLC (tR) = 2.25 min MS (APCI) m/z 368 [M + H]+ | B |
| 305 | 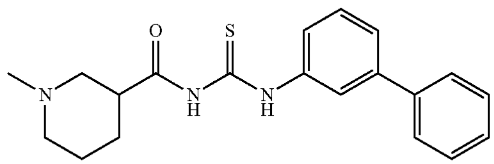 | 1-(3-phenylphenyl)-3-(1-methyl-piperidine-5-carbonyl)thiourea | HPLC (tR) = 2.18 min MS (APCI) m/z 354 [M + H]+ | B |
| 306 | 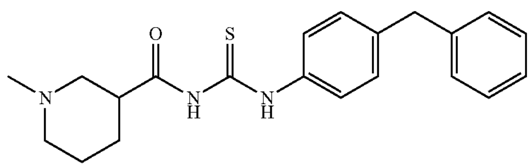 | 1-(4-benzylphenyl)-3-(1-methyl-piperidine-5-carbonyl)thiourea | HPLC (tR) = 2.27 min MS (APCI) m/z 368 [M + H]+ | B |
| 307 | 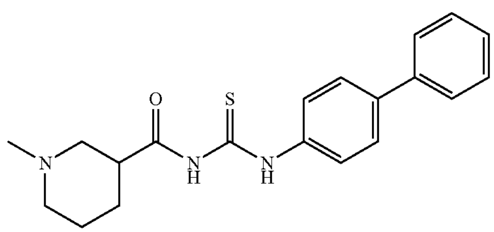 | 1-(4-phenylphenyl)-3-(1-methyl-piperidine-5-carbonyl)thiourea | HPLC (tR) = 2.18 min MS (APCI) m/z 354 [M + H]+ | B |
| 308 | 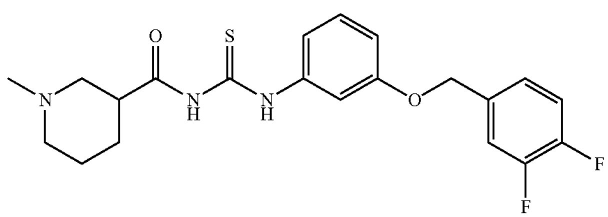 | 1-(3-(3,4-difluorobenzyloxy)phenyl)-3-(1-methylpiperidine-5-carbonyl)thiourea | HPLC (tR) = 2.32 min MS (APCI) m/z 420 [M + H]+ | B |

TABLE III-continued

| CPD # | STRUCTURE | NAME | MS | method |
|---|---|---|---|---|
| 309 | 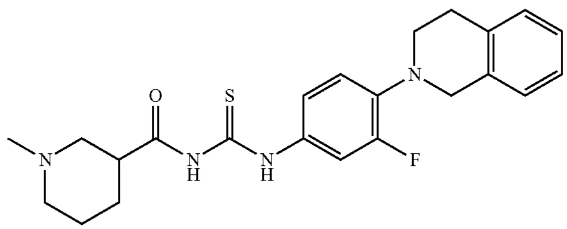 | 1-(4-(3,4-dihydroisoquinolin-2(1H)-yl)-3-fluorophenyl)-3-(1-methylpiperidine-5-carbonyl)thiourea | HPLC (tR) = 2.34 min MS (APCI) m/z 427 [M + H]+ | B |
| 310 | 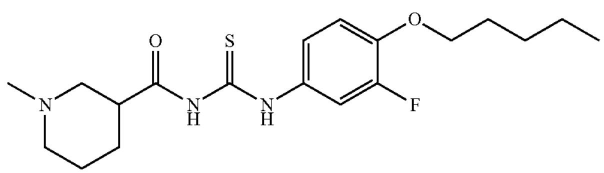 | 1-(3-fluoro-4-(pentyloxy)phenyl)-3-(1-methylpiperidine-5-carbonyl)thiourea | HPLC (tR) = 2.44 min MS (APCI) m/z 382 [M + H]+ | B |
| 311 | 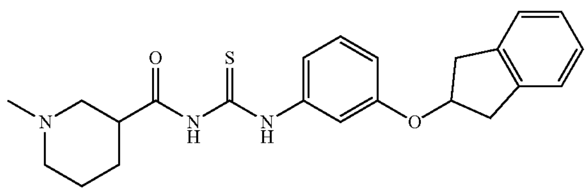 | 1-(4-phenyl-phenyl)-3-(1-phenyl-1H-pyrazole-5-carbonyl)thiourea | HPLC (tR) = 2.36 min MS (APCI) m/z 410 [M + H]+ | B |
| 312 | 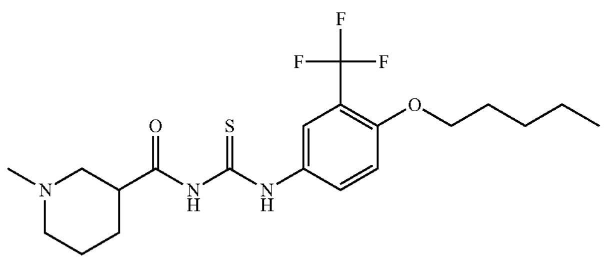 | 1-(1-methylpiperidine-5-carbonyl)-3-(4-(pentyloxy)-3-(trifluoromethyl)phenyl)thiourea | HPLC (tR) = 2.65 min MS (APCI) m/z 432 [M + H]+ | B |
| 313 | 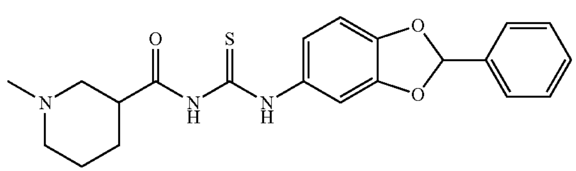 | 1-(1-methylpiperidine-5-carbonyl)-3-(2-phenylbenzo[d][1,3]dioxol-5-yl)thiourea | HPLC (tR) = 2.16 min MS (APCI) m/z 398 [M + H]+ | B |

TABLE III-continued

| CPD # | STRUCTURE | NAME | MS | method |
|---|---|---|---|---|
| 314 | 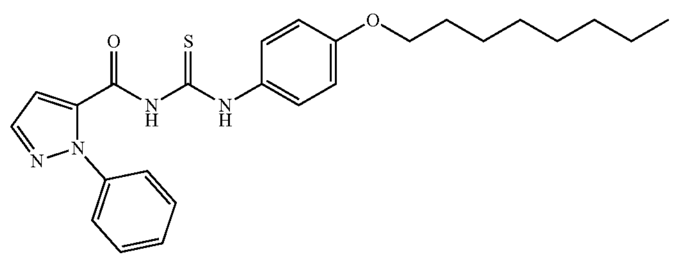 | 1-(4-(octyloxy)phenyl)-3-(1-phenyl-1H-pyrazole-5-carbonyl)thiourea | HPLC (tR) = 4.60 min MS (APCI) m/z 451 [M + H]+ | B |
| 315 | 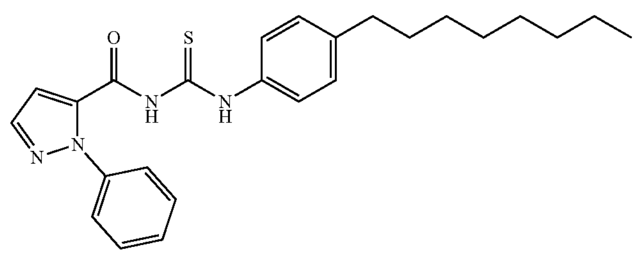 | 1-(4-octylphenyl)-3-(1-phenyl-1H-pyrazole-5-carbonyl)thiourea | HPLC (tR) = 4.88 min MS (APCI) m/z 435 [M + H]+ | B |
| 316 | 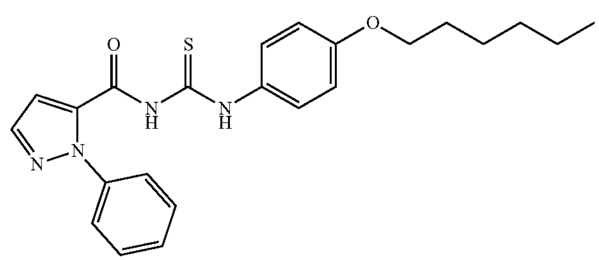 | 1-(4-(hexyloxy)phenyl)-3-(1-phenyl-1H-pyrazole-5-carbonyl)thiourea | HPLC (tR) = 4.19 min MS (APCI) m/z 423 [M + H]+ | B |

TABLE III-continued

| CPD # | STRUCTURE | NAME | MS | method |
|---|---|---|---|---|
| 317 | 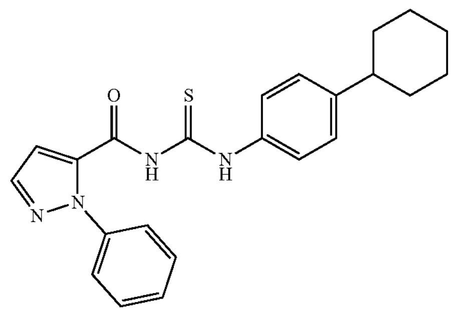 | 1-(4-cyclohexylphenyl)-3-(1-phenyl-1H-pyrazole-5-carbonyl)thiourea | HPLC (tR) = 4.19 min MS (APCI) m/z 405 [M + H]+ | B |
| 318 | 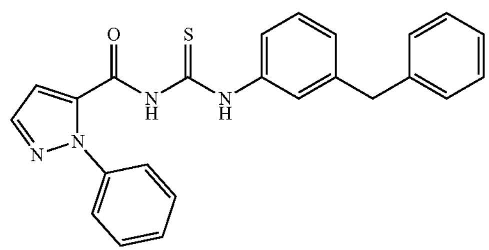 | 1-(3-benzylphenyl)-3-(1-phenyl-1H-pyrazole-5-carbonyl)thiourea | HPLC (tR) = 3.69 min MS (APCI) m/z 413 [M + H]+ | B |
| 319 | 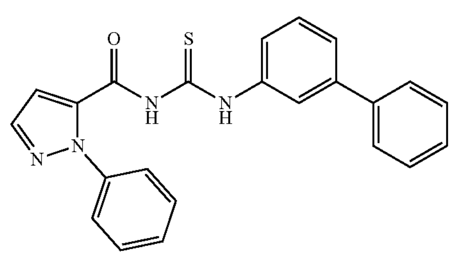 | 1-(3-phenyl-phenyl)-3-(1-phenyl-1H-pyrazole-5-carbonyl)thiourea | HPLC (tR) = 3.67 min MS (APCI) m/z 399 [M + H]+ | B |

TABLE III-continued

| CPD # | STRUCTURE | NAME | MS | method |
|---|---|---|---|---|
| 320 | 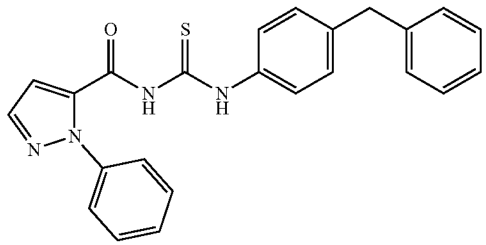 | 1-(4-benzylphenyl)-3-(1-phenyl-1H-pyrazole-5-carbonyl)thiourea | HPLC (tR) = 3.72 min MS (APCI) m/z 413 [M + H]+ | B |
| 321 | 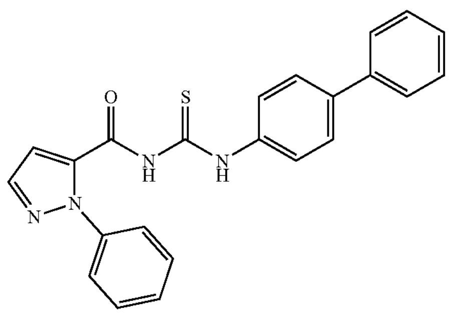 | 1-(4-phenyl-phenyl)-3-(1-phenyl-1H-pyrazole-5-carbonyl)thiourea | HPLC (tR) = 3.68 min MS (APCI) m/z 399 [M + H]+ | B |
| 322 | 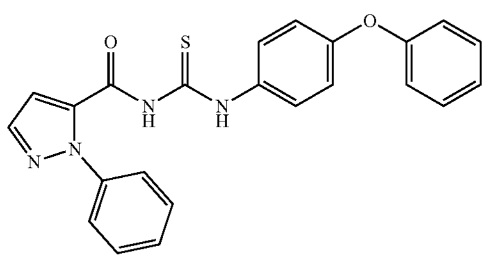 | 1-(4-phenoxyphenyl)-3-(1-phenyl-1H-pyrazole-5-carbonyl)thiourea | HPLC (tR) = 3.61 min MS (APCI) m/z 415 [M + H]+ | B |

TABLE III-continued

| CPD # | STRUCTURE | NAME | MS | method |
|---|---|---|---|---|
| 323 | 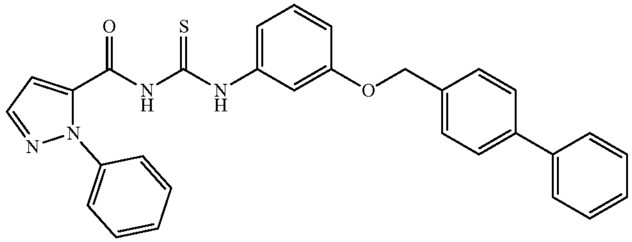 | 1-(3-(4-phenyl-benzyloxy)phenyl)-3-(1-phenyl-1H-pyrazole-5-carbonyl)thiourea | HPLC (tR) = 4.19 min MS (APCI) m/z 505 [M + H]+ | B |
| 324 | 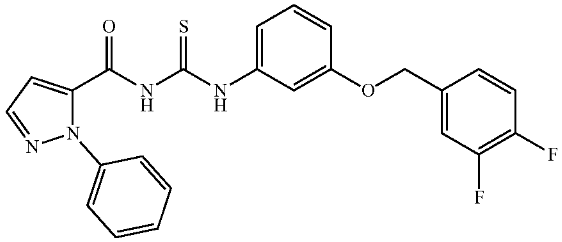 | 1-(3-(3,4-difluorobenzyloxy)phenyl)-3-(1-phenyl-1H-pyrazole-5-carbonyl)thiourea | HPLC (tR) = 3.75 min MS (APCI) m/z 465 [M + H]+ | B |
| 325 | 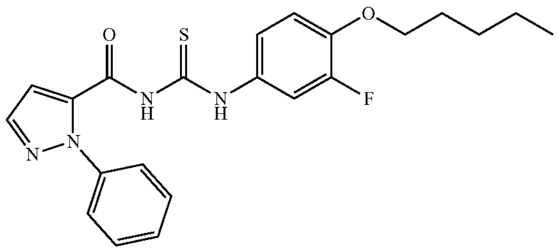 | 1-(3-fluoro-4-(pentyloxy)phenyl)-3-(1-phenyl-1H-pyrazole-5-carbonyl)thiourea | HPLC (tR) = 3.97 min MS (APCI) m/z 427 [M + H]+ | B |
| 326 | 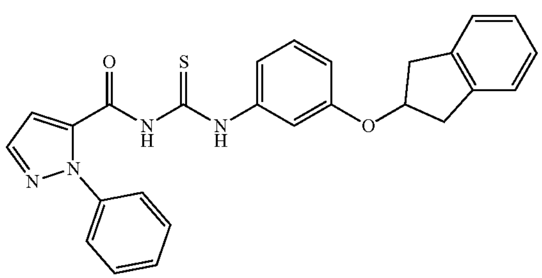 | 1-(3-(2,3-dihydro-1H-inden-2-yloxy)phenyl)-3-(1-phenyl-1H-pyrazole-5-carbonyl)thiourea | HPLC (tR) = 3.84 min MS (APCI) m/z 455 [M + H]+ | B |

TABLE III-continued

| CPD # | STRUCTURE | NAME | MS | method |
|---|---|---|---|---|
| 327 | 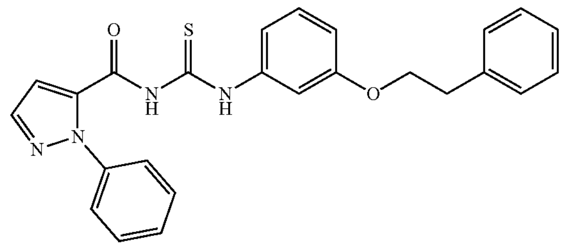 | 1-(3-phenethoxyphenyl)-3-(1-phenyl-1H-pyrazole-5-carbonyl)thiourea | HPLC (tR) = 3.80 min MS (APCI) m/z 443 [M + H]+ | B |
| 328 | 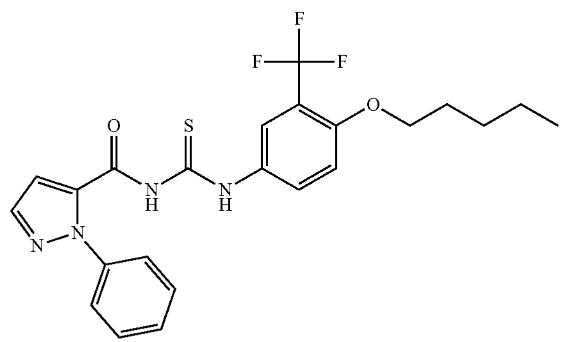 | 1-(4-(pentyloxy)-3-(trifluoromethyl)phenyl)-3-(1-phenyl-1H-pyrazole-5-carbonyl)thiourea | HPLC (tR) = 4.2 min MS (APCI) m/z 477 [M + H]+ | B |
| 329 | 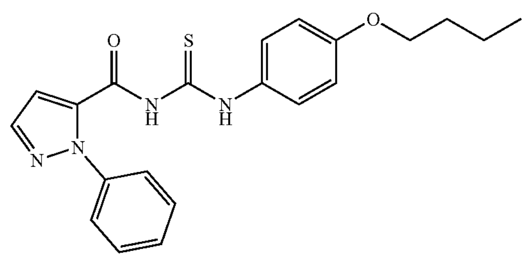 | 1-(4-butoxyphenyl)-3-(1-phenyl-1H-pyrazole-5-carbonyl)thiourea | HPLC (tR) = 3.75 min MS (APCI) m/z 395 [M + H]+ | B |
| 330 | 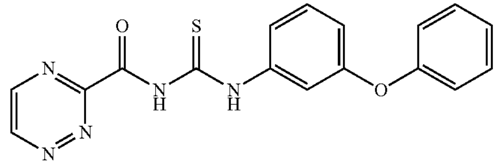 | 1-(3-phenoxyphenyl)-3-(1,2,4-triazine-3-carbonyl)thiourea | HPLC (tR) = 1.80 min MS (APCI) m/z 351.9 [M + H]+ | A |

TABLE III-continued

| CPD # | STRUCTURE | NAME | MS | method |
|---|---|---|---|---|
| 331 | 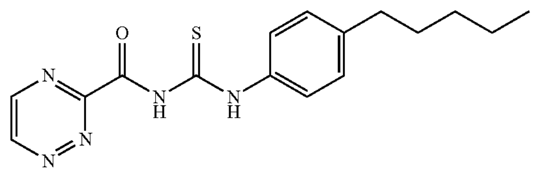 | 1-(4-pentylphenyl)-3-(1,2,4-triazine-3-carbonyl)thiourea | HPLC (tR) = 2.16 min MS (APCI) m/z 330.0 [M + H]+ | A |
| 332 | 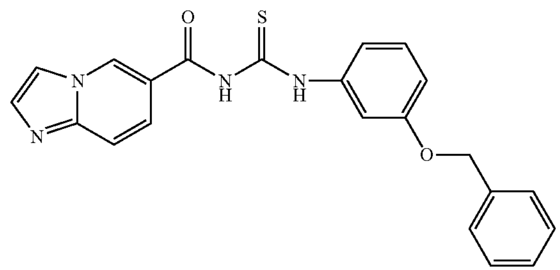 | 1-(3-(benzyloxy)phenyl)-3-(H-imidazo[1,2-a]pyridine-6-carbonyl)thiourea | HPLC (tR) = 0.52 min MS (APCI) m/z 403 [M + H]+ | B |
| 333 | 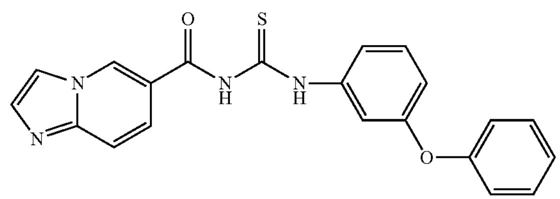 | 1-(H-imidazo[1,2-a]pyridine-6-carbonyl)-3-(3-phenoxyphenyl)thiourea | HPLC (tR) = 0.56 min MS (APCI) m/z 389 [M + H]+ | B |
| 334 | 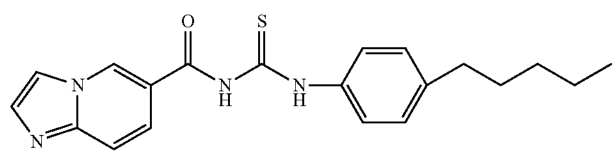 | 1-(H-imidazo[1,2-a]pyridine-6-carbonyl)-3-(4-pentylphenyl)thiourea | HPLC (tR) = 0.58 min MS (APCI) m/z 367 [M + H]+ | B |
| 335 | 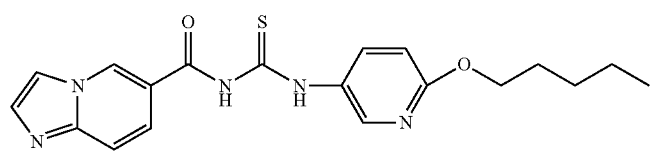 | 1-(H-imidazo[1,2-a]pyridine-6-carbonyl)-3-(6-(pentyloxy)pyridin-3-yl)thiourea | HPLC (tR) = 0.54 min MS (APCI) m/z 384 [M + H]+ | B |

TABLE III-continued

| CPD # | STRUCTURE | NAME | MS | method |
|---|---|---|---|---|
| 336 | 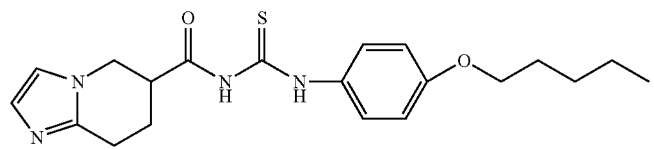 | 1-(4-(pentyloxy)phenyl)-3-(5,6,7,8-tetrahydroimidazo[1,2-a]pyridine-6-carbonyl)thiourea | HPLC (tR) = 1.16 min MS (APCI) m/z 387 [M + H]+ | B |
| 337 | 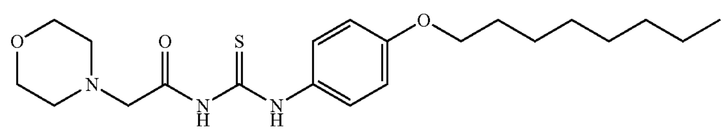 | 1-(2-morpholinoacetyl)-3-(4-(octyloxy)phenyl)thiourea | HPLC (tR) = 1.65 min MS (APCI) m/z 408 [M + H]+ | A |
| 338 | 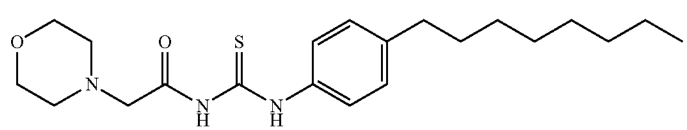 | 1-(2-morpholinoacetyl)-3-(4-octylphenyl)thiourea | HPLC (tR) = 1.73 min MS (APCI) m/z 392 [M + H]+ | A |
| 339 | 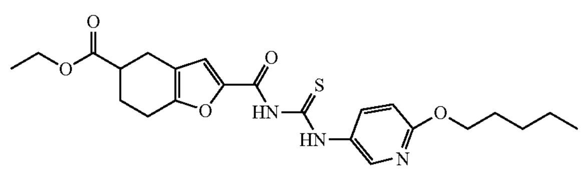 | ethyl 2-((3-(6-(pentyloxy)pyridin-3-yl)thioureido)carbonyl)-4,5,6,7-tetrahydrobenzofuran-5-carboxylate | HPLC (tR) = 2.24 min MS (APCI) m/z 461 [M + H]+ | B |
| 340 | 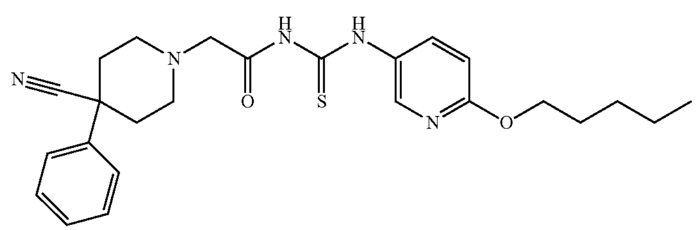 | 1-(2-(4-cyano-4-phenylpiperidin-1-yl)acetyl)-3-(6-(pentyloxy)pyridin-3-yl)thiourea | HPLC (tR) = 1.57 min MS (APCI) m/z 466.74 [M + H]+ | A |

TABLE III-continued

| CPD # | STRUCTURE | NAME | MS | method |
|---|---|---|---|---|
| 341 | 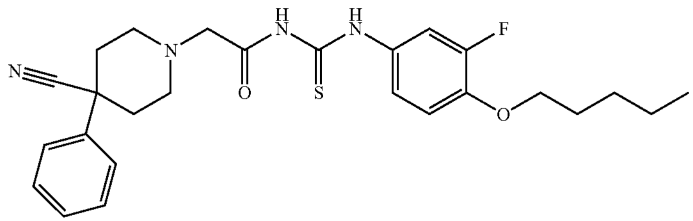 | 1-(2-(4-cyano-4-phenylpiperidin-1-yl)acetyl)-3-(3-fluoro-4-(pentyloxy)phenyl)thiourea | HPLC (tR) = 1.71 min MS (APCI) m/z 483.78 [M + H]+ | A |
| 342 | 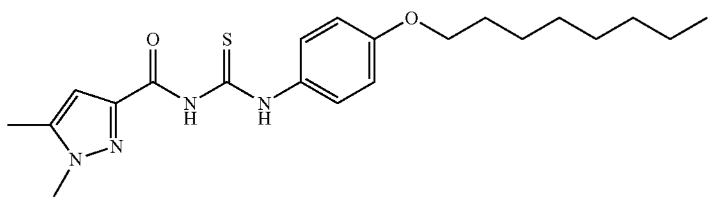 | 1-(1,5-dimethyl-1H-pyrazole-3-carbonyl)-3-(4-(octyloxy)phenyl)thiourea | HPLC (tR) = 2.06 min MS (APCI) m/z 403 [M + H]+ | A |
| 343 | 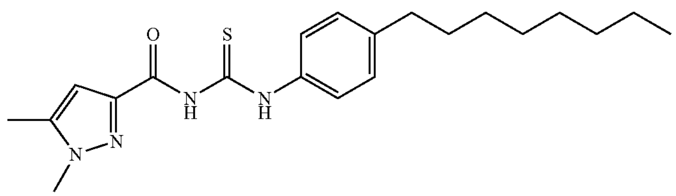 | 1-(1,5-dimethyl-1H-pyrazole-3-carbonyl)-3-(4-octylphenyl)thiourea | HPLC (tR) = 5.22 min MS (APCI) m/z 387 [M + H]+ | B |
| 344 | 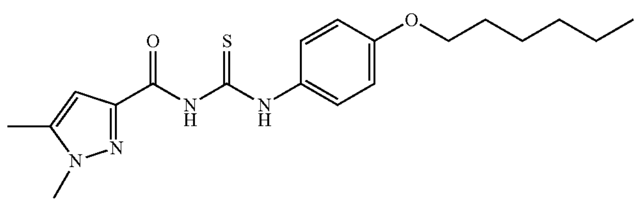 | 1-(1,5-dimethyl-1H-pyrazole-3-carbonyl)-3-(4-(hexyloxy)phenyl)thiourea | HPLC (tR) = 4.39 min MS (APCI) m/z 375 [M + H]+ | BB |
| 345 | 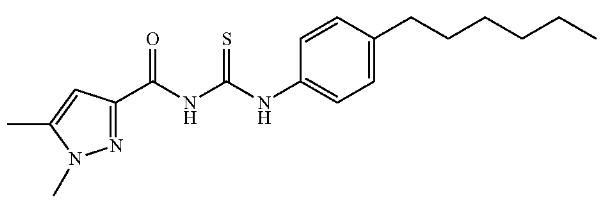 | 1-(1,5-dimethyl-1H-pyrazole-3-carbonyl)-3-(4-hexylphenyl)thiourea | HPLC (tR) = 4.68 min MS (APCI) m/z 359 [M + H]+ | B |

TABLE III-continued

| CPD # | STRUCTURE | NAME | MS | method |
|---|---|---|---|---|
| 346 | 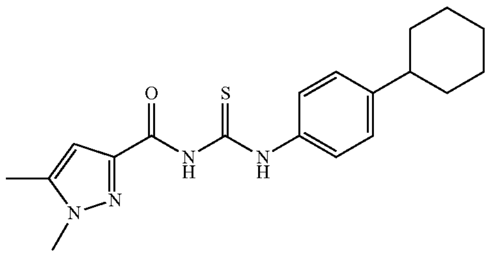 | 1-(4-cyclohexylphenyl)-3-(1,5-dimethyl-1H-pyrazole-3-carbonyl)thiourea | HPLC (tR) = 4.44 min MS (APCI) m/z 357 [M + H]+ | B |
| 347 | 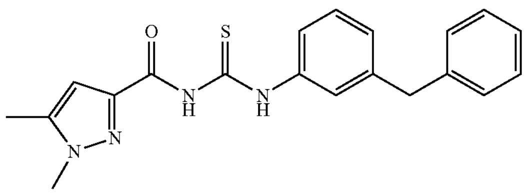 | 1-(3-benzylphenyl)-3-(1,5-dimethyl-1H-pyrazole-3-carbonyl)thiourea | HPLC (tR) = 3.84 min MS (APCI) m/z 365 [M + H]+ | B |
| 348 | 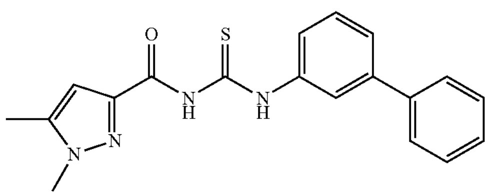 | 1-(3-phenyl-phenyl)-3-(1,5-dimethyl-1H-pyrazole-3-carbonyl)thiourea | HPLC (tR) = 3.85 min MS (APCI) m/z 351 [M + H]+ | B |
| 349 | 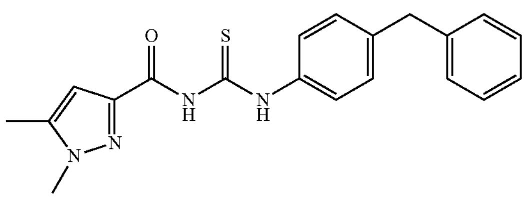 | 1-(4-benzylphenyl)-3-(1,5-dimethyl-1H-pyrazole-3-carbonyl)thiourea | HPLC (tR) = 3.87 min MS (APCI) m/z 365 [M + H]+ | B |

TABLE III-continued

| CPD # | STRUCTURE | NAME | MS | method |
|---|---|---|---|---|
| 350 | 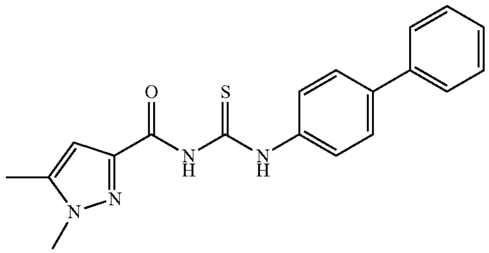 | 1-(1,5-dimethyl-1H-pyrazole-3-carbonyl)-3-(4-phenylphenyl)thiourea | HPLC (tR) = 3.91 min MS (APCI) m/z 351 [M + H]+ | B |
| 351 | 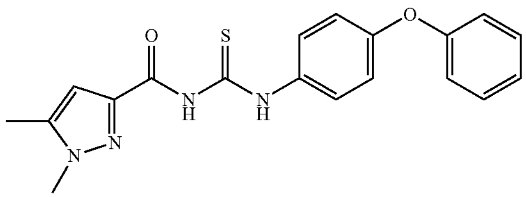 | 1-(1,5-dimethyl-1H-pyrazole-3-carbonyl)-3-(4-phenoxyphenyl)thiourea | HPLC (tR) = 3.83 min MS (APCI) m/z 367 [M + H]+ | B |
| 352 | 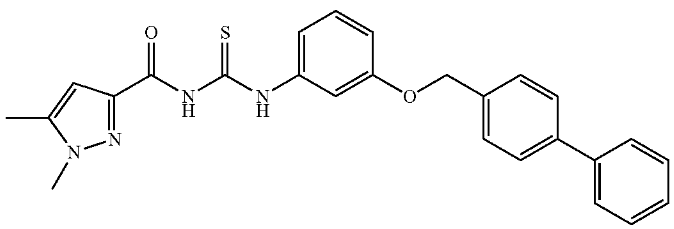 | 1-(3-(4-phenyl)phenyl)-3-(1,5-dimethyl-1H-pyrazole-3-carbonyl)thiourea | HPLC (tR) = 4.37 min MS (APCI) m/z 457 [M + H]+ | B |
| 353 | 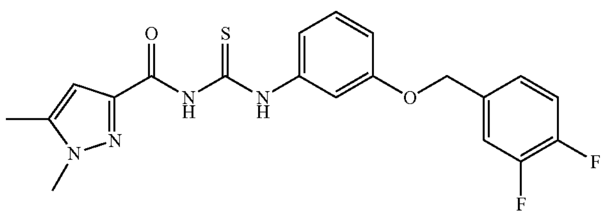 | 1-(3-(3,4-difluorobenzyloxy)phenyl)-3-(1,5-dimethyl-1H-pyrazole-3-carbonyl)thiourea | HPLC (tR) = 3.90 min MS (APCI) m/z 417 [M + H]+ | B |

TABLE III-continued

| CPD # | STRUCTURE | NAME | MS | method |
|---|---|---|---|---|
| 354 | 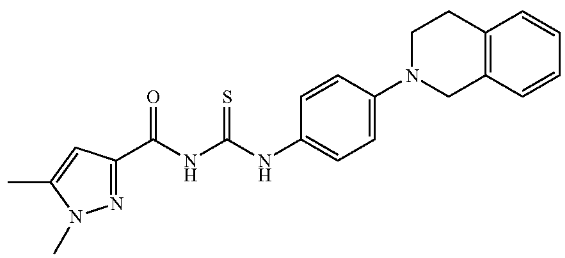 | 1-(4-(3,4-dihydroisoquinolin-2(1H)-yl)phenyl)-3-(1,5-dimethyl-1H-pyrazole-3-carbonyl)thiourea | HPLC (tR) = 3.27 min MS (APCI) m/z 406 [M + H]+ | B |
| 355 | 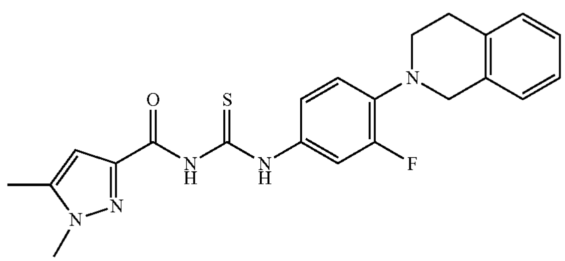 | 1-(4-(3,4-dihydroisoquinolin-2(1H)-yl)-3-fluorophenyl)-3-(1,5-dimethyl-1H-pyrazole-3-carbonyl)thiourea | HPLC (tR) = 4.08 min MS (APCI) m/z 424 [M + H]+ | B |
| 356 | 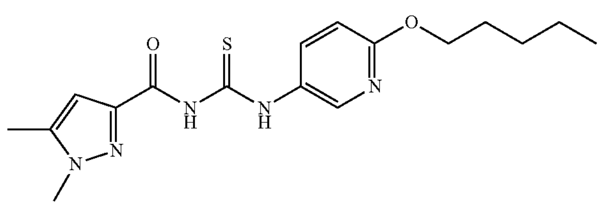 | 1-(1,5-dimethyl-1H-pyrazole-3-carbonyl)-3-(6-(pentyloxy)pyridin-3-yl)thiourea | HPLC (tR) = 3.93 min MS (APCI) m/z 362 [M + H]+ | B |
| 357 | 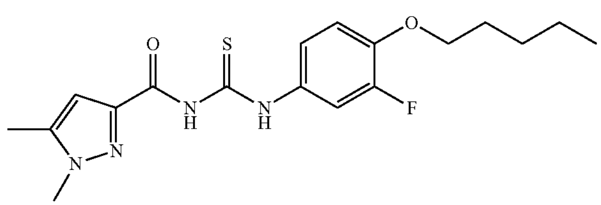 | 1-(1,5-dimethyl-1H-pyrazole-3-carbonyl)-3-(3-fluoro-4-(pentyloxy)phenyl)thiourea | HPLC (tR) = 4.16 min MS (APCI) m/z 379 [M + H]+ | B |

| CPD # | STRUCTURE | NAME | MS | method |
|---|---|---|---|---|
| 358 | 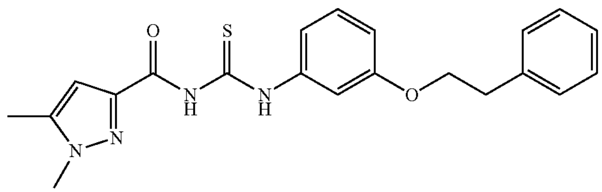 | 1-(1,5-dimethyl-1H-pyrazole-3-carbonyl)-3-(3-phenethoxyphenyl)thiourea | HPLC (tR) = 3.98 min MS (APCI) m/z 395 [M + H]+ | B |
| 359 | 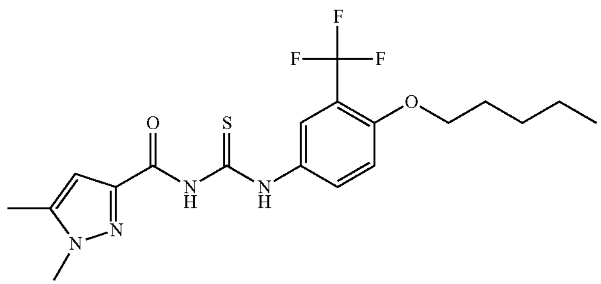 | 1-(1,5-dimethyl-1H-pyrazole-3-carbonyl)-3-(4-(pentyloxy)-3-(trifluoromethyl)phenyl)thiourea | HPLC (tR) = 4.34 min MS (APCI) m/z 429 [M + H]+ | B |
| 360 | 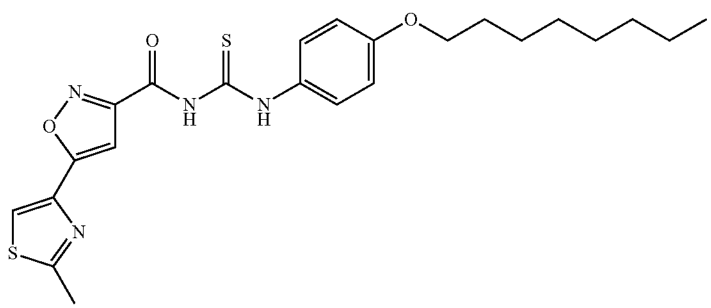 | 1-(5-(2-methylthiazol-4-yl)isoxazole-3-carbonyl)-3-(4-(octyloxy)phenyl)thiourea | HPLC (tR) = 5.09 min MS (APCI) m/z 473 [M + H]+ | B |

TABLE III-continued

| CPD # | STRUCTURE | NAME | MS | method |
|---|---|---|---|---|
| 361 | 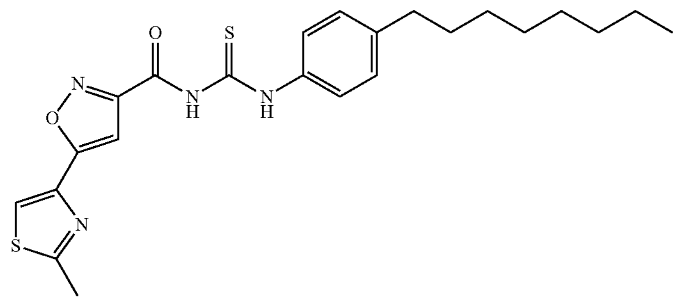 | 1-(5-(2-methylthiazol-4-yl)isoxazole-3-carbonyl)-3-(4-octylphenyl)thiourea | HPLC (tR) = 5.42 min MS (APCI) m/z 459 [M + H]+ | B |
| 362 | 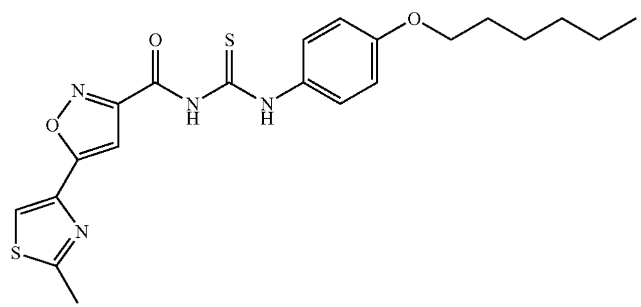 | 1-(4-(hexyloxy)phenyl)-3-(5-(2-methylthiazol-4-yl)isoxazole-3-carbonyl)thiourea | HPLC (tR) = 4.53 min MS (APCI) m/z 445 [M + H]+ | B |
| 363 | 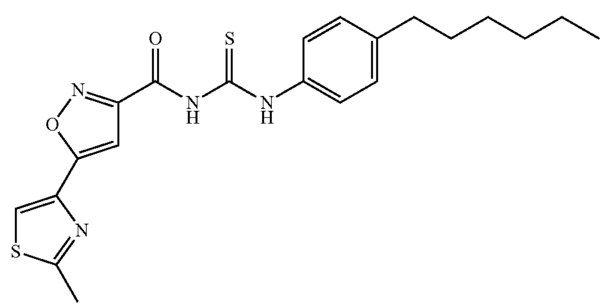 | 1-(4-hexylphenyl)-3-(5-(2-methylthiazol-4-yl)isoxazole-3-carbonyl)thiourea | HPLC (tR) = 4.83 min MS (APCI) m/z 429 [M + H]+ | B |

TABLE III-continued

| CPD # | STRUCTURE | NAME | MS | method |
|---|---|---|---|---|
| 364 | 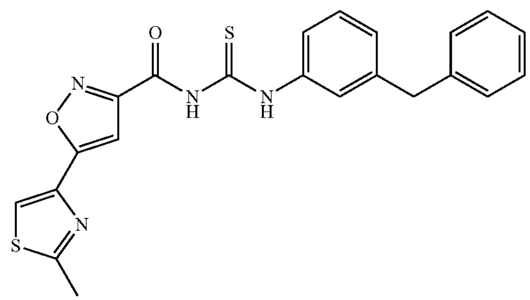 | 1-(3-benzylphenyl)-3-(5-(2-methylthiazol-4-yl)isoxazole-3-carbonyl)thiourea | HPLC (tR) = 3.98 min MS (APCI) m/z 435 [M + H]+ | B |
| 365 | 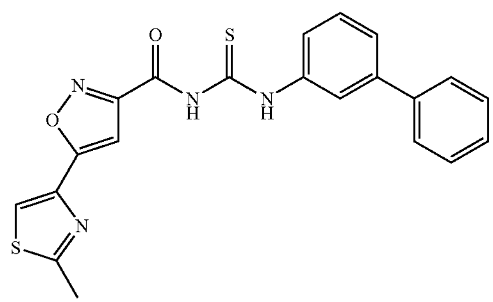 | 1-(3-phenyl-phenyl)-3-(5-(2-methylthiazol-4-yl)isoxazole-3-carbonyl)thiourea | HPLC (tR) = 3.94 min MS (APCI) m/z 421 [M + H]+ | B |
| 366 | 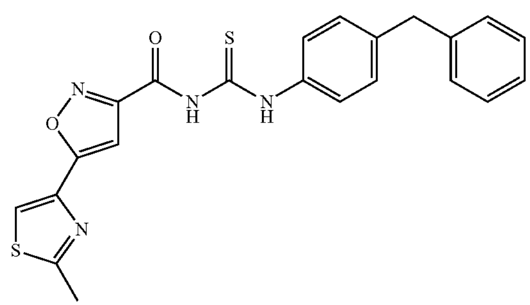 | 1-(4-benzylphenyl)-3-(5-(2-methylthiazol-4-yl)isoxazole-3-carbonyl)thiourea | HPLC (tR) = 3.98 min MS (APCI) m/z 435 [M + H]+ | B |

TABLE III-continued

| CPD # | STRUCTURE | NAME | MS | method |
|---|---|---|---|---|
| 367 | 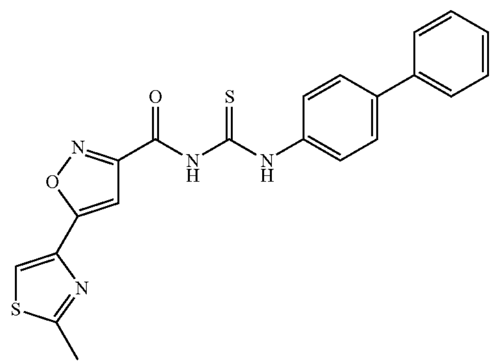 | 1-(4-phenyl-phenyl)-3-(5-(2-methylthiazol-4-yl)isoxazole-3-carbonyl)thiourea | HPLC (tR) = 4.00 min MS (APCI) m/z 421 [M + H]+ | B |
| 368 | 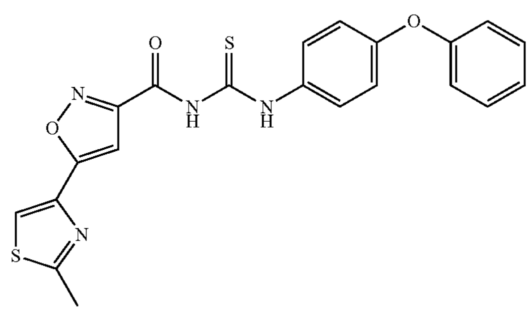 | 1-(3-phenoxyphenyl)-3-(1,2,4-triazine-3-carbonyl)thiourea | HPLC (tR) = 3.92 min MS (APCI) m/z 437 [M + H]+ | B |
| 369 | 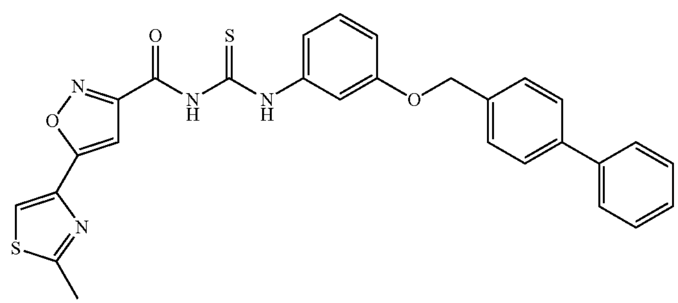 | 1-(3-(4-phenyl)phenyl)-3-(5-(2-methylthiazol-4-yl)isoxazole-3-carbonyl)thiourea | HPLC (tR) = 4.45 min MS (APCI) m/z 527 [M + H]+ | B |

TABLE III-continued

| CPD # | STRUCTURE | NAME | MS | method |
|---|---|---|---|---|
| 370 | 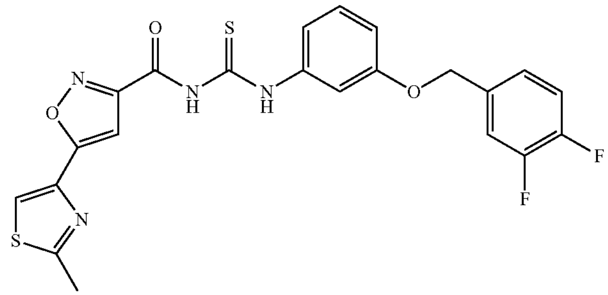 | 1-(3-(3,4-difluorobenzyloxy)phenyl)-3-(5-(2-methylthiazol-4-yl)isoxazole-3-carbonyl)thiourea | HPLC (tR) = 3.99 min MS (APCI) m/z 487 [M + H]+ | B |
| 371 | 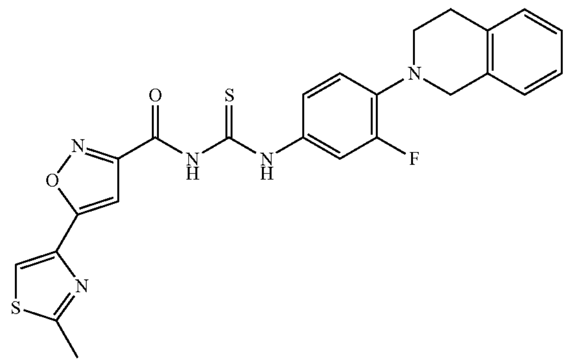 | 1-(4-(3,4-dihydroisoquinolin-2(1H)-yl)-3-fluorophenyl)-3-(5-(2-methylthiazol-4-yl)isoxazole-3-carbonyl)thiourea | HPLC (tR) = 4.20 min MS (APCI) m/z 494 [M + H]+ | B |
| 372 | 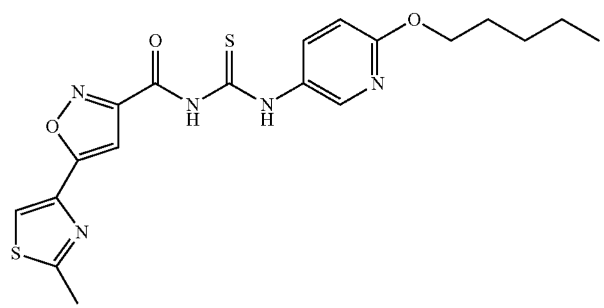 | 1-(5-(2-methylthiazol-4-yl)isoxazole-3-carbonyl)-3-(6-(pentyloxy)pyridin-3-yl)thiourea | HPLC (tR) = 4.03 min MS (APCI) m/z 432 [M + H]+ | B |

TABLE III-continued

| CPD # | STRUCTURE | NAME | MS | method |
|---|---|---|---|---|
| 373 | 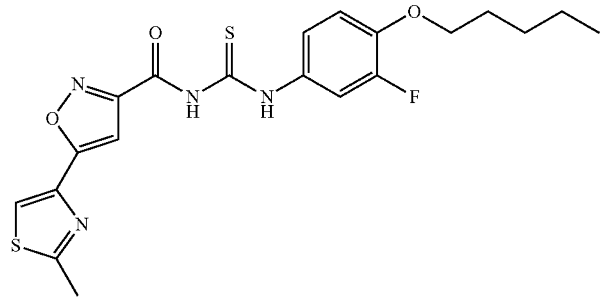 | 1-(3-fluoro-4-(pentyloxy)phenyl)-3-(5-(2-methylthiazol-4-yl)isoxazole-3-carbonyl)thiourea | HPLC (tR) = 4.23 min MS (APCI) m/z 449 [M + H]+ | B |
| 374 | 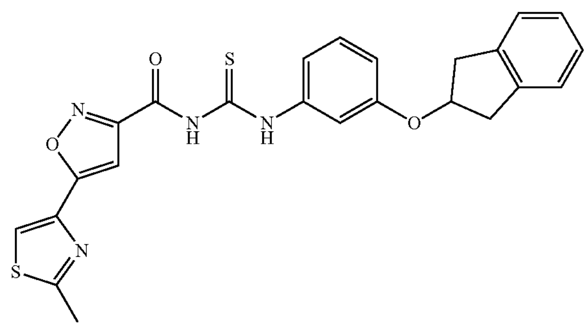 | 1-(3-(2,3-dihydro-1H-inden-2-yloxy)phenyl)-3-(5-(2-methylthiazol-4-yl)isoxazole-3-carbonyl)thiourea | HPLC (tR) = 4.14 min MS (APCI) m/z 477 [M + H]+ | B |
| 375 | 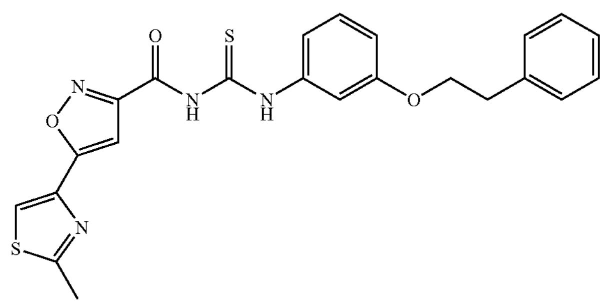 | 1-(5-(2-methylthiazol-4-yl)isoxazole-3-carbonyl)-3-(3-phenethoxyphenyl)thiourea | HPLC (tR) = 4.08 min MS (APCI) m/z 465 [M + H]+ | B |

TABLE III-continued

| CPD # | STRUCTURE | NAME | MS | method |
|---|---|---|---|---|
| 376 | 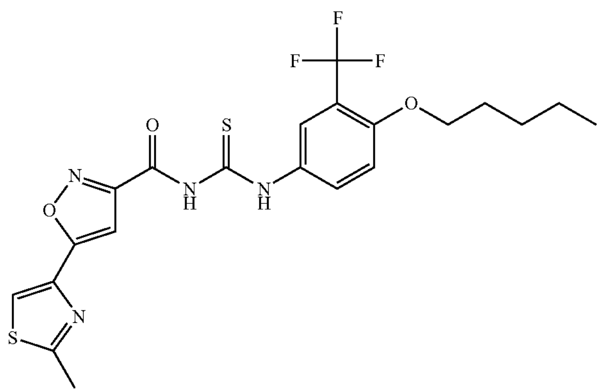 | 1-(5-(2-methylthiazol-4-yl)isoxazole-3-carbonyl)-3-(4-(pentyloxy)-3-(trifluoromethyl)phenyl)thiourea | HPLC (tR) = 4.45 min MS (APCI) m/z 499 [M + H]+ | B |
| 377 | 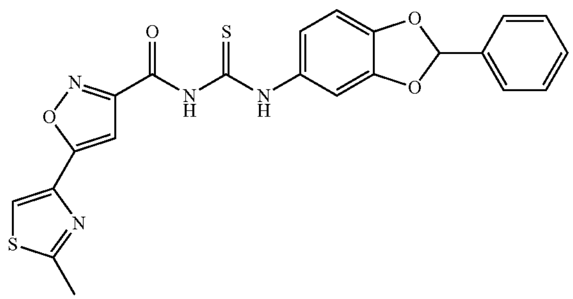 | 1-(5-(2-methylthiazol-4-yl)isoxazole-3-carbonyl)-3-(2-phenylbenzo[d][1,3]dioxol-5-yl)thiourea | HPLC (tR) = 3.82 min MS (APCI) m/z 465 [M + H]+ | B |
| 378 | 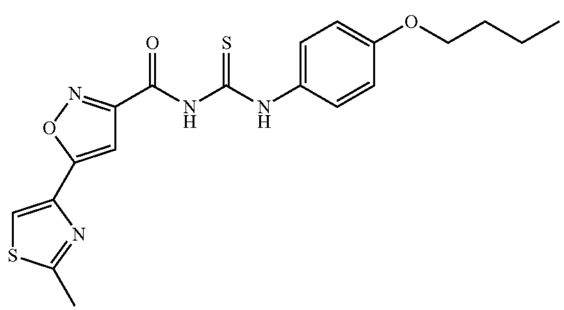 | 1-(4-butoxyphenyl)-3-(5-(2-methylthiazol-4-yl)isoxazole-3-carbonyl)thiourea | HPLC (tR) = 4.05 min MS (APCI) m/z 417 [M + H]+ | B |

TABLE III-continued

| CPD # | STRUCTURE | NAME | MS | method |
|---|---|---|---|---|
| 379 | 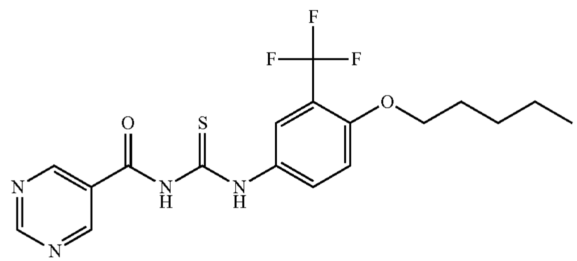 | 1-(4-(pentyloxy)-3-(trifluoromethyl)phenyl)-3-(pyrimidine-5-carbonyl)thiourea | HPLC (tR) = 3.92 min MS (APCI) m/z 413 [M + H]+ | B |
| 380 | 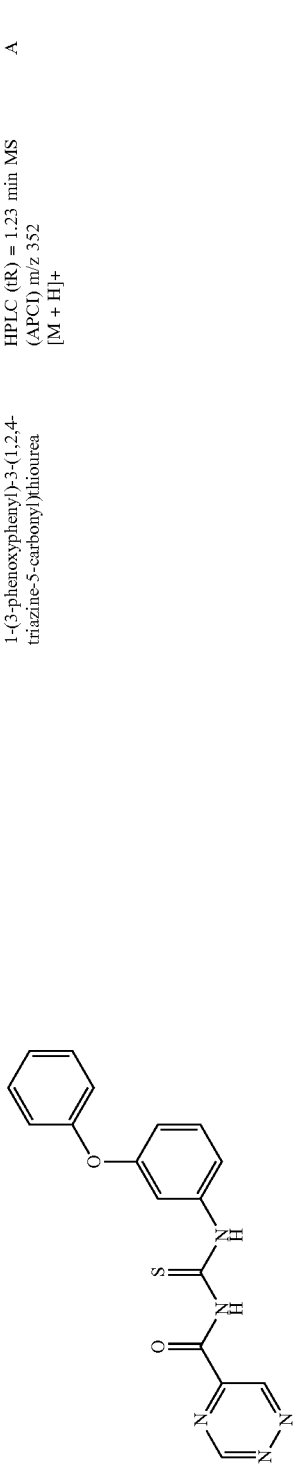 | 1-(3-phenoxyphenyl)-3-(1,2,4-triazine-5-carbonyl)thiourea | HPLC (tR) = 1.23 min MS (APCI) m/z 352 [M + H]+ | A |
| 381 | 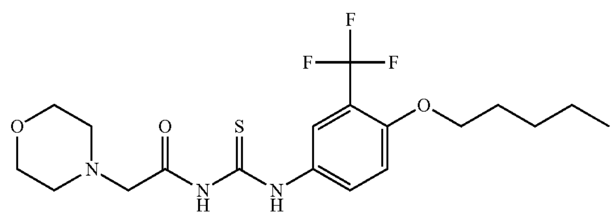 | 1-(2-morpholinoacetyl)-3-(4-(pentyloxy)-3-(trifluoromethyl)phenyl)thiourea | HPLC (tR) = 1.46 min MS (APCI) m/z 434 [M + H]+ | A |
| 382 | 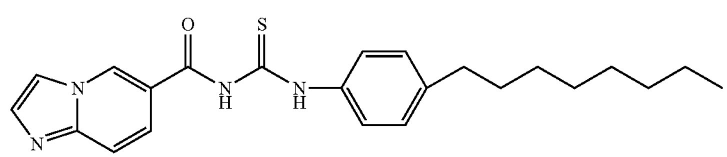 | 1-(H-imidazo[1,2-a]pyridine-6-carbonyl)-3-(4-octylphenyl)thiourea | HPLC (tR) = 2.01 min MS (APCI) m/z 409 [M + H]+ | B |

TABLE III-continued

| CPD # | STRUCTURE | NAME | MS | method |
|---|---|---|---|---|
| 383 | 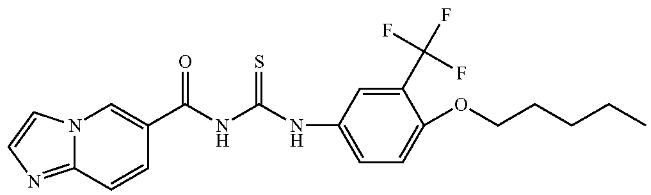 | 1-(H-imidazo[1,2-a]pyridine-6-carbonyl)-3-(4-(pentyloxy)-3-(trifluoromethyl)phenyl)thiourea | HPLC (tR) = 1.98 min MS (APCI) m/z 451 [M + H]+ | B |
| 384 | 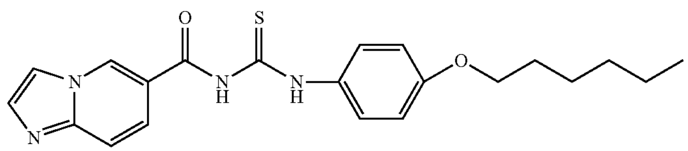 | 1-(4-(hexyloxy)phenyl)-3-(H-imidazo[1,2-a]pyridine-6-carbonyl)thiourea | HPLC (tR) = 2.01 min MS (APCI) m/z 397 [M + H]+ | B |
| 385 | 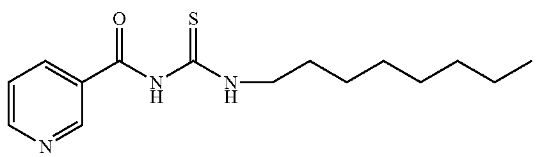 | 1-nicotinoyl-3-octylthiourea | HPLC (tR) = 1.85 min MS (APCI) m/z 294.46 [M + H]+ | A |
| 386 | 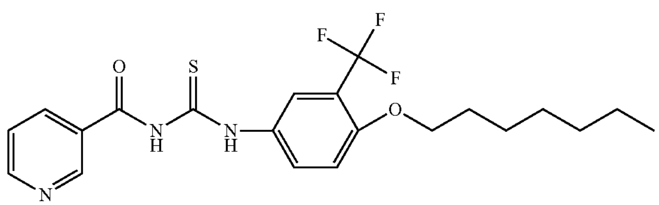 | 1-(4-(heptyloxy)-3-(trifluoromethyl)phenyl)-3-nicotinoylthiourea | HPLC (tR) = 2.36 min MS (APCI) m/z 440.67 [M + H]+ | A |
| 387 | 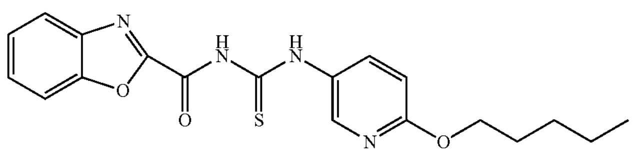 | 1-(benzo[d]oxazole-2-carbonyl)-3-(6-(pentyloxy)pyridin-3-yl)thiourea | HPLC (tR) = 2.02 min MS (APCI) m/z 385.4 [M + H]+ | A |
| 388 | 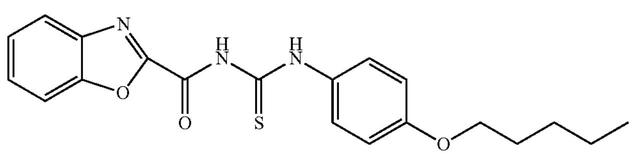 | 1-(benzo[d]oxazole-2-carbonyl)-3-(4-(pentyloxy)phenyl)thiourea | HPLC (tR) = 2.06 min MS (APCI) m/z 384.5 [M + H]+ | A |

TABLE III-continued

| CPD # | STRUCTURE | NAME | MS | method |
|---|---|---|---|---|
| 389 | 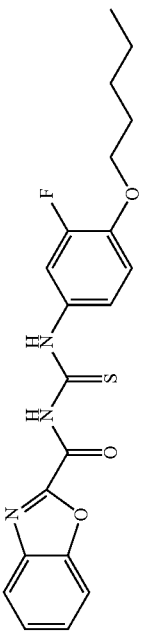 | 1-(benzo[d]oxazole-2-carbonyl)-3-(3-fluoro-4-(pentyloxy)phenyl)thiourea | HPLC (tR) = 2.08 min MS (APCI) m/z 402.6 [M + H]+ | A |
| 390 | 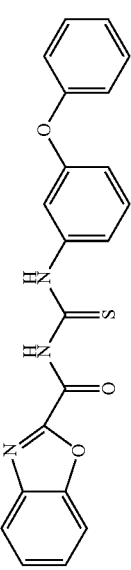 | 1-(benzo[d]oxazole-2-carbonyl)-3-(3-phenoxyphenyl)thiourea | HPLC (tR) = 1.90 min MS (APCI) m/z 390.5 [M + H]+ | A |
| 391 | 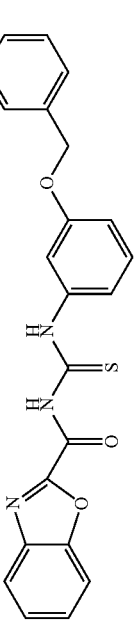 | 1-(benzo[d]oxazole-2-carbonyl)-3-(3-(benzyloxy)phenyl)thiourea | HPLC (tR) = 1.91 min MS (APCI) m/z 404.5 [M + H]+ | A |
| 392 | 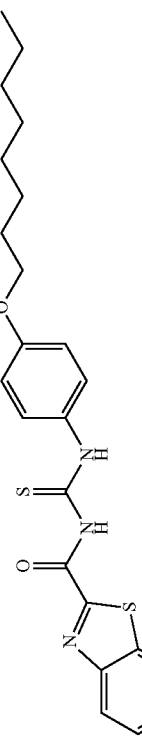 | 1-(benzo[d]thiazole-2-carbonyl)-3-(4-(octyloxy)phenyl)thiourea | HPLC (tR) = 5.86 min MS (APCI) m/z 442 [M + H]+ | B |
| 393 | 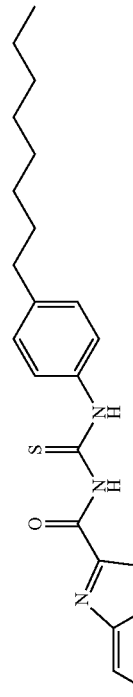 | 1-(benzo[d]thiazole-2-carbonyl)-3-(4-(octylphenyl)thiourea | HPLC (tR) = 6.37 min MS (APCI) m/z 426 [M + H]+ | B |

TABLE III-continued

| CPD # | STRUCTURE | NAME | MS | method |
|---|---|---|---|---|
| 394 | 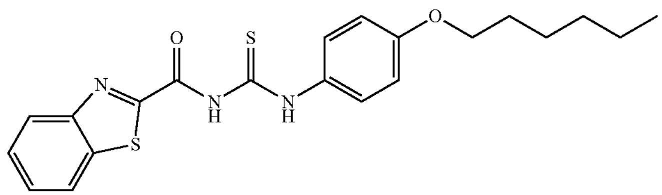 | 1-(benzo[d]thiazole-2-carbonyl)-3-(4-octyloxyphenyl)thiourea | HPLC (tR) = 5.17 min MS (APCI) m/z 414 [M + H]+ | B |
| 395 | 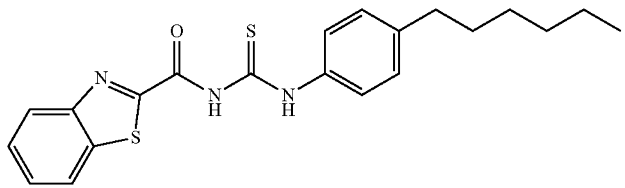 | 1-(2-morpholinoacetyl)-3-(4-(pentyloxy)-3-(trifluoromethyl)phenyl)thiourea | HPLC (tR) = 5.56 min MS (APCI) m/z 398 [M + H]+ | B |
| 396 | 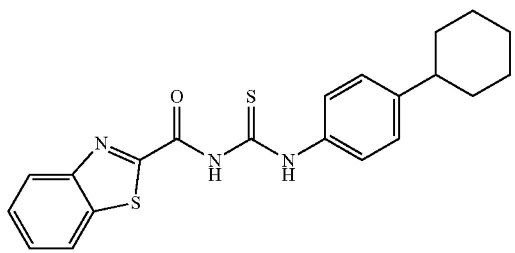 | 1-(benzo[d]thiazole-2-carbonyl)-3-(4-cyclohexylphenyl)thiourea | HPLC (tR) = 5.26 min MS (APCI) m/z 396 [M + H]+ | B |
| 397 | 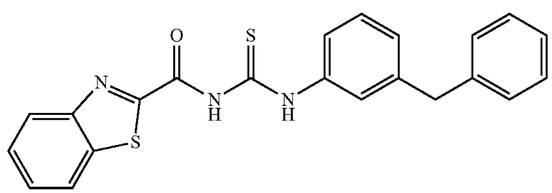 | 1-(benzo[d]thiazole-2-carbonyl)-3-(3-benzylphenyl)thiourea | HPLC (tR) = 4.49 min MS (APCI) m/z 404 [M + H]+ | B |
| 398 | 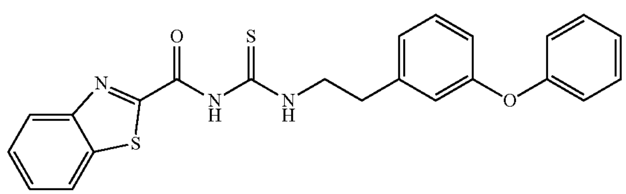 | 1-(3-phenoxyphenethyl)-3-(benzo[d]thiazole-2-carbonyl)thiourea | HPLC (tR) = 4.45 min MS (APCI) m/z 434 [M + H]+ | B |

TABLE III-continued

| CPD # | STRUCTURE | NAME | MS | method |
|---|---|---|---|---|
| 399 | 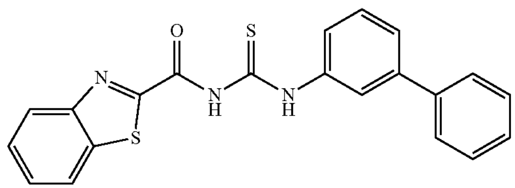 | 1-(benzo[d]thiazole-2-carbonyl)-3-(3-phenyl-phenyl)thiourea | HPLC (tR) = 4.49 min MS (APCI) m/z 390 [M + H]+ | B |
| 400 | 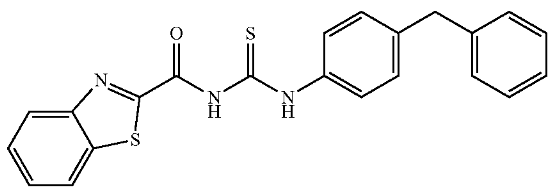 | 1-(benzo[d]thiazole-2-carbonyl)-3-(4-benzylphenyl)thiourea | HPLC (tR) = 4.47 min MS (APCI) m/z 404 [M + H]+ | B |
| 401 | 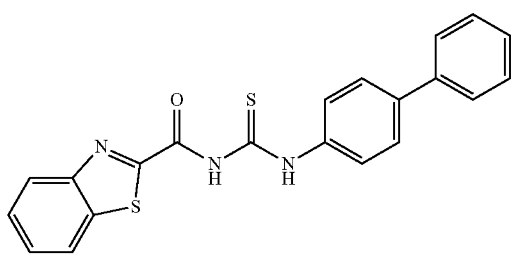 | 1-(benzo[d]thiazole-2-carbonyl)-3-(4-phenyl-phenyl)thiourea | HPLC (tR) = 4.55 min MS (APCI) m/z 390 [M + H]+ | B |
| 402 | 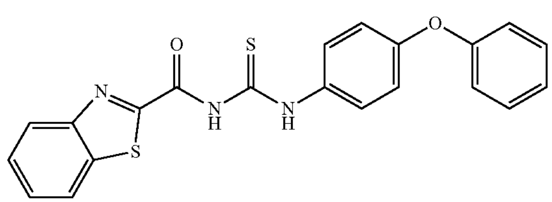 | 1-(benzo[d]thiazole-2-carbonyl)-3-(4-phenoxyphenyl)thiourea | HPLC (tR) = 4.47 min MS (APCI) m/z 406 [M + H]+ | B |

TABLE III-continued

| CPD # | STRUCTURE | NAME | MS | method |
|---|---|---|---|---|
| 403 | 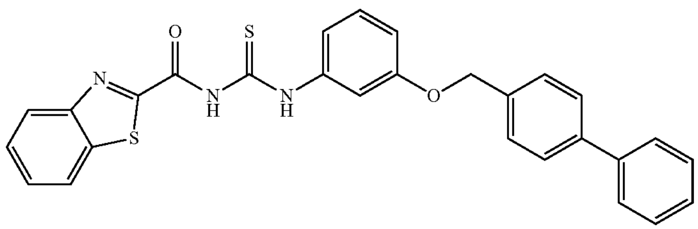 | 1-(3-(4-Phenyl-benzyloxy) phenyl)-3-(benzo[d] thiazole-2-carbonyl)thiourea | HPLC (tR) = 5.04 min MS (APCI) m/z 496 [M + H]+ | B |
| 404 | 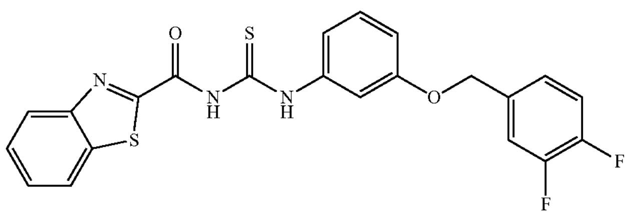 | 1-(3-(3,4-difluorobenzyloxy) phenyl)-3-(benzo[d] thiazole-2-carbonyl)thiourea | HPLC (tR) = 4.50 min MS (APCI) m/z 456 [M + H]+ | B |
| 405 | 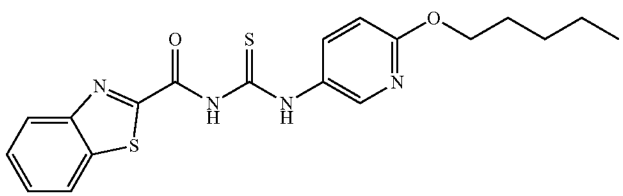 | 1-(benzo[d]thiazole-2-carbonyl)-3-(6-(pentyloxy)pyridin-3-yl)thiourea | HPLC (tR) = 4.61 min MS (APCI) m/z 401 [M + H]+ | B |
| 406 | 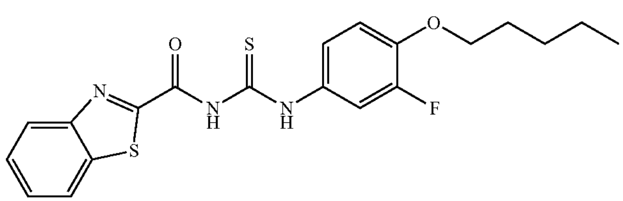 | 1-(benzo[d]thiazole-2-carbonyl)-3-(3-fluoro-4-(pentyloxy)phenyl)thiourea | HPLC (tR) = 4.83 min MS (APCI) m/z 418 [M + H]+ | B |

TABLE III-continued

| CPD # | STRUCTURE | NAME | MS | method |
|---|---|---|---|---|
| 407 | 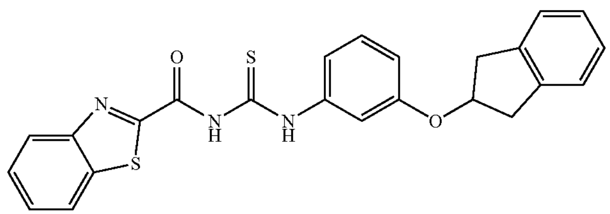 | 1-(benzo[d]thiazole-2-carbonyl)-3-(3-(2,3-dihydro-1H-inden-2-yloxy)phenyl)thiourea | HPLC (tR) = 4.65 min MS (APCI) m/z 446 [M + H]+ | B |
| 408 | 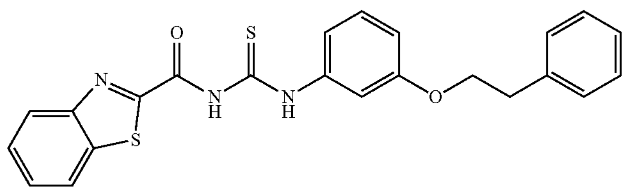 | 1-(benzo[d]thiazole-2-carbonyl)-3-(3-phenethoxyphenyl)thiourea | HPLC (tR) = 4.58 min MS (APCI) m/z 434 [M + H]+ | B |
| 409 | 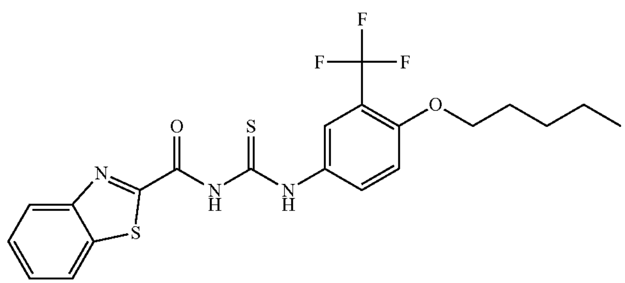 | 1-(benzo[d]thiazole-2-carbonyl)-3-(4-(pentyloxy)-3-(trifluoromethyl)phenyl)thiourea | HPLC (tR) = 5.00 min MS (APCI) m/z 468 [M + H]+ | B |
| 410 | 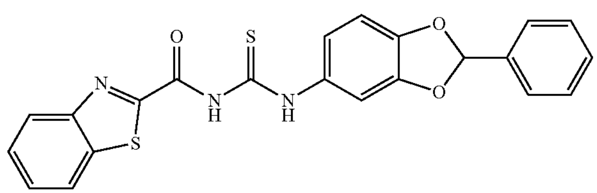 | 1-(benzo[d]thiazole-2-carbonyl)-3-(2-phenyl-benzo[d][1,3]dioxol-5-yl)thiourea | HPLC (tR) = 4.31 min MS (APCI) m/z 434 [M + H]+ | B |

| CPD # | STRUCTURE | NAME | MS | method |
|---|---|---|---|---|
| 411 | 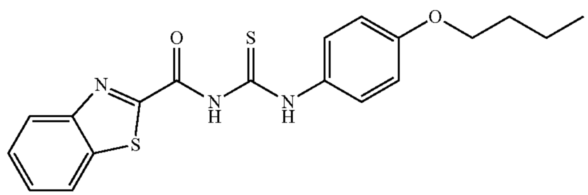 | 1-(benzo[d]thiazole-2-carbonyl)-3-(4-butoxyphenyl)thiourea | HPLC (tR) = 4.59 min MS (APCI) m/z 386 [M + H]+ | B |
| 412 | 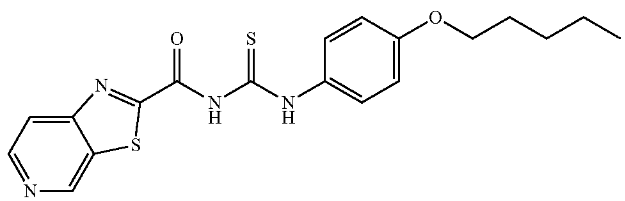 | 1-(4-(pentyloxy)phenyl)-3-(thiazolo[5,4-c]pyridine-2-carbonyl)thiourea | HPLC (tR) = 2.06 min MS (APCI) m/z 401.55 [M + H]+ | A |
| 413 | 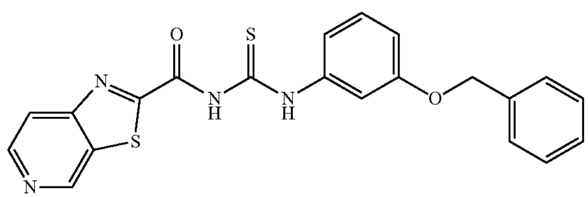 | 1-(3-(benzyloxy)phenyl)-3-(thiazolo[5,4-c]pyridine-2-carbonyl)thiourea | HPLC (tR) = 1.83 min MS (APCI) m/z 421.53 [M + H]+ | A |
| 414 | 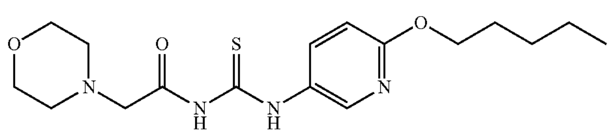 | 1-(2-morpholinoacetyl)-3-(6-(pentyloxy)pyridin-3-yl)thiourea | HPLC (tR) = 1.16 min MS (APCI) m/z 367.2 [M + H]+ | A |
| 415 | 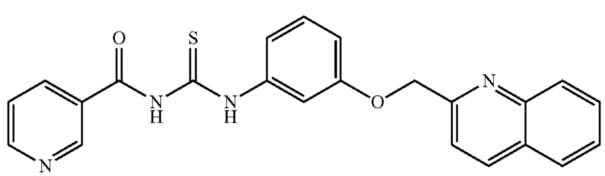 | 1-nicotinoyl-3-(3-(quinolin-2-ylmethoxy)phenyl)thiourea | HPLC (tR) = 1.29 min MS (APCI) m/z 415.1 [M + H]+ | A |

| CPD # | STRUCTURE | NAME | MS | method |
|---|---|---|---|---|
| 416 | 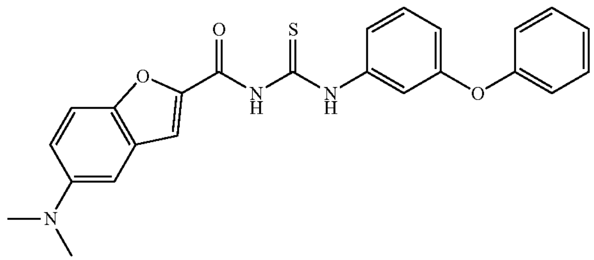 | 1-(5-(dimethylamino)benzofuran-2-carbonyl)-3-(3-phenoxyphenyl)thiourea | HPLC (tR) = 1.49 min MS (APCI) m/z 432.1 [M + H]+ | A |
| 417 | 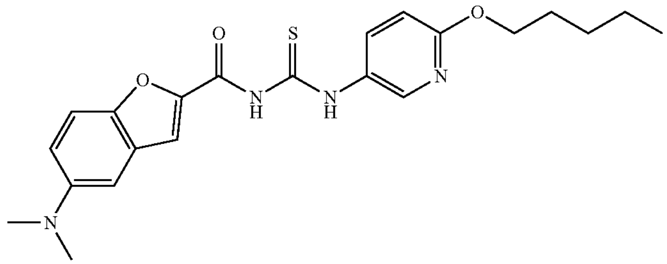 | 1-(5-(dimethylamino)benzofuran-2-carbonyl)-3-(6-(pentyloxy)pyridin-3-yl)thiourea | HPLC (tR) = 2.29 min MS (APCI) m/z 427.1 [M + H]+ | A |
| 418 | 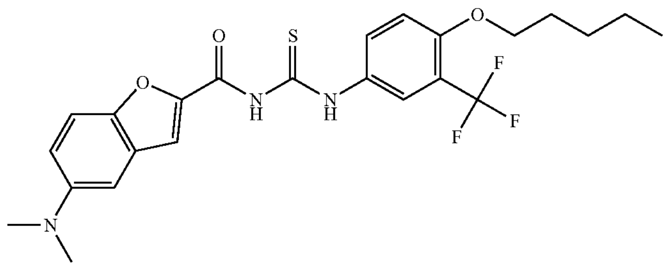 | 1-(5-(dimethylamino)benzofuran-2-carbonyl)-3-(4-(pentyloxy)-3-(trifluoromethyl)phenyl)thiourea | HPLC (tR) = 1.83 min MS (APCI) m/z 494.1 [M + H]+ | A |
| 419 | 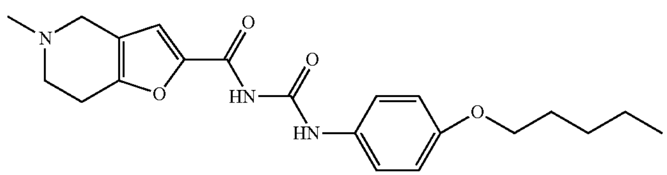 | 1-(5-methyl-4,5,6,7-tetrahydrofuro[3,2-c]pyridine-2-carbonyl)-3-(4-(pentyloxy)phenyl)thiourea | HPLC (tR) = 0.589 min MS (APCI) m/z 403 [M + H]+ | B |

TABLE III-continued

| CPD # | STRUCTURE | NAME | MS | method |
|---|---|---|---|---|
| 420 | 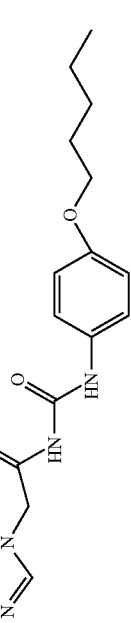 | 1-(2-(1H-imidazol-1-yl)acetyl)-3-(4-(pentyloxy)phenyl)thiourea | HPLC (tR) = 2.42 min MS (APCI) m/z 347 [M + H]+ | B |
| 421 | 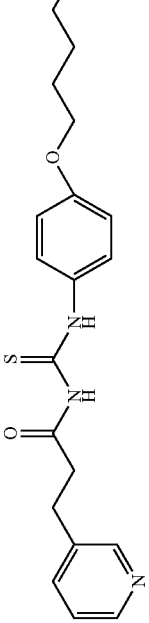 | 1-(4-(pentyloxy)phenyl)-3-(3-(pyridin-3-yl)propanoyl)thiourea | HPLC (tR) = 1.37 min MS (APCI) m/z 372 [M + H]+ | B |
| 422 | 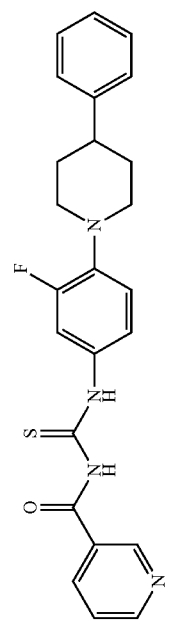 | 1-(3-fluoro-4-(4-phenylpiperidin-1-yl)phenyl)-3-nicotinoylthiourea | HPLC (tR) = 1.61 min MS (APCI) m/z 435 [M + H]+ | B |
| 423 | 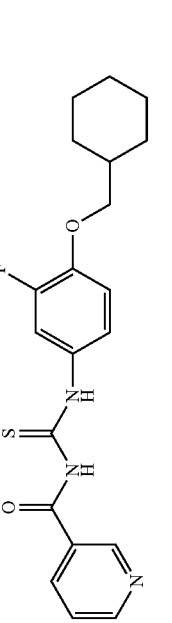 | 1-(4-(cyclohexylmethoxy)-3-fluorophenyl)-3-nicotinoylthiourea | HPLC (tR) = 1.94 min MS (APCI) m/z 389 [M + H]+ | B |
| 424 | 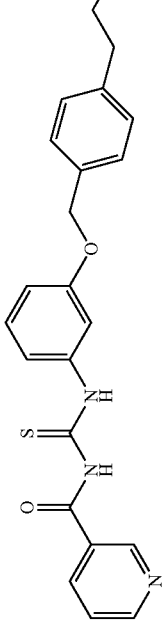 | 1-(3-(4-propylbenzyloxy)phenyl)-3-nicotinoylthiourea | HPLC (tR) = 1.94 min MS (APCI) m/z 406 [M + H]+ | A |

TABLE III-continued

| CPD # | STRUCTURE | NAME | MS | method |
|---|---|---|---|---|
| 425 | 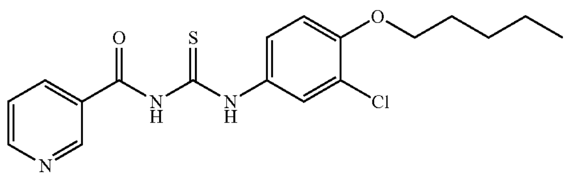 | 1-(3-chloro-4-(pentyloxy)phenyl)-3-nicotinoylthiourea | HPLC (tR) = 1.97 min MS (AFASTA) m/z 378; 380 [M + H]+ | A |
| 426 | 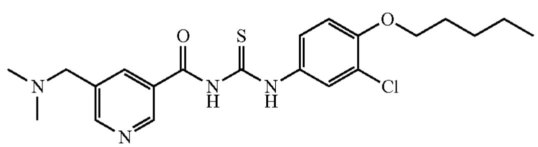 | 1-(3-chloro-4-(pentyloxy)phenyl)-3-(5-((dimethylamino)methyl)nicotinoyl)thiourea | HPLC (tR) = 1.63 min MS APCI m/z 469.65 [M + H]+ | A |
| 427 | 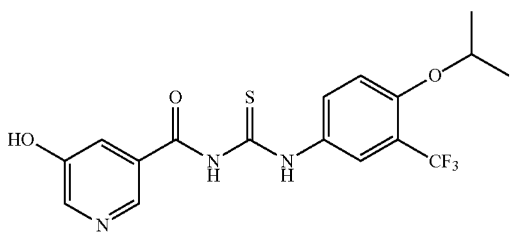 | 1-(3-hydroxynicotinoyl)-3-(4-isopropoxy-3-(trifluoromethyl)phenyl)thiourea | HPLC (tR) = 1.59 min MS APCI m/z 400.38 [M + H]+ | A |
| 428 | 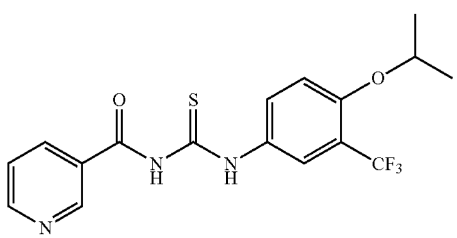 | 1-(4-isopropoxy-3-(trifluoromethyl)phenyl)-3-nicotinoylthiourea | HPLC (tR) = 1.69 min MS APCI m/z 384.38 [M + H]+ | A |

Example 7

ASSAY FOR IDENTIFYING COMPOUNDS WHICH INHIBIT HCV REPLICATION

The compounds claimed herein were tested for the ability to inhibit viral replication of the Hepatitis C replicon in cultured cells in which the HCV replicon construct has been incorporated. Bartenschlager, et al. described the HCV replicon system (Science, 285, pp. 110-113 (1999)). The replicon system is predictive of in vivo anti-HCV activity; compounds that are active in humans uniformly evidence activity in the replicon assay.

In this assay HCV replicon containing cells are treated with different concentrations of the test compound to ascertain the ability of the test compound to suppress replication of the HCV replicon. As a positive control, HCV replicon-containing cells are treated with different concentrations of interferon alpha, a known inhibitor of HCV replication. The replicon assay system includes Neomycin Phosphotransferase (NPT) as a component of the replicon itself in order to detect the transcription of replicon gene products in the host cell. Cells in which the HCV replicon is actively replicating have high levels of NPT; the level of NPT is proportional to HCV replication. Cells in which the HCV replicon is not replicating also have low levels of NPT and thus do not survive when treated with Neomycin. The NPT level of each sample is measured using a captured ELISA.

A protocol for testing compounds for the ability to inhibit viral replication of the Hepatitis C replicon cultured cells in which the replicon construct has been incorporated, follows.

7A. HCV Replicon and Replicon Expression

The HCV genome consists of a single ORF that encodes a 3000 amino acid polyprotein. The ORF is flanked on the 5' side by an untranslated region that serves as an internal ribosome entry site (IRES) and at the 3' side by a highly conserved sequence necessary for viral replication (3'-NTR). The structural proteins, necessary for viral infection, are located near the 5' end of the ORF. The non-structural proteins, designated NS2 to NS5B comprise the remainder of the ORF.

The HCV replicon contains, 5'-3', the HCV-IRES, the neomycin phosphotransferase (neo) gene, the IRES of encephalomyocarditis virus, which directs translation of HCV sequences NS3 to NS5B, and the 3'-NTR. The sequence of the HCV replicon has been deposited in GenBank (Accession no. AJ242652).

The replicon is transfected into Huh-7 cells using standard methods such as electroporation.

7B. Cell Maintenance

The equipment and materials include, but are not limited to, Huh-7 HCV replicon-containing cells, maintenance media (DMEM (Dulbecco's modified Eagle media) supplemented with 10% FBS, L-glutamine, non-essential amino acids, penicillin (100 units/ml), streptomycin (100 micrograms/ml), and 500 micrograms/ml of Geneticin G418), screening media (DMEM supplemented with 10% FBS, L-glutamine, and non-essential amino acid, penicillin (100 units/ml) and streptomycin (100 micrograms/ml)), 96 well tissue culture plates (flat bottom), 96 well plates (U bottom for drug dilution), Interferon alpha for positive control, fixation reagent (such as methanol:acetone), primary antibody (rabbit anti-NPTII), secondary antibody: Eu—N1 1, and enhancement solution.

HCV replicon-containing cells support high levels of viral RNA replicon replication when their density is suitable. Over-confluency will cause decreased viral RNA replication. Therefore, cells must be kept growing in log phase in the presence of 500 micrograms/ml of G418. Generally, cells should be passed twice a week at 1:4-6 dilution. Cell maintenance is conducted as follows:

HCV replicon-containing cells are examined under a microscope to ensure that cells growing well. Cells are rinsed once with PBS and 2 ml trypsin is added. The cell/trypsin mixture is incubated at 37° C. in a $CO_2$ incubator for 3-5 minutes. After incubation 10 ml of complete media is added to stop the trypsinization reaction. Cells are blown gently, put into a 15 ml tube, and spun at 1200 rpm for 4 minutes. The trypsin/medium solution is removed. Medium (5 ml) is added and the cells are mixed carefully. The cells are counted.

The cells are then seeded onto 96-well plates at a density of 6000-7500 cells/100 microliters/well (6-7.5×105 cells/10 ml/plate). The plates are then incubated at 37° C. in a 5% $CO_2$ incubator.

Cells are examined under a microscope approximated 24 hours after seeding and prior to adding drugs. If counting and dilution were performed correctly, cells are 60-70% confluent and nearly all cells should attach and spread evenly in the well.

7C. Treatment of HCV-Replicon Containing Cells with Test Compound

HCV replicon-containing cells are rinsed with once PBS once; 2 mls of trypsin is added. Cells are incubated at 37° C. in a 5% $CO_2$ incubator for 3-5 minutes. 10 mls of complete medium is added to stop the reaction. Cells are blown gently, put into a 15 ml tube, and spun at 1200 rpm for four minutes. The trypsin/medium solution is removed and 5 mls of medium (500 ml DMEM (high glucose)) from BRL catalog #12430-054; 50 mls 10% FBS, 5% Geneticin G418 (50 mg/ml, BRL 10131-035), 5 ml MEM non-essential amino acid (100×BRL #11140-050) and 5 ml pen-strep (BRL #15140-148) is added. The cells and media are mixed carefully Cells are plated with screening medium (500 ml DMEM (BRL #21063-029), 50 ml FBS (BRL #10082-147) and 5 ml MEM non-essential amino acid (BRL #11140-050) at 6000-7500 cells/100 µl/well of 96 well plate (6-7.5×10$^5$ cells/10 ml/plate). Plates are placed into 37° C. 5% $CO_2$ incubator overnight.

7D. Assay

The following morning, drugs (test compounds or interferon alpha) are diluted in 96 well U bottom plates with media or DMSO/media, depending on the final concentration chosen for screening. Generally for 6 concentrations of each test compounds ranging from 10 micromolar to 0.03 micromolar are applied. 100 µl of the test compound dilution is placed in wells of the 96 well plates containing the HCV replicon cells. Media without drug is added to some wells as a negative controls. DMSO is known to affect cell growth. Therefore, if drugs diluted in DMSO are used, all wells, including negative control (media only) and positive control (interferon alpha) wells, must contain the same concentration of DMSO, for single dose screening. The plates are incubated at 37° C. in a humidified 5% $CO_2$ environment for three days.

On day four, the NTPII assay is quantitated. The medium is poured from the plates and the plates are washed once in 200 µl of PBS. The PBS is then decanted and the plates tapped in a paper towel to remove any remaining PBS. Cells are fixed in situ with 100 μl/well of pre-cooled (−20° C.) methanol:acetone (1:1) and the plates are placed at −20° C. for 30 minutes.

The fixing solution is poured from the plates and the plates are allowed to air-dry completely (approximately one hour). The appearance of the dried cell layer is recorded and the density of the cells in the toxic wells is scored with the naked eye. Alternatively cell viability may be assessed using the MTS assay described below.

The wells are blocked with 200 μl of blocking solution (10% FBS; 3% NGS in PBS) for 30 minutes at room temperature. The blocking solution is removed and 100 μl of rabbit anti-NPTII diluted 1:1000 in blocking solution is added to each well. The plates are then incubated 45-60 minutes at room temperature. After incubation, wells are washed six times with PBS-0.05% Tween-20 solution. 100 μl of 1:15,000 diluted Europium (EU)-conjugated goat anti-rabbit in blocking buffer is added to each well and incubated at room temperature for 30-45 minutes. The plates are washed again and 100 μl of enhancement solution (Perkin Elmer #4001-0010) is added to each well. Each plate is shaken (approx. 30 rpm) in a plate shaker for three minutes. 95 μl is transferred from each well to a black plate; the EU signal is quantitated in a Perkin-Elmer VICTOR plate reader (EU-Lance).

Test Results:

Compounds 1-426, shown in Examples 3 to 5 and Tables I, II, and III have been tested in the above assay and found to inhibit replication of the HCV replicon with EC50 values of less than 10 micromolar.

Example 8

CYTOTOXICITY ASSAYS

To insure that the decrease in replicon replication is due to compound activity against the HCV replicon rather than nonspecific toxicity assays are used to quantitate compound cytotoxicity.

Example 8A

Cellular Protein Albumin Assay for Cytotoxicity

Cellular protein albumin measurements provide one marker of cytotoxicity. The protein levels obtained from cellular albumin assays may also be used to provide a normalization reference for antiviral activity of compounds. (Check on the meaning of this statement) In the protein albumin assay HCV replicon-containing cells are treated for three days with different concentrations of helioxanthin; a compound that is known to be cytotoxic at high concentrations. The cells are lysed and the cell lysate used to bind plate-bound goat anti-albumin antibody at room temperature (25° C. to 28° C.) for 3 hours. The plate is then washed 6 times with 1×PBS. After washing away the unbound proteins, mouse monoclonal anti-human serum albumin is applied to bind the albumin on the plate. The complex is then detected using phosphatase-labeled anti-mouse IgG as a second antibody.

Cell viability may also be determined via the CELLTITER 96 AQUEOUS ONE Solution Cell Proliferation Assay (Promega, Madison Wis.), a calorimetric assay for determining the number of viable cells. In this method, 10-20 μl MTS reagent is added to each well according to manufacturer's instructions before fixing the cells, plates are incubated at 37° C., and read at OD 490 nm. During the incubation period living cells covert the MTS reagent to a formazan product which absorbs at 490 nm. Thus the 490 nm absorbance is directly proportional to the number of living cells in culture.

A direct comparison of the Cellular Album and MTS methods for determining cytotoxicity may be obtained as follows: Cells are treated with different concentrations of test compound or Helioxanthin for a three day-period Prior to lysis for detection album as described above, the MTS reagent is added according to manufacturer's instruction to each well and incubate at 37 0C and read at OD 490 nm. The cellular album quantitation is then performed as described above.

Example 9

PHARMACEUTICAL FORMULATIONS

Examples 9A through 9G are examples of pharmaceutical compositions containing the compounds of Formula I. The abbreviation "V.I." stands for the viral inhibitor compounds of Formula I of the present invention.

Example 9A

Oral Drops 5 grams of V.I. is dissolved in 5 ml of 2-hydroxypropanoic acid and 15 ml polyethylene glycol at about 60° C. to about 80° C. After cooling to about 30°-40° C., 350 ml polyethylene glycol is added and the mixture was stirred well. A solution of 17.5 g sodium saccharin in 25 ml purified water is then added. Flavor and polyethylene glycol q.s. (quantity sufficient) to a volume of 500 ml are added while stirring to provide an oral drop solution comprising 10 mg/ml of V.I.

Example 9B

Capsules 20 grams of the V.I., 6 grams sodium lauryl sulfate, 56 grams starch, 56 grams lactose, 0.8 grams colloidal silicon dioxide, and 1.2 grams magnesium stearate are vigorously stirred together. The resulting mixture is subsequently filled into 1000 suitable hardened gelatin capsules, comprising each 20 mg of the active ingredient.

Example 9C

Film-Coated Tablets

Preparation of tablet core: A mixture of 10 grams of the V.I., 57 grams lactose and 20 grams starch is mixed well and thereafter humidified with a solution of 0.5 grams sodium dodecyl sulfate, and 1.0 grams polyvinylpyrrolidone (KOLLIDON-K 90) in about 20 ml of water. The wet powder mixture is sieved, dried, and sieved again. Then 100 grams microcrystalline cellulose (AVICEL) and 15 grams hydrogenated vegetable oil (STEROTEX) are added. The whole is mixed well and compressed into tablets, giving 1000 tablets, each containing 10 mg of the active ingredient.

Coating: Ethyl cellulose (0.5 grams, ETHOCEL 22 CPS) in 15 ml of dichloromethane is added to a solution of 1.0 grams methyl cellulose (Methocel 60 HG.RTM.) in 7.5 ml of denatured ethanol. Then 7.5 ml of dichloromethane and 0.25 ml 1,2,3-propanetriol are added. Polyethylene glycol (1.0 grams) is melted and dissolved in 7.5 ml of dichloromethane and added to the cellulose-containing solution. Magnesium Octadecanoate (0.25 grams), 0.5 grams polyvinylpyrrolidone, and 3.0 ml of concentrated color suspension (OPASPRAY K-1-2109) are added and the whole mixture homogenized. The tablet cores are coated with this mixture in a coating apparatus.

Example 9D

Injectible Solutions (i) 1.8 grams methyl 4-hydroxybenzoate and 0.2 grams propyl 4-hydroxybenzoate are dissolved in about 0.5 L of boiling water. After cooling to about 50° C., 4 grams lactic acid, 0.05 grams propylene glycol, and 4 grams of the A.M are added while stirring. The solution is cooled to room temperature and supplemented with water for injection q.s. giving a solution containing 4 mg/ml of V.I. The solution is sterilized by filtration and filled in sterile containers.

(ii) 100.0 g of an acid salt of a V.I. of the invention is dissolved in boiling water. After cooling to about 50° C., 37.5 grams lactic acid (90% by weight) are added while stirring. The solution is cooled to room temperature and water is added to 1 L. The solution is sterilized by filtration and filled in sterile containers.

(iii) 5.00 g of an acid salt of a V.I. of the invention is dissolved in boiling water. After cooling to about 50° C., 2.20 grams lactic acid (90% by weight) are added while stirring. The solution is cooled to room temperature and water is added to 100 ml.

Example 9E

Gel

A compound or salt of the invention may be formed as a gel for topical application.

A gel is prepared by suspending A.M (0.2 g-5.0 g) in benzyl alcohol at room temperature. A mixture of hydroxypropyl cellulose (2.5) grams and demineralized water (q.s. 100 g) is added to the suspension with stirring.

Example 9F

Cream

Phase I contains Sorbitan monostearate (2.0 g), Polyoxyethylene (20) sorbitan monostearate (1.5 g), Synthetic spermaceti (3.0 g) Cetyl stearyl alcohol (10.0 g) and 2-Octyldodecanol (13.5 g). The phase I mixture is heated to 75° C., stirred and mixed.

Phase II contains V.I. (1.0 g). Phase II is added to phase I, stirred and suspended.

Phase III contains Benzyl alcohol (1.0 g) and demineralized water (q.s. 100 g). Phase III is heated to 75° C. and added to phase II. The cream is mixed intensively and cooled slowly to room temperature, with further stirring. After cooling to room temperature the cream is homogenized.

Example 9G

Sprays

The active compound solutions or suspensions prepared according to Example 9D can also be processed to sprays. For this purpose, for example, a 60 to 90% active compound solution is mixed with 20 to 40% of the usual propellants, for example $N_2$, $N_2O$, $CO_2$, propane, butane, halogenohydrocarbons and the like.

What is claimed is:

1. A compound or a pharmaceutically acceptable salt thereof wherein the compound is
   1-(3-cyclopropyl-4-(pentyloxy)phenyl)-3-nicotinoylthiourea;
   methyl 2-oxo-2-(5-((3-(4-(pentyloxy)-3-(trifluoromethyl)phenyl)thioureido)carbonyl)pyridin-2-ylamino)acetate;
   methyl 2-(5-((3-(4-(heptyloxy)phenyl)thioureido)carbonyl)pyridin-2-ylamino)-2-oxoacetate;
   1-(2-(2-amino-2-oxoacetamido)nicotinoyl)-3-(4-(pentyloxy)-3-(trifluoromethyl)phenyl)thiourea;
   1-(6-(2-(dimethylamino)ethoxy)nicotinoyl)-3-(4-(pentyloxy)-3-(trifluoromethyl)phenyl)thiourea;
   1-(2-methylnicotinoyl)-3-(4-(pentyloxy)-3-(trifluoromethyl)phenyl)thiourea;
   1-(6-(4-methylpiperazin-1-yl)nicotinoyl)-3-(4-pentylphenyl)thiourea;
   1-(6-(4-methylpiperazin-1-yl)nicotinoyl)-3-(4-(pentyloxy)phenyl)thiourea;
   1-(3-fluoro-4-(pentyloxy)phenyl)-3-(6-(4-methylpiperazin-1-yl)nicotinoyl)thiourea;
   1-(6-(4-methylpiperazin-1-yl)nicotinoyl)-3-(4-(pentyloxy)-3-(trifluoromethyl)phenyl)thiourea;
   1-(3-methyl-4-(pentyloxy)phenyl)-3-(6-(4-methylpiperazin-1-yl)nicotinoyl)thiourea;
   1-(6-hydroxynicotinoyl)-3-(4-(pentyloxy)phenyl)thiourea;
   1-(6-hydroxynicotinoyl)-3-(4-pentylphenyl)thiourea;
   1-(3-fluoro-4-(pentyloxy)phenyl)-3-(6-hydroxynicotinoyl)thiourea;
   1-(6-hydroxynicotinoyl)-3-(4-(pentyloxy)-3-(trifluoromethyl)phenyl)thiourea;
   1-(5-hydroxynicotinoyl)-3-(4-(pentyloxy)-3-(trifluoromethyl)phenyl)thiourea;
   1-(3-fluoro-4-(pentyloxy)phenyl)-3-(5-hydroxynicotinoyl)thiourea;
   1-(6-(morpholine-4-carbonyl)nicotinoyl)-3-(4-(pentyloxy)-3-(trifluoromethyl)phenyl)thiourea;
   1-(6-((dimethylamino)methyl)nicotinoyl)-3-(4-(pentyloxy)-3-(trifluoromethyl)phenyl)thiourea;
   1-(6-acetamidonicotinoyl)-3-(4-(pentyloxy)-3-(trifluoromethyl)phenyl)thiourea;
   (5-((3-(4-(pentyloxy)-3-(trifluoromethyl)phenyl)thioureido) carbonyl)pyridin-2-yl)methyl acetate;
   1-(6-(hydroxymethyl)nicotinoyl)-3-(4-(pentyloxy)-3-(trifluoromethyl)phenyl)thiourea;
   1-(6-(morpholinomethyl)nicotinoyl)-3-(4-(pentyloxy)phenyl)thiourea;
   1-(6-(morpholinomethyl)nicotinoyl)-3-(4-(pentyloxy)-3-(trifluoromethyl)phenyl)thiourea;
   1-(6-((dimethylamino)methyl)nicotinoyl)-3-(4-pentylphenyl)thiourea;
   1-(4-(heptyloxy)phenyl)-3-(6-(morpholine-4-carbonyl)nicotinoyl)thiourea;
   1-(6-(morpholine-4-carbonyl)nicotinoyl)-3-(4-(octyloxy)phenyl)thiourea;
   1-(6-(morpholine-4-carbonyl)nicotinoyl)-3-(4-pentylphenyl)thiourea;
   1-(4-(heptyloxy)phenyl)-3-(6-((4-methylpiperazin-1-yl)methyl)nicotinoyl)thiourea;
   1-(6-((4-methylpiperazin-1-yl)methyl)nicotinoyl)-3-(4-(pentyloxy)-3-(trifluoromethyl)phenyl)thiourea;

1-(6-((dimethylamino)methyl)nicotinoyl)-3-(4-(pentyloxy)phenyl)thiourea;
1-(4-(heptyloxy)phenyl)-3-(6-hydroxynicotinoyl)thiourea;
1-(6-((dimethylamino)methyl)nicotinoyl)-3-(4-(hexyloxy)phenyl)thiourea;
1-(4-(hexyloxy)phenyl)-3-(6-(morpholinomethyl)nicotinoyl)thiourea;
1-(4-(heptyloxy)phenyl)-3-(6-(morpholinomethyl)nicotinoyl) thiourea;
1-(3-fluoro-4-(pentyloxy)phenyl)-3-(26-morpholinonicotinoyl)thiourea;
1-(6-cyanonicotinoyl)-3-(4-(pentyloxy)-3-(trifluoromethyl)phenyl)thiourea;
1-(6-cyanonicotinoyl)-3-(3-fluoro-4-(pentyloxy)phenyl)thiourea;
1-(2-cyanonicotinoyl)-3-(4-(pentyloxy)phenyl)thiourea;
1-(6-(2-morpholinoethoxy)nicotinoyl)-3-(4-(pentyloxy)-3-(trifluoromethyl)phenyl)thiourea;
1-(3-fluoro-4-(pentyloxy)phenyl)-3-(26-(2-morpholinoethoxy) nicotinoyl)thiourea;
1-(6-(2-morpholinoethoxy)nicotinoyl)-3-(4-(pentyloxy) phenyl)thiourea;
1-(6-(2-morpholinoethoxy)nicotinoyl)-3-(4-pentylphenyl)thiourea;
1-(6-(dimethylamino)nicotinoyl)-3-(4-(pentyloxy)-3-(trifluoromethyl)phenyl)thiourea;
1-(6-(dimethylamino)nicotinoyl)-3-(4-(pentyloxy)phenyl)thiourea;
1-(6-(dimethylamino)nicotinoyl)-3-(4-pentylphenyl)thiourea;
1-(5-(furan-3-yl)nicotinoyl)-3-(4-(pentyloxy)-3-(trifluoromethyl)phenyl)thiourea;
1-(3-fluoro-4-(pentyloxy)phenyl)-3-(5-(furan-3-yl)nicotinoyl)thiourea;
1-(5-(furan-3-yl)nicotinoyl)-3-(4-(pentyloxy)phenyl) thiourea;
1-(3-cyano-4-(pentyloxy)phenyl)-3-nicotinoylthiourea;
1-(5-bromonicotinoyl)-3-(4-(pentyloxy)-3-(triflorom ethyl)phenyl)thiourea;
1-(6-(dimethylcarbamoyl)nicotinoyl)-3-(4-(pentyloxy)-3-(trifluoromethyl)phenyl)thiourea;
1-(6-(dimethylcarbamoyl)nicotinoyl)-3-(3-fluoro-4-(pentyloxy)phenyl)thiourea;
1-(3-cyano-4-(pentyloxy)phenyl)-3-(6-(dimethylcarbamoyl) nicotinoyl)thiourea;
1-(6-(dimethylcarbamoyl)nicotinoyl)-3-(4-(pentyloxy) phenyl)thiourea;
1-(3-chloro-4-(pentyloxy)phenyl)-3-(6-cyanonicotinoyl) thiourea;
1-(5-cyanonicotinoyl)-3-(4-(pentyloxy)-3-(trifluoromethyl)phenyl)thiourea;
methyl 5-((3-(4-(pentyloxy)-3-(trifluoromethyl)phenyl) thioureido)carbonyl)nicotinate;
1-(3-fluoro-4-(pentyloxy)phenyl)-3-(6-(1-methylpiperazine-4-carbonyl)nicotinoyl)thiourea;
1-(3-chloro-4-(pentyloxy)phenyl)-3-(6-(1-methylpiperazine-4-carbonyl)nicotinoyl)thiourea;
1-(6-(1-methylpiperazine-4-carbonyl)nicotinoyl)-3-(4-(pentyloxy)phenyl)thiourea;
1-(3-chloro-4-(pentyloxy)phenyl)-3-nicotinoylthiourea;
1-(4-(pentyloxy)phenyl)-3-(6-(2-(pyrrolidin-1-yl)ethyl) nicotinoyl)thiourea;
1-(4-pentylphenyl)-3-(6-(2-(pyrrolidin-1-yl)ethyl)nicotinoyl)thiourea;
1-(2-(4-fluorophenoxy)nicotinoyl)-3-(4-pentylphenyl) thiourea;
1-nicotinoyl-3-(4-(octyloxy)phenyl)thiourea;
1-nicotinoyl-3-(4-octylphenyl)thiourea;
1-(4-(hexyloxy)phenyl)-3-nicotinoylthiourea;
1-(4-hexylphenyl)-3-nicotinoylthiourea;
1-(3-fluoro-4-(pentyloxy)phenyl)-3-nicotinoylthiourea;
1-nicotinoyl-3-(4-(pentyloxy)-3-(trifluoromethyl)phenyl) thiourea;
1-(4-butoxyphenyl)-3-nicotinoylthiourea;
1-(4-(heptyloxy)-3-(trifluoromethyl)phenyl)-3-nicotinoylthiourea;
1-(3-chloro-4-(pentyloxy)phenyl)-3-nicotinoylthiourea; or
1-(4-isopropoxy-3-(trifluoromethyl)phenyl)-3-nicotinoylthiourea.

2. A pharmaceutical composition comprising a compound or salt of claim 1 together with at least one pharmaceutically acceptable excipient.

3. The pharmaceutical composition of claim 2, wherein the composition is formulated for oral administration.

4. The pharmaceutical composition of claim 2, wherein the composition is formulated as an injectable fluid, an aerosol, a cream, a gel, a tablet, a pill, a capsule, a syrup, ophthalmic solution, or a transdermal patch.

5. A compound of claim 1 of the formula:

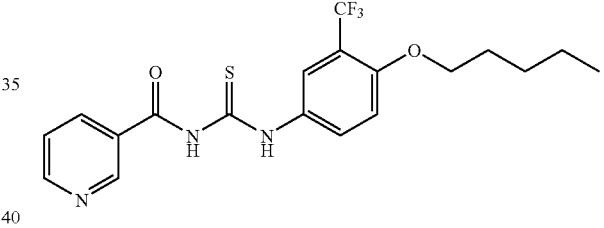

or a pharmaceutically acceptable salt thereof.

6. A compound of claim 1 of the formula:

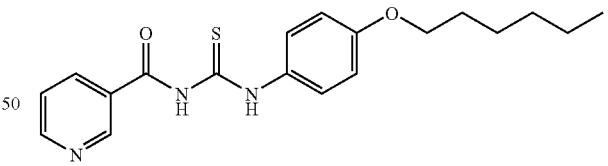

or a pharmaceutically acceptable salt thereof.

7. A compound of claim 1 of the formula:

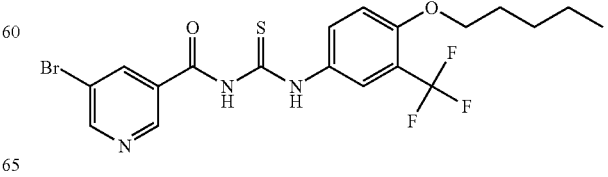

or a pharmaceutically acceptable salt thereof.

8. A compound of claim 1 the formula:

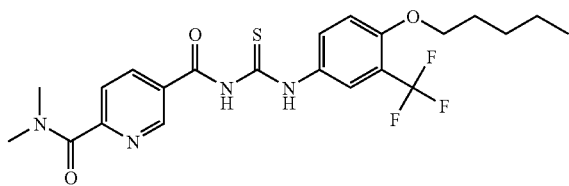

or a pharmaceutically acceptable salt thereof.

9. A compound of claim 1 the formula:

or a pharmaceutically acceptable salt thereof.

10. A compound of claim 1 the formula

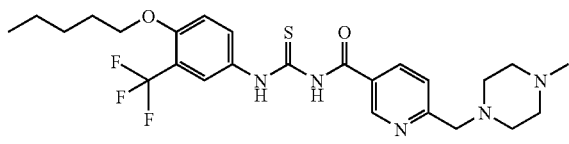

or a pharmaceutically acceptable salt thereof.

11. A compound of claim 1 the formula

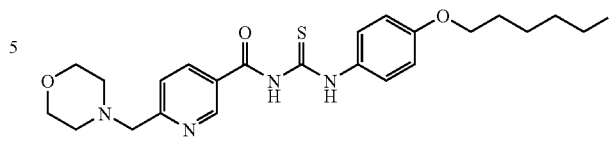

or a pharmaceutically acceptable salt thereof.

12. A compound of claim 1 which is 1-nicotinoyl-3-(4-(pentyloxy)-3-(trifluoromethyl)phenyl)thiourea.

13. A compound of claim 1, which is 1-(4-(hexyloxy)phenyl)-3-nicotinoylthiourea.

14. A compound of claim 1, which is 1-(5-bromonicotinoyl)-3-(4-(pentyloxy)-3-(trifluoromethyl)phenyl)thiourea.

15. A compound of claim 1, which is 1-(6-(dimethylcarbamoyl)nicotinoyl)-3-(4-(pentyloxy)-3-(trifluoromethyl)phenyl)thiourea.

16. A compound of claim 1, which is 1-(6-((dimethylamino)methyl)nicotinoyl)-3-(4-(pentyloxy)-3-(trifluoromethyl)phenyl)thiourea.

17. A compound of claim 1, which is 1-(6-((4-methylpiperazin-1-yl)methyl)nicotinoyl)-3-(4-(pentyloxy)-3-(trifluoromethyl)phenyl)thiourea.

18. A compound of claim 1, which is 1-(4-(hexyloxy)phenyl)-3-(6-(morpholinomethyl)nicotinoyl)thiourea.

19. A pharmaceutical composition of claim 2, wherein the compound is 1-nicotinoyl-3-(4-(pentyloxy)-3-(trifluoromethyl)phenyl)thiourea or a salt thereof.

* * * * *